(12) United States Patent
Uoto et al.

(10) Patent No.: US 8,404,691 B2
(45) Date of Patent: Mar. 26, 2013

(54) IMIDAZOTHIAZOLE DERIVATIVES HAVING PROLINE RING STRUCTURE

(75) Inventors: Kouichi Uoto, Tokyo (JP); Yuuichi Sugimoto, Tokyo (JP); Hiroyuki Naito, Tokyo (JP); Masaki Miyazaki, Tokyo (JP); Keisuke Yoshida, Tokyo (JP); Masashi Aonuma, Tokyo (JP)

(73) Assignee: Daiichi Sankyo Company, Limited (JP)

( * ) Notice: Subject to any disclaimer, the term of this patent is extended or adjusted under 35 U.S.C. 154(b) by 0 days.

(21) Appl. No.: 13/183,762

(22) Filed: Jul. 15, 2011

(65) Prior Publication Data

US 2011/0301176 A1 Dec. 8, 2011

Related U.S. Application Data

(63) Continuation of application No. PCT/JP2010/050372, filed on Jan. 15, 2010.

(30) Foreign Application Priority Data

Jan. 16, 2009 (JP) .................................. 2009-007536

(51) Int. Cl.
*A61K 31/496* (2006.01)
*C07D 513/04* (2006.01)

(52) U.S. Cl. ................ 514/253.1; 514/254.02; 544/364; 544/368

(58) Field of Classification Search .................. None
See application file for complete search history.

(56) References Cited

U.S. PATENT DOCUMENTS

2009/0312310 A1 12/2009 Kawato et al.

FOREIGN PATENT DOCUMENTS

| EP | 2298778 | 3/2011 |
|---|---|---|
| WO | WO 2003/051359 A1 | 6/2003 |
| WO | WO 2003/051360 A1 | 6/2003 |
| WO | WO 2005/002575 A1 | 1/2005 |
| WO | WO 2005/003097 A1 | 1/2005 |
| WO | WO 2005/110996 A1 | 11/2005 |
| WO | WO 2005/123691 A1 | 12/2005 |
| WO | WO 2007/063013 A1 | 6/2007 |
| WO | WO 2008/119741 A2 | 10/2008 |
| WO | WO 2008/125487 A1 | 10/2008 |

OTHER PUBLICATIONS

Cancer Drug Design and Discovery, Neidle, Stephen,ed. (Elsevier/Academic Press), pp. 427-431 (2008).*
Jones et al. Proc.Natl.Acad.Sci. vol. 95, pp. 15608-15612 (1998).*
Marine Cancer cell, vol. 18, pp. 399-400 (2010).*
Chow & Eckhart, "Sunitinib: From Rational Design to Clinical Efficacy," *J. Clin. Oncol.* (2007) 25:884-896.
Kerbel, "Human Tumor Xenografts as Predictive Preclinical Models for Anticancer Drug Activity in Humans," *Cancer Biol. & Ther.* (2003) 2:S134-S139.
Lee et al., "BMS-247550: A Novel Epothilone Analog with a Mode of Action Similar to Paclitaxel but Possessing Superior Antitumor Efficacy," *Clin. Cancer Res.* (2001) 7:1429-1437.
Luo et al., "Dasatinib (BMS-354825) Pharmacokinetics and Pharmacodynamic Biomarkers in Animal Models Predict Optimal Clinical Exposure," *Clin. Cancer Res.* (2006) 12:7180-7186.
Man et al, "Antitumor Effects in Mice of Low-dose (Metronomic) Cyclophosphamide Administered Continuously through the Drinking Water," *Cancer Res.* (2002) 62:2731-2735.
Yuan et al., "Novel targeted therapeutics: inhibitors of MDM2, ALK and PARP," *J. Hematol. Oncol.*, (2011) 4:16, 14 pages.
U.S. Appl. No. 13/416,061, Sugimoto et al. (English version as filed provided herewith).
International Search Report for PCT/JP2010/050372, dated Apr. 6, 2010.
International Preliminary Report on Patentability for PCT/JP2010/050372, dated Aug. 16, 2011.
Vassilev et al., "In Vivo Activation of the p53 Pathway by Small-Molecule Antagonists of MDM2," Science (2004) 303: 844-848.
Tovar et al. "Small-molecule MDM2 antagonists reveal aberrant p53 signaling in cancer: Implications for therapy," Proceedings of the National Academy of Sciences of the United States of America (2006) 103(6):1888-1893.

* cited by examiner

*Primary Examiner* — Emily Bernhardt
(74) *Attorney, Agent, or Firm* — Dorsey & Whitney LLP

(57) ABSTRACT

There is provided compounds that inhibit interaction between murine double minute 2 (Mdm2) protein and p53 protein and exhibits anti-tumor activity. Compounds include imidazothiazole derivatives that can inhibit interaction between Mdm2 protein and p53 protein and exhibits anti-tumor activity.

11 Claims, No Drawings

IMIDAZOTHIAZOLE DERIVATIVES HAVING PROLINE RING STRUCTURE

This application is a continuation of PCT Patent Application No. PCT/JP2010/050372, filed Jan. 15, 2010, which claims priority to Japanese Application No. 2009-007536, filed Jan. 16, 2009, which is incorporated herein by reference in its entirety.

TECHNICAL FIELD

The present invention relates to a compound having a proline ring structure having anti-tumor activity by inhibition of murine double minute 2 (Mdm2) or a salt thereof.

BACKGROUND ART p53 is known as an important factor for inhibiting canceration of cells. p53 is a transcription factor that induces the expression of genes involved in the cell cycle and cellular apoptosis in response to various stresses. p53 is thought to inhibit canceration of cells by a transcription regulating function thereof. In fact, deletion or mutation of the p53 gene is observed in about half of human cancer cases.

Meanwhile, overexpression of murine double minute 2 (Mdm2), a type of E3 ubiquitin ligase, is known as a factor for canceration of cells that are cancerated in spite of the presence of normal p53. Mdm2 is a protein of which expression is induced by p53. Mdm2 negatively regulates p53 by mediating degradation of p53 by binding to the transcription activity domain of p53 to decrease the transcription activity of p53, exporting p53 out of the nucleus, and further acting as a ubiquitination ligase against p53. Therefore, it is thought that inactivation of functions of and degradation of p53 are promoted in cells in which Mdm2 is overexpressed, resulting in canceration (Non Patent Document 1).

Paying attention to such functions of Mdm2, many approaches have been attempted using substances that inhibit the suppression of p53 functions by Mdm2, as candidate anti-tumor agents. Examples of the Mdm2 inhibitors targeting the Mdm2-p53 binding site have been reported, which include imidazoline derivatives having two sites substituted with halogenobenzene (for example, refer to Non Patent Documents 1 and 2 and Patent Documents 1 to 8) and imidazothiazole derivatives having two sites substituted with halogenobenzene (for example, refer to Patent Document 9). However, no report has demonstrated that these compounds actually showed efficacy in clinical practice.

CITATION LIST

Patent Documents

[Patent Document 1] WO2003/51359
[Patent Document 2] WO2003/51360
[Patent Document 3] WO2005/3097
[Patent Document 4] WO2005/2575
[Patent Document 5] WO2005/110996
[Patent Document 6] WO2005/123691
[Patent Document 7] WO2007/63013
[Patent Document 8] WO2008/125487
[Patent Document 9] WO2008/072655

Non Patent Documents

[Non Patent Document 1] Science, 2004, 303, 844-848
[Non Patent Document 2] Proceedings of the National Academy of Sciences of the United States of America, 2006, 103, 1888-1893

SUMMARY OF INVENTION

Problem to be Solved by the Invention

The present invention provides a novel Mdm2 inhibiting compound. Furthermore, the present invention provides an anti-tumor agent containing the Mdm2 inhibiting compound.

Means for Solving the Problem

As a result of extensive studies, the present inventors have found that a compound having a structure represented by the following general formula (1) or a salt thereof had potent Mdm2 inhibiting activity and accomplished the present invention.

More specifically, the present invention provides:

[1] A compound represented by general formula (1) or a salt thereof:

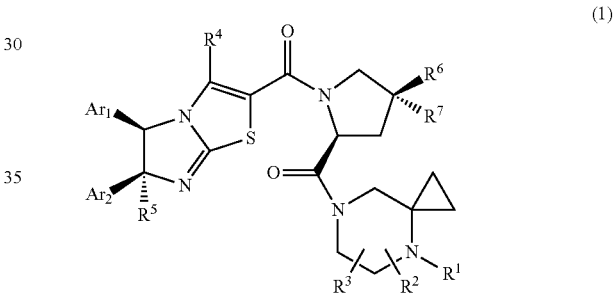

(1)

wherein $Ar_1$ represents a phenyl group which may have one or more substituents selected from a halogen atom, a cyano group, and a $C_1$-$C_6$ alkyl group;

$Ar_2$ represents a phenyl group which may have one or more substituents selected from a halogen atom, a $C_1$-$C_6$ alkyl group, and a cyano group, or a pyridyl group which may have one or more substituents selected from a halogen atom, a $C_1$-$C_6$ alkyl group, and a cyano group;

$R^1$ represents a $C_1$-$C_6$ alkyl group which may have one or more substituents selected from a halogen atom, a hydroxy group, a $C_1$-$C_6$ alkoxy group, a carbamoyl group, an amino group, a $C_1$-$C_6$ alkanoyl group, and a cyano group, a $C_1$-$C_6$ alkanoyl group which may have one or more substituents selected from a halogen atom, a hydroxy group, a $C_1$-$C_6$ alkoxy group, a carbamoyl group, an amino group, and a cyano group, a hydrogen atom, or a hydroxy group;

$R^2$ and $R^3$ each independently represent a $C_1$-$C_6$ alkyl group which may have one or more substituents selected from a halogen atom, a hydroxy group, a $C_1$-$C_6$ alkoxy group, a carbamoyl group, an amino group, a $C_1$-$C_6$ alkanoyl group, and a cyano group, a carboxy group, or a hydrogen atom, or $R^2$ and $R^3$ may together form an oxo group, or $R^2$ and $R^3$ together with the carbon atoms to which $R^2$ and $R^3$ are respectively bonded may form a 3- to 5-membered saturated hydrocarbon ring in a spiro or condensed form;

$R^4$ represents a $C_1$-$C_6$ alkyl group which may have one or more substituents selected from a halogen atom, a hydroxy group, a $C_1$-$C_6$ alkoxy group, a carbamoyl group, an amino group, a $C_1$-$C_6$ alkanoyl group, and a cyano group;

$R^5$ represents a $C_1$-$C_6$ alkyl group which may have one or more substituents selected from a halogen atom, a hydroxy group, a $C_1$-$C_6$ alkoxy group, a carbamoyl group, an amino group, a $C_1$-$C_6$ alkanoyl group, and a cyano group;

$R^6$ represents a halogen atom or a hydrogen atom; and $R^7$ represents a halogen atom.

[2] A compound represented by general formula (2) or a salt thereof:

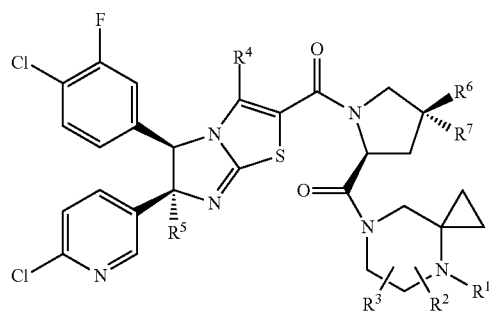

(2)

wherein $R^1$ represents a $C_1$-$C_6$ alkyl group which may have one or more substituents selected from a halogen atom, a hydroxy group, a $C_1$-$C_6$ alkoxy group, a carbamoyl group, an amino group, a $C_1$-$C_6$ alkanoyl group, and a cyano group, a $C_1$-$C_6$ alkanoyl group which may have one or more substituents selected from a halogen atom, a hydroxy group, a $C_1$-$C_6$ alkoxy group, a carbamoyl group, an amino group, and a cyano group, a hydrogen atom, or a hydroxy group;

$R^2$ and $R^3$ each independently represent a $C_1$-$C_6$ alkyl group which may have one or more substituents selected from a halogen atom, a hydroxy group, a $C_1$-$C_6$ alkoxy group, a carbamoyl group, an amino group, a $C_1$-$C_6$ alkanoyl group, and a cyano group, a carboxy group, or a hydrogen atom, or $R^2$ and $R^3$ may together form an oxo group, or $R^2$ and $R^3$ together with the carbon atoms to which $R^2$ and $R^3$ are respectively bonded may form a 3- to 5-membered saturated hydrocarbon ring in a spiro or condensed form;

$R^4$ represents a $C_1$-$C_6$ alkyl group which may have one or more substituents selected from a halogen atom, a hydroxy group, a $C_1$-$C_6$ alkoxy group, a carbamoyl group, an amino group, a $C_1$-$C_6$ alkanoyl group, and a cyano group;

$R^5$ represents a $C_1$-$C_6$ alkyl group which may have one or more substituents selected from a halogen atom, a hydroxy group, a $C_1$-$C_6$ alkoxy group, a carbamoyl group, an amino group, a $C_1$-$C_6$ alkanoyl group, and a cyano group;

$R^6$ represents a halogen atom or a hydrogen atom; and $R^7$ represents a halogen atom.

[3] A compound according to [1] or [2] or a salt thereof, wherein $R^1$ is a $C_1$-$C_6$ alkyl group, a $C_1$-$C_6$ alkanoyl group which may be substituted with one or more halogen atoms, or a hydrogen atom.

[4] A compound according to any one of [1] to [3] or a salt thereof, wherein $R^4$ is a $C_1$-$C_6$ alkyl group.

[5] A compound according to any one of [1] to [4] or a salt thereof, wherein $R^5$ is a $C_1$-$C_6$ alkyl group.

[6] A compound represented by the following formula:

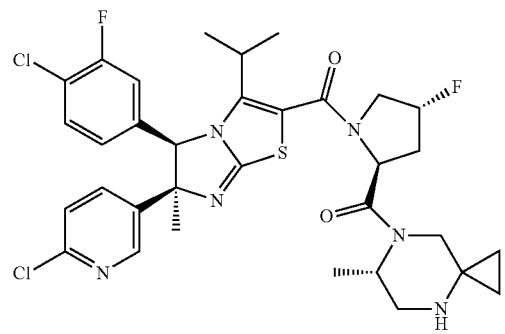 [SMILES: CC(C)C1=C(C(=O)N2C[C@H](F)C[C@H]2C(=O)N2CC3(CC3)NC[C@@H]2C)SC2=N[C@@](C)(c3ccc(Cl)nc3)[C@@H](c3ccc(Cl)c(F)c3)N21]

[7] A compound represented by the following formula:

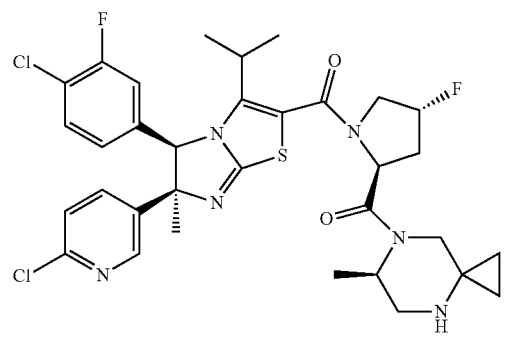 [SMILES: CC(C)C1=C(C(=O)N2C[C@H](F)C[C@H]2C(=O)N2CC3(CC3)NC[C@H]2C)SC2=N[C@@](C)(c3ccc(Cl)nc3)[C@@H](c3ccc(Cl)c(F)c3)N21]

[8] A compound represented by the following formula:

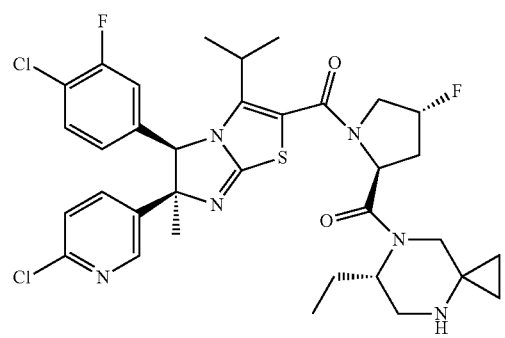 [SMILES: CC[C@H]1CNC2(CC2)CN1C(=O)[C@@H]1C[C@@H](F)CN1C(=O)C1=C(C(C)C)N2C(=N[C@@](C)(c3ccc(Cl)nc3)[C@H]2c2ccc(Cl)c(F)c2)S1]

[9] A compound represented by the following formula:

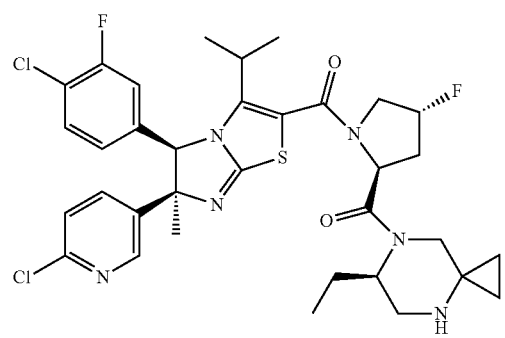 [SMILES: CC[C@@H]1CNC2(CC2)CN1C(=O)[C@@H]1C[C@@H](F)CN1C(=O)C1=C(C(C)C)N2C(=N[C@@](C)(c3ccc(Cl)nc3)[C@H]2c2ccc(Cl)c(F)c2)S1]

[10] A compound represented by the following formula:

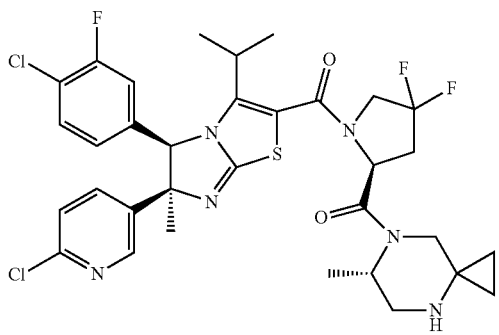 [SMILES: CC(C)C1=C(C(=O)N2CC(F)(F)C[C@H]2C(=O)N2CC3(CC3)NC[C@@H]2C)SC2=N[C@@](C)(c3ccc(Cl)nc3)[C@@H](c3ccc(Cl)c(F)c3)N21]

[11] An inhibitor of Mdm2 comprising a compound according to any one of [1] to [10] or a salt thereof.

[12] An inhibitor of p53-Mdm2 binding comprising a compound according to any one of [1] to [10] or a salt thereof.

[13] A medicament comprising a compound according to any one of [1] to [10] or a salt thereof as an active ingredient.

[14] A pharmaceutical composition comprising a compound according to any one of [1] to [10] or a salt thereof and a pharmaceutically acceptable carrier.

[15] Use of a compound according to any one of [1] to [10] or a salt thereof for the manufacture of a medicament.

[16] An anticancer agent comprising a compound according to any one of [1] to [10] or a salt thereof as an active ingredient.

[17] A method for treating cancer, comprising administering a compound according to any one of [1] to [10] or a salt thereof.

[18] An anticancer agent according to [16], wherein the cancer is any selected from lung cancer, breast cancer, prostate cancer, colon cancer, acute myeloid leukemia, malignant lymphoma, retinoblastoma, neuroblastoma, and sarcoma.

[19] A method for treating cancer according to [17], wherein the cancer is any selected from lung cancer, breast cancer, prostate cancer, colon cancer, acute myeloid leukemia, malignant lymphoma, retinoblastoma, neuroblastoma, and sarcoma.

Advantages of the Invention

The present invention provides a novel imidazothiazole derivative represented by the above formula (1), which has Mdm2 inhibiting activity. Such a novel compound is useful as an anti-tumor agent.

DESCRIPTION OF EMBODIMENTS

In the present invention, "Mdm2" means a protein encoded by the murine double minute 2 gene. "Mdm2" includes Mdm2 proteins encoded by a complete length of the Mdm2 gene, Mdm2 proteins encoded by mutated Mdm2 genes (including deletion mutants, substitution mutants, and addition mutants), and so forth. In the present invention, "Mdm2" also includes homologues derived from various animal species such as, for example, human Mdm2 homologue (HDM2).

In the present invention, "p53" means a protein encoded by the p53 gene. "p53" means the p53 protein encoded by a full length p53 gene or a p53 protein that has a mutation (including mutations by deletion, substitution, and addition), but functions normally.

In the present invention, "Mdm2 inhibitor" means a factor that restores p53 functions suppressed by Mdm2 by acting on either Mdm2 or p53, or on both p53 and Mdm2. The p53 functions are not particularly limited so long as they are functions which p53 normally has. Examples thereof include inhibition of canceration of cells by inducing the expression of genes involved in the cell cycle or cellular apoptosis. Examples of Mdm2 inhibitors include factors that inhibit binding of Mdm2 to p53 (hereinafter, referred to as p53-Mdm2 binding inhibitors) or factors that inhibit ubiquitination of p53 by Mdm2 (hereinafter, referred to as Mdm2 ubiquitin ligase inhibitors).

In the present invention, "inhibitor of suppression of p53 transcription activity" means a factor that restores the functions of p53 as a transcription factor suppressed by Mdm2.

In the present invention, "inhibitor of p53 degradation" means a factor that inhibits degradation of p53 in proteasomes by inhibiting ubiquitination of p53 by Mdm2.

In the present invention, the terms "tumor" and "cancer" are used interchangeably. Furthermore, in the present invention, tumor, malignant tumor, cancer, malignant neoplasm, carcinoma, sarcoma, and the like may be collectively referred to as "tumor" or "cancer."

In the present invention, "$C_1$-$C_6$ alkyl group" means a straight, branched, or cyclic alkyl group having 1 to 6 carbon atoms. Examples of a "$C_1$-$C_6$ alkyl group" include a methyl group, an ethyl group, a propyl group, an isopropyl group, a cyclopropyl group, a butyl group, a tert-butyl group, a cyclobutyl group, a cyclopentyl group, and a cyclohexyl group.

"$C_1$-$C_6$ alkoxy group" means an alkoxy group having a straight, branched, or cyclic alkyl group having 1 to 6 carbon atoms. Examples of a "$C_1$-$C_6$ alkoxy group" include a methoxy group, an ethoxy group, a propoxy group, an isopropoxy group, a butoxy group, and a cyclopentyloxy group.

"$C_1$-$C_6$ alkanoyl group" means an alkanoyl group having a straight, branched, or cyclic alkyl group having 1 to 6 carbon atoms. Examples of a "$C_1$-$C_6$ alkanoyl group" include a formyl group, an acetyl group, a propionyl group, and a methylpropionyl group.

Examples of "halogen atom" include a fluorine atom, a chlorine atom, a bromine atom, and an iodine atom.

"Oxo group" means a group represented by "=O" unless otherwise specified.

Hereafter, each substituent in formula (1) will be explained.

In the following general formula (1),

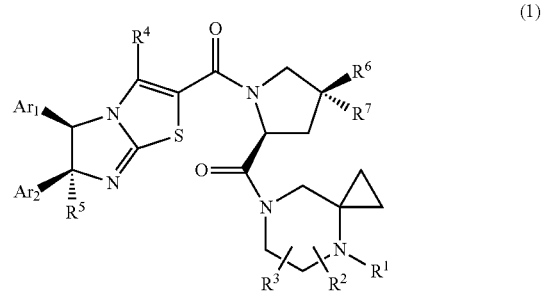

$R^1$ represents a $C_1$-$C_6$ alkyl group which may have one or more substituents selected from a halogen atom, a hydroxy group, a $C_1$-$C_6$ alkoxy group, a carbamoyl group, an amino group, a $C_1$-$C_6$ alkanoyl group, and a cyano group, a $C_1$-$C_6$ alkanoyl group which may have one or more substituents selected from a halogen atom, a hydroxy group, a $C_1$-$C_6$ alkoxy group, a carbamoyl group, an amino group, and a cyano group, a hydrogen atom, or a hydroxy group.

Here, the "$C_1$-$C_6$ alkyl group which may have one or more substituents" and the "$C_1$-$C_6$ alkanoyl group which may have one or more substituents" preferably have 0 to 3 substituents. The substituent(s) is preferably a halogen atom, a hydroxy group, a $C_1$-$C_6$ alkoxy group, a carbamoyl group, an amino group, a $C_1$-$C_6$ alkanoyl group, or a cyano group. The substituent(s) is more preferably a halogen atom, a hydroxy group, or a $C_1$-$C_6$ alkoxy group.

The "$C_1$-$C_6$ alkyl group which may have one or more substituents" is more preferably an unsubstituted $C_1$-$C_6$ alkyl group or a $C_1$-$C_6$ alkyl group having one or more halogen atoms, hydroxy groups, or $C_1$-$C_6$ alkoxy groups as a substituent, yet more preferably an unsubstituted $C_1$-$C_6$ alkyl group or a $C_1$-$C_6$ alkyl group having 1 to 3 fluorine atoms as a substituent.

The "$C_1$-$C_6$ alkanoyl group which may have one or more substituents" is preferably an unsubstituted $C_1$-$C_6$ alkanoyl group or a $C_1$-$C_6$ alkanoyl group having 1 to 3 halogen atoms as a substituent, particularly preferably a formyl group, an acetyl group, or a trifluoromethylcarbonyl group.

$R^1$ is preferably an unsubstituted $C_1$-$C_6$ alkyl group or a $C_1$-$C_6$ alkyl group substituted with halogen atom(s), an unsubstituted $C_1$-$C_6$ alkanoyl group or a $C_1$-$C_6$ alkanoyl group substituted with halogen atom(s), or a hydrogen atom.

$R^2$ and $R^3$ each independently represent a $C_1$-$C_6$ alkyl group which may have one or more substituents selected from a halogen atom, a hydroxy group, a $C_1$-$C_6$ alkoxy group, a carbamoyl group, an amino group, a $C_1$-$C_6$ alkanoyl group, and a cyano group, a carboxy group, or a hydrogen atom, or $R^2$ and $R^3$ may together form an oxo group, or $R^2$ and $R^3$ together with the carbon atoms to which $R^2$ and $R^3$ are respectively bonded may form a 3- to 5-membered saturated hydrocarbon ring in a spiro or condensed form.

Here, the "$C_1$-$C_6$ alkyl group which may have one or more substituents" has the same meaning as defined above in $R^1$ and also has the same preferred examples.

When both $R^2$ and $R^3$ are respectively a carboxy group or one of $R^2$ and $R^3$ is a carboxy group, compounds in which the carboxy group is esterified or amidated are also included in the scope of the present invention. Examples thereof include compounds in which the carboxy group is ethyl esterified, phenyl esterified, carboxymethyl esterified, dimethylaminomethyl esterified, pivaloyloxymethyl esterified, ethoxycarbonyloxyethyl esterified, amidated, or methylamidated.

The phrase "$R^2$ and $R^3$ together with the carbon atoms to which $R^2$ and $R^3$ are respectively bonded may form a 3- to 5-membered saturated hydrocarbon ring in a spiro or condensed form" means that $R^2$ and $R^3$ may be bonded to form a 3- to 5-membered saturated hydrocarbon ring in a spiro form when $R^2$ and $R^3$ are substituents bonded to the same carbon atom, or $R^2$ and $R^3$ may be bonded to form a 3- to 5-membered saturated hydrocarbon ring in a condensed form when $R^2$ and $R^3$ are bonded to different carbon atoms. Examples of the "3- to 5-membered saturated hydrocarbon ring" include a cyclopropane ring, a cyclobutane ring, and a cyclopentane ring.

Preferably, $R^2$ and $R^3$ are each independently a hydrogen atom, a $C_1$-$C_6$ alkyl group which may have substituent(s), or a carboxy group. The substituent substituted on the $C_1$-$C_6$ alkyl group is preferably a fluorine atom or a hydroxy group. More preferably, $R^2$ and $R^3$ are respectively a hydrogen atom, or one of $R^2$ and $R^3$ is a hydrogen atom and the other moiety is a methyl group or an ethyl group, or $R^2$ and $R^3$ which are $C_1$-$C_6$ alkyl groups bonded to the same carbon atom form a 3- to 4-membered saturated hydrocarbon ring in a spiro form, together with the carbon atom to which they are bonded. Both $R^2$ and $R^3$ are preferably substituents at the 6-position on a piperazine ring.

$R^4$ represents a $C_1$-$C_6$ alkyl group which may have one or more substituents. Here, the "$C_1$-$C_6$ alkyl group which may have one or more substituents" has the same meaning as defined above in $R^1$.

$R^4$ is preferably an unsubstituted $C_1$-$C_6$ alkyl group, more preferably an unsubstituted $C_1$-$C_3$ alkyl group, yet more preferably an isopropyl group.

$R^5$ represents a $C_1$-$C_6$ alkyl group which may have one or more substituents. Here, the "$C_1$-$C_6$ alkyl group which may have one or more substituents" has the same meaning as defined above in $R^1$.

$R^5$ is preferably an unsubstituted $C_1$-$C_6$ alkyl group, more preferably an unsubstituted $C_1$-$C_3$ alkyl group, yet more preferably a methyl group or an ethyl group.

$R^6$ represents a halogen atom or a hydrogen atom. $R^6$ is preferably a fluorine atom, a chlorine atom, a bromine atom, or a hydrogen atom, more preferably a fluorine atom or a hydrogen atom.

$R^7$ represents a halogen atom. $R^7$ is preferably a fluorine atom, a chlorine atom, or a bromine atom, more preferably a fluorine atom.

$An$ represents a phenyl group which may have one or more substituents. $Ar_1$ is preferably a phenyl group having 1 to 3 $C_1$-$C_6$ alkyl groups, cyano groups, or halogen atoms as a substituent, more preferably a phenyl group having 1 to 3 halogen atoms as a substituent. The substituent may be positioned at any position. More preferably, $Ar_1$ is a 4-chlorophenyl group or a 3-fluoro-4-chlorophenyl group.

$Ar_2$ represents a phenyl group which may have one or more substituents or a pyridyl group which may have one or more substituents. $Ar_2$ is preferably a phenyl group having 1 to 3 halogen atoms, $C_1$-$C_6$ alkyl groups, or cyano groups as a substituent or a pyridyl group having 1 to 3 halogen atoms, $C_1$-$C_6$ alkyl groups, or cyano groups as a substituent. The substituent may be positioned at any position. More preferably, $Ar_2$ is a 4-chlorophenyl group or a 6-chloropyridin-3-yl group.

The absolute configurations of $Ar_1$ and $Ar_2$ in the imidazothiazole skeleton are preferably 5R and 6S, respectively.

Furthermore, the compound represented by the formula (1) of the present invention is preferably a compound represented by the following general formula (2):

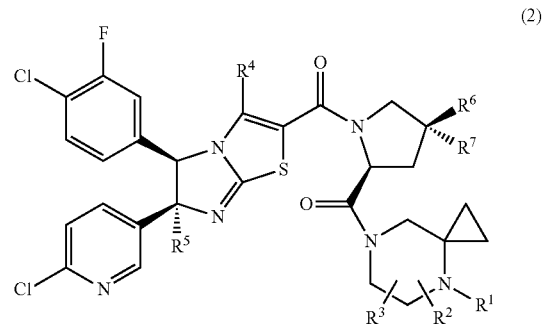

(2)

Here, definitions, examples, and preferred examples of $R^1$, $R^2$, $R^3$, $R^4$, $R^5$, $R^6$, and $R^7$ are the same as described above in general formula (1).

Furthermore, the compound of the present invention is preferably one compound selected from the following group:

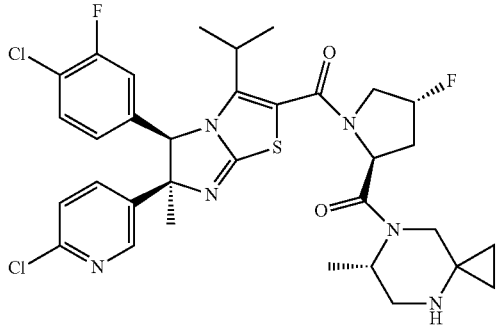

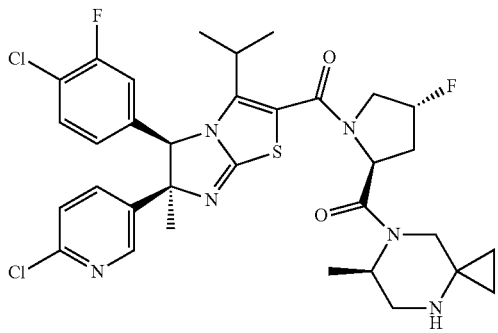

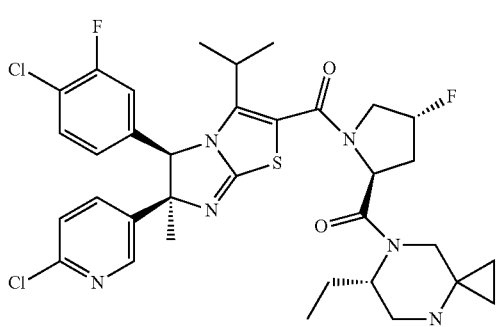

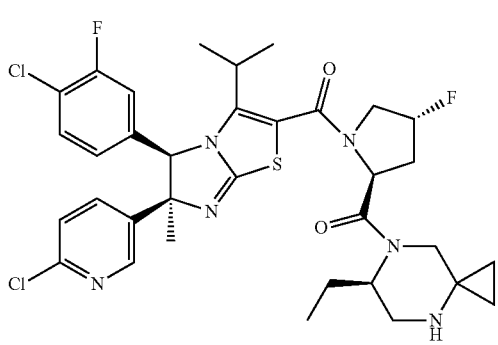

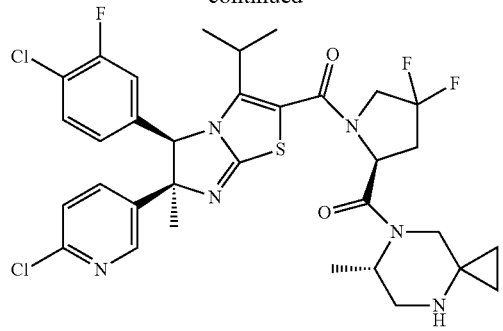

The compound represented by formula (1) of the present invention may have stereoisomers or optical isomers due to asymmetric carbon atoms, and all these stereoisomers, optical isomers, and mixtures thereof are included in the present invention.

In one embodiment of the present invention, a compound having an absolute configuration represented by formula (3) is preferred:

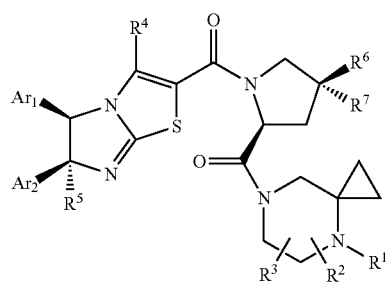

(3)

wherein $Ar_1$, $Ar_2$, $R^1$ to $R^7$ have the same meanings as defined above.

Furthermore, the compound of general formula (1) is preferably a compound, a salt or a hydrate thereof described in any of the Examples and/or Tables 1 to 12 described later.

The compound represented by general formula (1) of the present invention can form a pharmaceutically acceptable salt, if desired, when having a basic group such as an amino group. Examples of such salts can include: hydrohalides such as hydrochloride and hydroiodide; inorganic acid salts such as nitrate, perchlorate, sulfate, and phosphate; lower alkanesulfonates such as methanesulfonate, trifluoromethanesulfonate, and ethanesulfonate; arylsulfonates such as benzenesulfonate and p-toluenesulfonate; organic acid salts such as formic acid, acetic acid, malic acid, fumarate, succinate, citrate, tartrate, oxalate, and maleate; and amino acid salts such as ornithine salt, glutamate, and aspartate. Hydrohalides and organic acid salts are preferred.

The compound represented by general formula (1) of the present invention may generally form a base addition salt when having an acidic group such as a carboxy group. Examples of pharmaceutically acceptable salts can include: alkali metal salts such as sodium salt, potassium salt, and lithium salt; alkaline earth metal salts such as calcium salt and magnesium salt; inorganic salts such as ammonium salt; and organic amine salts such as dibenzylamine salt, morpholine salt, phenylglycine alkyl ester salt, ethylenediamine salt, N-methylglucamine salt, diethylamine salt, triethylamine salt, cyclohexylamine salt, dicyclohexylamine salt, N,N'- dibenzylethylenediamine salt, diethanolamine salt, N-benzyl-N-(2-phenylethoxy)amine salt, piperazine salt, tetramethylammonium salt, and tris(hydroxymethyl)aminomethane salt.

The compound represented by general formula (1) of the present invention or the salt thereof may be present in a free or solvate form. The compound represented by general formula (1) of the present invention or the salt thereof may be present in a hydrate form, for example, by absorbing moisture in the air. The solvate is not particularly limited so long as it is pharmaceutically acceptable. Specifically, the solvate is preferably a hydrate, an ethanol solvate, or the like. Moreover, the compound represented by general formula (1) of the present invention may be in an N-oxide form when containing a nitrogen atom. These solvate and N-oxide forms are also included in the present invention.

The compound represented by general formula (1) of the present invention may have various isomers such as geometrical isomers (e.g., cis and trans forms), tautomers, and optical isomers (e.g., d and l forms), depending on the types or combinations of substituents. The compound of the present invention also encompasses all these isomers, stereoisomers, and mixtures of these isomers and stereoisomers in any ratio, unless otherwise specified.

The compound represented by general formula (1) of the present invention may contain an isotope in a non-natural proportion as one or more constituent atoms. Examples of an isotope include deuterium ($^2$H), tritium ($^3$H), iodine-125 ($^{125}$I), and carbon-14 ($^{14}$C). These compounds are useful as a therapeutic or preventive agent, a research reagent (e.g., an assay reagent), and a diagnostic agent (e.g., an in vivo diagnostic imaging agent). All isotopic variants of the compound represented by general formula (1) are included in the scope of the present invention, regardless of the presence or absence of radioactivity.

Moreover, the present invention also encompasses a compound that is converted to the compound (1) as an active ingredient in the pharmaceutical composition of the present invention due to a reaction induced by an enzyme, gastric acid, or the like under physiological conditions in vivo, i.e., a compound that is converted to the compound (1) through enzymatic oxidation, reduction, hydrolysis, or the like or a "pharmaceutically acceptable prodrug compound" that is converted to the compound (1) through hydrolysis or the like induced by gastric acid or the like.

Examples of a prodrug can include: compounds in which an amino group in the compound (1) is acylated, alkylated, or phosphorylated (e.g., compounds in which the amino group is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, or tert-butylated); compounds in which a hydroxy group in the compound (1) is acylated, alkylated, phosphorylated, or borated (e.g., compounds in which the hydroxy group is acetylated, palmitoylated, propanoylated, pivaloylated, succinylated, fumarylated, alanylated, or dimethylaminomethylcarbonylated); and compounds in which a carboxy group in the compound (1) is esterified or amidated (e.g., compounds in which the carboxy group is ethyl esterified, phenyl esterified, carboxymethyl esterified, dimethylaminomethyl esterified, pivaloyloxymethyl esterified, ethoxycarbonyloxyethyl esterified, amidated, or methylamidated).

A prodrug of the compound of the present invention can be produced from the compound (1) according to a method known in the art. Moreover, a prodrug of the compound of the present invention also includes those converted to the compound (1) under physiological conditions as described in "Development of Pharmaceutical Products", vol. 7, Molecule Design, p. 163-198, Hirokawa-Shoten Ltd. (1990).

Specific examples of the compound represented by general formula (1) of the present invention can include compounds described in, for example, the following Compound Tables 1 to 12. These compounds can be synthesized according to [Production Method 1] to [Production Method 4] described later or methods described in the Examples. In the tables, $R^1$, $R^2$, $R^3$, $R^4$, $R^5$, $R^6$, $R^7$, $Ar_1$, and $Ar_2$ means groups represented by the following general formula (1a).

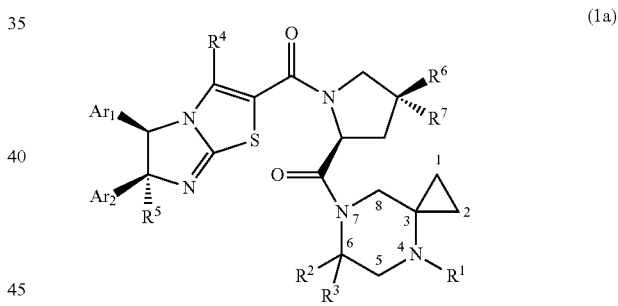

(1a)

TABLE 1

| No. | $R^1$ | $R^2$ | $R^3$ | $R^4$ | $R^5$ | $R^6$ | $R^7$ | $Ar_1$ | $Ar_2$ |
|---|---|---|---|---|---|---|---|---|---|
| 1 | H | H | H | CH(CH$_3$)$_2$ | CH$_3$ | H | F | *-C$_6$H$_3$(F)(Cl) | *-C$_6$H$_4$-Cl |
| 2 | H | CH$_3$ | H | CH(CH$_3$)$_2$ | CH$_3$ | H | F | *-C$_6$H$_3$(F)(Cl) | *-C$_6$H$_4$-Cl |

TABLE 1-continued
| No. | R¹ | R² | R³ | R⁴ | R⁵ | R⁶ | R⁷ | Ar₁ | Ar₂ |
|---|---|---|---|---|---|---|---|---|---|
| 3 | H | CH₃ | CH₃ | CH(CH₃)₂ | CH₃ | H | F | 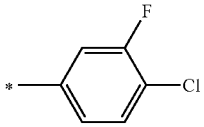 |  |
| 4 | H | CH₂CH₃ | H | CH(CH₃)₂ | CH₃ | H | F | 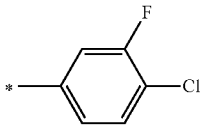 |  |
| 5 | H | CH(CH₃)₂ | H | CH(CH₃)₂ | CH₃ | H | F | 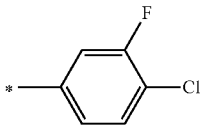 |  |
| 6 | H | CH₂CH(CH₃)₂ | H | CH(CH₃)₂ | CH₃ | H | F | 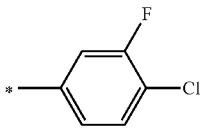 |  |
| 7 | H | CH₂OH | H | CH(CH₃)₂ | CH₃ | H | F | 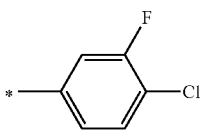 |  |
| 8 | H | CO₂H | H | CH(CH₃)₂ | CH₃ | H | F | 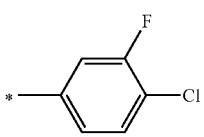 |  |
| 9 | H | CH₂F | H | CH(CH₃)₂ | CH₃ | H | F | 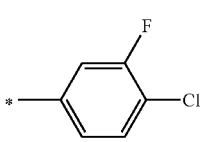 |  |
| 10 | H | CHF₂ | H | CH(CH₃)₂ | CH₃ | H | F | 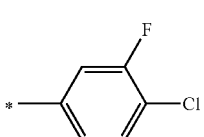 | 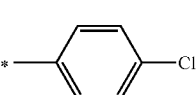 |
| 11 | H | cyclopropyl | | CH(CH₃)₂ | CH₃ | H | F | 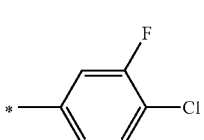 | 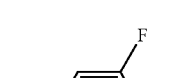 |
| 12 | H | cyclobutyl | | CH(CH₃)₂ | CH₃ | H | F | 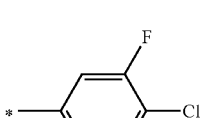 |  |
| 13 | CH₃ | H | H | CH(CH₃)₂ | CH₃ | H | F | 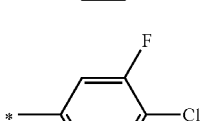 | 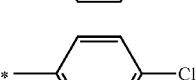 |

TABLE 1-continued
| No. | R¹ | R² | R³ | R⁴ | R⁵ | R⁶ | R⁷ | Ar₁ | Ar₂ |
|---|---|---|---|---|---|---|---|---|---|
| 14 | CH₃ | CH₃ |  | H | CH(CH₃)₂ | CH₃ | H | F | 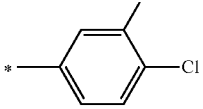 | 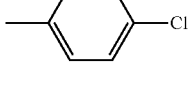 |
| 15 | CH₃ | CH₃ |  | CH₃ | CH(CH₃)₂ | CH₃ | H | F | 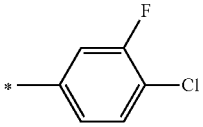 | 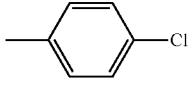 |
TABLE 2
| No. | R¹ | R² | R³ | R⁴ | R⁵ | R⁶ | R⁷ | Ar₁ | Ar₂ |
|---|---|---|---|---|---|---|---|---|---|
| 16 | CH₃ | CH₂CH₃ | H | CH(CH₃)₂ | CH₃ | H | F | 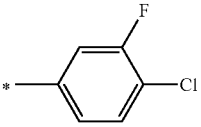 | 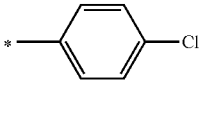 |
| 17 | CH₃ | CH(CH₃)₂ | H | CH(CH₃)₂ | CH₃ | H | F | 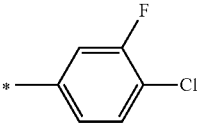 | 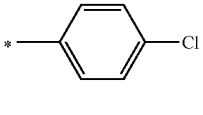 |
| 18 | CH₃ | CH₂CH(CH₃)₂ | H | CH(CH₃)₂ | CH₃ | H | F | 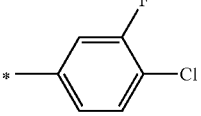 | 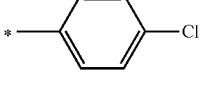 |
| 19 | CH₃ | CH₂F | H | CH(CH₃)₂ | CH₃ | H | F | 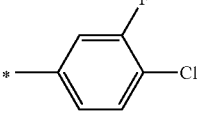 | 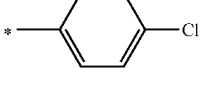 |
| 20 | CH₃ | CHF₂ | H | CH(CH₃)₂ | CH₃ | H | F | 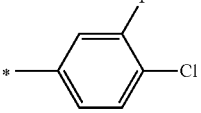 | 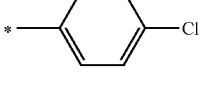 |
| 21 | CH₃ | cyclopropyl |  | CH(CH₃)₂ | CH₃ | H | F | 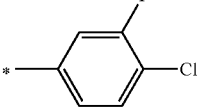 | 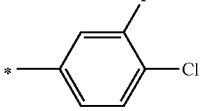 |
| 22 | CH₃ | cyclobutyl |  | CH(CH₃)₂ | CH₃ | H | F | 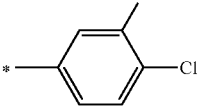 | 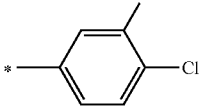 |
| 23 | CH₂CH₂OH | CH₃ | H | CH(CH₃)₂ | CH₃ | H | F | 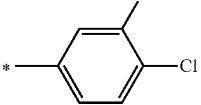 | 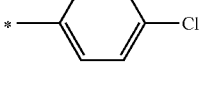 |

TABLE 2-continued
| No. | R¹ | R² | R³ | R⁴ | R⁵ | R⁶ | R⁷ | Ar₁ | Ar₂ |
|---|---|---|---|---|---|---|---|---|---|
| 24 | CHO | CH₃ | H | CH(CH₃)₂ | CH₃ | H | F | 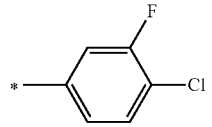 | 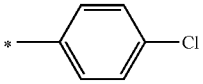 |
| 25 | CHO | CH₂CH₃ | H | CH(CH₃)₂ | CH₃ | H | F | 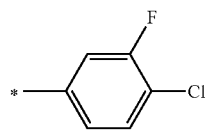 | 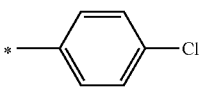 |
| 26 | COCH₃ | CH₃ | H | CH(CH₃)₂ | CH₃ | H | F | 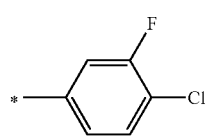 |  |
| 27 | COCH₃ | CH₂CH₃ | H | CH(CH₃)₂ | CH₃ | H | F | 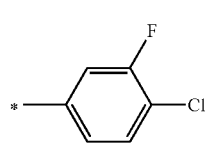 | 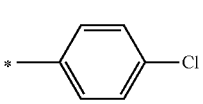 |
| 28 | COCF₃ | CH₃ | H | CH(CH₃)₂ | CH₃ | H | F | 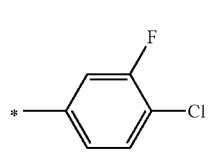 | 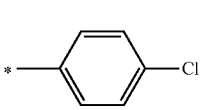 |
| 29 | COCF₃ | CH₂CH₃ | H | CH(CH₃)₂ | CH₃ | H | F | 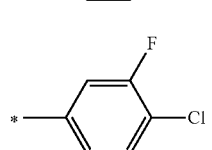 | 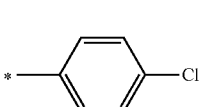 |
| 30 | H | H | H | CH(CH₃)₂ | CH₃ | F | F | 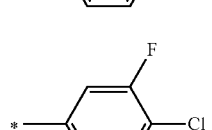 | 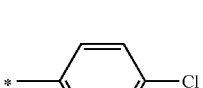 |
TABLE 3
| No. | R¹ | R² | R³ | R⁴ | R⁵ | R⁶ | R⁷ | Ar₁ | Ar₂ |
|---|---|---|---|---|---|---|---|---|---|
| 31 | H | CH₃ | H | CH(CH₃)₂ | CH₃ | F | F | 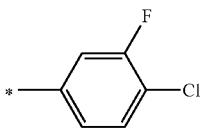 | 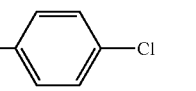 |
| 32 | H | CH₃ | CH₃ | CH(CH₃)₂ | CH₃ | F | F | 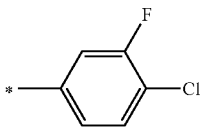 | 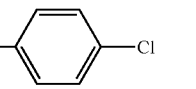 |
| 33 | H | CH₂CH₃ | H | CH(CH₃)₂ | CH₃ | F | F | 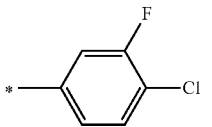 | 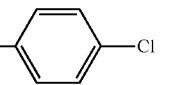 |

TABLE 3-continued
| No. | R¹ | R² | R³ | R⁴ | R⁵ | R⁶ | R⁷ | Ar₁ | Ar₂ |
|---|---|---|---|---|---|---|---|---|---|
| 34 | H | CH(CH₃)₂ | H | CH(CH₃)₂ | CH₃ | F | F | 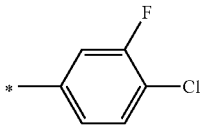 | 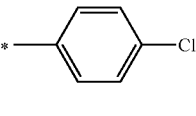 |
| 35 | H | CH₂CH(CH₃)₂ | H | CH(CH₃)₂ | CH₃ | F | F | 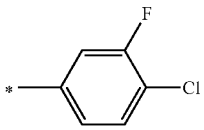 | 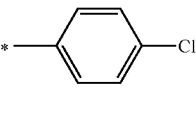 |
| 36 | H | CH₂OH | H | CH(CH₃)₂ | CH₃ | F | F | 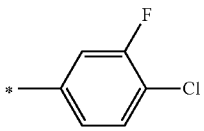 | 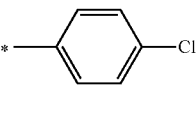 |
| 37 | H | CO₂H | H | CH(CH₃)₂ | CH₃ | F | F | 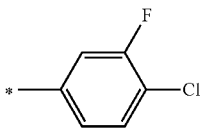 | 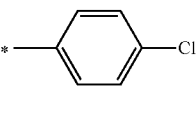 |
| 38 | H | CH₂F | H | CH(CH₃)₂ | CH₃ | F | F | 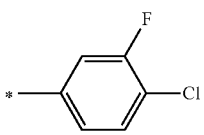 | 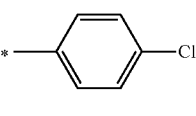 |
| 39 | H | CHF₂ | H | CH(CH₃)₂ | CH₃ | F | F | 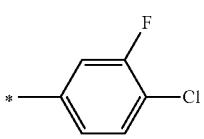 | 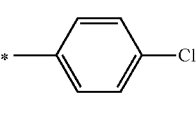 |
| 40 | H | cyclopropyl | | CH(CH₃)₂ | CH₃ | F | F | 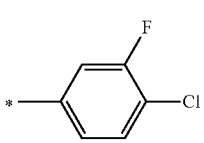 | 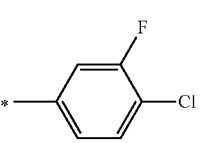 |
| 41 | H | cyclobutyl | | CH(CH₃)₂ | CH₃ | F | F | 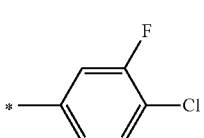 | 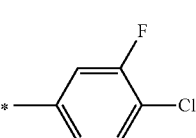 |
| 42 | CH₃ | H | H | CH(CH₃)₂ | CH₃ | F | F | 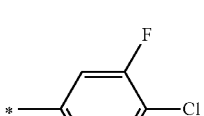 | 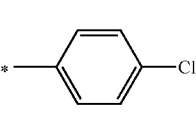 |
| 43 | CH₃ | CH₃ | H | CH(CH₃)₂ | CH₃ | F | F | 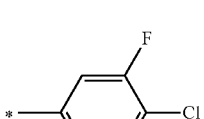 | 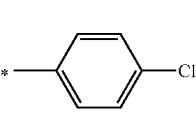 |
| 44 | CH₃ | CH₃ | CH₃ | CH(CH₃)₂ | CH₃ | F | F | 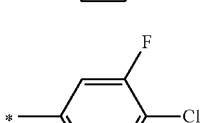 | 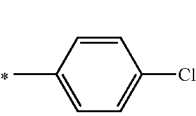 |

TABLE 3-continued

| No. | $R^1$ | $R^2$ | $R^3$ | $R^4$ | $R^5$ | $R^6$ | $R^7$ | $Ar_1$ | $Ar_2$ |
|---|---|---|---|---|---|---|---|---|---|
| 45 | $CH_3$ | $CH_2CH_3$ | H | $CH(CH_3)_2$ | $CH_3$ | F | F | 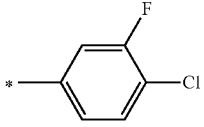 | 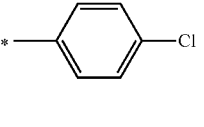 |

TABLE 4

| No. | $R^1$ | $R^2$ | $R^3$ | $R^4$ | $R^5$ | $R^6$ | $R^7$ | $Ar_1$ | $Ar_2$ |
|---|---|---|---|---|---|---|---|---|---|
| 46 | $CH_3$ | $CH(CH_3)_2$ | H | $CH(CH_3)_2$ | $CH_3$ | F | F | 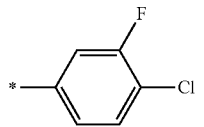 | 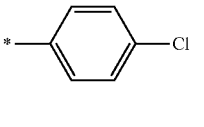 [SMILES: *c1ccc(Cl)cc1] |
| 47 | $CH_3$ | $CH_2CH(CH_3)_2$ | H | $CH(CH_3)_2$ | $CH_3$ | F | F | 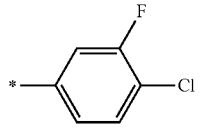 | 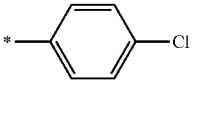 |
| 48 | $CH_3$ | $CH_2F$ | H | $CH(CH_3)_2$ | $CH_3$ | F | F | 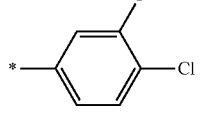 | 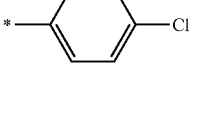 |
| 49 | $CH_3$ | $CHF_2$ | H | $CH(CH_3)_2$ | $CH_3$ | F | F | 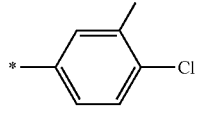 | 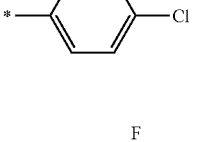 |
| 50 | $CH_3$ | cyclopropyl | | $CH(CH_3)_2$ | $CH_3$ | F | F | 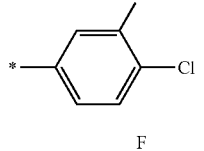 | 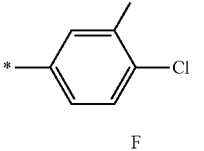 |
| 51 | $CH_3$ | cyclobutyl | | $CH(CH_3)_2$ | $CH_3$ | F | F | 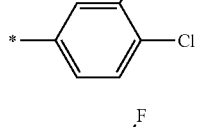 | 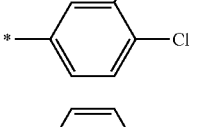 |
| 52 | $CH_2CH_2OH$ | $CH_3$ | H | $CH(CH_3)_2$ | $CH_3$ | F | F | 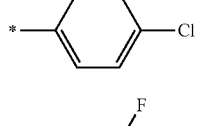 | 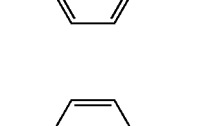 |
| 53 | CHO | $CH_3$ | H | $CH(CH_3)_2$ | $CH_3$ | F | F | 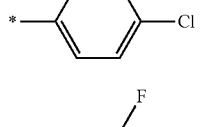 | 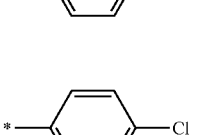 |
| 54 | CHO | $CH_2CH_3$ | H | $CH(CH_3)_2$ | $CH_3$ | F | F | 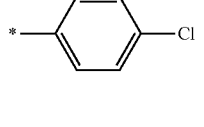 | 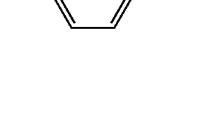 |

TABLE 4-continued
| No. | R¹ | R² | R³ | R⁴ | R⁵ | R⁶ | R⁷ | Ar₁ | Ar₂ |
|---|---|---|---|---|---|---|---|---|---|
| 55 | COCH₃ | CH₃ | H | CH(CH₃)₂ | CH₃ | F | F | 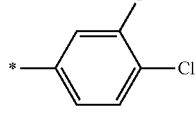 |  |
| 56 | COCH₃ | CH₂CH₃ | H | CH(CH₃)₂ | CH₃ | F | F | 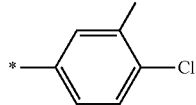 | 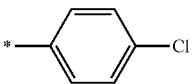 [SMILES: *c1ccc(Cl)cc1] |
| 57 | COCF₃ | CH₃ | H | CH(CH₃)₂ | CH₃ | F | F | 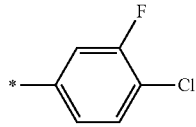 | 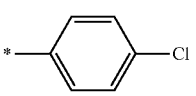 [SMILES: *c1ccc(Cl)cc1] |
| 58 | COCF₃ | CH₂CH₃ | H | CH(CH₃)₂ | CH₃ | F | F | 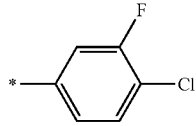 | 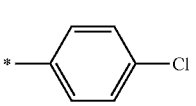 |
| 59 | H | H | H | CH(CH₃)₂ | CH₃ | H | F | 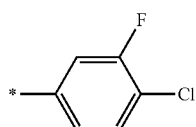 | 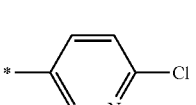 |
| 60 | H | CH₃ | H | CH(CH₃)₂ | CH₃ | H | F | 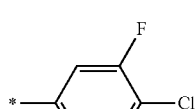 | 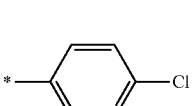 |
TABLE 5
| No. | R¹ | R² | R³ | R⁴ | R⁵ | R⁶ | R⁷ | Ar₁ | Ar₂ |
|---|---|---|---|---|---|---|---|---|---|
| 61 | H | CH₃ | CH₃ | CH(CH₃)₂ | CH₃ | H | F | 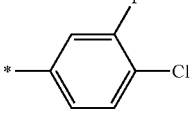 | 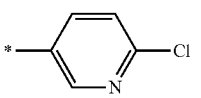 |
| 62 | H | CH₂CH₃ | H | CH(CH₃)₂ | CH₃ | H | F | 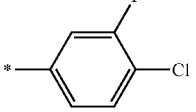 | 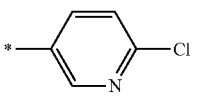 [SMILES: *c1ccc(Cl)nc1] |
| 63 | H | CH(CH₃)₂ | H | CH(CH₃)₂ | CH₃ | H | F | 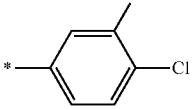 | 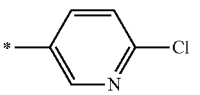 |
| 64 | H | CH₂CH(CH₃)₂ | H | CH(CH₃)₂ | CH₃ | H | F | 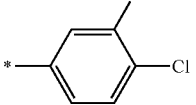 | 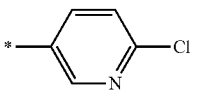 [SMILES: *c1ccc(Cl)nc1] |

TABLE 5-continued
| No. | R¹ | R² | R³ | R⁴ | R⁵ | R⁶ | R⁷ | Ar₁ | Ar₂ |
|---|---|---|---|---|---|---|---|---|---|
| 65 | H | CH₂OH | H | CH(CH₃)₂ | CH₃ | H | F | 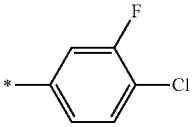 | 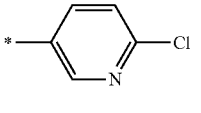 |
| 66 | H | CO₂H | H | CH(CH₃)₂ | CH₃ | H | F | 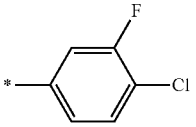 | 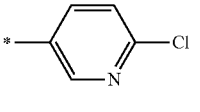 |
| 67 | H | CH₂F | H | CH(CH₃)₂ | CH₃ | H | F | 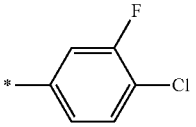 | 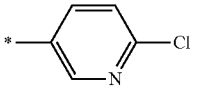 |
| 68 | H | CHF₂ | H | CH(CH₃)₂ | CH₃ | H | F | 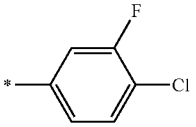 | 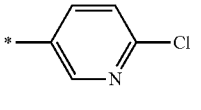 |
| 69 | H | cyclopropyl | | CH(CH₃)₂ | CH₃ | H | F | 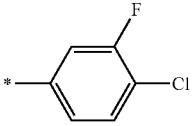 | 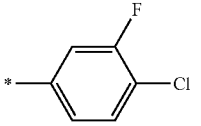 |
| 70 | H | cyclobutyl | | CH(CH₃)₂ | CH₃ | H | F | 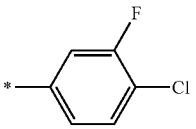 | 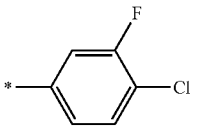 |
| 71 | CH₃ | H | H | CH(CH₃)₂ | CH₃ | H | F | 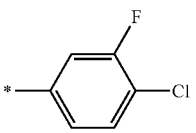 | 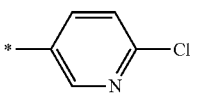 |
| 72 | CH₃ | CH₃ | H | CH(CH₃)₂ | CH₃ | H | F | 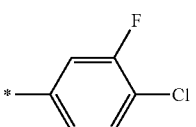 | 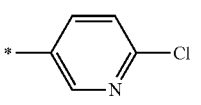 |
| 73 | CH₃ | CH₃ | CH₃ | CH(CH₃)₂ | CH₃ | H | F | 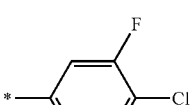 | 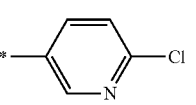 |
| 74 | CH₃ | CH₂CH₃ | H | CH(CH₃)₂ | CH₃ | H | F | 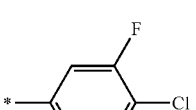 | 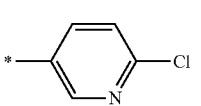 |
| 75 | CH₃ | CH(CH₃)₂ | H | CH(CH₃)₂ | CH₃ | H | F | 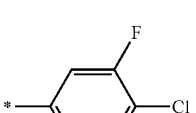 | 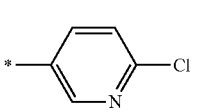 |

TABLE 6
| No. | R¹ | R² | R³ | R⁴ | R⁵ | R⁶ | R⁷ | Ar₁ | Ar₂ |
|---|---|---|---|---|---|---|---|---|---|
| 76 | $CH_3$ | $CH_2CH(CH_3)_2$ | H | $CH(CH_3)_2$ | $CH_3$ | H | F | 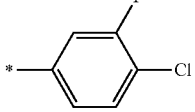 | 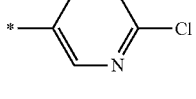 |
| 77 | $CH_3$ | $CH_2F$ | H | $CH(CH_3)_2$ | $CH_3$ | H | F | 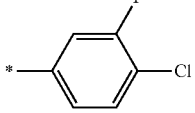 | 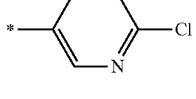 |
| 78 | $CH_3$ | $CHF_2$ | H | $CH(CH_3)_2$ | $CH_3$ | H | F | 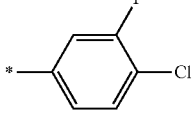 | 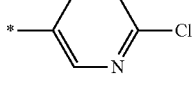 |
| 79 | $CH_3$ | cyclopropyl |  | $CH(CH_3)_2$ | $CH_3$ | H | F | 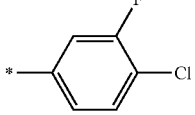 | 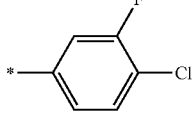 |
| 80 | $CH_3$ | cyclobutyl |  | $CH(CH_3)_2$ | $CH_3$ | H | F | 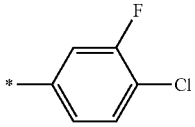 | 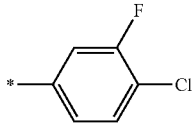 |
| 81 | $CH_2CH_2OH$ | $CH_3$ | H | $CH(CH_3)_2$ | $CH_3$ | H | F | 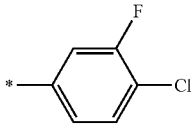 | 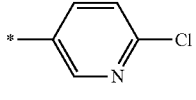 |
| 82 | CHO | $CH_3$ | H | $CH(CH_3)_2$ | $CH_3$ | H | F | 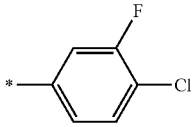 | 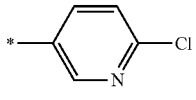 |
| 83 | CHO | $CH_2CH_3$ | H | $CH(CH_3)_2$ | $CH_3$ | H | F | 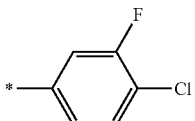 | 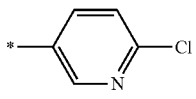 |
| 84 | $COCH_3$ | $CH_3$ | H | $CH(CH_3)_2$ | $CH_3$ | H | F | 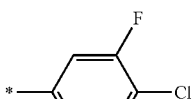 | 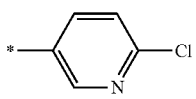 |
| 85 | $COCH_3$ | $CH_2CH_3$ | H | $CH(CH_3)_2$ | $CH_3$ | H | F | 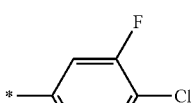 | 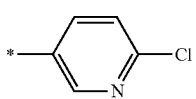 |
| 86 | $COCF_3$ | $CH_3$ | H | $CH(CH_3)_2$ | $CH_3$ | H | F | 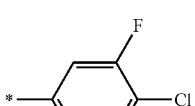 | 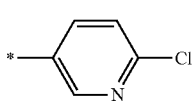 |

TABLE 6-continued
| No. | R¹ | R² | R³ | R⁴ | R⁵ | R⁶ | R⁷ | Ar₁ | Ar₂ |
|---|---|---|---|---|---|---|---|---|---|
| 87 | COCF₃ | CH₂CH₃ | H | CH(CH₃)₂ | CH₃ | H | F | 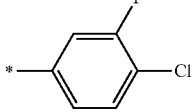 | 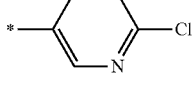 |
| 88 | H | H | H | CH(CH₃)₂ | CH₃ | F | F | 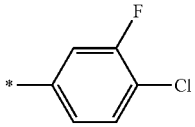 | 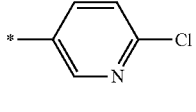 |
| 89 | H | CH₃ | H | CH(CH₃)₂ | CH₃ | F | F | 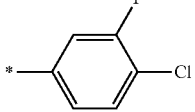 | 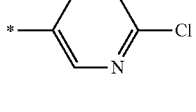 |
| 90 | H | CH₃ | CH₃ | CH(CH₃)₂ | CH₃ | F | F | 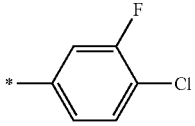 | 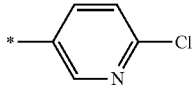 |
TABLE 7
| No. | R¹ | R² | R³ | R⁴ | R⁵ | R⁶ | R⁷ | Ar₁ | Ar₂ |
|---|---|---|---|---|---|---|---|---|---|
| 91 | H | CH₂CH₃ | H | CH(CH₃)₂ | CH₃ | F | F | 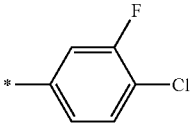 | 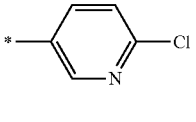 |
| 92 | H | CH(CH₃)₂ | H | CH(CH₃)₂ | CH₃ | F | F | 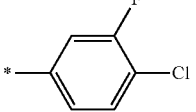 | 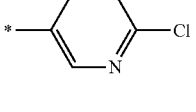 |
| 93 | H | CH₂CH(CH₃)₂ | H | CH(CH₃)₂ | CH₃ | F | F | 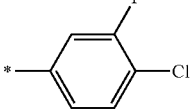 | 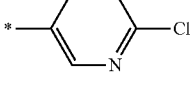 |
| 94 | H | CH₂OH | H | CH(CH₃)₂ | CH₃ | F | F | 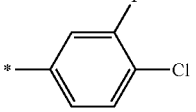 | 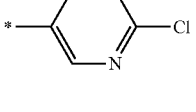 |
| 95 | H | CO₂H | H | CH(CH₃)₂ | CH₃ | F | F | 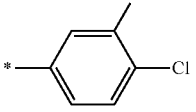 | 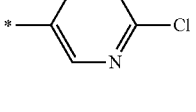 |
| 96 | H | CH₂F | H | CH(CH₃)₂ | CH₃ | F | F | 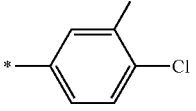 | 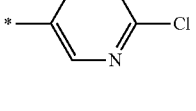 |

TABLE 7-continued
| No. | R¹ | R² | R³ | R⁴ | R⁵ | R⁶ | R⁷ | Ar₁ | Ar₂ |
|---|---|---|---|---|---|---|---|---|---|
| 97 | H | CHF₂ | H | CH(CH₃)₂ | CH₃ | F | F | 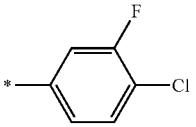 | 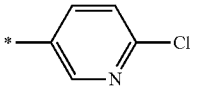 |
| 98 | H | cyclopropyl | | CH(CH₃)₂ | CH₃ | F | F | 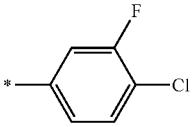 | 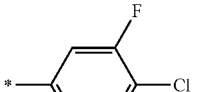 |
| 99 | H | cyclobutyl | | CH(CH₃)₂ | CH₃ | F | F | 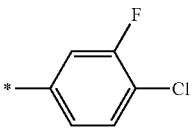 | 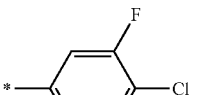 |
| 100 | CH₃ | H | H | CH(CH₃)₂ | CH₃ | F | F | 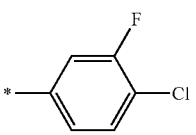 | 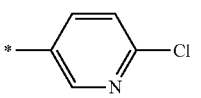 |
| 101 | CH₃ | CH₃ | H | CH(CH₃)₂ | CH₃ | F | F | 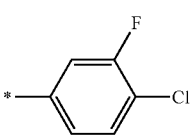 | 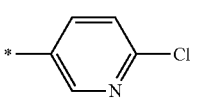 |
| 102 | CH₃ | CH₃ | CH₃ | CH(CH₃)₂ | CH₃ | F | F | 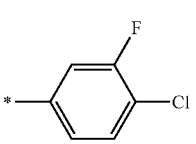 | 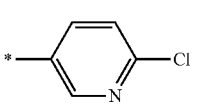 |
| 103 | CH₃ | CH₂CH₃ | H | CH(CH₃)₂ | CH₃ | F | F | 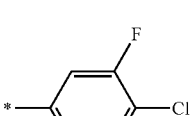 | 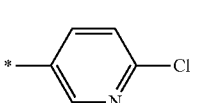 |
| 104 | CH₃ | CH(CH₃)₂ | H | CH(CH₃)₂ | CH₃ | F | F | 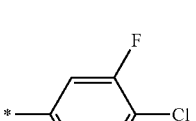 | 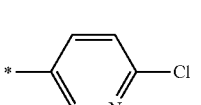 |
| 105 | CH₃ | CH₂CH(CH₃)₂ | H | CH(CH₃)₂ | CH₃ | F | F | 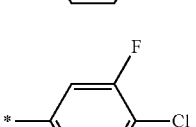 | 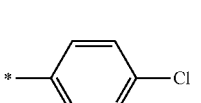 |
TABLE 8
| No. | R¹ | R² | R³ | R⁴ | R⁵ | R⁶ | R⁷ | Ar₁ | Ar₂ |
|---|---|---|---|---|---|---|---|---|---|
| 106 | CH₃ | CH₂F | H | CH(CH₃)₂ | CH₃ | F | F | 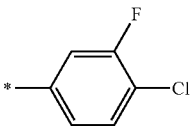 | 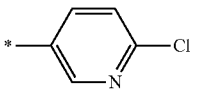 |

TABLE 8-continued
| No. | R¹ | R² | R³ | R⁴ | R⁵ | R⁶ | R⁷ | Ar₁ | Ar₂ |
|---|---|---|---|---|---|---|---|---|---|
| 107 | CH₃ | CHF₂ | H | CH(CH₃)₂ | CH₃ | F | F | 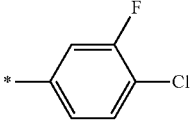 | 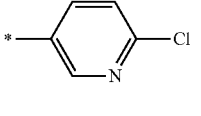 |
| 108 | CH₃ | cyclopropyl | | CH(CH₃)₂ | CH₃ | F | F | 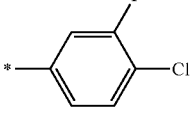 | 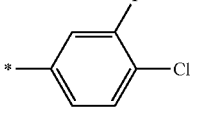 |
| 109 | CH₃ | cyclobutyl | | CH(CH₃)₂ | CH₃ | F | F | 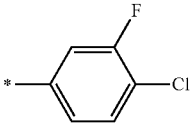 | 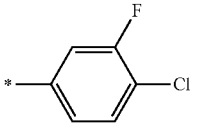 |
| 110 | CH₂CH₂OH | CH₃ | H | CH(CH₃)₂ | CH₃ | F | F | 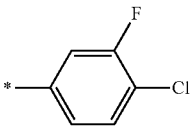 | 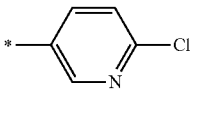 |
| 111 | CHO | CH₃ | H | CH(CH₃)₂ | CH₃ | F | F | 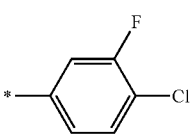 | 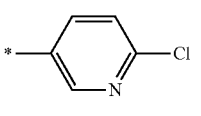 |
| 112 | CHO | CH₂CH₃ | H | CH(CH₃)₂ | CH₃ | F | F | 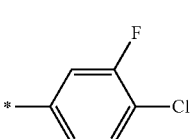 | 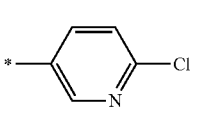 |
| 113 | COCH₃ | CH₃ | H | CH(CH₃)₂ | CH₃ | F | F | 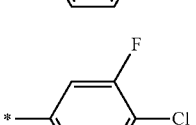 | 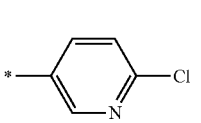 |
| 114 | COCH₃ | CH₂CH₃ | H | CH(CH₃)₂ | CH₃ | F | F | 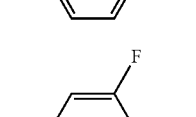 | 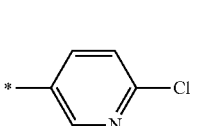 |
| 115 | COCF₃ | CH₃ | H | CH(CH₃)₂ | CH₃ | F | F | 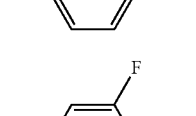 | 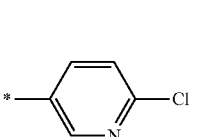 |
| 116 | COCF₃ | CH₂CH₃ | H | CH(CH₃)₂ | CH₃ | F | F | 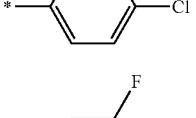 | 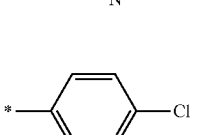 |
| 117 | H | CH₃ | H | CH(CH₃)₂ | CH₃ | H | F | 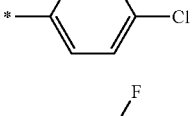 | 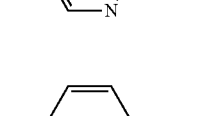 |

TABLE 8-continued
| No. | R¹ | R² | R³ | R⁴ | R⁵ | R⁶ | R⁷ | Ar₁ | Ar₂ |
|---|---|---|---|---|---|---|---|---|---|
| 118 | H | CH₂CH₃ | H | CH(CH₃)₂ | CH₃ | H | F | 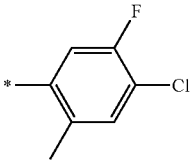 | 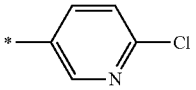 |
| 119 | H | CH(CH₃)₂ | H | CH(CH₃)₂ | CH₃ | H | F | 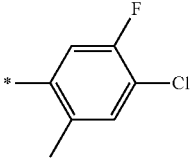 | 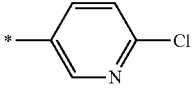 |
| 120 | H | CH₂F | H | CH(CH₃)₂ | CH₃ | H | F | 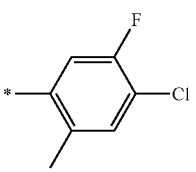 | 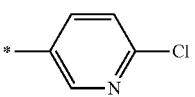 |
TABLE 9
| No. | R¹ | R² | R³ | R⁴ | R⁵ | R⁶ | R⁷ | Ar₁ | Ar₂ |
|---|---|---|---|---|---|---|---|---|---|
| 121 | H | CHF₂ | H | CH(CH₃)₂ | CH₃ | H | F | 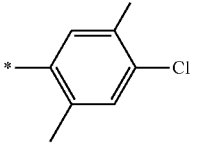 | 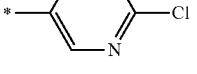 |
| 122 | H | cyclopropyl | | CH(CH₃)₂ | CH₃ | H | F | 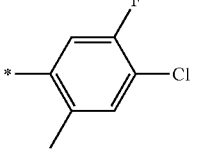 | 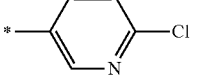 |
| 123 | CH₃ | CH₃ | H | CH(CH₃)₂ | CH₃ | H | F | 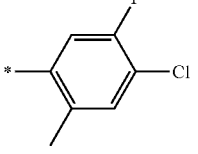 | 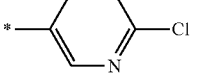 |
| 124 | CH₃ | CH₂CH₃ | H | CH(CH₃)₂ | CH₃ | H | F | 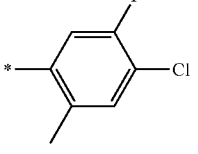 | 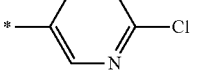 |
| 125 | CH₃ | CH(CH₃)₂ | H | CH(CH₃)₂ | CH₃ | H | F | 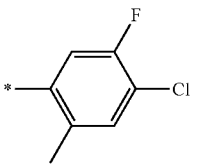 | 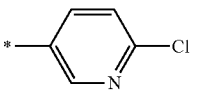 |

TABLE 9-continued
| No. | R¹ | R² | R³ | R⁴ | R⁵ | R⁶ | R⁷ | Ar₁ | Ar₂ |
|---|---|---|---|---|---|---|---|---|---|
| 126 | CH₃ | CH₂F | H | CH(CH₃)₂ | CH₃ | H | F | 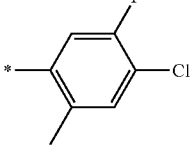 | 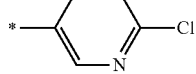 |
| 127 | CH₃ | CHF₂ | H | CH(CH₃)₂ | CH₃ | H | F | 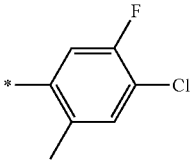 |  |
| 128 | CH₃ | cyclopropyl | | CH(CH₃)₂ | CH₃ | H | F | 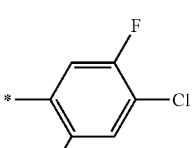 |  |
| 129 | H | CH₃ | H | CH(CH₃)₂ | CH₃ | F | F | 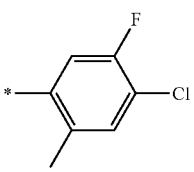 |  |
| 130 | H | CH₂CH₃ | H | CH(CH₃)₂ | CH₃ | F | F | 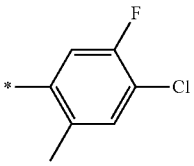 |  |
| 131 | H | CH(CH₃)₂ | H | CH(CH₃)₂ | CH₃ | F | F | 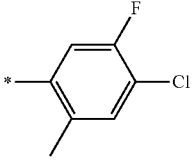 | 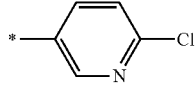 |
| 132 | H | CH₂F | H | CH(CH₃)₂ | CH₃ | F | F | 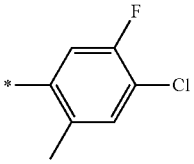 | 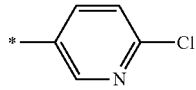 |
| 133 | H | CHF₂ | H | CH(CH₃)₂ | CH₃ | F | F | 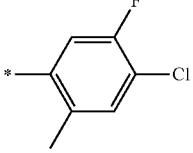 | 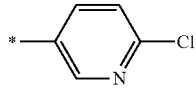 |
| 134 | H | cyclopropyl | | CH(CH₃)₂ | CH₃ | F | F | 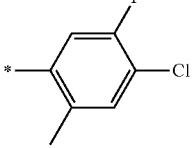 | 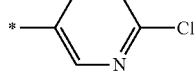 |

TABLE 9-continued
| No. | R¹ | R² | R³ | R⁴ | R⁵ | R⁶ | R⁷ | Ar₁ | Ar₂ |
|---|---|---|---|---|---|---|---|---|---|
| 135 | CH₃ | CH₃ | H | CH(CH₃)₂ | CH₃ | F | F | 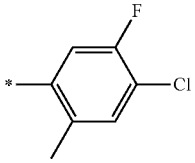 | 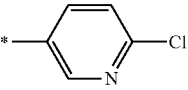 |
TABLE 10
| No. | R¹ | R² | R³ | R⁴ | R⁵ | R⁶ | R⁷ | Ar₁ | Ar₂ |
|---|---|---|---|---|---|---|---|---|---|
| 136 | CH₃ | CH₂CH₃ | H | CH(CH₃)₂ | CH₃ | F | F | 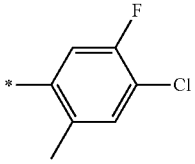 | 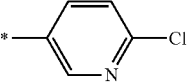 |
| 137 | CH₃ | CH(CH₃)₂ | H | CH(CH₃)₂ | CH₃ | F | F | 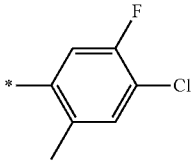 | 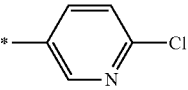 |
| 138 | CH₃ | CH₂F | H | CH(CH₃)₂ | CH₃ | F | F | 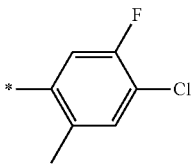 | 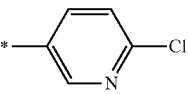 |
| 139 | CH₃ | CHF₂ | H | CH(CH₃)₂ | CH₃ | F | F | 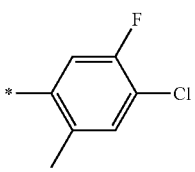 | 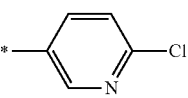 |
| 140 | CH₃ | cyclopropyl | | CH(CH₃)₂ | CH₃ | F | F | 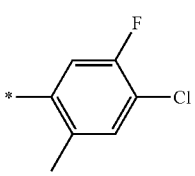 | 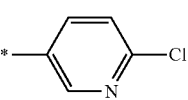 |
| 141 | H | CH₃ | H | CH(CH₃)₂ | CH₃ | H | F | 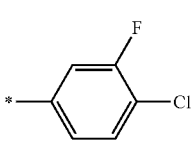 | 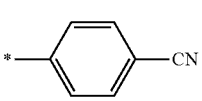 |
| 142 | H | CH₂CH₃ | H | CH(CH₃)₂ | CH₃ | H | F | 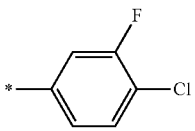 | 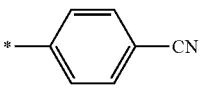 |
| 143 | H | CH₃ | H | CH(CH₃)₂ | CH₃ | F | F | 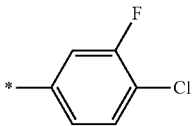 | 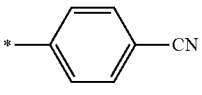 |

TABLE 10-continued
| No. | R¹ | R² | R³ | R⁴ | R⁵ | R⁶ | R⁷ | Ar₁ | Ar₂ |
|---|---|---|---|---|---|---|---|---|---|
| 144 | H | CH₂CH₃ | H | CH(CH₃)₂ | CH₃ | F | F | 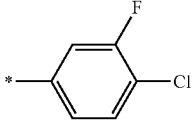 | 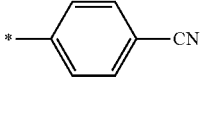 |
| 145 | H | CH₃ | H | CH(CH₃)₂ | CH₃ | H | F | 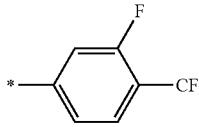 | 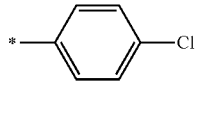 |
| 146 | H | CH₂CH₃ | H | CH(CH₃)₂ | CH₃ | H | F | 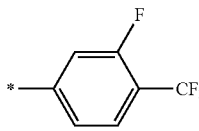 | 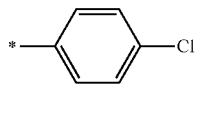 [SMILES: *c1ccc(Cl)cc1] |
| 147 | H | CH₃ | H | CH(CH₃)₂ | CH₃ | F | F | 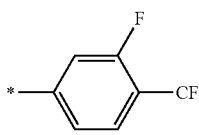 | 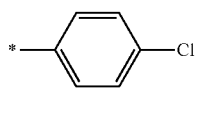 |
| 148 | H | CH₂CH₃ | H | CH(CH₃)₂ | CH₃ | F | F | 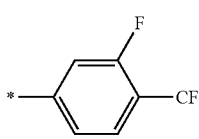 | 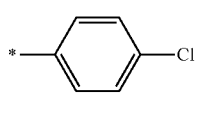 |
| 149 | H | CH₃ | H | CH(CH₃)₂ | CH₃ | H | F | 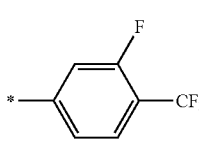 | 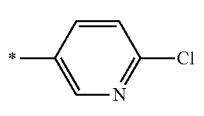 [SMILES: *c1ccc(Cl)nc1] |
| 150 | H | CH₂CH₃ | H | CH(CH₃)₂ | CH₃ | H | F | 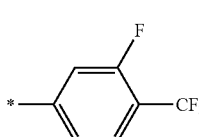 | 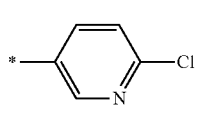 |
TABLE 11
| No. | R¹ | R² | R³ | R⁴ | R⁵ | R⁶ | R⁷ | Ar₁ | Ar₂ |
|---|---|---|---|---|---|---|---|---|---|
| 151 | H | CH₃ | H | CH(CH₃)₂ | CH₃ | F | F | 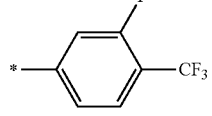 | 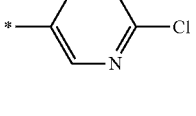 |
| 152 | H | CH₂CH₃ | H | CH(CH₃)₂ | CH₃ | F | F | 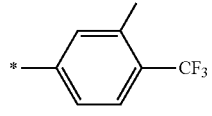 | 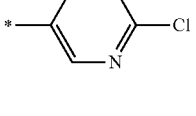 |
| 153 | H | CH₃ | H | CH(CH₃)₂ | CH₃ | H | F | 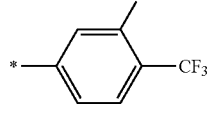 | 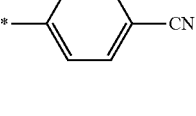 |

TABLE 11-continued
| No. | R¹ | R² | R³ | R⁴ | R⁵ | R⁶ | R⁷ | Ar₁ | Ar₂ |
|---|---|---|---|---|---|---|---|---|---|
| 154 | H | CH₂CH₃ | H | CH(CH₃)₂ | CH₃ | H | F | 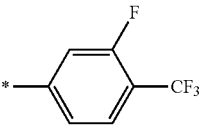 | 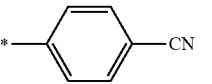 |
| 155 | H | CH₃ | H | CH(CH₃)₂ | CH₃ | F | F | 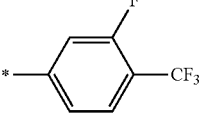 | 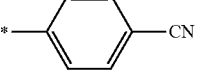 |
| 156 | H | CH₂CH₃ | H | CH(CH₃)₂ | CH₃ | F | F | 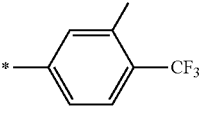 | 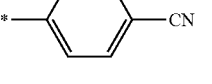 |
| 157 | H | CH₃ | H | CH(CH₃)₂ | CH₃ | H | F | 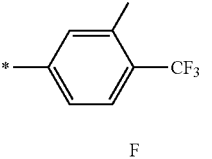 | 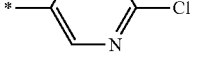 |
| 158 | H | CH₂CH₃ | H | CH(CH₃)₂ | CH₃ | H | F | 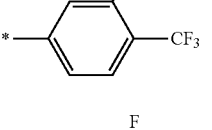 | 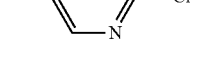 |
| 159 | H | CH₃ | H | CH(CH₃)₂ | CH₃ | F | F | 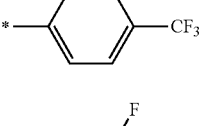 | 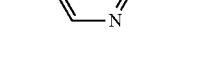 |
| 160 | H | CH₂CH₃ | H | CH(CH₃)₂ | CH₃ | F | F | 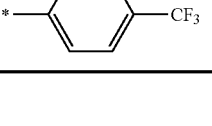 | 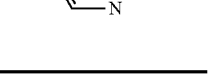 |
TABLE 12
| No. | R¹ | R² | R³ | R⁴ | R⁵ | R⁶ | R⁷ | Ar₁ | Ar₂ |
|---|---|---|---|---|---|---|---|---|---|
| 161 | H | H | H | CH(CH₃)₂ | CH₃ | H | F | 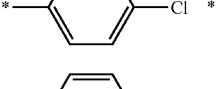 | 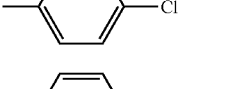 |
| 162 | H | CH₃ | H | CH(CH₃)₂ | CH₃ | H | F | 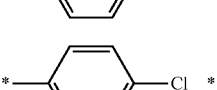 | 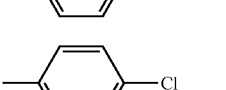 |
| 163 | H | CH₂CH₃ | H | CH(CH₃)₂ | CH₃ | H | F | 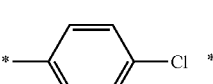 | 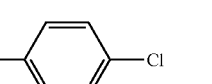 |
| 164 | H | H | H | CH(CH₃)₂ | CH₃ | H | F | 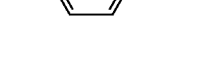 | 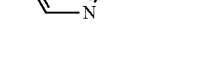 |

TABLE 12-continued

| No. | R¹ | R² | R³ | R⁴ | R⁵ | R⁶ | R⁷ | Ar₁ | Ar₂ |
|---|---|---|---|---|---|---|---|---|---|
| 165 | H | CH₃ | H | CH(CH₃)₂ | CH₃ | H | F | 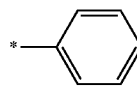 | 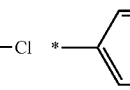 |
| 166 | H | CH₂CH₃ | H | CH(CH₃)₂ | CH₃ | H | F | 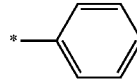 | 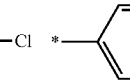 |

Next, a representative method for producing a compound represented by general formula (1) will be explained. The compound of the present invention can be produced by various production methods and the following production methods are illustrative and should not be construed in any limitative way. Reactions shown below can be performed by protecting substituents with appropriate protective groups, if necessary, and the types of protective groups are not particularly limited.

[Production Method 1]

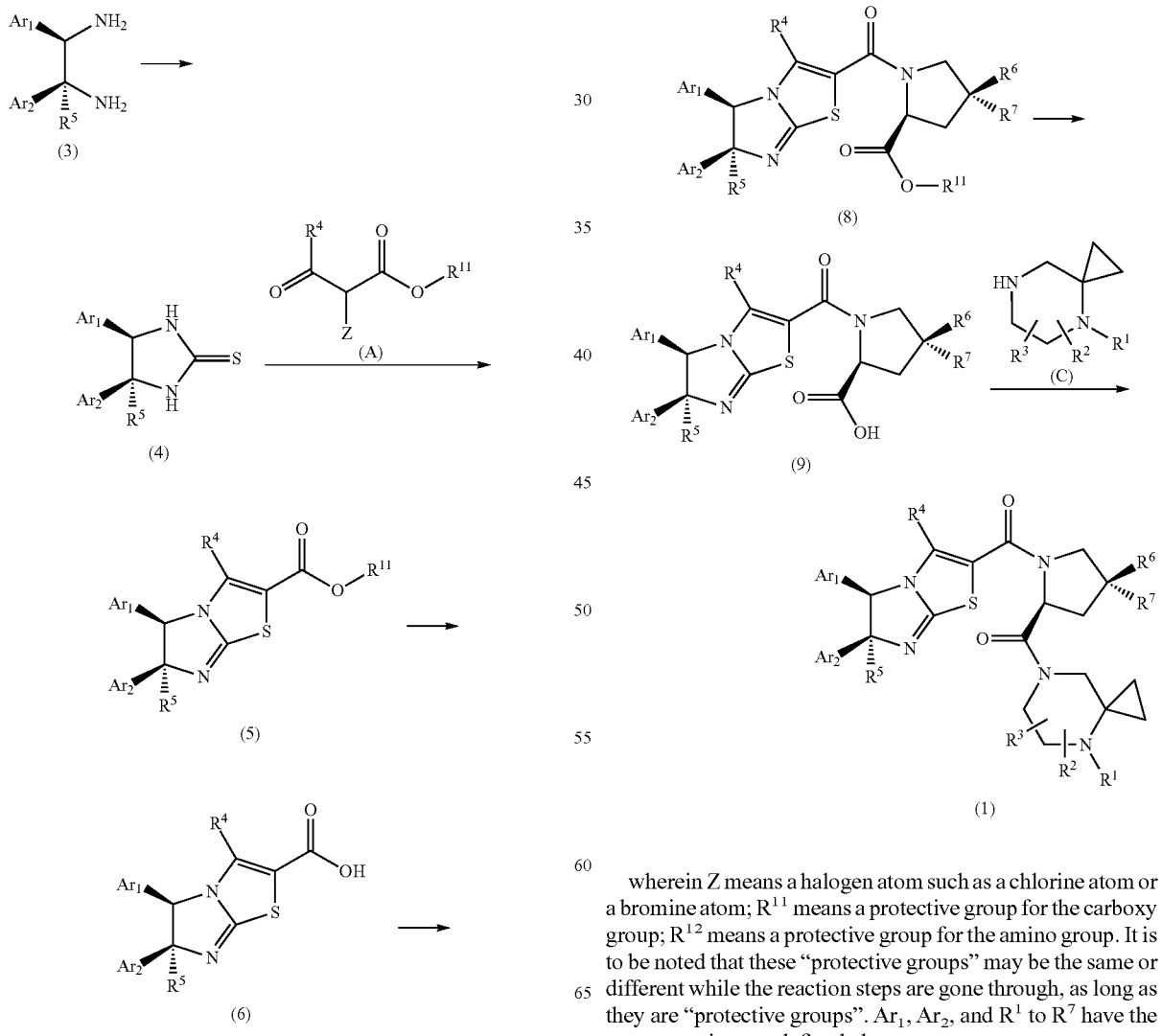

wherein Z means a halogen atom such as a chlorine atom or a bromine atom; $R^{11}$ means a protective group for the carboxy group; $R^{12}$ means a protective group for the amino group. It is to be noted that these "protective groups" may be the same or different while the reaction steps are gone through, as long as they are "protective groups". $Ar_1$, $Ar_2$, and $R^1$ to $R^7$ have the same meanings as defined above.

Examples of the protective group for the carboxy group include substituted or unsubstituted alkyl groups or aralkyl groups such as a methyl group, an ethyl group, a tert-butyl group, and a benzyl group.

Synthesis of Compound (4)

A compound (4) can be obtained by reacting an optically active diamine compound (3) having the positional configuration shown above with carbon disulfide or 1,1'-thiocarbonyldiimidazole. Here, the solvent used in the reaction is not particularly limited and examples thereof include ethanol, tetrahydrofuran, dioxane, acetonitrile, dimethylformamide, dichloromethane, chloroform, toluene, and mixed solvents thereof. The reaction temperature is usually in the range from −78 to 100° C. or the boiling point of the solvent, preferably in the range from around room temperature to 100° C.

Synthesis of Compound (5)

A compound (5) can be obtained by reacting compound (4) with a compound (A). Here, the solvent used in the reaction is not particularly limited and examples thereof include ethanol, tetrahydrofuran, dioxane, acetonitrile, dimethylformamide, chloroform, toluene, and mixed solvents thereof. The reaction temperature is usually in the range from −78 to 100° C. or the boiling point of the solvent, preferably in the range from around room temperature to 100° C.

Synthesis of Compound (6)

This step is performed for the deprotection of $R^{11}$.

Although deprotection reaction conditions differ depending on the type of $R^{11}$, $R^{11}$ may be deprotected by hydrolysis. When $R^{11}$ is a methyl group, an ethyl group, a benzyl group, or the like, a compound (6) can be obtained by treating compound (5) with a base (e.g., sodium hydroxide, potassium hydroxide, lithium hydroxide, or potassium tert-butoxide) or hydrochloric acid, p-toluenesulfonic acid, or the like. Here, examples of the solvent used in the reaction include methanol, ethanol, water, tetrahydrofuran, dioxane, and mixed solvents thereof. However, organic solvents that can be mixed with water in an arbitrary ratio are preferred. The reaction temperature is usually in the range from −78 to 100° C. or the boiling point of the solvent, preferably in the range from around room temperature to 100° C. When $R^{11}$ is a tert-butyl group or the like, compound (5) is preferably treated with trifluoroacetic acid or hydrochloric acid or the like. Here, the solvent used in the reaction is not particularly limited and examples thereof include dichloromethane, chloroform, and mixed solvents thereof. The reaction temperature is usually in the range from −78 to 100° C. or the boiling point of the solvent, preferably in the range from −20° C. to around room temperature.

Synthesis of Compound (7)

A compound (7) can be obtained by reacting compound (6) with an acid halogenating reagent such as thionyl chloride, oxalyl chloride, phosphorus oxychloride, or 1-chloro-N,N,2-trimethyl-1-propenylamine. Here, the solvent used in the reaction is not particularly limited and examples thereof include dichloromethane, chloroform, toluene, and mixed solvents thereof. Alternatively, the reaction can be performed in the absence of a solvent. The reaction temperature is usually in the range from −78 to 100° C. or the boiling point of the solvent, preferably in the range from 0 to 100° C.

Synthesis of Compound (8)

A compound (8) can be obtained by reacting compound (7) with a compound (B) in the presence of a base. Examples of the base used can include organic bases such as triethylamine, diisopropylethylamine, 4-dimethylaminopyridine, N-methylmorpholine, pyridine, and 2,6-lutidine, and diazabicyclo[5.4.0]undec-7-ene, and inorganic bases such as potassium carbonate, sodium carbonate, and sodium bicarbonate. Here, the solvent used in the reaction is not particularly limited and examples thereof include dichloromethane, chloroform, tetrahydrofuran, ethyl acetate, toluene, and mixed solvents thereof. However, dried solvents are preferred. The reaction temperature is usually in the range from −78 to 100° C. or the boiling point of the solvent, preferably in the range from −10° C. to around room temperature. Moreover, in another method, a compound (8) can be obtained by reacting compound (6) with a compound (B) in the presence of a condensing agent. Here, examples of the condensing agent used can include N,N'-dicyclohexylcarbodiimide and 1-ethyl-3-(3-dimethylaminopropyl)carbodiimide. The solvent used in the reaction is not particularly limited and examples thereof include dichloromethane, dimethylformamide, tetrahydrofuran, ethyl acetate, and mixed solvents thereof. The reaction temperature is usually in the range from −78 to 100° C. or the boiling point of the solvent, preferably in the range from 0 to 50° C. Moreover, a base such as triethylamine, diisopropylethylamine, N-methylmorpholine, or 4-dimethylaminopyridine can be added, if necessary. Furthermore, 1-hydroxybenzotriazole, N-hydroxysuccinimide, or the like may be added as a reaction accelerator.

Synthesis of Compound (9)

A compound (9) can be obtained by performing deprotection under the reaction conditions used in the method for producing compound (6) above.

Synthesis of Compound (1)

A compound (1) can be obtained from compound (9) and a compound (C) under reaction conditions described above in another method for producing compound (8) above using a condensing agent. Moreover, in another method, a compound (1) can be obtained by reacting compound (9) and a compound (C) with an acid halogenating reagent such as 1-chloro-N,N,2-trimethyl-1-propenylamine in the presence of a base. Here, examples of the base used can include organic bases such as triethylamine, diisopropylethylamine, 4-dimethylaminopyridine, N-methylmorpholine, pyridine, 2,6-lutidine, and diazabicyclo[5.4.0]undec-7-ene, and inorganic bases such as potassium carbonate, sodium carbonate, and sodium bicarbonate. The solvent used in the reaction is not particularly limited and examples thereof include dichloromethane, chloroform, toluene, and mixed solvents thereof. The reaction temperature is usually in the range from −78 to 100° C. or the boiling point of the solvent, preferably in the range from −20 to 50° C.

The compound (1) of the present invention can also be produced by the following method.

[Production Method 2]

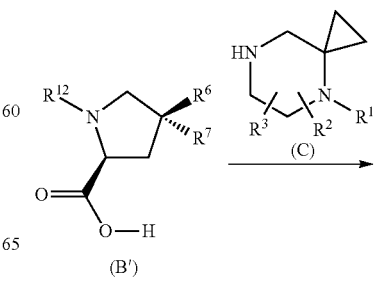
(B')

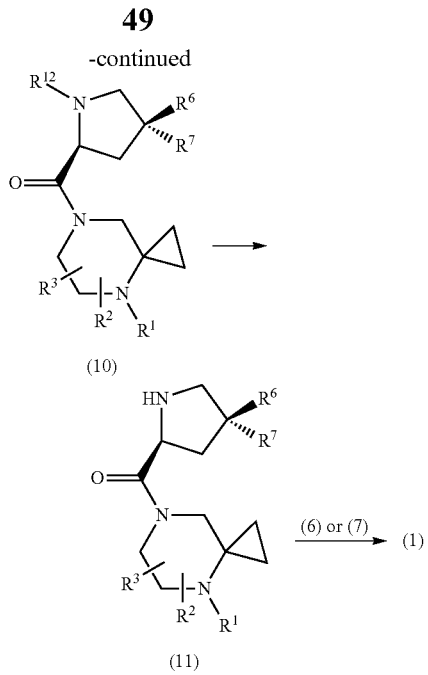

wherein $R^{12}$ means a protective group for the amino group; and $R^1$ to $R^3$, $R^6$, and $R^7$ have the same meanings as defined above.

Examples of the protective group for the amino group include a benzyloxycarbonyl group, a tert-butyloxycarbonyl group, and a benzyl group.

Synthesis of Compound (10)

A compound (10) can be obtained from a compound (B') and a compound (C) under the reaction conditions used in the method for producing compound (1) (amidation of compound (9) with a compound (C)) according to Production Method 1 above.

Synthesis of Compound (11)

Deprotection reaction conditions differ depending on the type of $R^{12}$. The synthesis may be performed under reaction conditions usually used in this field. When $R^{12}$ is a benzyloxycarbonyl group or a benzyl group or the like, deprotection can be performed by adding a reduction catalyst such as palladium carbon and reacting compound (10) in a hydrogen atmosphere or in the presence of a hydrogen source such as ammonium formate. Here, the solvent used in the reaction is not particularly limited and examples thereof include alcohols such as methanol and ethanol, tetrahydrofuran, dioxane, ethyl acetate, water, and mixed solvents thereof. The reaction temperature is usually in the range from −78 to 100° C. or the boiling point of the solvent, preferably in the range from 0° C. to around room temperature. Moreover, when $R^{12}$ is a tert-butyloxycarbonyl group or the like, deprotection can be performed by treating the compound (10) with trifluoroacetic acid or hydrochloric acid or the like. Here, the reaction solvent used in the reaction is not particularly limited and examples thereof include dichloromethane, chloroform, tetrahydrofuran, dioxane, methanol, ethanol, water, and mixed solvents thereof. The reaction temperature is usually in the range from −78 to 100° C. or the boiling point of the solvent, preferably in the range from 0° C. to around room temperature.

Synthesis of Compound (1)

A compound (1) can be obtained from compound (11) and compound (6) or compound (7) under the reaction conditions used in the method for producing compound (8) (amidation of compound (B) with a compound (6) or a compound (7)) according to Production Method 1 above.

When $R^1$ in compound (1) of the present invention is a tert-butoxycarbonyl group, a benzyloxycarbonyl group, or a trifluoroacetyl group, or the like usually used as a protective group, a compound (1) wherein $R^1$ is a hydrogen atom can be obtained under the reaction conditions used in the method for producing compound (11) (deprotection of $R^{12}$ in compound (10)) according to Production Method 2 above or by treatment with a base such as sodium hydroxide, potassium hydroxide, sodium carbonate, or potassium carbonate in a mixed solvent of methanol or ethanol and water. Furthermore, when $R^1$ is a hydrogen atom, it can be converted to the defined substituent using a conventional organic chemical method. For example, $R^1$ can be converted to an alkyl group or the like by treatment with a reducing agent such as sodium cyanoborohydride or sodium triacetoxyborohydride in the presence of an aldehyde derivative. Moreover, $R^1$ can be converted to an alkanoyl group or an alkylsulfonyl group by reaction with an acid chloride derivative in the presence of a base such as triethylamine.

The starting material compound (3) can be synthesized according to the method described in the document (Synlett, 1998, 623 or US2005/26916). Moreover, compound (3) can also be synthesized by the following method.

[Production Method 3]

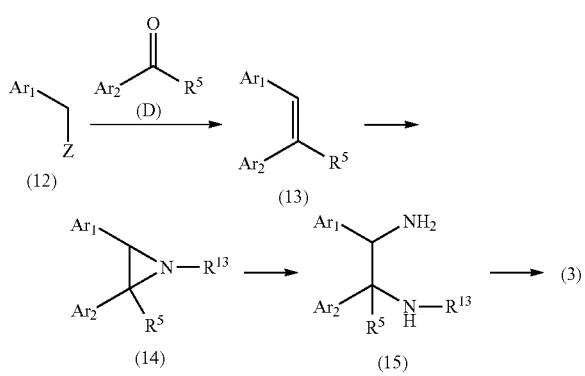

wherein Z means a halogen atom such as a chlorine atom or a bromine atom; $R^{13}$ means a trichloroethyloxysulfonyl group, a p-toluenesulfonyl group, or the like; and $Ar_1$, $Ar_2$, and $R^5$ have the same meanings as defined above.

Synthesis of Compound (13)

A compound (13) can be obtained by treating a phosphonium salt or a phosphonic acid ester obtained from a reaction of a compound (12) and an organic phosphorous compound such as triphenylphosphine or triethyl phosphite with a base such as alkyl lithium, lithium diisopropylamide, lithium bis (trimethylsilyl)amide, sodium hydride, or potassium tert-butoxide and then reacting the resulting product with a compound (D). Here, the solvent used in this reaction is not particularly limited and examples thereof include diethyl ether, tetrahydrofuran, toluene, dimethylformamide, dimethyl sulfoxide, and mixed solvents thereof. However, dried solvents are preferred. The reaction temperature is usually in the range from −78 to 100° C. or the boiling point of the solvent, preferably in the range from −78° C. to room temperature.

Synthesis of Compound (14)

A compound (14) can be synthesized according to synthesis methods reported in various documents (e.g., Tetrahedron Lett., 2005, 46 4031; J. Am. Chem. Soc., 2002, 124, 136672; J. Am. Chem. Soc., 2001, 123, 7707; Synlett, 2004, 525; and Japanese Patent Laid-Open No. 2000-72743). For example, a compound (14) can be obtained by reacting compound (13) with an alkoxysulfonamide derivative or an arylsulfonamide derivative in the presence of a rhodium catalyst after addition of an oxidizing agent such as iodosobenzene acetate and a base such as magnesium oxide. Here, the solvent used in this reaction is not particularly limited and examples thereof include diethyl ether, tetrahydrofuran, toluene, acetonitrile, and mixed solvents thereof. However, dried solvents are preferred. The reaction temperature is usually in the range from −78 to 100° C. or the boiling point of the solvent, preferably in the range from −20 to 80° C.

Synthesis of Compound (15)

A compound (15) can be obtained by treating the compound (14) with ammonia water. Here, the solvent used in this reaction is not particularly limited and examples thereof include methanol, ethanol, water, tetrahydrofuran, dioxane, and mixed solvents thereof. However, organic solvents that can be mixed with water in an arbitrary ratio are preferred. The reaction temperature is usually in the range from −78 to 100° C. or the boiling point of the solvent, preferably in the range from room temperature to 80° C.

Synthesis of Compound (3)

A compound (3) can be obtained by treating compound (15) with hydrochloric acid, sulfuric acid, or trifluoroacetic acid, or the like. Here, the solvent used in this reaction is not particularly limited and examples thereof include methanol, ethanol, water, tetrahydrofuran, dioxane, and mixed solvents thereof. However, organic solvents that can be mixed with water in an arbitrary ratio are preferred. The reaction temperature is usually in the range from −78 to 100° C. or the boiling point of the solvent, preferably in the range from room temperature to 80° C.

[Production Method 4]

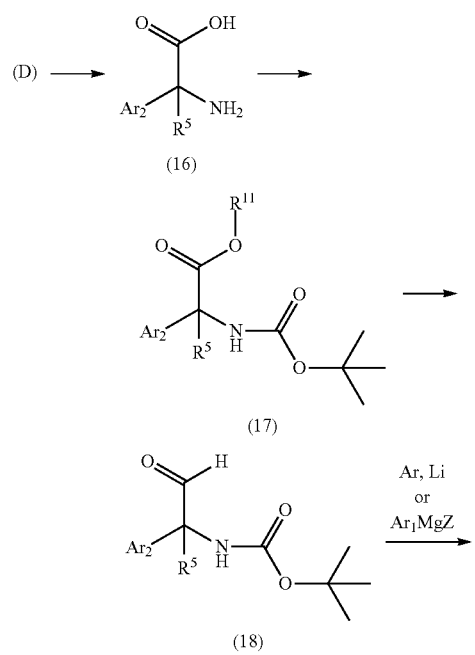

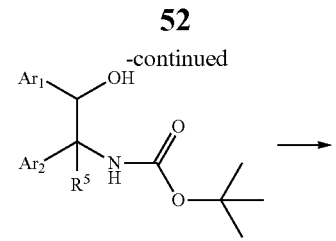

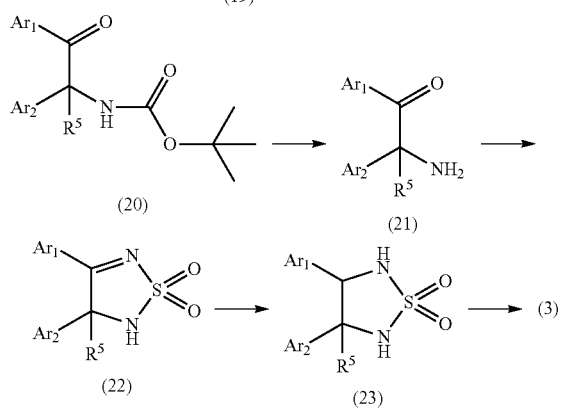

wherein $R^{11}$ means a protective group for the carboxyl group; Z means a halogen atom such as a chlorine atom or a bromine atom and $Ar_1$, $Ar_2$, and $R^5$ have the same meanings as defined above.

Synthesis of Compound (16)

A compound (16) can be obtained by treating an aminonitrile form obtained from a reaction (Strecker reaction) of a compound (D) with potassium cyanide or sodium cyanide, ammonium chloride, and ammonia water with a mineral acid (e.g., hydrochloric acid or sulfuric acid) or an organic acid (e.g., p-toluenesulfonic acid or methanesulfonic acid). Here, the solvent used in the reaction is not particularly limited and examples thereof include methanol, ethanol, water, tetrahydrofuran, dioxane, and mixed solvents thereof. The reaction temperature is usually in the range from −20 to 100° C. or the boiling point of the solvent, preferably in the range from around room temperature to 100° C.

Synthesis of Compound (17)

Each of the carboxyl group and the amino group in the compound (16) may be protected according to a standard method. Here, the order in which protective groups are introduced is not particularly limited. Hereinafter, each reaction will be described. Esterification can be performed by treatment with a halogenating reagent such as hydrogen chloride, sulfuric acid, or thionyl chloride in a lower alcohol appropriate for $R^{11}$, such as methanol or ethanol. The reaction temperature is usually in the range from −78 to 100° C. or the boiling point of the solvent, preferably in the range from 0 to 100° C. Moreover, the tert-butoxycarbonylation of the amino group can be performed by reaction with di-tert-butyl dicarbonate in the presence of a base such as triethylamine, diisopropylethylamine, or 4-dimethylaminopyridine. Here, the solvent used in the reaction is not particularly limited and examples thereof include dichloromethane, chloroform, tetrahydrofuran, ethyl acetate, acetonitrile, toluene, and mixed solvents thereof. However, dried solvents are preferred. The reaction temperature is usually in the range from −78 to 100° C. or the boiling point of the solvent, preferably in the range from 0 to 100° C.

Synthesis of Compound (18)

The ester group in compound (17) can be reduced by reaction using a water-reactive reagent such as lithium aluminum hydride at a temperature equal to or lower than room temperature (preferably −40 to 0° C.) in an aprotic solvent such as diethyl ether, tetrahydrofuran, or dioxane to give an alcohol form. Moreover, similarly, the reaction using sodium borohydride or the like can be performed at a temperature equal to or lower than room temperature (preferably −20° C. to around room temperature) using a protic solvent such as methanol, ethanol, or water, or a mixed solvent of the protic solvent and the aprotic solvent to give an alcohol form. A compound (18) can be obtained by reacting the alcohol form thus obtained with an oxidizing agent such as chromic acid [pyridinium chlorochromate (PCC), pyridinium dichromate (PDC), etc.], dimethyl sulfoxide with oxalyl chloride (Swern oxidation), dimethyl sulfoxide with acetic anhydride, dimethyl sulfoxide with a sulfur trioxide-pyridine complex, 1,1,1-triacetoxy-1,1-dihydro-1,2-benziodoxol-3(1H)-one (Dess-Martin reagent), or 2,2,6,6-tetramethyl-1-piperidinyloxy (TEMPO) with hypochlorous acid. Here, the solvent used in the reaction is not particularly limited and examples thereof include dichloromethane, chloroform, tetrahydrofuran, ethyl acetate, dimethyl sulfoxide, water, toluene, and mixed solvents thereof. The reaction temperature is usually in the range from −78 to 100° C. or the boiling point of the solvent, preferably in the range from −78° C. to around room temperature.

Synthesis of Compound (19)

A compound (19) can be obtained by reacting compound (18) with an aryl lithium compound ($Ar_1Li$) or a Grignard reagent ($Ar_1MgZ$). The corresponding aryl lithium compound or Grignard reagent is a commercially available product or can be synthesized according to a standard method. The Grignard reagent can be synthesized from the corresponding aryl halide and magnesium metal, and the organic lithium reagent can be synthesized by halogen-metal exchange from the corresponding aryl halide and a commercially available alkyl lithium reagent or the like.

Here, the solvent used in the reaction is not particularly limited and examples thereof include diethyl ether, tetrahydrofuran, dioxane, toluene, and mixed solvents thereof. However, dried solvents are preferred. The reaction temperature is usually in the range from −78 to 100° C. or the boiling point of the solvent, preferably in the range from −78° C. to around room temperature.

Synthesis of Compound (20)

A compound (20) can be obtained by appropriately selecting and using the oxidation reaction conditions described in the method for producing compound (19).

Synthesis of Compound (21)

A compound (21) can be obtained under the reaction conditions used in the method for producing the compound (11) according to Production Method 2 above, wherein $R^{12}$ is a tert-butyloxycarbonyl group.

Synthesis of Compound (22)

A compound (22) can be obtained by heating compound (21) in the presence of sulfamide and a base such as 1,8-diazabicyclo[5.4.0]undec-7-ene. Here, the solvent used in the reaction is not particularly limited and examples thereof include diethyl ether, tetrahydrofuran, dioxane, ethyl acetate, methanol, ethanol, isopropyl alcohol, ethylene glycol, acetonitrile, toluene, and mixed solvents thereof. The reaction temperature is usually in the range from −78 to 180° C. or the boiling point of the solvent, preferably in the range from 70 to 150° C.

Synthesis of Compound (23)

A compound (23) can be obtained from compound (22) by appropriately selecting and using the reduction reaction conditions described in the method for producing compound (18).

Synthesis of Compound (3)

A compound (3) can be synthesized from compound (23) according to the method described in the document (Synlett, 1998, 623-624 and US2005/0026916). Moreover, in another method, a compound (3) can be obtained from compound (23) by hydrolyzation in the presence of a base such as pyridine or ethylenediamine. Here, examples of the solvent used in the reaction include methanol, ethanol, water, tetrahydrofuran, dioxane, ethylene glycol, and mixed solvents thereof. However, organic solvents that can be mixed with water in an arbitrary ratio are preferred. The reaction temperature is usually in the range from 0 to 180° C. or the boiling point of the solvent, preferably in the range from 60 to 120° C.

The racemic compound (3) obtained by the production method can be optically resolved according to the method described in the document (US2005/26916, Japanese Patent Laid-Open No. 2005-75754, and Tetrahedron Asymmetry, 1995, 6, 3). For example, the racemic compound (3) can be treated with an optical resolving agent such as L-(+)-tartaric acid in a mixed solvent of methanol or ethanol and water to give crystalline tartrate. This tartrate is treated with a base such as sodium hydroxide to give an optically active diamine (3) having the positional configuration shown above.

The starting material compound (A) is a commercially available product or can be synthesized according to the method described in the document (Tetrahedron Asymmetry, 1995, 6, 2199).

The starting material compounds (B) and (C) are commercially available products or can be synthesized according to methods described in the Reference Examples.

The starting material compound (D) is a commercially available product or can be synthesized according to the method described in various documents (e.g., J. Med. Chem. 2000, 43, 4781).

In one embodiment of the present invention, the compound of the present invention can be used as a p53-Mdm2 binding inhibitor and/or an Mdm2 ubiquitin ligase inhibitor because it inhibits the binding of p53 with Mdm2 and the ubiquitination of p53 by Mdm2.

The condition of the p53-Mdm2 binding can be examined by a method conventionally used by those skilled in the art to examine binding conditions between proteins (for example, immunological techniques, surface plasmon resonance techniques, etc.). Examples of methods for examining the condition of the Mdm2-p53 binding using an immunological technique include an immuno-sedimentation method and enzyme-linked-immuno-sorbent assay (ELISA). An antibody used in such immunological techniques may be an anti-Mdm2 antibody and/or an anti-p53 antibody that can directly detect Mdm2 and/or p53. When Mdm2 and/or p53 is labeled with a tag (for example, a GST tag or a histidine tag) or the like, an antibody suitable for labeling (for example, an anti-GST antibody or an anti-histidine antibody) can be used. Methods for examining the condition of the Mdm2-p53 binding using an immunological technique are described in, for example, WO2003/51359, WO2003/51360, U.S. Patent Application Publication No. 2004/259867 or 2004/259884, and WO2005/110996. Methods for examining the condition of the Mdm2-p53 binding using a surface plasmon resonance technique are described in, for example, Science, vol. 303, p. 844-848, 2004.

Ubiquitin ligase activity of Mdm2 against p53 can be examined by an ubiquitin ligase assay conventionally used by those skilled in the art. The ubiquitin ligase activity can be detected by, for example, comparing ubiquitination of p53 by ubiquitin activation enzyme (E1), ubiquitin binding enzyme (E2), and ubiquitin ligase (E3) (Mdm2) in the presence and absence of a test compound (for example, refer to WO2001/75145 and WO2003/76608).

In another embodiment, the compound of the present invention can be used as an inhibitor of suppression of the p53 transcription activity because it restores functions of p53 as a transcription factor that is suppressed by Mdm2 by inhibiting the binding of Mdm2 to the p53 transcription activation domain. The inhibitor of suppression of the p53 transcription activity can be obtained by, for example, measuring the mRNA level or the protein level of a protein whose transcription is regulated by p53 (for example, p21$^{Waf1/Cip1}$) in the presence or absence of a test compound by an mRNA measuring method (for example, Northern blot) or a protein measuring method (for example, Western blot) conventionally used by those skilled in the art and selecting the test compound as an inhibitor of suppression of the p53 transcription activity when the mRNA level or the protein level is increased in the presence of the test compound as compared with that in the absence of the test compound. Furthermore, the inhibitor of suppression of the p53 transcription activity can also be identified by a reporter assay using the reporter activity of a reporter gene including a p53 responsive element as an indicator.

In another embodiment, the compound of the present invention can be used as a p53 degradation inhibitor because it inhibits ubiquitination of p53 by Mdm2 and thereby prevents the degradation of p53 in proteasomes. The p53 degradation inhibitor can be obtained by, for example, measuring the protein level of p53 in the presence or absence of a test compound by a protein measuring method (for example, Western blot) conventionally used by those skilled in the art and selecting the test compound as a p53 degradation inhibitor when the protein level is increased in the presence of the test compound as compared with that in the absence of the test compound.

In another embodiment, the compound of the present invention can be used as an anti-tumor agent because it normalizes functions of p53 as a cancer-restraining gene by inhibition of the Mdm2-p53 binding and/or ubiquitination of p53 by Mdm2.

Cellular growth inhibiting activity can be examined by methods for testing growth inhibition conventionally used by those skilled in the art. The cell growth inhibition activity can be determined by, for example, comparing the levels of cellular growth (for example, tumor cells) in the presence or absence of a test compound as described in the following Test Example 2. The levels of cellular growth can be examined by using, for example, a test system for measuring living cells. Examples of the method for measuring living cells include the [$^3$H]-thymidine uptake test, the BrdU method, the MTT assay, and so forth.

Moreover, in vivo anti-tumor activity can be examined by methods for testing anti-tumor activity conventionally used by those skilled in the art. The in vivo anti-tumor activity of the present invention can be confirmed by, for example, transplanting various tumor cells to mice, rats, or the like; after confirming the engraftment of the transplanted cells, orally or intravenously administering the compound of the present invention to the animals; a few days or a few weeks later, comparing tumor growth in a drug-non-administered group with that in the compound-administered group.

The compound of the present invention can be used for the treatment of tumors or cancers, for example, lung cancer, digestive system cancer, ovary cancer, uterine cancer, breast cancer, liver cancer, head/neck region cancer, blood cancer, renal cancer, and testicular tumors, more preferably lung cancer, breast cancer, prostate cancer, colon cancer, acute myeloid leukemia, malignant lymphoma, retinoblastoma, neuroblastoma, and sarcoma. However, the present invention is not limited to these cancers.

A pharmaceutical composition of the present invention can contain a compound of the present invention and a pharmaceutically acceptable carrier and can be administered as various injections such as intravenous injection, intramuscular injection, and subcutaneous injection or by various methods such as oral administration or percutaneous administration. Pharmaceutically acceptable carrier means a pharmacologically acceptable material that is involved in transport of the compound of the present invention or a composition containing the compound of present invention (for example, an excipient, a diluent, an additive, a solvent, etc.) from a given organ to another organ.

A formulation can be prepared by selecting a suitable formulation form (for example, oral formulation or injection) depending on the administration method and using various conventionally used methods for preparing a formulation. Examples of oral formulations include tablets, powders, granules, capsules, pills, lozenges, solutions, syrups, elixirs, emulsions, oily or aqueous suspensions, and so forth. In oral administration, the free compound or a salt form may be used. An aqueous formulation can be prepared by forming an acid adduct with a pharmacologically acceptable acid or by forming an alkali metal salt such as sodium. As an injection, a stabilizer, a preservative, a dissolving aid, and the like can be used in the formulation. After filling a solution that may contain these aids and the like in a vessel, a formulation for use may be prepared as a solid formulation by lyophilization or the like. Furthermore, one dose may be filled in one vessel, or two or more doses may be filled in a vessel.

Examples of solid formulations include tablets, powders, granules, capsules, pills, and lozenges. These solid formulations may contain pharmaceutically acceptable additives together with a compound of the present invention. Examples of additives include fillers, extenders, binders, disintegrating agents, dissolution promoting agents, skin wetting agents, and lubricants, and these can be selected and mixed as required to prepare a formulation.

Examples of liquid formulations include solutions, syrups, elixirs, emulsions, and suspensions. These liquid formulations may contain pharmaceutically acceptable additives together with a compound of the present invention. Examples of additives include suspending agents and emulsifiers, and these are selected and mixed as required to prepare a formulation.

The compound of the present invention can be used in cancer treatment of mammals, in particular, humans. The dose and the administration interval can be suitably selected depending on the site of the disease, the patient's height, body weight, sex, or medical history, according to a physician's judgment. When the compound of the present invention is administered to a human, the dose range is approx. 0.01 to 500 mg/kg body weight per day, preferably, approx 0.1 to 100 mg/kg body weight. Preferably, the compound of the present invention is administered to a human once a day, or the dose is divided two to four times, and administration is repeated at an appropriate interval. Furthermore, the daily dose may exceed the above-mentioned dose at a physician's discretion, if necessary.

The compound of the present invention may be used in combination with an additional anti-tumor agent. Examples thereof include anti-tumor antibiotics, anti-tumor plant constituents, BRMs (biological response modifiers), hormones, vitamins, anti-tumor antibodies, molecular target drugs, and other anti-tumor agents.

More specifically, examples of alkylating agents include: alkylating agents such as nitrogen mustard, nitrogen mustard N-oxide, and chlorambucil; aziridine alkylating agents such as carboquone and thiotepa; epoxide alkylating agents such as dibromomannitol and dibromodulcitol; nitrosourea alkylating agents such as carmustine, lomustine, semustine, nimustine hydrochloride, streptozocin, chlorozotocin, and ranimustine; and busulfan, improsulfan tosylate, and dacarbazine.

Examples of various metabolic antagonists include: purine metabolic antagonists such as 6-mercaptopurine, 6-thioguanine, and thioinosine; pyrimidine metabolic antagonists such as fluorouracil, tegafur, tegafur-uracil, carmofur, doxifluridine, broxuridine, cytarabine, and enocitabine; and folic acid metabolic antagonists such as methotrexate and trimetrexate.

Examples of anti-tumor antibiotics include: anti-tumor anthracycline antibiotics such as mitomycin C, bleomycin, peplomycin, daunorubicin, aclarubicin, doxorubicin, pirarubicin, THP-adriamycin, 4'-epidoxorubicin, and epirubicin; and chromomycin A3 and actinomycin D.

Examples of anti-tumor plant constituents include: vinca alkaloids such as vindesine, vincristine, and vinblastine; taxanes such as paclitaxel and docetaxel; and epipodophyllotoxins such as etoposide and teniposide.

Examples of BRMs include tumor necrosis factors and indomethacin.

Examples of hormones include hydrocortisone, dexamethasone, methylprednisolone, prednisolone, prasterone, betamethasone, triamcinolone, oxymetholone, nandrolone, metenolone, fosfestrol, ethinylestradiol, chlormadinone, and medroxyprogesterone.

Examples of vitamins include vitamin C and vitamin A.

Examples of anti-tumor antibodies and molecular target drugs include trastuzumab, rituximab, cetuximab, nimotuzumab, denosumab, bevacizumab, infliximab, imatinib mesilate, gefitinib, erlotinib, sunitinib, lapatinib, and sorafenib.

Examples of other anti-tumor agents include cisplatin, carboplatin, oxaliplatin, tamoxifen, camptothecin, ifosfamide, cyclophosphamide, melphalan, L-asparaginase, aceglatone, sizofuran, picibanil, procarbazine, pipobroman, neocarzinostatin, hydroxyurea, ubenimex, and krestin.

The present invention also includes a method for preventing and/or treating cancer, comprising administering a compound of the present invention or a salt thereof.

The present invention further includes use of a compound of the present invention, a salt, or a solvate thereof for the manufacture of the medicament.

Hereinafter, the present invention will be specifically explained with reference to the Examples. However, the present invention is not limited to these examples, and they should not be construed in any limitative way. Furthermore, reagents, solvents, and starting materials in the specification can be readily obtained from commercially available supply sources unless otherwise specified.

EXAMPLES

Example 1

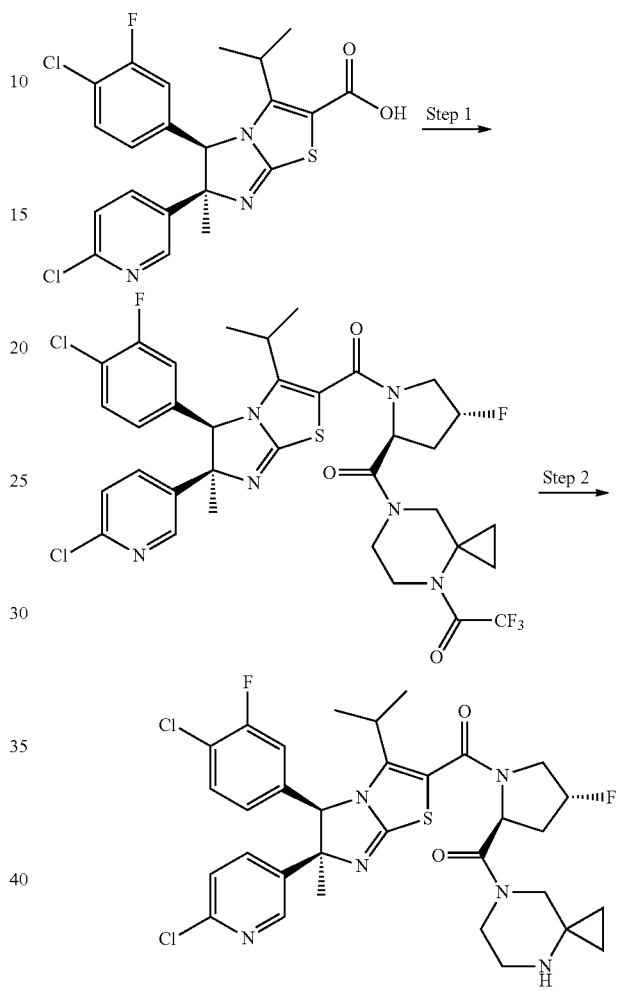

Step 1: 7-[(4R)-1-{[(5R,6S)-5-(4-chloro-3-fluorophenyl)-6-(6-chloropyridin-3-yl)-3-isopropyl-6-methyl-5,6-dihydroimidazo[2,1-b][1,3]thiazol-2-yl]carbonyl}-4-fluoro-L-prolyl]-4-(trifluoroacetyl)-4,7-diazaspiro[2.5]octane Thionyl chloride (0.50 ml) and dimethylformamide (2 drops) were added to a 1,2-dichloroethane (10 ml) suspension of the compound (470 mg, 1.00 mmol) obtained in Step 13 of Reference Example 1, the resulting mixture was stirred under heating at 70° C. for 1 hour and then the solvent was concentrated under reduced pressure. The residue obtained was dissolved in tetrahydrofuran (10 ml) and added dropwise to a tetrahydrofuran (10 ml) solution of the compound (380 mg, 1.20 mmol) obtained in Step 2 of Reference Example 3 and triethylamine (0.42 ml, 3.00 mmol) under ice cooling and the resulting mixture was stirred at room temperature for 20 hours. The reaction mixture was diluted with ethyl acetate and the organic layer was washed with saturated aqueous sodium bicarbonate solution and saturated brine and dried over anhydrous sodium sulfate. The solvent was evaporated under reduced pressure and the residue obtained was purified by NH-silica gel column chromatography [n-hexane:ethyl acetate=1:5 (v/v)] to give the title compound (399 mg, 51%) as a colorless solid.

$^1$H-NMR (400 MHz, DMSO-d$_6$, 90° C.) δ: 0.93 (3H, d, J=7.1 Hz), 0.93 (3H, d, J=7.1 Hz), 0.98-1.12 (4H, m), 1.77 (3H, s), 2.05-2.15 (1H, m), 2.54-2.60 (1H, m), 2.61-2.67 (1H, m), 3.49-3.57 (2H, m), 3.63-3.83 (5H, m), 3.87-3.97 (1H, m), 5.06-5.09 (1H, m), 5.36 (1H, d, J=53.7 Hz), 5.51 (1H, s), 6.73-6.77 (1H, m), 6.91-6.97 (1H, m), 7.17 (1H, d, J=8.3 Hz), 7.34 (1H, t, J=7.9 Hz), 7.65 (1H, dd, J=8.3, 2.7 Hz), 8.26 (1H, d, J=2.4 Hz).

MS (ESI) m/z: 771 [(M+H)$^+$].

Step 2: 7-[(4R)-1-{[(5R,6S)-5-(4-chloro-3-fluorophenyl)-6-(6-chloropyridin-3-yl)-3-isopropyl-6-methyl-5,6-dihydroimidazo[2,1-b][1,3]thiazol-2-yl]carbonyl}-4-fluoro-L-prolyl]-4,7-diazaspiro[2.5]octane The compound (390 mg, 0.51 mmol) obtained in Step 1 above was dissolved in 10% aqueous methanol (8 ml), potassium carbonate (400 mg, 2.89 mmol) was added and the resulting mixture was stirred under heating at 40° C. for 2 hours. The solvent was concentrated under reduced pressure and then the residue obtained was diluted with ethyl acetate, washed with saturated brine, and then dried over anhydrous sodium sulfate. The solvent was evaporated under reduced pressure and the residue obtained was purified by silica gel column chromatography [chloroform:methanol=15:1 (v/v)] to give the title compound (190 mg, 55%) as a colorless solid.

$^1$H-NMR (400 MHz, DMSO-d$_6$, 90° C.) δ: 0.44-0.52 (4H, m), 0.93 (3H, d, J=6.8 Hz), 0.94 (3H, d, J=6.8 Hz), 1.78 (3H, s), 2.05-2.15 (1H, m), 2.56-2.64 (1H, m), 2.61-2.69 (1H, m), 2.73-2.79 (2H, m), 3.31-3.39 (2H, m), 3.43-3.50 (2H, m), 3.74 (1H, dd, J=35.8, 12.1 Hz), 3.91 (1H, dd, J=19.2, 12.6 Hz), 5.02-5.06 (1H, m), 5.35 (1H, d, J=53.7 Hz), 5.52 (1H, s), 6.73-6.78 (1H, m), 6.92-6.99 (1H, m), 7.18 (1H, dd, J=8.3, 0.7 Hz), 7.35 (1H, t, J=8.1 Hz), 7.66 (1H, dd, J=8.3, 2.7 Hz), 8.27 (1H, d, J=2.4 Hz).

MS (ESI) m/z: 675 [(M+H)$^+$].

Anal. Calcd. for $C_{32}H_{34}Cl_2F_2N_6O_2S \cdot 0.25H_2O$: C, 56.51; H, 5.11; N, 12.36; F, 5.59; Cl, 10.43; S, 4.71.

Found: C, 56.33; H, 5.10; N, 12.20; F, 5.55; Cl, 10.21; S, 4.73.

Example 2

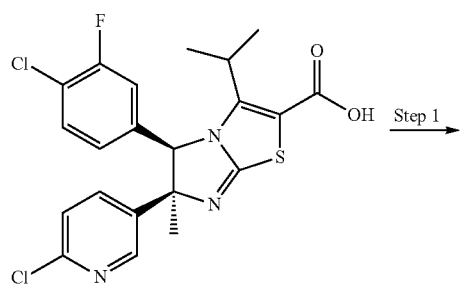

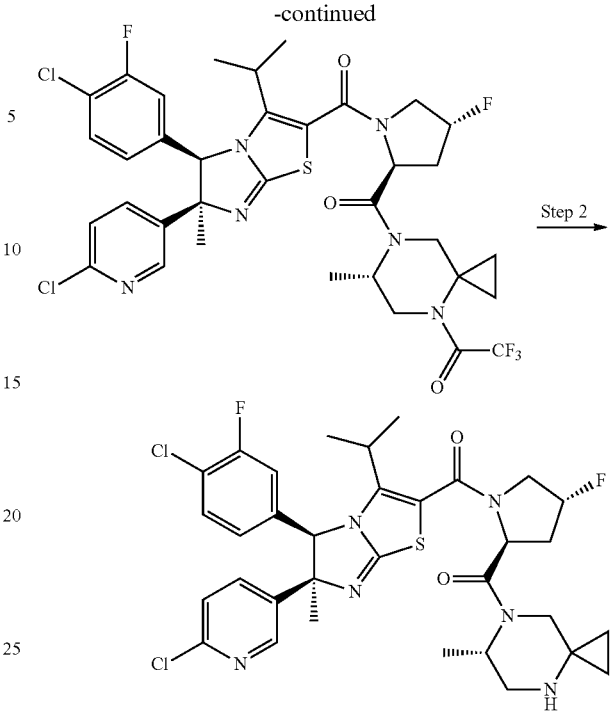

Step 1: (6S)-7-[(4R)-1-{[(5R,6S)-5-(4-chloro-3-fluorophenyl)-6-(6-chloropyridin-3-yl)-3-isopropyl-6-methyl-5,6-dihydroimidazo[2,1-b][1,3]thiazol-2-yl]carbonyl}-4-fluoro-L-prolyl]-6-methyl-4-(trifluoroacetyl)-4,7-diazaspiro[2.5]octane Triethylamine (0.12 ml, 0.86 mmol), 1-(3-dimethylaminopropyl)-3-ethylcarbodiimide hydrochloride (100 mg, 0.52 mmol), and 1-hydroxybenzotriazole (53 mg, 0.43 mmol) were added to a dimethylformamide (3 ml) solution of the compound (200 mg, 0.43 mmol) obtained in Step 13 of Reference Example 1 and the compound (159 mg, 0.47 mmol) obtained in Step 2 of Reference Example 5 and the resulting mixture was stirred at room temperature for 24 hours. The reaction mixture was diluted with ethyl acetate, washed with saturated aqueous sodium bicarbonate solution, water, and saturated brine, and then dried over anhydrous sodium sulfate. The solvent was evaporated under reduced pressure and the residue obtained was purified by silica gel column chromatography [n-hexane:ethyl acetate=1:1 (v/v)] to give the title compound (286 mg, 85%) as a pale yellow solid.

$^1$H-NMR (400 MHz, DMSO-d$_6$, 100° C.) δ: 0.72-0.74 (2H, m), 0.92 (3H, d, J=7.1 Hz), 0.96 (3H, d, J=7.1 Hz), 1.12 (3H, brd, J=6.1 Hz), 1.30 (1H, m), 1.49 (1H, m), 1.78 (3H, s), 2.17 (1H, m), 2.58-2.65 (2H, m), 3.54-3.57 (3H, m), 3.78-3.92 (3H, m), 4.69 (1H, m), 5.01 (1H, m), 5.39 (1H, d, J=53.1 Hz), 5.51 (1H, s), 6.76 (1H, d, J=8.3 Hz), 6.95 (1H, d, J=8.3 Hz), 7.17 (1H, d, J=8.3 Hz), 7.34 (1H, t, J=8.3 Hz), 7.65 (1H, dd, J=8.3, 2.7 Hz), 8.26 (1H, d, J=2.7 Hz).

MS (ESI) m/z: 785 [(M+H)$^+$].

Step 2: (6S)-7-[(4R)-1-{[(5R,6S)-5-(4-chloro-3-fluorophenyl)-6-(6-chloropyridin-3-yl)-3-isopropyl-6-methyl-5,6-dihydroimidazo[2,1-b][1,3]thiazol-2-yl]carbonyl}-4-fluoro-L-prolyl]-6-methyl-4,7-diazaspiro[2.5]octane The compound obtained in Step 1 above was reacted in the same way as in Step 2 of Example 1 to give the title compound as a colorless solid.

¹H-NMR (400 MHz, DMSO-d₆, 100° C.) δ: 0.35-0.41 (2H, m), 0.57-0.59 (2H, m), 0.92 (3H, d, J=7.1 Hz), 0.95 (3H, d, J=7.1 Hz), 1.21-1.22 (3H, brd, J=5.6 Hz), 1.28 (1H, m), 1.78 (3H, s), 2.14 (1H, m), 2.55-2.66 (3H, m), 3.21-3.44 (2H, m), 3.75 (1H, ddd, J=36.6, 12.8, 2.9 Hz), 3.92 (1H, dd, J=18.2, 12.8 Hz), 4.33 (1H, m), 4.97 (1H, m), 5.36 (1H, d, J=52.9 Hz), 5.50 (1H, s), 6.75 (1H, d, J=8.3 Hz), 6.95 (1H, d, J=8.3 Hz), 7.17 (1H, dd, J=8.3, 0.6 Hz), 7.34 (1H, t, J=8.3 Hz), 7.65 (1H, dd, J=8.3, 2.4 Hz), 8.26 (1H, dd, J=2.4, 0.6 Hz).

MS (ESI) m/z: 689 [(M+H)⁺].

Anal. Calcd. for $C_{33}H_{36}Cl_2F_2N_6O_2S \cdot 1.25H_2O$: C, 55.65; H, 5.45; N, 11.80.

Found: C, 55.25; H, 5.23; N, 11.32.

Example 3

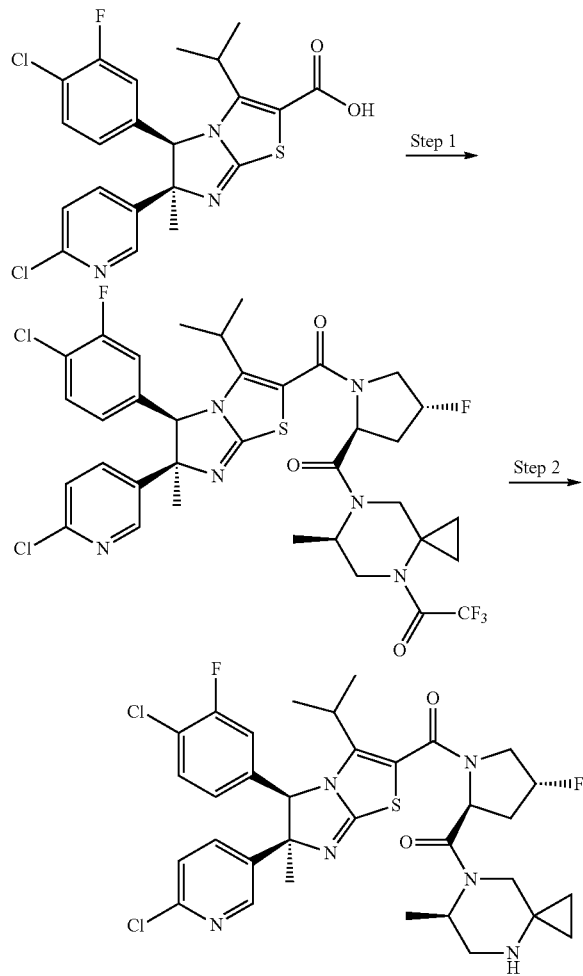

Step 1: (6R)-7-[(4R)-1-{[(5R,6S)-5-(4-chloro-3-fluorophenyl)-6-(6-chloropyridin-3-yl)-3-isopropyl-6-methyl-5,6-dihydroimidazo[2,1-b][1,3]thiazol-2-yl]carbonyl}-4-fluoro-L-prolyl]-6-methyl-4-(trifluoroacetyl)-4,7-diazaspiro[2.5]octane The compound obtained in Step 13 of Reference Example 1 was reacted in the same way as in Step 1 of Example 2 using the compound obtained in Step 2 of Reference Example 7 instead of the compound obtained in Step 2 of Reference Example 5 to give the title compound as a colorless solid.

¹H-NMR (400 MHz, DMSO-d₆, 100° C.) δ: 0.71-0.73 (1H, m), 0.89-0.92 (1H, m), 0.93 (6H, d, J=7.1 Hz), 1.10-1.13 (3H, m), 1.30-1.32 (1H, m), 1.47-1.49 (1H, m), 1.77 (3H, s), 2.06-2.08 (1H, m), 2.61-2.68 (1H, m), 3.51-3.54 (3H, m), 3.71-3.81 (1H, m), 3.90-3.95 (2H, m), 4.61 (1H, brs), 5.04 (1H, t, J=8.1 Hz), 5.34 (1H, d, J=54.0 Hz), 5.50 (1H, s), 6.74 (1H, d, J=7.8 Hz), 6.93 (1H, d, J=7.8 Hz), 7.16 (1H, dd, J=8.3, 0.7 Hz), 7.33 (1H, t, J=7.8 Hz), 7.64 (1H, dd, J=8.3, 2.4 Hz), 8.25 (1H, t, J=1.3 Hz).

Step 2: (6R)-7-[(4R)-1-{[(5R,6S)-5-(4-chloro-3-fluorophenyl)-6-(6-chloropyridin-3-yl)-3-isopropyl-6-methyl-5,6-dihydroimidazo[2,1-b][1,3]thiazol-2-yl]carbonyl}-4-fluoro-L-prolyl]-6-methyl-4,7-diazaspiro[2.5]octane The compound obtained in Step 1 above was reacted in the same way as in Step 2 of Example 1 to give the title compound as a colorless solid.

¹H-NMR (400 MHz, DMSO-d₆, 100° C.) δ: 0.35-0.37 (2H, m), 0.55-0.57 (2H, m), 0.92 (3H, d, J=7.1 Hz), 0.93 (3H, d, J=7.1 Hz), 1.26 (3H, brs), 1.76 (3H, s), 1.99-2.02 (1H, m), 2.32-2.34 (1H, m), 2.61-2.68 (3H, m), 2.86-2.92 (1H, m), 3.30-3.32 (1H, m), 3.72 (1H, dd, J=36.3, 11.9 Hz), 3.90 (1H, dd, J=19.9, 12.8 Hz), 4.17-4.20 (1H, m), 5.00 (1H, t, J=8.0 Hz), 5.32 (1H, d, J=53.1 Hz), 5.48 (1H, s), 6.73 (1H, d, J=8.3 Hz), 6.92 (1H, d, J=8.3 Hz), 7.15 (1H, d, J=8.3 Hz), 7.31 (1H, t, J=7.9 Hz), 7.63 (1H, dd, J=8.3, 2.7 Hz), 8.24 (1H, d, J=2.7 Hz).

MS (ESI) m/z: 689 [(M+H)⁺].

Anal. Calcd. for $C_{33}H_{36}Cl_2F_2N_6O_2S \cdot 1.25H_2O$: C, 55.65; H, 5.45; N, 11.80.

Found: C, 55.26; H, 5.19; N, 11.85.

Example 4

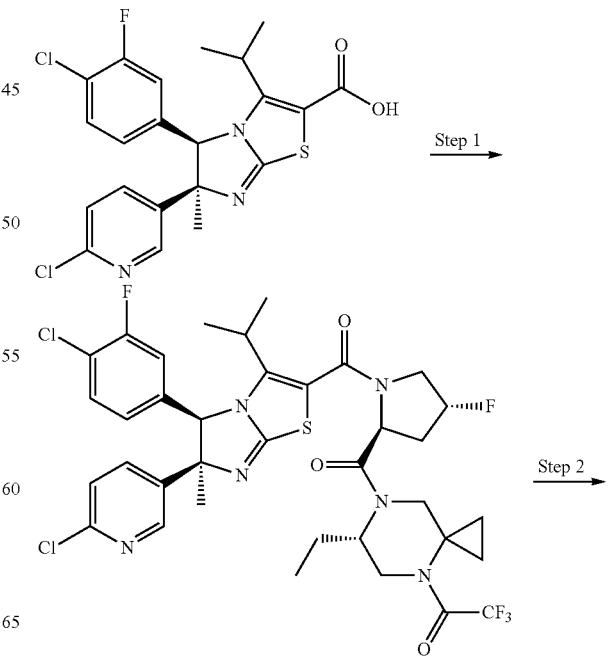

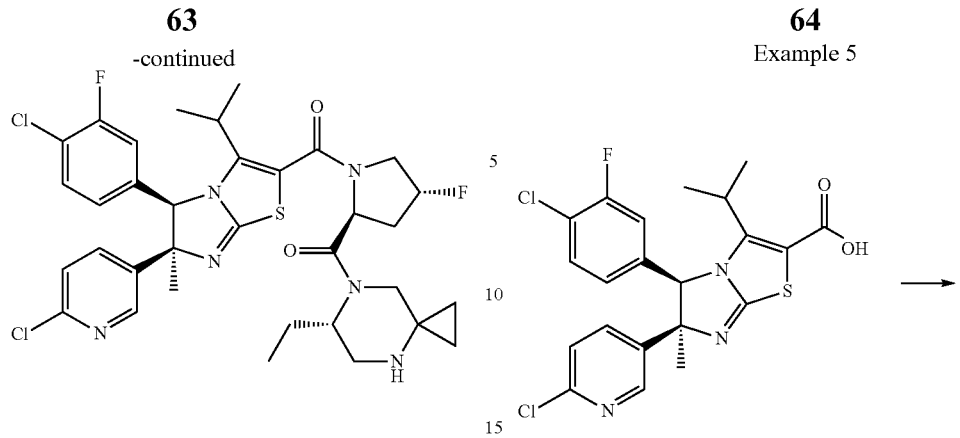

Step 1: (6S)-7-[(4R)-1-{[(5R,6S)-5-(4-chloro-3-fluorophenyl)-6-(6-chloropyridin-3-yl)-3-isopropyl-6-methyl-5,6-dihydroimidazo[2,1-b][1,3]thiazol-2-yl]carbonyl}-4-fluoro-L-prolyl]-6-ethyl-4-(trifluoroacetyl)-4,7-diazaspiro[2.5]octane The compound obtained in Step 13 of Reference Example 1 was reacted in the same way as in Step 1 of Example 2 using the compound obtained in Step 2 of Reference Example 9 instead of the compound obtained in Step 2 of Reference Example 5 to give the title compound as a colorless solid.

$^1$H-NMR (400 MHz, DMSO-d$_6$, 90° C.) δ: 0.67-0.74 (2H, m), 0.80-0.85 (3H, m), 0.91 (3H, d, J=7.1 Hz), 0.94 (3H, d, J=6.8 Hz), 1.25-1.33 (1H, m), 1.43-1.53 (3H, m), 1.77 (3H, s), 2.17-2.27 (2H, m), 2.55-2.63 (1H, m), 3.37-3.97 (6H, m), 4.06-4.13 (1H, m), 4.49-4.53 (1H, m), 5.40 (1H, d, J=52.2 Hz), 5.51 (1H, s), 6.72-6.78 (1H, m), 6.92-6.99 (1H, m), 7.17 (1H, d, J=8.3 Hz), 7.34 (1H, t, J=8.1 Hz), 7.65 (1H, dd, J=8.4, 2.6 Hz), 8.26 (1H, d, J=2.2 Hz).

MS (ESI) m/z: 799 [(M+H)$^+$].

Step 2: (6S)-7-[(4R)-1-{[(5R,6S)-5-(4-chloro-3-fluorophenyl)-6-(6-chloropyridin-3-yl)-3-isopropyl-6-methyl-5,6-dihydroimidazo[2,1-b][1,3]thiazol-2-yl]carbonyl}-4-fluoro-L-prolyl]-6-ethyl-4,7-diazaspiro[2.5]octane The compound obtained in Step 1 above was reacted in the same way as in Step 2 of Example 1 to give the title compound as a colorless solid.

$^1$H-NMR (400 MHz, DMSO-d$_6$, 90° C.) δ: 0.31-0.39 (2H, m), 0.50-0.58 (2H, m), 0.78-0.84 (3H, m), 0.91 (3H, d, J=7.3 Hz), 0.93 (3H, d, J=7.1 Hz), 1.65-1.73 (2H, m), 1.77 (3H, s), 2.09-2.22 (1H, m), 2.30-2.36 (1H, m), 2.56-2.63 (1H, m), 2.72-2.77 (2H, m), 3.46-3.58 (2H, m), 3.70-3.95 (2H, m), 4.12-4.20 (1H, m), 4.89-4.95 (1H, m), 5.37 (1H, d, J=53.2 Hz), 5.50 (1H, s), 6.72-6.79 (1H, m), 6.91-6.99 (1H, m), 7.17 (1H, d, J=8.3 Hz), 7.34 (1H, t, J=7.9 Hz), 7.65 (1H, dd, J=8.4, 2.6 Hz), 8.26 (1H, d, J=2.4 Hz).

MS (ESI) m/z: 703 [(M+H)$^+$].

Anal. Calcd. for C$_{34}$H$_{38}$Cl$_2$F$_2$N$_6$O$_2$S.0.25H$_2$O: C, 57.66; H, 5.48; N, 11.87; F, 5.37; Cl, 10.01; S, 4.53.

Found: C, 57.56; H, 5.49; N, 11.74; F, 5.32; Cl, 9.78; S, 4.49.

Example 5

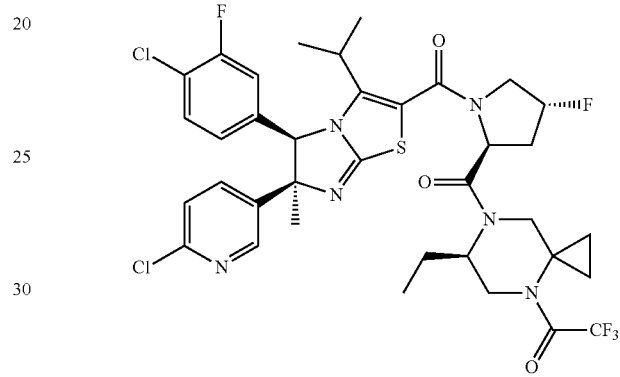

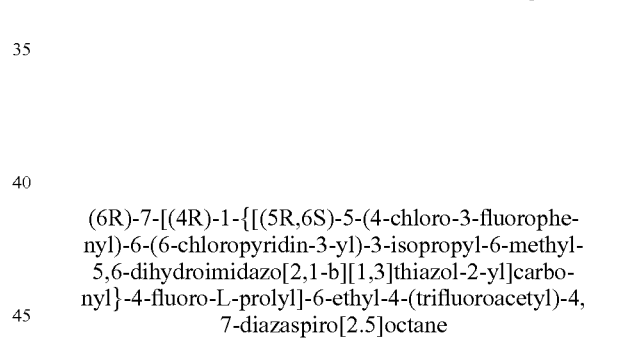

(6R)-7-[(4R)-1-{[(5R,6S)-5-(4-chloro-3-fluorophenyl)-6-(6-chloropyridin-3-yl)-3-isopropyl-6-methyl-5,6-dihydroimidazo[2,1-b][1,3]thiazol-2-yl]carbonyl}-4-fluoro-L-prolyl]-6-ethyl-4-(trifluoroacetyl)-4,7-diazaspiro[2.5]octane The compound obtained in Step 13 of Reference Example 1 was reacted in the same way as in Step 1 of Example 2 using the compound obtained in Step 2 of Reference Example 11 instead of the compound obtained in Step 2 of Reference Example 5 to give the title compound as a colorless solid.

$^1$H-NMR (400 MHz, DMSO-d$_6$, 90° C.) δ: 0.69-0.75 (2H, m), 0.79-0.86 (3H, m), 0.94 (6H, d, J=7.1 Hz), 1.05-1.14 (1H, m), 1.26-1.33 (1H, m), 1.45-1.53 (3H, m), 1.78 (3H, s), 1.92-2.12 (1H, m), 2.60-2.70 (1H, m), 3.27-3.49 (2H, m), 3.64-3.84 (2H, m), 3.89-3.99 (1H, m), 4.14-4.25 (1H, m), 4.58-4.64 (1H, m), 5.06-5.12 (1H, m), 5.35 (1H, d, J=55.7 Hz), 5.52 (1H, s), 6.74-6.79 (1H, m), 6.92-6.98 (1H, m), 7.18 (1H, d, J=8.3 Hz), 7.35 (1H, t, J=7.9 Hz), 7.66 (1H, dd, J=8.2, 2.3 Hz), 8.27 (1H, d, J=2.2 Hz).

MS (ESI) m/z: 799 [(M+H)$^+$].

Anal. Calcd. for C$_{36}$H$_{37}$Cl$_2$F$_5$N$_6$O$_3$S.0.5H$_2$O: C, 53.47; H, 4.74; N, 10.39; F, 11.75; Cl, 8.77; S, 3.97.

Found: C, 52.97; H, 4.52; N, 10.37; F, 12.45; Cl, 7.90; S, 3.94.

Example 6

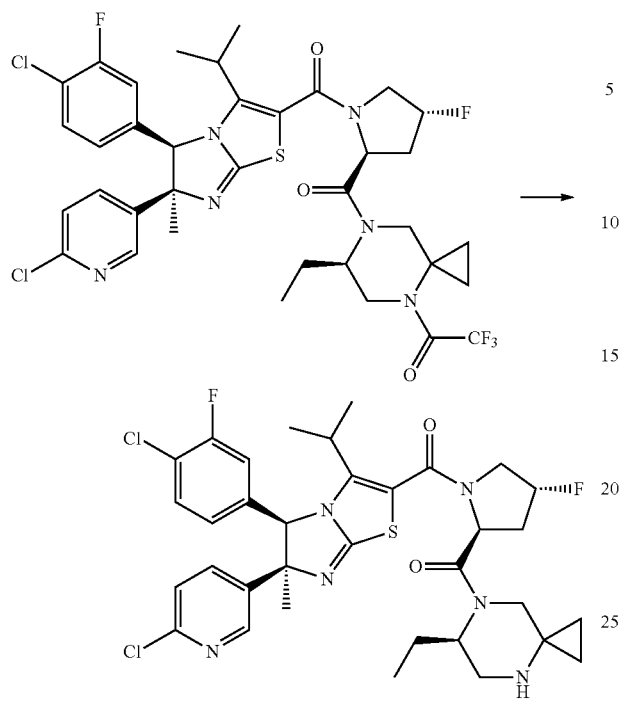

(6R)-7-[(4R)-1-{[(5R,6S)-5-(4-chloro-3-fluorophenyl)-6-(6-chloropyridin-3-yl)-3-isopropyl-6-methyl-5,6-dihydroimidazo[2,1-b][1,3]thiazol-2-yl]carbonyl}-4-fluoro-L-prolyl]-6-ethyl-4,7-diazaspiro[2.5]octane The compound obtained in Example 5 was reacted in the same way as in Step 2 of Example 1 to give the title compound as a colorless solid.

$^1$H-NMR (400 MHz, DMSO-d$_6$, 70° C.) δ: 0.25-0.38 (2H, m), 0.49-0.55 (1H, m), 0.57-0.64 (1H, m), 0.78-0.98 (3H, m), 0.93 (6H, d, J=7.1 Hz), 1.62-1.72 (1H, m), 1.77 (3H, s), 1.86-2.13 (1H, m), 2.40-2.45 (1H, m), 2.59-2.67 (1H, m), 2.69-2.84 (3H, m), 3.49 (1H, dd, J=13.3, 6.5 Hz), 3.63-3.82 (2H, m), 3.86-3.97 (1H, m), 4.17-4.24 (1H, m), 4.98-5.06 (1H, m), 5.33 (1H, dd, J=53.1, 20.1 Hz), 5.53 (1H, s), 6.71-6.75 (1H, m), 6.93-6.99 (1H, m), 7.19 (1H, d, J=8.3 Hz), 7.35 (1H, t, J=7.4 Hz), 7.66 (1H, dd, J=8.4, 2.3 Hz), 8.26 (1H, d, J=2.2 Hz).

MS (ESI) m/z: 703 [(M+H)$^+$].

Anal. Calcd. for C$_{34}$H$_{38}$Cl$_2$F$_2$N$_6$O$_2$S.0.25H$_2$O: C, 57.66; H, 5.48; N, 11.87; F, 5.36; Cl, 10.01; S, 4.53.

Found: C, 57.71; H, 5.40; N, 11.65; F, 4.99; Cl, 9.43; S, 4.43.

Example 7

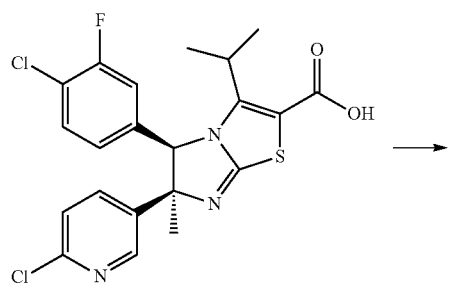

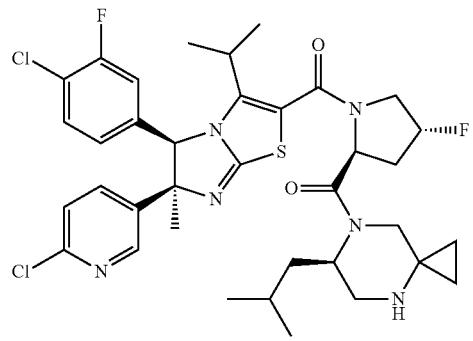

(6R)-7-[(4R)-1-{[(5R,6S)-5-(4-chloro-3-fluorophenyl)-6-(6-chloropyridin-3-yl)-3-isopropyl-6-methyl-5,6-dihydroimidazo[2,1-b][1,3]thiazol-2-yl]carbonyl}-4-fluoro-L-prolyl]-6-isobutyl-4,7-diazaspiro[2.5]octane The compound obtained in Step 13 of Reference Example 1 was reacted in the same way as in Step 1 of Example 2 using the compound obtained in Step 2 of Reference Example 13 instead of the compound obtained in Step 2 of Reference Example 5 and then reacted in the same way as in Step 2 of Example 1 to give the title compound as a pale yellow solid.

$^1$H-NMR (400 MHz, DMSO-d$_6$, 100° C.) δ: 0.22-0.76 (4H, m), 0.83-1.03 (13H, m), 1.40-1.56 (1H, m), 1.59-1.76 (1H, m), 1.79 (3H, s), 1.81-3.04 (7H, m), 3.06-3.22 (1H, m), 3.44-3.63 (1H, m), 3.64-3.85 (1H, m), 3.92 (1H, dd, J=19.9, 12.8 Hz), 4.92-5.10 (1H, m), 5.22-5.46 (1H, m), 5.51 (1H, s), 6.76 (1H, d, J=8.1 Hz), 6.95 (1H, d, J=8.1 Hz), 7.18 (1H, d, J=8.3 Hz), 7.34 (1H, t, J=8.1 Hz), 7.66 (1H, dd, J=8.3, 2.4 Hz), 8.27 (1H, d, J=2.4 Hz).

MS (ESI) m/z: 731 [(M+H)$^+$].

Anal. Calcd. for C$_{36}$H$_{42}$Cl$_2$F$_2$N$_6$O$_2$S.0.5H$_2$O: C, 58.37; H, 5.85; N, 11.35.

Found: C, 58.42; H, 5.77; N, 11.17.

Example 8

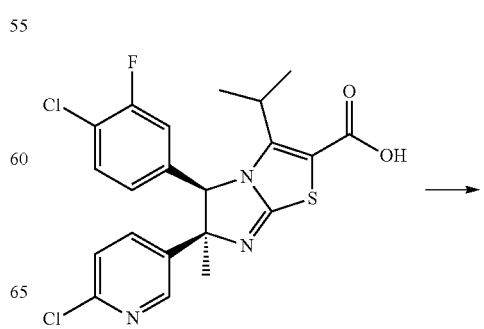

67

-continued

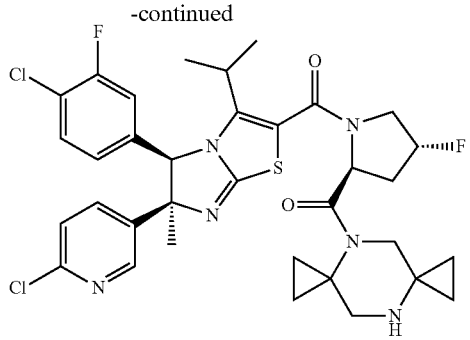

4-[(4R)-1-{[(5R,6S)-5-(4-chloro-3-fluorophenyl)-6-(6-chloropyridin-3-yl)-3-isopropyl-6-methyl-5,6-dihydroimidazo[2,1-b][1,3]thiazol-2-yl]carbonyl}-4-fluoro-L-prolyl]-4,9-diazaspiro[2.2.2.2]decane The compound obtained in Step 13 of Reference Example 1 was reacted in the same way as in Step 1 of Example 2 using the compound obtained in Step 2 of Reference Example 15 instead of the compound obtained in Step 2 of Reference Example 5 and then reacted in the same way as in Step 2 of Example 1 to give the title compound as a colorless solid.

$^1$H-NMR (400 MHz, DMSO-$d_6$, 100° C.) δ: 0.60 (4H, d, J=5.1 Hz), 0.87 (1H, t, J=7.0 Hz), 0.94 (6H, t, J=6.8 Hz), 1.08-1.23 (5H, m), 1.79 (3H, s), 2.13 (1H, dd, J=36.3, 6.2 Hz), 2.59-2.74 (3H, m), 3.58 (2H, dd, J=34.9, 12.9 Hz), 3.79-4.00 (2H, m), 5.21 (1H, s), 5.39 (1H, d, J=53.5 Hz), 5.51 (1H, s), 6.76 (1H, d, J=7.8 Hz), 6.95 (1H, d, J=9.3 Hz), 7.17 (1H, d, J=8.3 Hz), 7.34 (1H, t, J=7.9 Hz), 7.65 (1H, dd, J=8.4, 2.3 Hz), 8.26 (1H, d, J=2.4 Hz).

MS (ESI) m/z: 701 [(M+H)$^+$].

Anal. Calcd. for $C_{34}H_{36}Cl_2F_2N_6O_2S \cdot 1.75H_2O$: C, 55.69; H, 5.43; N, 11.46.

Found: C, 55.58; H, 5.32; N, 11.01.

Example 9

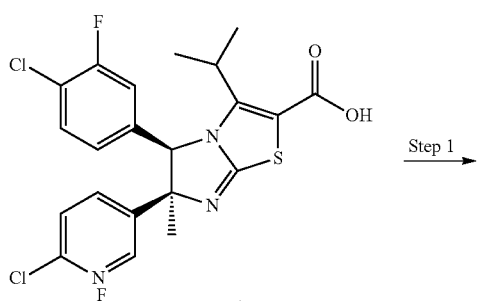

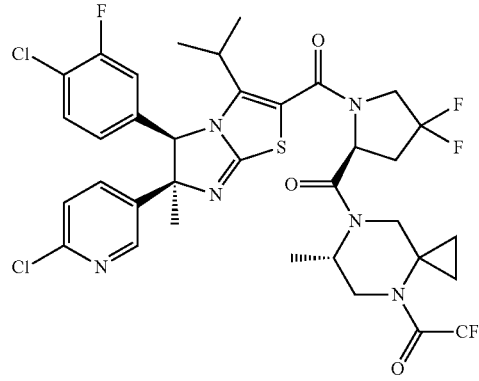

68

-continued

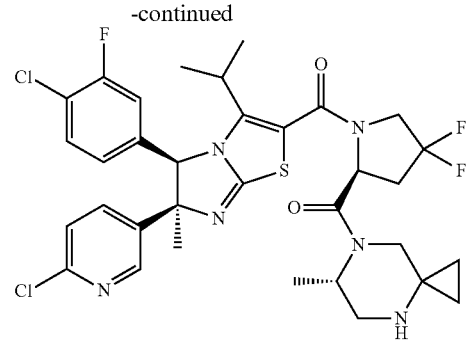

Step 1: (6S)-7-(1-{[(5R,6S)-5-(4-chloro-3-fluorophenyl)-6-(6-chloropyridin-3-yl)-3-isopropyl-6-methyl-5,6-dihydroimidazo[2,1-b][1,3]thiazol-2-yl]carbonyl}-4,4-difluoro-L-prolyl)-6-methyl-4-(trifluoroacetyl)-4,7-diazaspiro[2.5]octane The compound obtained in Step 13 of Reference Example 1 was reacted in the same way as in Step 1 of Example 2 using the compound obtained in Step 2 of Reference Example 16 instead of the compound obtained in Step 2 of Reference Example 5 to give the title compound as a colorless solid.

$^1$H-NMR (400 MHz, DMSO-$d_6$, 100° C.) δ: 0.73 (2H, brs), 0.90-0.95 (6H, m), 1.12 (3H, brs), 1.25-1.31 (1H, m), 1.48-1.50 (1H, m), 1.77 (3H, s), 2.31-2.45 (2H, m), 2.58-2.65 (1H, m), 2.91-2.96 (2H, m), 3.38-3.58 (3H, m), 3.93-4.19 (2H, m), 4.65 (1H, brs), 5.10 (1H, br), 5.50 (1H, s), 6.77 (1H, d, J=7.5 Hz), 6.96 (1H, d, J=10.0 Hz), 7.17 (1H, d, J=8.2 Hz), 7.32 (1H, t, J=8.0 Hz), 7.64 (1H, dd, J=8.2, 2.2 Hz), 8.25 (1H, d, J=2.2 Hz).

MS (ESI) m/z: 803 [(M+H)$^+$].

Step 2: (6S)-7-(1-{[(5R,6S)-5-(4-chloro-3-fluorophenyl)-6-(6-chloropyridin-3-yl)-3-isopropyl-6-methyl-5,6-dihydroimidazo[2,1-b][1,3]thiazol-2-yl]carbonyl}-4,4-difluoro-L-prolyl)-6-methyl-4,7-diazaspiro[2.5]octane The compound obtained in Step 1 above was reacted in the same way as in Step 2 of Example 1 to give the title compound as a colorless solid.

$^1$H-NMR (400 MHz, DMSO-$d_6$, 100° C.) δ: 0.39 (2H, t, J=7.7 Hz), 0.57 (2H, t, J=7.7 Hz), 0.92 (6H, t, J=7.6 Hz), 1.18-1.29 (5H, m), 1.77 (3H, s), 2.28-2.41 (1H, m), 2.62-2.68 (2H, m), 3.39 (3H, br), 3.90-4.01 (1H, m), 4.09 (1H, t, J=12.5 Hz), 4.28 (1H, br), 5.10 (1H, br), 5.50 (1H, s), 6.76 (1H, d, J=7.8 Hz), 6.96 (1H, d, J=9.5 Hz), 7.16 (1H, dd, J=8.3, 0.5 Hz), 7.32 (1H, t, J=8.0 Hz), 7.64 (1H, dd, J=8.3, 2.5 Hz), 8.24 (1H, d, J=2.0 Hz).

MS (ESI) m/z: 707 [(M+H)$^+$].

Anal. Calcd. for $C_{33}H_{35}Cl_2F_3N_6O_2S \cdot 0.5H_2O$: C, 55.31; H, 5.06; N, 11.73.

Found: C, 55.69; H, 5.28; N, 11.52.

Example 10

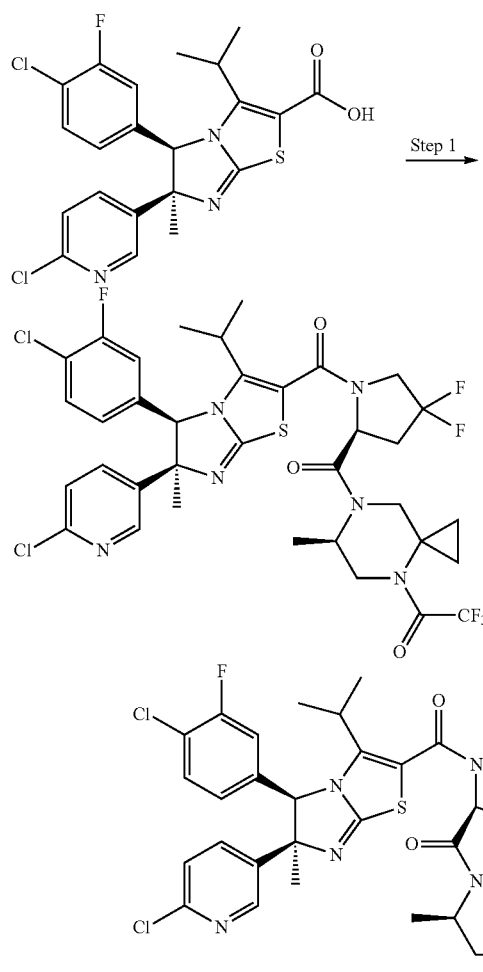

Step 1: (6R)-7-(1-{[(5R,6S)-5-(4-chloro-3-fluorophenyl)-6-(6-chloropyridin-3-yl)-3-isopropyl-6-methyl-5,6-dihydroimidazo[2,1-b][1,3]thiazol-2-yl]carbonyl}-4,4-difluoro-L-prolyl)-6-methyl-4-(trifluoroacetyl)-4,7-diazaspiro[2.5]octane The compound obtained in Step 13 of Reference Example 1 was reacted in the same way as in Step 1 of Example 2 using the compound obtained in Step 2 of Reference Example 17 instead of the compound obtained in Step 2 of Reference Example 5 to give the title compound as a colorless solid.

MS (ESI) m/z: 803 [(M+H)+].

Step 2: (6R)-7-(1-{[(5R,6S)-5-(4-chloro-3-fluorophenyl)-6-(6-chloropyridin-3-yl)-3-isopropyl-6-methyl-5,6-dihydroimidazo[2,1-b][1,3]thiazol-2-yl]carbonyl}-4,4-difluoro-L-prolyl)-6-methyl-4,7-diazaspiro[2.5]octane The compound obtained in Step 1 above was reacted in the same way as in Step 2 of Example 1 to give the title compound as a colorless solid.

¹H-NMR (400 MHz, DMSO-d₆, 100° C.) δ: 0.38 (1H, br), 0.58 (3H, br), 0.93 (6H, t, J=7.3 Hz), 1.23-1.28 (3H, m), 1.78 (3H, s), 2.32 (1H, br), 2.46-2.50 (2H, m), 2.66-2.72 (2H, m), 2.93-3.01 (3H, m), 3.94-4.12 (2H, m), 5.13 (1H, dd, J=9.6, 5.1 Hz), 5.51 (1H, s), 6.76 (1H, d, J=8.0 Hz), 6.95 (1H, d, J=9.8 Hz), 7.16 (1H, dd, J=8.0, 0.5 Hz), 7.32 (1H, t, J=8.0 Hz), 7.64 (1H, dd, J=8.3, 2.5 Hz), 8.24 (1H, d, J=2.5 Hz).

MS (ESI) m/z: 707 [(M+H)+].

Anal. Calcd. for C₃₃H₃₅Cl₂F₃N₆O₂S.0.5H₂O: C, 55.31; H, 5.06; N, 11.73.

Found: C, 55.49; H, 5.18; N, 11.47.

Example 11

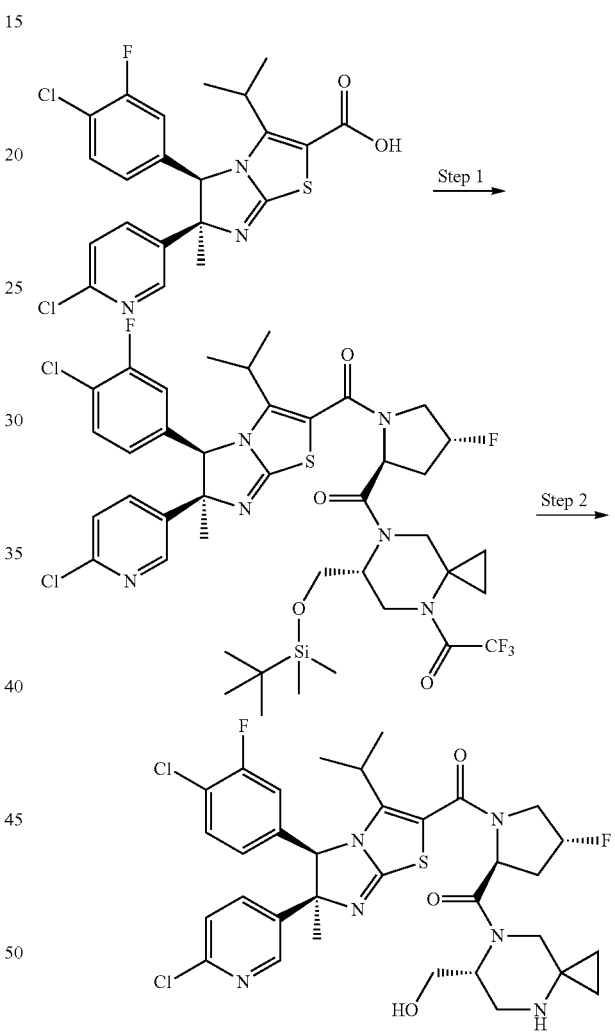

Step 1: (6R)-6-({[tert-butyl(dimethyl)silyl]oxy}methyl)-7-[(4R)-1-{[(5R,6S)-5-(4-chloro-3-fluorophenyl)-6-(6-chloropyridin-3-yl)-3-isopropyl-6-methyl-5,6-dihydroimidazo[2,1-b][1,3]thiazol-2-yl]carbonyl}-4-fluoro-L-prolyl]-4-(trifluoroacetyl)-4,7-diazaspiro[2.5]octane The compound obtained in Step 13 of Reference Example 1 was reacted in the same way as in Step 1 of Example 2 using the compound obtained in Reference Example 19 instead of the compound obtained in Step 2 of Reference Example 5 to give the title compound as a colorless solid.

¹H-NMR (400 MHz, DMSO-d₆, 90° C.) δ: −0.01 (3H, s), 0.00 (3H, s), 0.63-0.76 (2H, m), 0.83 (9H, s), 0.88 (3H, d, J=7.1 Hz), 0.92 (3H, d, J=7.1 Hz), 1.23-1.30 (1H, m), 1.38-1.47 (1H, m), 1.74 (3H, s), 2.07-2.29 (2H, m), 2.52-2.62 (1H, m), 3.47-3.96 (7H, m), 4.10-4.22 (1H, m), 4.41-4.53 (1H, m), 4.92-5.04 (1H, m), 5.37 (1H, d, J=53.0 Hz), 5.49 (1H, s), 6.70-6.74 (1H, m), 6.89-6.95 (1H, m), 7.14 (1H, d, J=8.5 Hz), 7.31 (1H, t, J=8.1 Hz), 7.62 (1H, dd, J=8.3, 2.4 Hz), 8.23 (1H, d, J=2.4 Hz).

MS (ESI) m/z: 915 [(M+1)⁺].

Step 2: {(6R)-7-[(4R)-1-{[(5R,6S)-5-(4-chloro-3-fluorophenyl)-6-(6-chloropyridin-3-yl)-3-isopropyl-6-methyl-5,6-dihydroimidazo[2,1-b][1,3]thiazol-2-yl]carbonyl}-4-fluoro-L-prolyl]-4,7-diazaspiro[2.5]oct-6-yl}methanol Tetra-n-butylammonium fluoride (1 M tetrahydrofuran solution) (0.42 ml, 0.42 mmol) was added to a tetrahydrofuran (4 ml) solution of the compound (255 mg, 0.28 mmol) obtained in Step 1 above and the resulting mixture was stirred at room temperature for 3 hours. The solvent was concentrated under reduced pressure, then the residue obtained was diluted with ethyl acetate and the organic layer was washed with saturated aqueous sodium bicarbonate solution and saturated brine and dried over anhydrous sodium sulfate. The solvent was evaporated under reduced pressure and the residue obtained was purified by NH-silica gel column chromatography [chloroform:methanol=40:1 (v/v)] to give the title compound (102 mg, 52%) as a colorless solid.

¹H-NMR (400 MHz, DMSO-d₆, 90° C.) δ: 0.33-0.41 (2H, m), 0.51-0.59 (2H, m), 0.92 (3H, d, J=7.1 Hz), 0.95 (3H, d, J=7.1 Hz), 1.78 (3H, s), 2.11-2.31 (2H, m), 2.56-2.64 (1H, m), 3.50-3.97 (6H, m), 4.09-4.18 (1H, m), 4.47-4.64 (1H, m), 4.83-4.94 (1H, m), 5.08-5.19 (1H, m), 5.37 (1H, d, J=53.2 Hz), 5.51 (1H, s), 6.72-6.78 (1H, m), 6.93-7.00 (1H, m), 7.18 (1H, d, J=8.3 Hz), 7.35 (1H, t, J=7.9 Hz), 7.66 (1H, dq, J=8.4, 1.2 Hz), 8.27 (1H, d, J=2.2 Hz).

MS (ESI) m/z: 705 [(M+H)⁺].

Anal. Calcd. for $C_{33}H_{36}Cl_2F_2N_6O_3S \cdot 0.5H_2O$: C, 55.46; H, 5.22; N, 11.60; F, 5.32; Cl, 9.92; S, 4.49.

Found: C, 55.42; H, 5.24; N, 11.73; F, 5.28; Cl, 9.77; S, 4.43.

Example 12

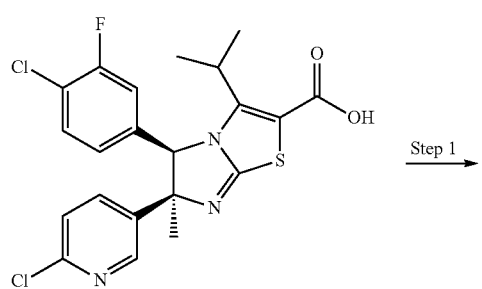

Step 1

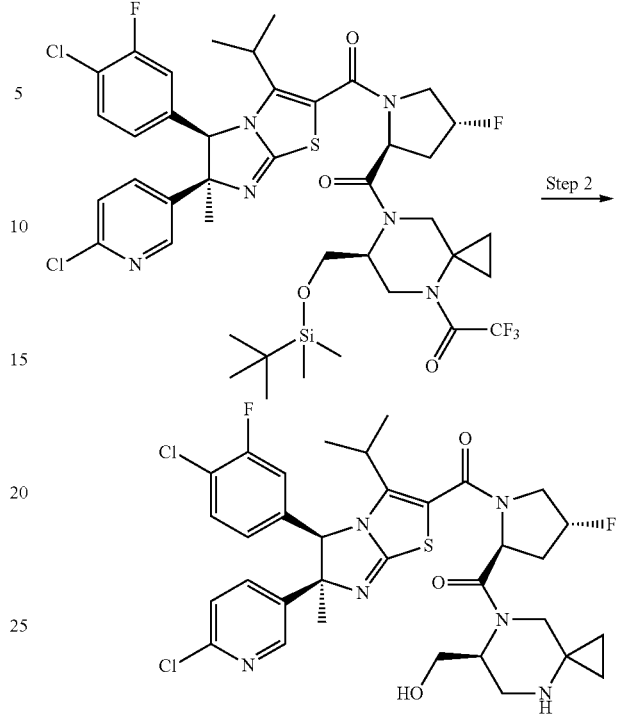

Step 1: (6S)-6-({[tert-butyl(dimethyl)silyl]oxy}methyl)-7-[(4R)-1-{[(5R,6S)-5-(4-chloro-3-fluorophenyl)-6-(6-chloropyridin-3-yl)-3-isopropyl-6-methyl-5,6-dihydroimidazo[2,1-b][1,3]thiazol-2-yl]carbonyl}-4-fluoro-L-prolyl]-4-(trifluoroacetyl)-4,7-diazaspiro[2.5]octane The compound obtained in Step 13 of Reference Example 1 was reacted in the same way as in Step 1 of Example 2 using the compound obtained in Reference Example 20 instead of the compound obtained in Step 2 of Reference Example 5 to give the title compound as a colorless solid.

¹H-NMR (400 MHz, DMSO-d₆, 90° C.) δ: 0.00 (3H, s), 0.01 (3H, s), 0.67-0.75 (1H, m), 0.82-0.88 (1H, m), 0.84 (9H, s), 0.87-0.94 (6H, m), 1.26-1.36 (1H, m), 1.39-1.47 (1H, m), 1.74 (3H, s), 1.90-2.10 (2H, m), 2.56-2.65 (1H, m), 3.40-3.95 (7H, m), 4.16-4.29 (1H, m), 4.44-4.56 (1H, m), 4.99-5.12 (1H, m), 5.32 (1H, d, J=54.2 Hz), 5.48 (1H, s), 6.69-6.74 (1H, m), 6.88-6.93 (1H, m), 7.14 (1H, d, J=8.3 Hz), 7.30 (1H, t, J=8.1 Hz), 7.62 (1H, dd, J=8.3, 2.7 Hz), 8.23 (1H, d, J=2.2 Hz).

MS (ESI) m/z: 915 [(M+H)⁺].

Step 2: {(6S)-7-[(4R)-1-{[(5R,6S)-5-(4-chloro-3-fluorophenyl)-6-(6-chloropyridin-3-yl)-3-isopropyl-6-methyl-5,6-dihydroimidazo[2,1-b][1,3]thiazol-2-yl]carbonyl}-4-fluoro-L-prolyl]-4,7-diazaspiro[2.5]oct-6-yl}methanol The compound obtained in Step 1 above was reacted in the same way as in Step 2 of Example 11 to give the title compound as a colorless solid.

¹H-NMR (400 MHz, DMSO-d₆, 90° C.) δ: 0.25-0.40 (2H, m), 0.48-0.66 (2H, m), 0.93 (3H, d, J=7.8 Hz), 0.94 (3H, d, J=7.1 Hz), 1.78 (3H, s), 1.97-2.15 (2H, m), 2.64-2.69 (1H, m), 2.75-2.85 (2H, m), 3.45-3.53 (1H, m), 3.65-3.97 (4H, m), 4.20-4.30 (1H, m), 4.41-4.51 (1H, m), 5.06 (1H, t, J=8.1 Hz), 5.34 (1H, d, J=57.1 Hz), 5.51 (1H, s), 6.71-6.77 (1H, m), 6.91-6.98 (1H, m), 7.18 (1H, d, J=8.3 Hz), 7.34 (1H, t, J=8.1 Hz), 7.66 (1H, dd, J=8.3, 2.4 Hz), 8.26 (1H, d, J=2.4 Hz).

MS (ESI) m/z: 705 [(M+H)⁺].

Anal. Calcd. for $C_{33}H_{36}Cl_2F_2N_6O_3S \cdot 0.75H_2O$: C, 55.11; H, 5.25; N, 11.60; F, 5.28; Cl, 9.86; S, 4.46.

Found: C, 55.00; H, 5.14; N, 11.62; F, 5.27; Cl, 9.75; S, 4.45.

Example 13

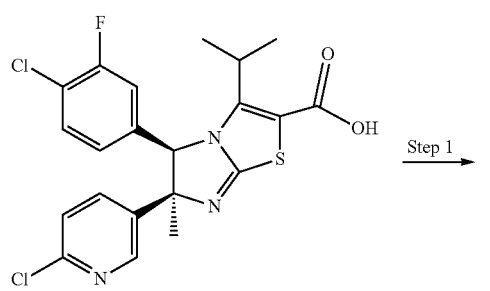

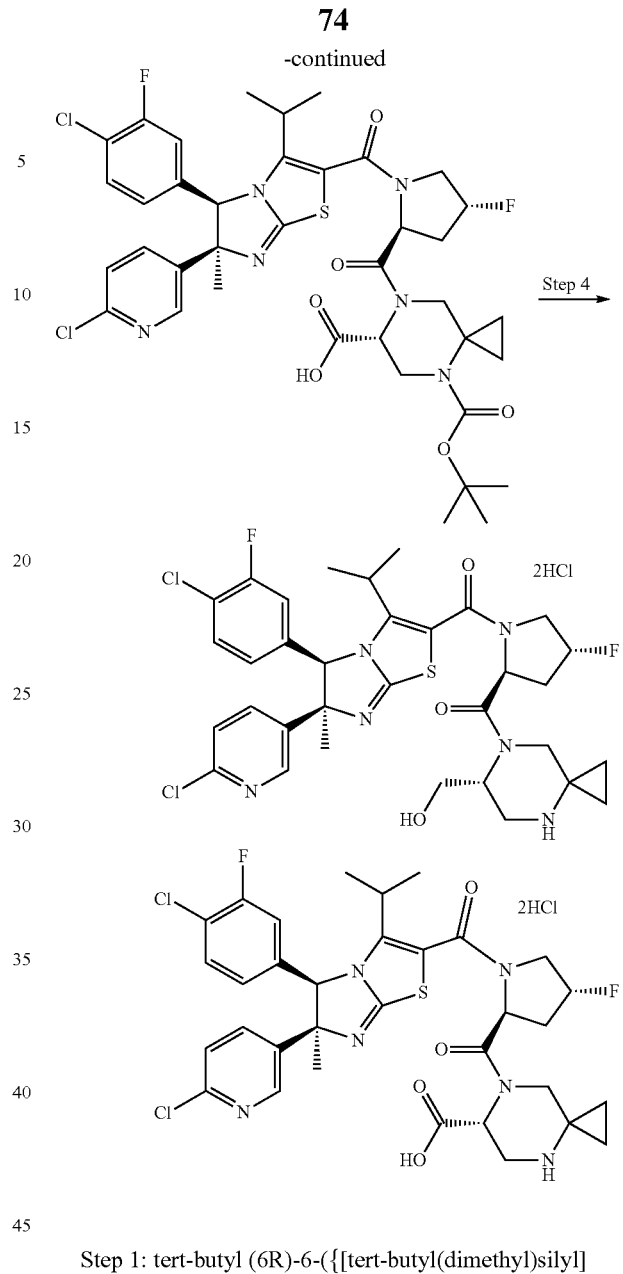

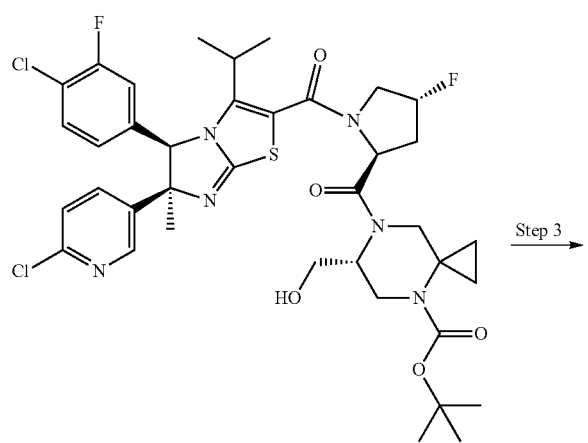

Step 1: tert-butyl (6R)-6-({[tert-butyl(dimethyl)silyl]oxy}methyl)-7-[(4R)-1-{[(5R,6S)-5-(4-chloro-3-fluorophenyl)-6-(6-chloropyridin-3-yl)-3-isopropyl-6-methyl-5,6-dihydroimidazo[2,1-b][1,3]thiazol-2-yl]carbonyl}-4-fluoro-L-prolyl]-4,7-diazaspiro[2.5]octane-4-carboxylate The compound obtained in Step 13 of Reference Example 1 was reacted in the same way as in Step 1 of Example 1 using the compound obtained in Reference Example 22 instead of the compound obtained in Step 2 of Reference Example 3 to give the title compound as a pale yellow solid.

¹H-NMR (400 MHz, DMSO-d₆, 90° C.) δ: 0.05 (6H, s), 0.46-0.54 (2H, m), 0.88 (9H, s), 0.92 (3H, d, J=7.1 Hz), 0.95 (3H, d, J=6.8 Hz), 1.03-1.10 (1H, m), 1.28-1.35 (1H, m), 1.42 (9H, s), 1.78 (3H, s), 2.17-2.36 (2H, m), 2.57-2.63 (1H, m), 3.14-3.26 (2H, m), 3.48-3.77 (2H, m), 3.84-3.99 (4H, m), 4.37-4.48 (1H, m), 4.99-5.13 (1H, m), 5.39 (1H, d, J=52.5 Hz), 5.52 (1H, s), 6.74-6.78 (1H, m), 6.93-6.99 (1H, m), 7.17 (1H, d, J=8.3 Hz), 7.34 (1H, t, J=8.1 Hz), 7.66 (1H, dd, J=8.3, 2.4 Hz), 8.26 (1H, d, J=2.0 Hz).

MS (ESI) m/z: 920 [(M+1)]⁺.

Step 2: tert-butyl (6R)-7-[(4R)-1-{[(5R,6S)-5-(4-chloro-3-fluorophenyl)-6-(6-chloropyridin-3-yl)-3-isopropyl-6-methyl-5,6-dihydroimidazo[2,1-b][1,3]thiazol-2-yl]carbonyl}-4-fluoro-L-prolyl]-6-(hydroxymethyl)-4,7-diazaspiro[2.5]octane-4-carboxylate The compound obtained in Step 1 above was reacted in the same way as in Step 2 of Example 11 to give the title compound as a light brown solid.

$^1$H-NMR (400 MHz, DMSO-$d_6$, 90° C.) δ: 0.43-0.53 (2H, m), 0.92 (3H, d, J=5.1 Hz), 0.96 (3H, d, J=6.8 Hz), 1.01-1.08 (1H, m), 1.29-1.34 (1H, m), 1.42 (9H, s), 1.78 (3H, s), 2.17-2.31 (2H, m), 2.56-2.61 (1H, m), 3.17-3.24 (1H, m), 3.46-3.54 (2H, m), 3.56-3.62 (1H, m), 3.70-3.77 (1H, m), 3.84-4.01 (2H, m), 4.32-4.36 (1H, m), 4.64-4.70 (1H, m), 5.09-5.15 (1H, m), 5.38 (1H, d, J=51.3 Hz), 5.51 (1H, s), 6.72-6.79 (1H, m), 6.93-6.99 (1H, m), 7.18 (1H, d, J=7.8 Hz), 7.31-7.38 (1H, m), 7.62-7.68 (1H, m), 8.24-8.29 (1H, m).

MS (ESI) m/z: 805 [(M+1)]$^+$.

Step 3: (6R)-4-(tert-butoxycarbonyl)-7-[(4R)-1-{[(5R,6S)-5-(4-chloro-3-fluorophenyl)-6-(6-chloropyridin-3-yl)-3-isopropyl-6-methyl-5,6-dihydroimidazo[2,1-b][1,3]thiazol-2-yl]carbonyl}-4-fluoro-L-prolyl]-4,7-diazaspiro[2.5]octane-6-carboxylic acid The compound (100 mg, 0.12 mmol) obtained in Step 2 above was dissolved in a mixed solvent of acetonitrile (1.5 ml) and water (1.5 ml), iodobenzene diacetate (88 mg, 0.26 mmol) and 2,2,6,6-tetramethylpiperidine 1-oxyl (20 mg, 0.12 mmol) were added and the resulting mixture was stirred at room temperature for 4 hours. Aqueous sodium thiosulfate solution (4 ml) was added, followed by extraction with ethyl acetate. The organic layer was washed with saturated brine and dried over anhydrous sodium sulfate. The solvent was evaporated under reduced pressure and the residue obtained was purified by silica gel chromatography [chloroform:methanol=40:1→10:1 (v/v)] to give the title compound (58 mg, 59%) as a colorless solid.

$^1$H-NMR (400 MHz, DMSO-$d_6$, 90° C.) δ: 0.49-0.61 (2H, m), 0.92 (3H, d, J=7.1 Hz), 0.95 (3H, d, J=7.1 Hz), 1.07-1.16 (1H, m), 1.27-1.34 (1H, m), 1.39 (9H, s), 1.78 (3H, s), 2.07-2.20 (2H, m), 2.59-2.65 (1H, m), 3.16-3.22 (1H, m), 3.33-3.41 (1H, m), 3.74 (1H, dd, J=36.4, 11.0 Hz), 3.87-4.04 (2H, m), 4.35-4.48 (1H, m), 4.67-4.74 (1H, m), 5.03-5.10 (1H, m), 5.35 (1H, d, J=53.0 Hz), 5.51 (1H, s), 6.74-6.78 (1H, m), 6.93-6.99 (1H, m), 7.18 (1H, d, J=8.3 Hz), 7.35 (1H, t, J=8.1 Hz), 7.66 (1H, dd, J=8.4, 2.6 Hz), 8.26 (1H, d, J=2.2 Hz).

MS (ESI) m/z: 819 [(M+1)]$^+$.

Step 4: (6R)-7-[(4R)-1-{[(5R,6S)-5-(4-chloro-3-fluorophenyl)-6-(6-chloropyridin-3-yl)-3-isopropyl-6-methyl-5,6-dihydroimidazo[2,1-b][1,3]thiazol-2-yl]carbonyl}-4-fluoro-L-prolyl]-4,7-diazaspiro[2.5]octane-6-carboxylic acid dihydrochloride The compound obtained in Step 3 above was reacted in the same way as in Step 2 of Reference Example 3 to give the title compound as a pale yellow solid.

$^1$H-NMR (400 MHz, DMSO-$d_6$, 90° C.) δ: 0.85-0.90 (1H, m), 0.92 (3H, d, J=6.8 Hz), 0.98-1.02 (1H, m), 1.03 (3H, d, J=7.1 Hz), 1.10-1.19 (2H, m), 2.00 (3H, s), 2.17-2.23 (1H, m), 2.26-2.33 (1H, m), 2.61-2.68 (1H, m), 3.29-3.35 (2H, m), 3.68-3.74 (1H, m), 3.77-3.86 (1H, m), 4.02 (1H, dd, J=19.8, 13.4 Hz), 5.17-5.31 (2H, m), 5.42 (1H, d, J=53.5 Hz), 5.52-5.56 (1H, m), 5.93 (1H, s), 6.83-6.90 (1H, m), 7.11-7.17 (1H, m), 7.27 (1H, d, J=8.5 Hz), 7.40 (1H, t, J=7.9 Hz), 7.68 (1H, dd, J=8.4, 2.6 Hz), 8.29 (1H, d, J=2.2 Hz).

MS (ESI) m/z: 719 [(M+1)]$^+$.

The compound obtained in Step 13 of Reference Example 1 and the compound obtained in Reference Example 23 were reacted in the same way as in Example 13 above to give the compound in the following table.

TABLE 13

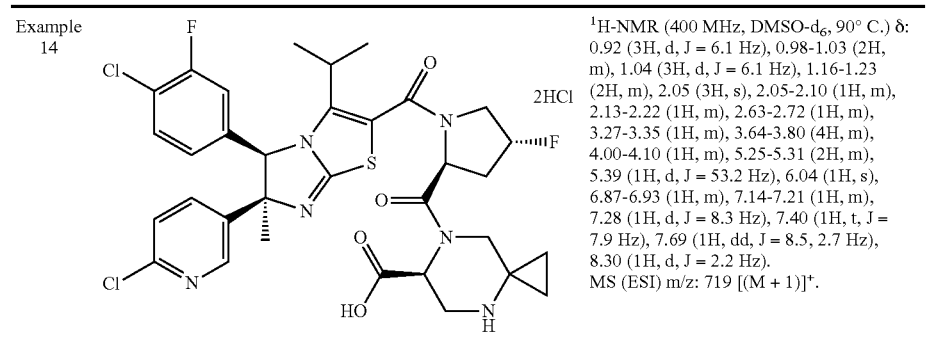

Example 14 · 2HCl $^1$H-NMR (400 MHz, DMSO-$d_6$, 90° C.) δ: 0.92 (3H, d, J = 6.1 Hz), 0.98-1.03 (2H, m), 1.04 (3H, d, J = 6.1 Hz), 1.16-1.23 (2H, m), 2.05 (3H, s), 2.05-2.10 (1H, m), 2.13-2.22 (1H, m), 2.63-2.72 (1H, m), 3.27-3.35 (1H, m), 3.64-3.80 (4H, m), 4.00-4.10 (1H, m), 5.25-5.31 (2H, m), 5.39 (1H, d, J = 53 Hz), 6.04 (1H, s), 6.87-6.93 (1H, m), 7.14-7.21 (1H, m), 7.28 (1H, d, J = 8.3 Hz), 7.40 (1H, t, J = 7.9 Hz), 7.69 (1H, dd, J = 8.5, 2.7 Hz), 8.30 (1H, d, J = 2.2 Hz).
MS (ESI) m/z: 719 [(M + 1)]$^+$.

Example 15

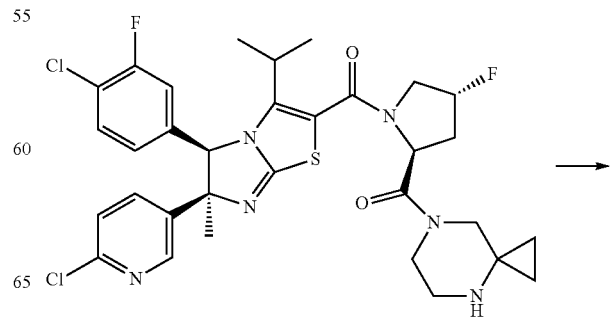

-continued

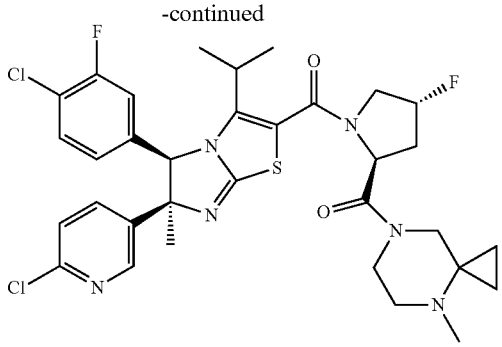

7-[(4R)-1-{[(5R,6S)-5-(4-chloro-3-fluorophenyl)-6-(6-chloropyridin-3-yl)-3-isopropyl-6-methyl-5,6-dihydroimidazo[2,1-b][1,3]thiazol-2-yl]carbonyl}-4-fluoro-L-prolyl]-4-methyl-4,7-diazaspiro[2.5]octane Sodium triacetoxyborohydride (267 mg, 1.26 mmol) was added to a 1,4-dioxane (10 ml) solution of the compound (340 mg, 0.503 mmol) obtained in Step 2 of Example 1 and 37% aqueous paraformaldehyde solution (0.41 ml, 5.05 mmol) at room temperature and the resulting mixture was stirred for 17 hours. Saturated aqueous sodium bicarbonate solution was added, followed by extraction with ethyl acetate. The organic layer was washed with water and saturated brine and dried over anhydrous sodium sulfate and the solvent was concentrated under reduced pressure. The residue obtained was purified by silica gel chromatography [chloroform:methanol=50:1 (v/v)) to give the title compound (309 mg, 89%) as a colorless solid.

$^1$H-NMR (400 MHz, $d_6$-DMSO, 100° C.) δ: 0.43-0.48 (2H, m), 0.56-0.62 (2H, m), 0.93 (6H, d, J=7.1 Hz), 1.77 (3H, s), 2.03-2.18 (1H, m), 3.30 (3H, s), 2.60-2.67 (2H, m), 2.73-2.78 (2H, m), 3.34 (2H, brs), 3.54 (2H, brs), 3.68-3.78 (1H, m), 3.80-3.95 (1H, m), 5.04 (1H, t, J=7.8 Hz), 5.34 (1H, d, J=53.0 Hz), 5.50 (1H, s), 6.75 (1H, d, J=8.0 Hz), 6.93 (1H, d, J=9.0 Hz), 7.16 (1H, d, J=8.3 Hz), 7.33 (1H, t, J=8.0 Hz), 7.64 (1H, dd, J=8.3, 2.3 Hz), 8.25 (1H, d, J=2.3 Hz).

MS (ESI) m/z: 689 [(M+1)]$^+$.

The compound obtained in Step 2 of Example 2 or the compound obtained in Step 2 of Example 3 was reacted in the same way as in Example 15 above to give the compounds in the following table.

TABLE 14

| Example 16 | 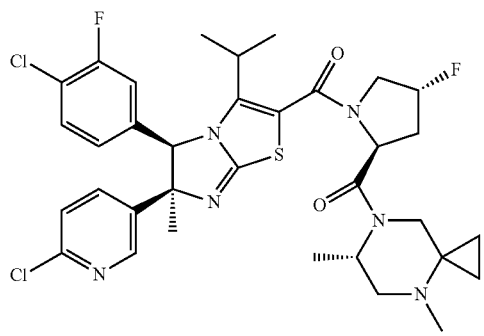 | $^1$H-NMR (400 MHz, $d_6$-DMSO, 100° C.) δ: 0.20-0.25 (1H, m), 0.46-0.51 (1H, m), 0.61-0.65 (1H, m), 0.84-0.90 (1H, m), 0.91 (3H, d, J = 7.1 Hz), 0.94 (3H, d, J = 7.1 Hz), 1.25-1.28 (3H, m), 1.77 (3H, s), 2.08 (3H, s), 2.10-2.21 (1H, m), 2.50-2.64 (4H, m), 3.18-3.26 (1H, m), 3.53-3.60 (1H, m), 3.68-3.78 (1H, m), 3.80-3.95 (1H, m), 4.37-4.40 (1H, m), 4.98 (1H, t, J = 7.8 Hz), 5.34 (1H, d, J = 53 Hz), 5.49 (1H, s), 6.75 (1H, d, J = 8.0 Hz), 6.93 (1H, d, J = 9.0 Hz), 7.16 (1H, d, J = 8.3 Hz), 7.33 (1H, t, J = 8.0 Hz), 7.64 (1H, dd, J = 8.3, 2.4 Hz), 8.25 (1H, d, J = 2.4 Hz). MS (ESI) m/z: 703 [(M + 1)]$^+$. |
| Example 17 | 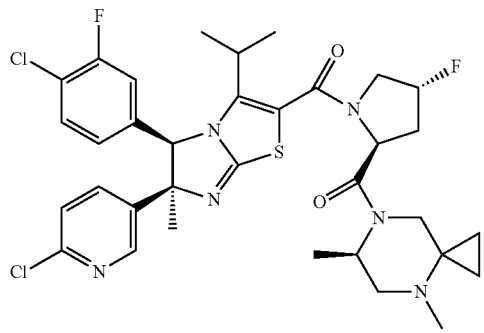 | $^1$H-NMR (400 MHz, $d_6$-DMSO, 100° C.) δ: 0.30 (1H, br), 0.45-0.50 (1H, m), 0.60-0.64 (1H, m), 0.85-0.90 (1H, m), 0.92 (3H, d, J = 7.1 Hz), 0.93 (3H, d, J = 7.1 Hz), 1.25-1.35 (3H, m), 1.77 (3H, s), 1.92-2.07 (1H, m), 2.09 (3H, s), 2.62-2.68 (4H, m), 3.22-3.34 (1H, m), 3.43-3.51 (1H, m), 3.67-3.79 (1H, m), 3.86-3.95 (1H, m), 4.27-4.35 (1H, m), 5.00 (1H, t, J = 7.8 Hz), 5.34 (1H, d, J = 53 Hz), 5.49 (1H, s), 6.74 (1H, d, J = 8.3 Hz), 6.92 (1H, d, J = 9.5 Hz), 7.16 (1H, d, J = 8.3 Hz), 7.33 (1H, t, J = 8.0 Hz), 7.64 (1H, dd, J = 8.3, 2.5 Hz), 8.25 (1H, d, J = 2.5 Hz). MS (ESI) m/z: 703 [(M + 1)]$^+$. |

The following compounds were synthesized according to the descriptions of the general production methods and Examples 1 to 12.

TABLE 15

| Example 18 | (structure) | ¹H-NMR (400 MHz, d₆-DMSO, 100° C.) δ: 0.43-0.49 (4H, m), 0.88 (3H, d, J = 7.1 Hz), 0.91 (3H, d, J = 7.1 Hz), 1.73 (3H, s), 2.01-2.31 (1H, m), 2.55-2.66 (2H, m), 2.71-2.76 (2H, m), 3.31-3.36 (2H, m), 3.43-3.47 (2H, m), 3.67-3.80 (1H, m), 3.85-3.93 (1H, m), 5.03 (1H, t, J = 7.8 Hz), 5.32 (1H, d, J = 53 Hz), 5.39 (1H, s), 6.89 (2H, d, J = 8.5 Hz), 7.03-7.07 (2H, m), 7.11 (2H, d, J = 8.5 Hz), 7.22-7.25 (2H, m). MS (ESI) m/z: 656 [(M + 1)]⁺. |
|---|---|---|
| Example 19 | (structure) | ¹H-NMR (400 MHz, d₆-DMSO, 100° C.) δ: 0.35-0.39 (2H, m), 0.54-0.59 (2H, m), 0.86 (3H, d, J = 7.1 Hz), 0.92 (3H, d, J = 7.1 Hz), 1.20 (3H, brd, J = 6.1 Hz), 1.73 (3H, s), 2.05-2.21 (1H, m), 2.51-2.65 (3H, m), 2.88-2.91 (1H, m), 3.23 (1H, br), 3.45 (1H, br), 3.67-3.71 (1H, m), 3.76-3.93 (1H, m), 4.31 (1H, br), 4.96 (1H, br), 5.34 (1H, d, J = 53 Hz), 5.38 (1H, s), 6.89 (2H, d, J = 7.5 Hz), 7.04-7.07 (2H, m), 7.11 (2H, d, J = 7.5 Hz), 7.22-7.25 (2H, m). MS (ESI) m/z: 670 [(M + 1)]⁺. |
| Example 20 | (structure) | ¹H-NMR (400 MHz, d₆-DMSO, 100° C.) δ: 0.35 (1H, br), 0.56 (2H, br), 0.86 (1H, br), 0.88 (3H, d, J = 7.1 Hz), 0.90 (3H, d, J = 7.1 Hz), 1.25 (3H, brs), 1.73 (3H, s), 2.01 (1H, br), 2.57-2.69 (3H, m), 2.87-2.92 (1H, m), 3.35 (2H, br), 3.66-3.78 (1H, m), 3.85-3.93 (1H, m), 4.52 (1H, br), 5.00 (1H, t, J = 8.1 Hz), 5.32 (1H, d, J = 53 Hz), 5.38 (1H, s), 6.88 (2H, d, J = 8.6 Hz), 7.03-7.07 (2H, m), 7.10 (2H, d, J = 8.6 Hz), 7.22-7.25 (2H, m). MS (ESI) m/z: 670 [(M + 1)]⁺. |

TABLE 16

| Example 21 | (structure) | ¹H-NMR (400 MHz, d₆-DMSO, 100° C.) δ: 0.33-0.38 (2H, m), 0.52-0.58 (2H, m), 0.80-0.83 (3H, m), 0.86 (3H, d, J = 7.1 Hz), 0.92 (3H, d, J = 7.1 Hz), 1.66-1.70 (2H, m), 1.73 (3H, s), 2.10-2.24 (1H, m), 2.43-2.65 (3H, m), 2.73-2.78 (1H, m), 3.65 (2H, br), 3.70-3.80 (1H, m), 3.82-3.94 (1H, m), 4.05 (1H, br), 4.98 (1H, br), 5.36 (1H, d, J = 53 Hz), 5.38 (1H, s), 6.90 (2H, d, J = 8.3 Hz), 7.04-7.07 (2H, m), 7.11 (2H, d, J = 8.3 Hz), 7.22-7.25 (2H, m). MS (ESI) m/z: 684 [(M + 1)]⁺. |
|---|---|---|
| Example 22 | (structure) | ¹H-NMR (400 MHz, d₆-DMSO, 100° C.) δ: 0.32-0.36 (1H, m), 0.50-0.57 (3H, m), 0.83-0.86 (3H, m), 0.88 (3H, d, J = 7.1 Hz), 0.91 (3H, d, J = 7.1 Hz), 1.62-1.68 (2H, m), 1.73 (3H, s), 2.09-2.22 (1H, m), 2.59-2.64 (2H, m), 2.81-2.85 (2H, m), 3.10 (1H, br), 3.50 (1H, br), 3.66-3.78 (1H, m), 3.85-3.93 (1H, m), 4.21 (1H, br), 5.02 (1H, t, J = 8.0 Hz), 5.36 (1H, d, J = 53 Hz), 5.38 (1H, s), 6.89 (2H, d, J = 8.3 Hz), 7.03-7.07 (2H, m), 7.10 (2H, d, J = 8.3 Hz), 7.22-7.25 (2H, m). MS (ESI) m/z: 684 [(M + 1)]⁺. |

TABLE 16-continued

| Example 23 | 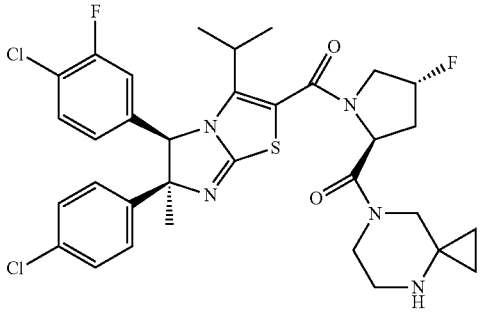 [SMILES: CC(C)C1=C(C(=O)N2C[C@H](F)C[C@H]2C(=O)N2CCNC3(CC3)C2)SC2=N[C@@](C)(c3ccc(Cl)cc3)[C@@H](c3ccc(Cl)c(F)c3)N21] | $^1$H-NMR (400 MHz, d$_6$-DMSO, 100° C.) δ: 0.44-0.48 (4H, m), 0.91 (3H, d, J = 7.1 Hz), 0.93 (3H, d, J = 7.1 Hz), 1.74 (3H, s), 2.02-2.34 (1H, m), 2.53-2.66 (2H, m), 2.72-2.76 (2H, m), 3.32-3.37 (2H, m), 3.42-3.48 (2H, m), 3.67-3.80 (1H, m), 3.86-3.93 (1H, m), 5.03 (1H, t, J = 7.8 Hz), 5.33 (1H, d, J = 53 Hz), 5.43 (1H, s), 6.71 (1H, d, J = 8.0 Hz), 6.88 (1H, d, J = 10.0 Hz), 7.07-7.10 (2H, m), 7.24-7.29 (3H, m). MS (ESI) m/z: 674 [(M + 1)]$^+$. |

TABLE 17

| Example 24 | 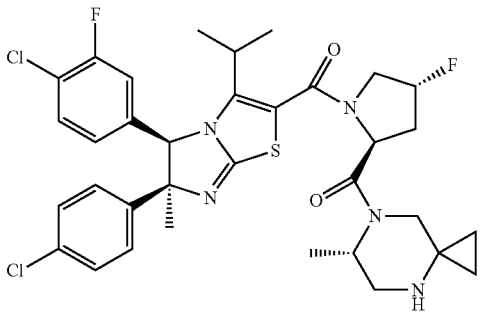 [SMILES: CC(C)C1=C(C(=O)N2C[C@H](F)C[C@H]2C(=O)N2CC3(CC3)NC[C@@H]2C)SC2=N[C@@](C)(c3ccc(Cl)cc3)[C@@H](c3ccc(Cl)c(F)c3)N21] | $^1$H-NMR (400 MHz, d$_6$-DMSO, 100° C.) δ: 0.33-0.38 (2H, m), 0.54-0.58 (2H, m), 0.89 (3H, d, J = 6.8 Hz), 0.93 (3H, d, J = 6.8 Hz), 1.19 (3H, brd, J = 6.5 Hz), 1.73 (3H, s), 2.07-2.19 (1H, m), 2.54-2.64 (3H, m), 2.87-2.91 (1H, m), 3.19 (1H, br), 3.44 (1H, br), 3.67-3.70 (1H, m), 3.76-3.93 (1H, m), 4.31 (1H, br), 4.95 (1H, br), 5.35 (1H, d, J = 53.6 Hz), 5.44 (1H, s), 6.71 (1H, d, J = 7.8 Hz), 6.88 (1H, d, J = 9.1 Hz), 7.07-7.10 (2H, m), 7.25-7.30 (3H, m). MS (ESI) m/z: 688 [(M + 1)]$^+$. |
| Example 25 | 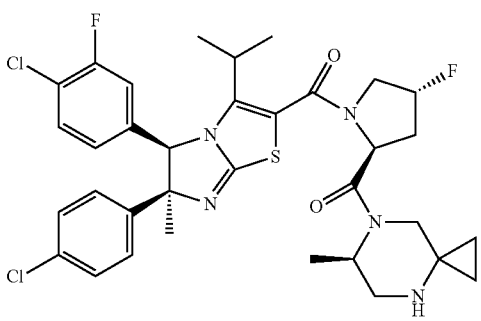 [SMILES: CC(C)C1=C(C(=O)N2C[C@H](F)C[C@H]2C(=O)N2CC3(CC3)NC[C@H]2C)SC2=N[C@@](C)(c3ccc(Cl)cc3)[C@@H](c3ccc(Cl)c(F)c3)N21] | $^1$H-NMR (400 MHz, d$_6$-DMSO, 100° C.) δ: 0.35 (1H, br), 0.55 (2H, br), 0.88 (1H, br), 0.91 (3H, d, J = 6.9 Hz), 0.92 (3H, d, J = 6.9 Hz), 1.20 (3H, brs), 1.73 (3H, s), 1.98 (1H, br), 2.59-2.68 (3H, m), 2.87-2.91 (1H, m), 3.41 (2H, br), 3.68-3.78 (1H, m), 3.85-3.93 (1H, m), 4.50 (1H, br), 5.00 (1H, t, J = 8.2 Hz), 5.33 (1H, d, J = 53 Hz), 5.38 (1H, s), 6.71 (1H, d, J = 8.2 Hz), 6.88 (1H, d, J = 10.0 Hz), 7.08-7.11 (2H, m), 7.24-7.29 (3H, m). MS (ESI) m/z: 688 [(M + 1)]$^+$. |
| Example 26 | 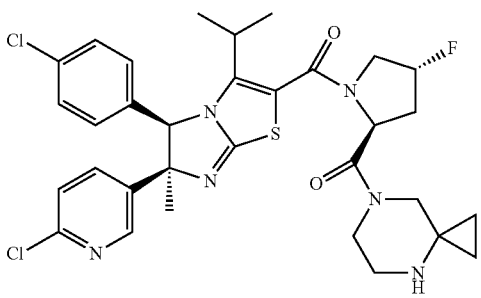 [SMILES: CC(C)C1=C(C(=O)N2C[C@H](F)C[C@H]2C(=O)N2CCNC3(CC3)C2)SC2=N[C@@](C)(c3ccc(Cl)nc3)[C@@H](c3ccc(Cl)cc3)N21] | $^1$H-NMR (400 MHz, d$_6$-DMSO, 100° C.) δ: 0.44-0.48 (4H, m), 0.90 (3H, d, J = 7.1 Hz), 0.91 (3H, d, J = 7.1 Hz), 1.76 (3H, s), 2.01-2.36 (1H, m), 2.53-2.66 (2H, m), 2.72-2.76 (2H, m), 3.28-3.37 (2H, m), 3.44-3.48 (2H, m), 3.67-3.79 (1H, m), 3.86-3.94 (1H, m), 5.04 (1H, t, J = 7.8 Hz), 5.33 (1H, d, J = 53 Hz), 5.46 (1H, s), 6.92 (2H, d, J = 8.3 Hz), 7.11-7.18 (3H, m), 7.62 (1H, dd, J = 8.3, 2.4 Hz), 8.23 (1H, d, J = 2.4 Hz). MS (ESI) m/z: 657 [(M + 1)]$^+$. |

TABLE 18

| Example 27 | 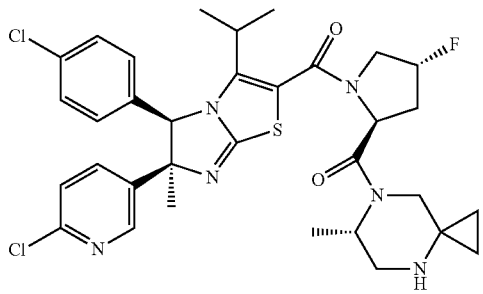 [SMILES: CC(C)C1=C(C(=O)N2C[C@H](F)C[C@H]2C(=O)N2CC3(CC3)NC[C@@H]2C)SC2=N[C@@](C)(c3ccc(Cl)nc3)[C@@H](c3ccc(Cl)cc3)N21] | $^1$H-NMR (400 MHz, $d_6$-DMSO, 100° C.) δ: 0.36-0.38 (2H, m), 0.54-0.58 (2H, m), 0.89 (3H, d, J = 7.1 Hz), 0.92 (3H, d, J = 7.1 Hz), 1.20 (3H, brd, J = 5.8 Hz), 1.76 (3H, s), 2.05-2.21 (1H, m), 2.50-2.65 (3H, m), 2.88-2.91 (1H, m), 3.24 (1H, br), 3.44 (1H, br), 3.67-3.71 (1H, m), 3.76-3.94 (1H, m), 4.31 (1H, br), 4.97 (1H, br), 5.34 (1H, d, J = 53 Hz), 5.45 (1H, s), 6.92 (2H, d, J = 8.3 Hz), 7.11-7.17 (3H, m), 7.62 (1H, dd, J = 8.3, 2.7 Hz), 8.22 (1H, d, J = 2.7 Hz). MS (ESI) m/z: 671 [(M + 1)]$^+$. |
|---|---|---|
| Example 28 | 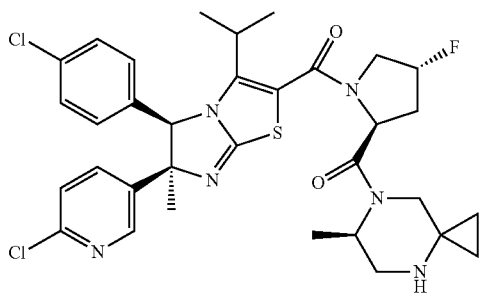 [SMILES: CC(C)C1=C(C(=O)N2C[C@H](F)C[C@H]2C(=O)N2CC3(CC3)NC[C@H]2C)SC2=N[C@@](C)(c3ccc(Cl)nc3)[C@@H](c3ccc(Cl)cc3)N21] | $^1$H-NMR (400 MHz, $d_6$-DMSO, 100° C.) δ: 0.36 (1H, br), 0.56 (2H, br), 0.85 (1H, br), 0.90 (6H, d, J = 7.1 Hz), 1.25 (3H, brs), 1.76 (3H, s), 2.17 (1H, br), 2.60-2.69 (3H, m), 2.88-2.92 (1H, m), 3.39 (2H, br), 3.66-3.78 (1H, m), 3.86-3.94 (1H, m), 4.45 (1H, br), 5.00 (1H, t, J = 8.3 Hz), 5.33 (1H, d, J = 54 Hz), 5.45 (1H, s), 6.91 (2H, d, J = 8.4 Hz), 7.11-7.17 (3H, m), 7.61 (1H, dd, J = 8.4, 2.7 Hz), 8.23 (1H, d, J = 2.7 Hz). MS (ESI) m/z: 671 [(M + 1)]$^+$. |
| Example 29 | 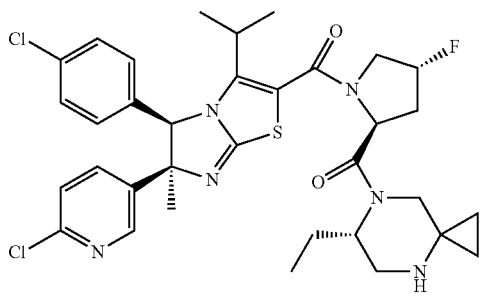 [SMILES: CC[C@H]1CNC2(CC2)CN1C(=O)[C@@H]1C[C@@H](F)CN1C(=O)C1=C(C(C)C)N2C(=N[C@@](C)(c3ccc(Cl)nc3)[C@H]2c2ccc(Cl)cc2)S1] | $^1$H-NMR (400 MHz, $d_6$-DMSO, 100° C.) δ: 0.34-0.38 (2H, m), 0.52-0.57 (2H, m), 0.81-0.83 (3H, m), 0.88 (3H, d, J = 7.1 Hz), 0.91 (3H, d, J = 7.1 Hz), 1.68-1.72 (2H, m), 1.76 (3H, s), 2.12-2.27 (1H, m), 2.50-2.65 (3H, m), 2.73-2.76 (1H, m), 3.69 (2H, br), 3.70-3.80 (1H, m), 3.82-3.95 (1H, m), 4.12 (1H, br), 4.97 (1H, br), 5.36 (1H, d, J = 54 Hz), 5.45 (1H, s), 6.92 (2H, d, J = 8.3 Hz), 7.11-7.18 (3H, m), 7.62 (1H, dd, J = 8.3, 2.2 Hz), 8.23 (1H, d, J = 2.2 Hz). MS (ESI) m/z: 685 [(M + 1)]$^+$. |

TABLE 19

| Example 30 | 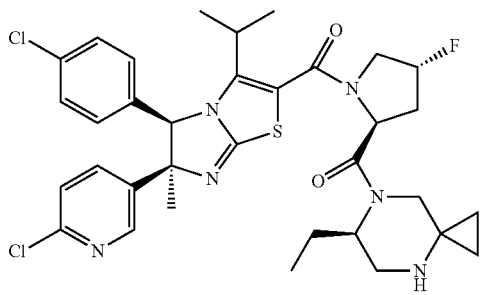 [SMILES: CC[C@@H]1CNC2(CC2)CN1C(=O)[C@@H]1C[C@@H](F)CN1C(=O)C1=C(C(C)C)N2C(=N[C@@](C)(c3ccc(Cl)nc3)[C@H]2c2ccc(Cl)cc2)S1] | $^1$H-NMR (400 MHz, $d_6$-DMSO, 100° C.) δ: 0.33-0.37 (1H, m), 0.51-0.57 (3H, m), 0.82-0.87 (3H, m), 0.90 (6H, d, J = 7.1 Hz), 1.68-1.72 (2H, m), 1.76 (3H, s), 1.99-2.13 (1H, m), 2.60-2.65 (2H, m), 2.81-2.94 (2H, m), 3.11 (1H, br), 3.49 (1H, br), 3.66-3.78 (1H, m), 3.86-3.95 (1H, m), 4.21 (1H, br), 5.02 (1H, t, J = 8.0 Hz), 5.36 (1H, d, J = 55 Hz), 5.45 (1H, s), 6.92 (2H, d, J = 8.0 Hz), 7.11-7.17 (3H, m), 7.61 (1H, dd, J = 8.0, 2.4 Hz), 8.22 (1H, d, J = 2.4 Hz). MS (ESI) m/z: 685 [(M + 1)]$^+$. |
|---|---|---|
| Example 31 | 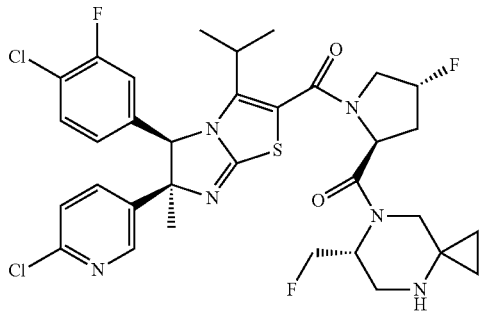 [SMILES: CC(C)C1=C(C(=O)N2C[C@H](F)C[C@H]2C(=O)N2CC3(CC3)NC[C@@H]2CF)SC2=N[C@@](C)(c3ccc(Cl)nc3)[C@@H](c3ccc(Cl)c(F)c3)N21] | $^1$H-NMR (400 MHz, $d_6$-DMSO, 100° C.) δ: 0.55 (4H, brs), 0.92 (3H, d, J = 7.2 Hz), 0.94 (3H, d, J = 7.2 Hz), 1.77 (3H, s), 2.10-2.30 (2H, m), 2.53-2.66 (2H, m), 2.86-2.94 (1H, m), 3.05-3.20 (1H, m), 3.39 (1H, br), 3.51-3.54 (1H, m), 3.76-3.98 (3H, m), 4.97 (1H, br), 5.04 (1H, t, J = 7.8 Hz), 5.37 (1H, d, J = 54 Hz), 5.48 (1H, s), 6.75 (1H, d, J = 8.3 Hz), 6.92 (1H, d, J = 8.8 Hz), 7.14 (1H, d, J = 8.3 Hz), 7.31 (1H, t, J = 8.0 Hz), 7.63 (1H, dd, J = 8.3, 2.5 Hz), 8.24 (1H, d, J = 2.5 Hz). MS (ESI) m/z: 707 [(M + 1)]$^+$. |

Reference Example 1
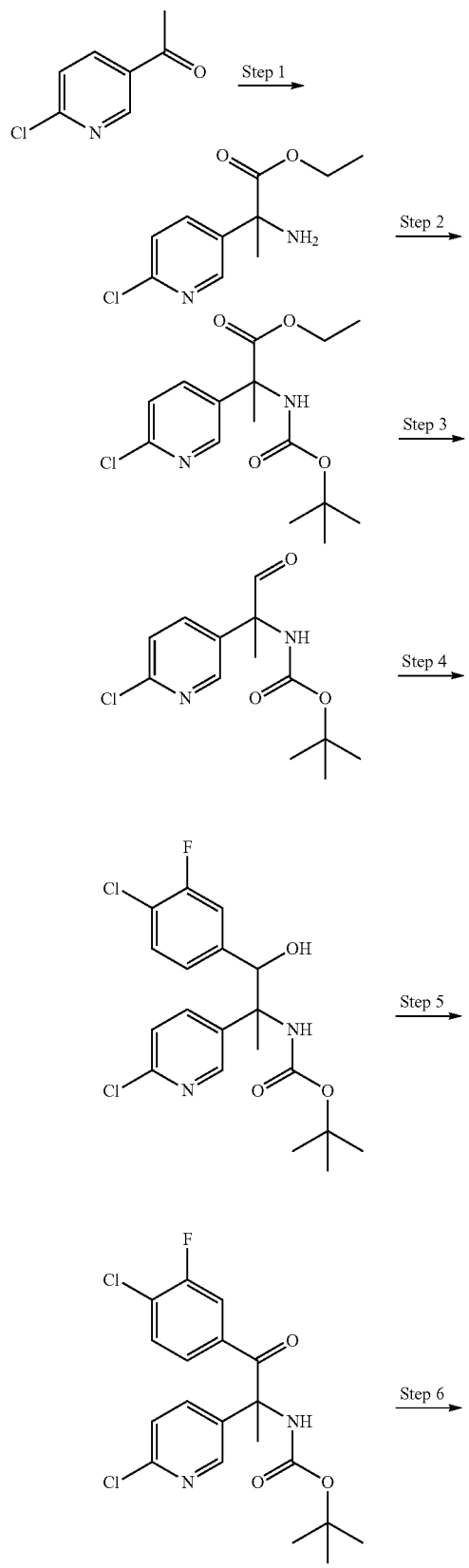
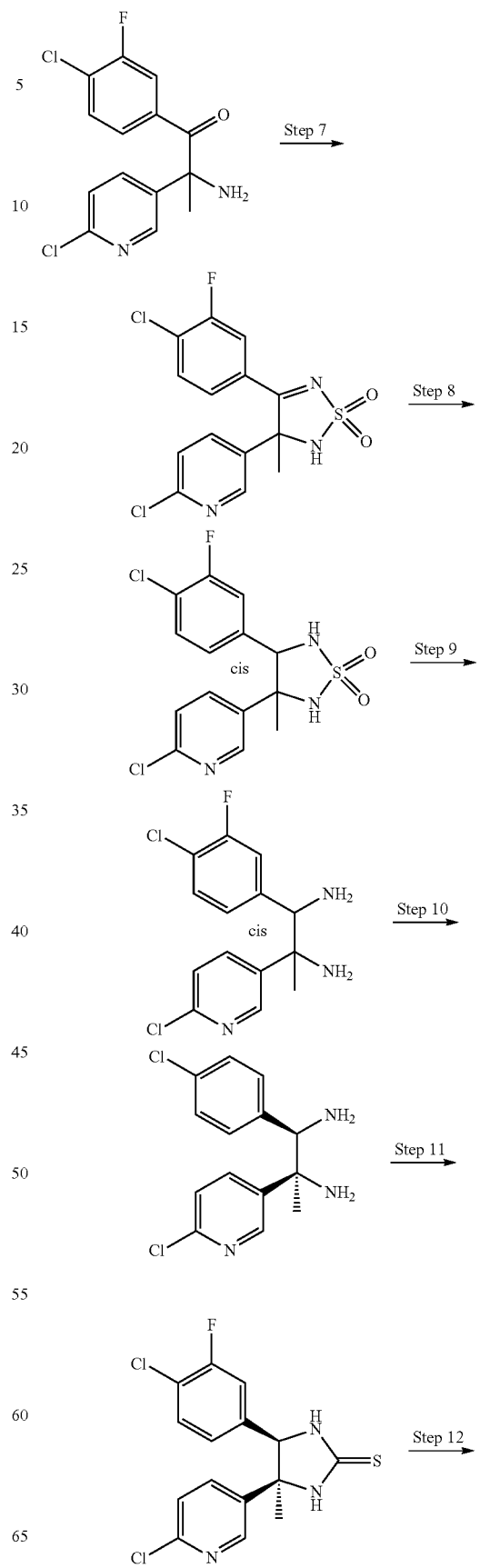

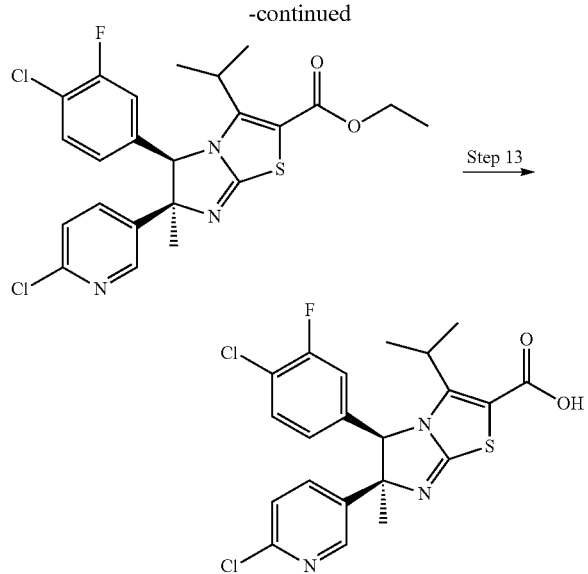

Step 1: ethyl 2-(6-chloropyridin-3-yl)propanoate

A methanol (200 ml) solution of ammonium chloride (6.88 g, 129 mmol) and 1-(6-chloropyridin-3-yl)ethanone (10.0 g, 64.3 mmol) was added to an aqueous concentrated ammonia solution (100 ml) of potassium cyanide (10.7 g, 161 mmol) under ice cooling and the resulting mixture was returned to room temperature while being stirred for 3 days. The reaction solution was concentrated under reduced pressure and the residue was subjected to extraction with dichloromethane. The organic layer was dried over anhydrous magnesium sulfate and then the solvent was evaporated under reduced pressure. Concentrated hydrochloric acid (100 ml) was added to the residue obtained under ice cooling and then the resulting mixture was heated to reflux for 2 hours. The reaction mixture was concentrated under reduced pressure and then subjected to azeotropic distillation with toluene and thionyl chloride (10 ml) was added dropwise to an ethanol (100 ml) solution of the residue obtained under ice cooling. The resulting mixture was heated to reflux for 3 hours, then the reaction mixture was concentrated under reduced pressure and the residue obtained was diluted with dichloromethane and then washed with saturated aqueous sodium bicarbonate solution and saturated brine. The organic layer was dried over anhydrous magnesium sulfate and the solvent was evaporated under reduced pressure. The residue obtained was purified by silica gel column chromatography (ethyl acetate) to give the title compound (7.24 g, 49%) as a pale yellow oil.

$^1$H-NMR (400 MHz, CDCl$_3$) δ: 1.25 (3H, t, J=7.1 Hz), 1.70 (3H, s), 1.98 (2H, brs), 4.19 (2H, q, J=7.1 Hz), 7.30 (1H, d, J=8.3 Hz), 7.85 (1H, dd, J=8.3, 2.4 Hz), 8.56 (1H, d, J=2.4 Hz).

Step 2: ethyl 2-[(tert-butoxycarbonyl)amino]-2-(6-chloropyridin-3-yl)propanoate

Triethylamine (1.22 ml, 8.75 mmol) and di-tert-butyl dicarbonate (1.12 ml, 4.81 mmol) were added to a tetrahydrofuran (20 ml) solution of the compound (1.00 g, 4.37 mmol) obtained in Step 1 above and the resulting mixture was heated to reflux for 18 hours. Further di-tert-butyl dicarbonate (0.51 ml, 2.19 mmol) was added and the resulting mixture was heated to reflux for 18 hours. The reaction mixture was concentrated under reduced pressure and then the residue obtained was diluted with ethyl acetate, washed with 10% aqueous citric acid solution and saturated brine, and then dried over anhydrous magnesium sulfate. The solvent was evaporated under reduced pressure and the residue obtained was purified by silica gel column chromatography [n-hexane:ethyl acetate=2:18 (v/v)] to give the title compound (1.20 g, 84%) as a pale yellow oil.

$^1$H-NMR (400 MHz, CDCl$_3$) δ: 1.19 (3H, t, J=7.2 Hz), 1.38 (9H, brs), 1.99 (3H, s), 4.08-4.26 (2H, m), 7.30 (1H, d, J=8.5 Hz), 7.74 (1H, dd, J=8.5, 2.7 Hz), 8.47 (1H, d, J=2.7 Hz)

Step 3: tert-butyl[1-(6-chloropyridin-3-yl)-1-methyl-2-oxoethyl]carbamate

A tetrahydrofuran (100 ml) solution of the compound (5.70 g, 17.3 mmol) obtained in Step 2 above was added dropwise to a tetrahydrofuran (20 ml) suspension of lithium aluminum hydride (1.43 g, 34.7 mmol) under ice cooling and the resulting mixture was stirred at the same temperature for 1 hour. 1 N aqueous sodium hydroxide solution (6 ml) was added to the reaction mixture under ice cooling and the precipitated insoluble matter was removed by filtration. The filtrate was concentrated under reduced pressure and the residue obtained was dissolved in dimethyl sulfoxide (100 ml). Triethylamine (60 ml) and a sulfur trioxide-pyridine complex (5.52 g, 34.7 mmol) were added at room temperature and the resulting mixture was stirred for 2 hours. The reaction mixture was poured into water, followed by extraction with ethyl acetate. The organic layer was washed with saturated brine. The organic layer was dried over anhydrous magnesium sulfate, then the solvent was evaporated under reduced pressure and the residue obtained was purified by silica gel column chromatography [n-hexane:ethyl acetate=2:1 (v/v)] to give the title compound (2.77 g, 56%) as a pale yellow oil.

$^1$H-NMR (400 MHz, CDCl$_3$) δ: 1.43 (9H, s), 1.79 (3H, s), 5.73 (1H, brs), 7.36 (1H, d, J=8.5 Hz), 7.69 (1H, dd, J=8.5, 2.7 Hz), 8.42 (1H, s), 9.34 (1H, s).

Step 4: tert-butyl[2-(4-chloro-3-fluorophenyl)-1-(6-chloropyridin-3-yl)-2-hydroxy-1-methylethyl]carbamate A tetrahydrofuran (20 ml) solution of the compound (6.47 g, 22.7 mmol) obtained in Step 3 above was added dropwise to 4-chloro-3-fluorophenyl magnesium bromide (0.5 M tetrahydrofuran solution) (100 ml, 50.0 mmol) under ice cooling and the resulting mixture was stirred at the same temperature for 1 hour. An aqueous solution of saturated ammonium chloride was added to the reaction mixture to terminate the reaction, followed by extraction with ethyl acetate. The organic layer was dried over anhydrous magnesium sulfate and then the solvent was evaporated under reduced pressure. An n-hexane/ethyl acetate mixed solvent was added to the residue obtained and the resulting precipitate was collected by filtration and dried to give the title compound (7.92 g, 84%) as a white solid.

$^1$H-NMR (400 MHz, CDCl$_3$) δ: 1.45 (9H, brs), 1.56 (3H, brs), 5.08 (2H, brs), 6.86 (1H, brs), 7.09 (1H, d, J=8.8 Hz), 7.31-7.35 (2H, m), 7.68 (1H, d, J=7.3 Hz), 8.44 (1H, s).
MS (API) m/z: 415 [(M+1)$^+$].

Step 5: tert-butyl[2-(4-chloro-3-fluorophenyl)-1-(6-chloropyridin-3-yl)-1-methyl-2-oxoethyl]carbamate Acetic anhydride (2.3 ml, 24.7 mmol) was added to a dimethyl sulfoxide (8 ml) solution of the compound (1.14 g, 2.75 mmol) obtained in Step 4 above under ice cooling and the resulting mixture was gradually returned to room temperature while being stirred for 18 hours. The reaction mixture was diluted with ethyl acetate, washed with 6% aqueous sodium perchlorate solution, 10% aqueous sodium thiosulfate solution, and saturated brine, and then dried over anhydrous magnesium sulfate. The solvent was evaporated under reduced pressure and the residue obtained was purified by silica gel column chromatography [n-hexane:ethyl acetate=4:1 (v/v)] to give the title compound (1.10 g, 97%) as a pale yellow solid.

$^1$H-NMR (400 MHz, CDCl$_3$) δ: 1.31 (9H, s), 2.03 (3H, s), 6.28 (1H, brs), 7.26-7.37 (3H, m), 7.49 (1H, d, J=9.5 Hz), 7.71 (1H, d, J=6.3 Hz), 8.45 (1H, s).

Step 6: 2-amino-1-(4-chloro-3-fluorophenyl)-2-(6-chloropyridin-3-yl)propan-1-one A dioxane (1 ml) solution of the compound (1.23 g, 2.55 mmol) obtained in Step 5 above was added to a 4 N hydrochloric acid/dioxane solution (5 ml) under ice cooling and the resulting mixture was gradually warmed and stirred at room temperature for 2 hours. The reaction mixture was diluted with water and washed with an n-hexane/ethyl acetate mixed solvent and then the aqueous layer was made alkaline by the addition of 15% aqueous sodium hydroxide solution, followed by extraction with dichloromethane. The organic layer was dried over anhydrous magnesium sulfate, then the solvent was evaporated under reduced pressure and the residue obtained was purified by silica gel column chromatography [n-hexane:ethyl acetate=1:1 (v/v)] to give the title compound (0.75 g, 95%) as a pale yellow solid.

MS (API) m/z: 313 [(M+1)$^+$].

Step 7: 2-chloro-5-[4-(4-chloro-3-fluorophenyl)-3-methyl-1,1-dioxido-2,3-dihydro-1,2,5-thiadiazol-3-yl]pyridine A molecular sieve 4 A (4.5 g), sulfamide (2.75 g, 28.6 mmol), and 1,8-diazabicyclo[5.4.0]undec-7-ene (1.45 g, 9.52 mmol) were added to a dioxane (60 ml) solution of the compound (2.99 g, 9.55 mmol) obtained in Step 6 above and the resulting mixture was stirred under heating at 95° C. for 18 hours. Further sulfamide (2.75 g, 28.6 mmol) was added and the resulting mixture was stirred under heating for 24 hours. The reaction mixture was concentrated under reduced pressure and then the residue obtained was diluted with ethyl acetate, washed with 10% aqueous citric acid solution and saturated brine, and then dried over anhydrous magnesium sulfate. A diisopropyl ether/ethyl acetate mixed solvent was added to the residue obtained and the resulting precipitate was collected by filtration and dried to give the title compound (2.86 g, 80%) as a colorless solid.

$^1$H-NMR (400 MHz, CDCl$_3$) δ: 2.25 (3H, s), 7.29-7.47 (3H, m), 7.59 (1H, dd, J=9.5, 2.0 Hz), 7.68 (1H, dd, J=8.5, 2.9 Hz), 8.53 (1H, d, J=2.9 Hz).

Step 8: 2-chloro-5-[(3R*,4S*)-4-(4-chloro-3-fluorophenyl)-3-methyl-1,1-dioxido-1,2,5-thiadiazolidin-3-yl]pyridine Sodium borohydride (1.00 g, 26.4 mmol) was gradually added to an ethanol (63 ml) solution of the compound (7.13 g, 19.1 mmol) obtained in Step 7 above under ice cooling and the resulting mixture was stirred at the same temperature for 2 hours. The reaction mixture was concentrated under reduced pressure and then the residue obtained was diluted with ethyl acetate, washed with 1 N aqueous hydrochloric acid solution and saturated brine, and then dried over anhydrous magnesium sulfate. The solvent was evaporated under reduced pressure and the residue obtained was purified by silica gel column chromatography [n-hexane:ethyl acetate=1:2 (v/v)] to give the title compound (4.36 g, 59%) as a pale yellow solid.

$^1$H-NMR (400 MHz, CDCl$_3$) δ: 1.85 (3H, s), 3.23-3.32 (4H, m), 4.92 (1H, d, J=5.6 Hz), 6.74-6.76 (1H, m), 6.80-6.83 (1H, m), 7.23-7.26 (2H, m), 7.55-7.60 (1H, m), 7.94-7.95 (1H, m).

Step 9: (1R*,2S*)-1-(4-chloro-3-fluorophenyl)-2-(6-chloropyridin-3-yl)propane-1,2-diamine Ethylenediamine (7.40 ml, 111 mmol) was added to a dioxane (80 ml) solution of the compound (4.15 g, 11.0 mmol) obtained in Step 8 above and the resulting mixture was stirred under heating at 100° C. for 18 hours. The reaction mixture was concentrated under reduced pressure and the residue obtained was diluted with chloroform, washed with 1 N aqueous sodium hydroxide solution and saturated brine, and then dried over anhydrous magnesium sulfate. The solvent was evaporated under reduced pressure and the residue obtained was purified by silica gel column chromatography [chloroform:methanol=93:7 (v/v)] to give the title compound (3.35 g, 97%) as a pale yellow oil.

$^1$H-NMR (400 MHz, CDCl$_3$) δ: 1.54 (3H, s), 1.58 (4H, brs), 4.08 (1H, s), 6.72 (1H, dd, J=8.3, 2.0 Hz), 6.96 (1H, dd, J=10.3, 2.0 Hz), 7.21 (1H, t, J=7.9 Hz), 7.23 (1H, dd, J=8.3, 0.7 Hz), 7.59 (1H, dd, J=8.5, 2.7 Hz), 8.36 (1H, dd, J=2.7, 0.7 Hz).

MS (ESI) m/z: 314 [(M+1)$^+$].

Step 10: (1R,2S)-1-(4-chloro-3-fluorophenyl)-2-(6-chloropyridin-3-yl)propane-1,2-diamine L-(+)-tartaric acid (6.3 g, 42.0 mmol) was added to an ethanol (200 ml) solution of the compound (12.6 g, 40.0 mmol) obtained in Step 9 above and the resulting mixture was heated to reflux at 110° C. for 30 minutes. Water (8 ml) was added, the resulting mixture was further heated to reflux for 10 minutes, then returned to room temperature, and left overnight and then the precipitated solid was collected by filtration. The solid obtained was made into an alkaline solution by the addition of 5 N aqueous sodium hydroxide solution, followed by extraction with diethyl ether. The organic layer was dried over potassium carbonate and then the solvent was evaporated under reduced pressure to give the title compound (5.68 g, 45%) as a colorless solid.

$^1$H-NMR (400 MHz, CDCl$_3$) δ: 1.54 (3H, s), 1.56 (4H, brs), 4.08 (1H, s), 6.72 (1H, dd, J=8.3, 2.0 Hz), 6.96 (1H, dd, J=10.4, 2.1 Hz), 7.20-7.24 (2H, m), 7.59 (1H, dd, J=8.4, 2.6 Hz), 8.36 (1H, dd, J=2.7, 0.7 Hz).

MS (ESI) m/z: 314 [(M+1)$^+$].

[α]$_D$=+55.5° (C=1.00, chloroform, 20° C.).

Step 11: (4S,5R)-5-(4-chloro-3-fluorophenyl)-4-(6-chloropyridin-3-yl)-4-methylimidazolidine-2-thione Carbon disulfide (0.58 ml, 9.21 mmol) was added to an ethanol (30 ml) solution of the compound (1.93 g, 6.14 mmol) obtained in Step 10 above at room temperature and the resulting mixture was heated to reflux for 20 hours. After cooling, the reaction mixture was concentrated under reduced pressure and the residue obtained was diluted with ethyl acetate, washed with saturated brine, and then dried over anhydrous magnesium sulfate. The solvent was evaporated under reduced pressure and the residue obtained was purified by silica gel column chromatography [chloroform:methanol=40:1 (v/v)] to give the title compound (1.94 g, 89%) as a colorless solid.

$^1$H-NMR (400 MHz, CDCl$_3$) δ: 1.94 (3H, s), 5.00 (1H, s), 6.67 (1H, d, J=7.8 Hz), 6.68 (1H, brs), 6.75 (1H, dd, J=9.5, 2.0 Hz), 7.10 (1H, brs), 7.15 (1H, d, J=8.3 Hz), 7.21 (1H, t, J=7.8 Hz), 7.31 (1H, dd, J=8.5, 2.7 Hz), 8.01 (1H, d, J=2.2 Hz).

MS (ESI) m/z: 356 [(M+1)$^+$].

Step 12: ethyl (5R,6S)-5-(4-chloro-3-fluorophenyl)-6-(6-chloropyridin-3-yl)-3-isopropyl-6-methyl-5,6-dihydroimidazo[2,1-b][1,3]thiazole-2-carboxylate Ethyl 2-chloro-4-methyl-3-oxopentanoate (1.36 g, 7.09 mmol) was added to an ethanol (20 ml) solution of the compound (1.94 g, 5.45 mmol) obtained in Step 11 above at room temperature and the resulting mixture was heated to reflux for 16 hours. The reaction mixture was returned to room temperature and the reaction solvent was evaporated under reduced pressure. The residue obtained was diluted with ethyl acetate and the organic layer was washed with saturated aqueous sodium bicarbonate solution and saturated brine and dried over anhydrous magnesium sulfate. The solvent was evaporated under reduced pressure and the residue obtained was purified by silica gel column chromatography [n-hexane:ethyl acetate=3:1 (v/v)] to give the title compound (2.06 g, 76%) as a colorless solid.

$^1$H-NMR (400 MHz, CDCl$_3$) δ: 0.90 (3H, d, J=7.3 Hz), 1.04 (3H, d, J=7.1 Hz), 1.34 (3H, t, J=7.2 Hz), 1.83 (3H, s), 4.26 (2H, q, J=7.2 Hz), 5.10 (1H, s), 6.51-6.62 (2H, m), 7.04 (1H, d, J=8.3 Hz), 7.16 (1H, t, J=7.7 Hz), 7.51-7.55 (1H, m), 8.20-8.22 (1H, m).

MS (ESI) m/z: 494 [(M+1)$^+$].

Step 13: (5R,6S)-5-(4-chloro-3-fluorophenyl)-6-(6-chloropyridin-3-yl)-3-isopropyl-6-methyl-5,6-dihydroimidazo[2,1-b][1,3]thiazole-2-carboxylic acid 1 N aqueous sodium hydroxide solution (6 ml) was added to an ethanol (30 ml) solution of the compound (2.06 g, 4.17 mmol) obtained in Step 12 above and the resulting mixture was stirred under heating at 60° C. for 16 hours. After cooling, the solvent was concentrated under reduced pressure and the residue obtained was diluted with water and then washed with diethyl ether. The aqueous layer was made into an acidic solution by the gradual addition of 1 N aqueous hydrochloric acid solution under ice cooling, followed by extraction with ethyl acetate. The organic layer was washed with saturated brine and then dried over anhydrous magnesium sulfate. The solvent was evaporated under reduced pressure, a diethyl ether/n-hexane mixed solvent was added to the residue and the resulting precipitate was collected by filtration and dried to give the title compound (1.51 g, 87%) as a pale yellow solid.

$^1$H-NMR (400 MHz, DMSO-d$_6$) δ: 0.79 (3H, d, J=7.1 Hz), 0.98 (3H, d, J=7.1 Hz), 1.73 (3H, s), 3.32-3.40 (1H, m), 5.71 (1H, s), 6.38-6.48 (1H, m), 7.23 (1H, d, J=8.3 Hz), 7.34-7.46 (2H, m), 7.66 (1H, dd, J=8.3, 2.4 Hz), 8.25 (1H, d, J=2.4 Hz).

MS (ESI) m/z: 466 [(M+1)$^+$].

[α]$_D$=+120.5° (C=1.00, methanol, 25° C.).

Reference Example 2

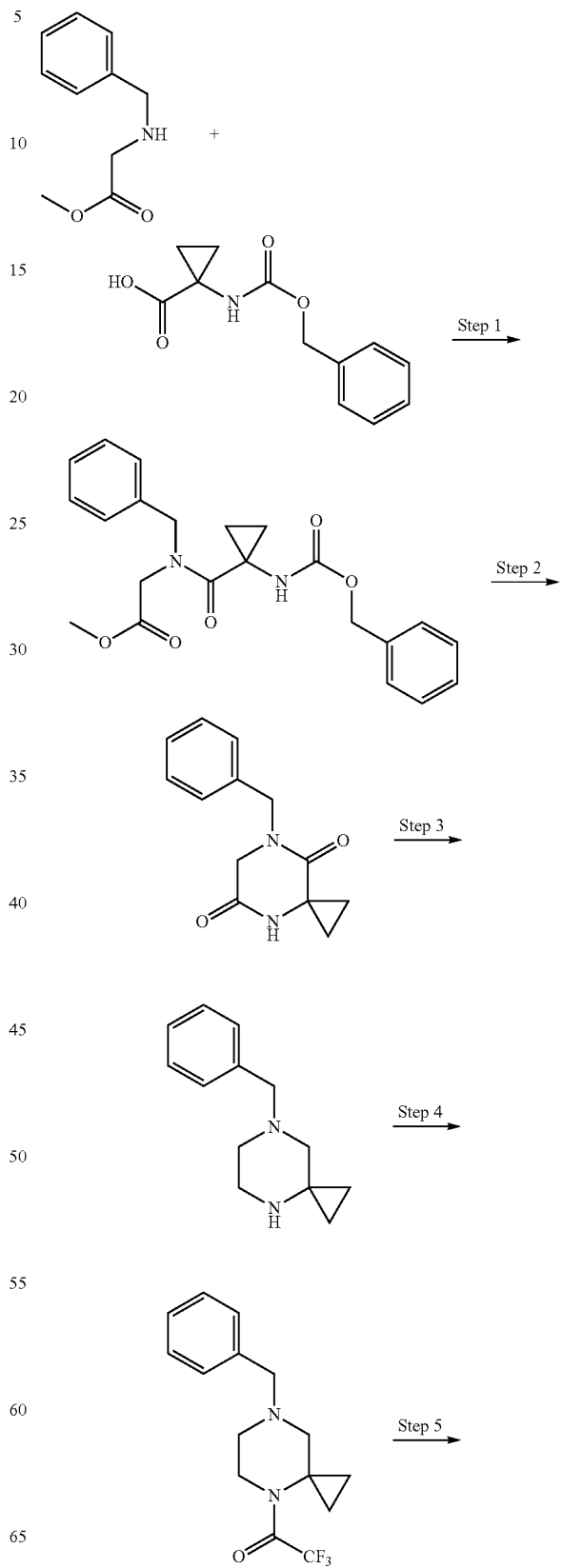

-continued

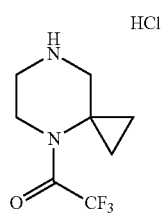

Step 1: ethyl N-benzyl-N-[(1-{[(benzyloxy)carbonyl]amino}cyclopropyl)carbonyl]glycinate 1-(3-dimethylaminopropyl)-3-ethylcarbodiimide hydrochloride (21.0 g, 110 mmol) and 1-hydroxybenzotriazole (2.70 g, 20 mmol) were added to a dichloromethane (235 ml) solution of 1-{[(benzyloxy)carbonyl]amino}cyclopropanecarboxylic acid (23.5 g, 100 mmol) and ethyl N-benzylglycinate (19.3 g, 100 mmol) under ice cooling and the resulting mixture was stirred at room temperature for 24 hours. The solvent was concentrated under reduced pressure and then the residue was diluted with ethyl acetate, washed with 1 N aqueous hydrochloric acid solution, saturated aqueous sodium bicarbonate solution, and saturated brine, and then dried over anhydrous sodium sulfate. The solvent was evaporated under reduced pressure and the residue obtained was purified by silica gel column chromatography [n-hexane:ethyl acetate=2:1 (v/v)] to give the title compound (35.7 g, 87%) as a colorless solid.

$^{1}$H-NMR (400 MHz, CDCl$_3$) δ: 1.13 (2H, br), 1.22 (3H, t, J=7.4 Hz), 1.25 (2H, br), 1.66 (2H, s), 3.91 (1H, br), 4.12 (2H, q, J=7.4 Hz), 4.91 (2H, brs), 5.36 (2H, brs), 7.19-7.31 (10H, m).

Step 2: 7-benzyl-4,7-diazaspiro[2.5]octane-5,8-dione

5% palladium carbon (3.6 g) was added to an ethanol (700 ml) solution of the compound (35.5 g, 86.5 mmol) obtained in Step 1 above and the resulting mixture was subjected to catalytic reduction for 2 hours in a hydrogen atmosphere. The catalyst was removed by filtration through celite, then the filtrate was concentrated under reduced pressure and the residue obtained was purified by silica gel column chromatography [ethyl acetate:n-hexane=1:1 (v/v)] to give the title compound (20 g, 100%) as a colorless solid.

$^{1}$H-NMR (400 MHz, CDCl$_3$) δ: 0.93-1.00 (2H, m), 1.55-1.59 (2H, m), 3.91 (2H, s), 4.60 (2H, s), 7.25-7.37 (5H, m), 7.86 (1H, brs).

MS (ESI) m/z: 231 [(M+H)$^+$].

Step 3: 7-benzyl-4,7-diazaspiro[2.5]octane

A borane-tetrahydrofuran complex (0.93 M tetrahydrofuran solution) (375 ml, 0.35 mol) was added to a tetrahydrofuran (200 ml) solution of the compound (20 g, 86.8 mmol) obtained in Step 2 above under ice cooling and then the resulting mixture was heated to reflux for 19 hours. Methanol (130 ml) was added to the reaction mixture under ice cooling, the resulting mixture was stirred for 60 minutes and then the solvent was concentrated under reduced pressure. Ethanol (450 ml), water (150 ml), and triethylamine (150 ml) were added to the residue obtained, the resulting mixture was heated to reflux for 2 hours and then the solvent was concentrated under reduced pressure. The residue obtained was diluted with ethyl acetate, washed with saturated aqueous sodium bicarbonate solution and saturated brine, and then dried over anhydrous sodium sulfate. The solvent was evaporated under reduced pressure and the residue obtained was purified by silica gel column chromatography [chloroform:methanol=10:1 (v/v)] to give the title compound (10.4 g, 59%) as a colorless oil.

$^{1}$H-NMR (400 MHz, CDCl$_3$) δ: 0.41-0.44 (2H, m), 0.57-0.60 (2H, m), 1.49 (1H, br), 2.22 (2H, s), 2.45 (2H, brs), 2.97 (2H, t, J=4.9 Hz), 3.50 (2H, s), 7.22-7.32 (5H, m).

Step 4: 7-benzyl-4-(trifluoroacetyl)-4,7-diazaspiro[2.5]octane

Trifluoroacetic anhydride (8.50 ml, 61.1 mmol) was added dropwise to a dichloromethane (200 ml) solution of the compound (10.3 g, 50.9 mmol) obtained in Step 3 above and triethylamine (17 ml, 122 mmol) under ice cooling and the resulting mixture was stirred at the same temperature for 1 hour. Saturated aqueous sodium bicarbonate solution was added to the reaction mixture and the resulting mixture was diluted with chloroform, then washed with saturated brine, and dried over anhydrous sodium sulfate. The solvent was evaporated under reduced pressure to give the title compound (15.5 g, 100%) as a colorless oil.

MS (ESI) m/z: 299 [(M+H)$^+$].

Step 5: 4-(trifluoroacetyl)-4,7-diazaspiro[2.5]octane hydrochloride

1 N hydrochloric acid/ethanol (105 ml, 105 mmol) and 5% palladium carbon (3 g) were added to an ethanol (250 ml) solution of the compound (15.5 g, 51 mmol) obtained in Step 4 above and the resulting mixture was subjected to catalytic reduction for 15 hours in a hydrogen atmosphere. The catalyst was removed by filtration through celite and then the filtrate was concentrated under reduced pressure. An ethanol/diethyl ether mixed solvent was added to the residue obtained and the deposited solid was collected by filtration to give the title compound (10.3 g, 83%) as a colorless solid.

$^{1}$H-NMR (400 MHz, DMSO-d$_6$, 80° C.) δ: 1.18 (4H, s), 3.16 (2H, s), 3.25 (2H, t, J=5.1 Hz), 3.89 (2H, brs), 9.71 (2H, br).

MS (ESI) m/z: 209 [(M+H)$^+$].

Reference Example 3

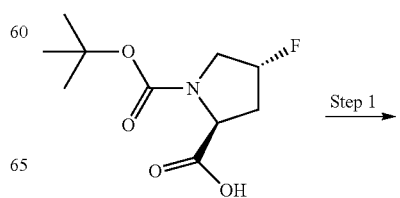

Step 1

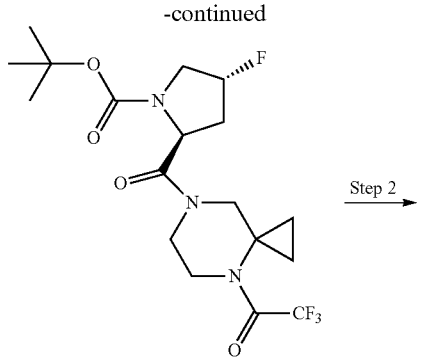

Step 1: tert-butyl (2S,4R)-4-fluoro-2-{[4-(trifluoro-acetyl)-4,7-diazaspiro[2.5]oct-7-yl]carbonyl}pyrrolidine-1-carboxylate 1-hydroxybenzotriazole (46 mg, 0.34 mmol) and 1-(3-dimethylaminopropyl)-3-ethylcarbodiimide hydrochloride (502 mg, 2.61 mmol) were added to a dimethylformamide (8 ml) solution of (4R)-1-(tert-butoxycarbonyl)-4-fluoro-L-proline (400 mg, 1.71 mmol) and the resulting mixture was stirred at room temperature for 15 minutes. Subsequently, the compound (460 mg, 2.05 mmol) obtained in Step 5 of Reference Example 2 and diisopropylethylamine (0.45 ml, 2.57 mmol) were added and the resulting mixture was stirred at room temperature for 16 hours. The reaction mixture was diluted with ethyl acetate and the organic layer was washed with saturated aqueous sodium bicarbonate solution and saturated brine and then dried over anhydrous sodium sulfate. The solvent was evaporated under reduced pressure and the residue obtained was purified by silica gel column chromatography [n-hexane:ethyl acetate=1:1 (v/v)] to give the title compound (560 mg, 77%) as a colorless solid.

$^1$H-NMR (400 MHz, DMSO-$d_6$, 90° C.) δ: 0.98-1.10 (4H, m), 1.37 (9H, s), 1.95-2.09 (1H, m), 2.49-2.54 (1H, m), 3.41-3.54 (3H, m), 3.60-3.75 (5H, m), 4.73-4.80 (1H, m), 5.26 (1H, d, J=53.7 Hz).

MS (ESI) m/z: 424 [(M+H)$^+$].

Step 2: 7-[(4R)-4-fluoro-L-prolyl]-4-(trifluoro-acetyl)-4,7-diazaspiro[2.5]octane Trifluoroacetic acid (10 ml) was added to a dichloromethane (10 ml) solution of the compound (560 mg, 1.32 mmol) obtained in Step 1 above and the resulting mixture was stirred at room temperature for 1 hour. The reaction solvent was concentrated under reduced pressure and then saturated aqueous sodium bicarbonate solution (30 ml) was added, followed by extraction with chloroform three times. The organic layer was washed with saturated brine and dried over anhydrous sodium sulfate. The solvent was evaporated under reduced pressure to give the title compound (380 mg, 89%) as a pale yellow solid.

$^1$H-NMR (400 MHz, DMSO-$d_6$, 90° C.) δ: 0.98-1.11 (4H, m), 2.00-2.07 (1H, m), 2.10-2.16 (1H, m), 2.68-2.77 (1H, m), 3.04-3.14 (1H, m), 3.51 (2H, s), 3.63-3.78 (4H, m), 4.05-4.13 (1H, m), 5.23 (1H, d, J=53.5 Hz).

MS (ESI) m/z: 324 [(M+H)$^+$].

Reference Example 4

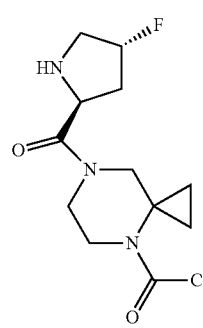

-continued

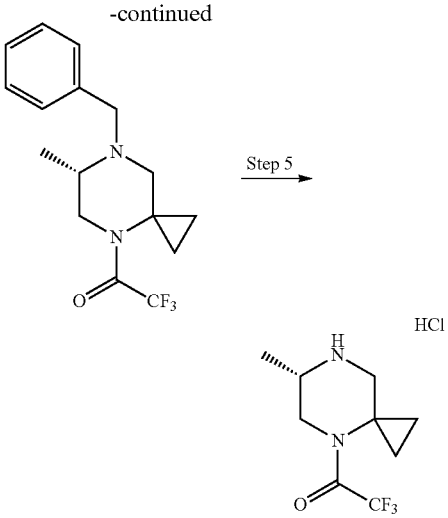

Step 1: methyl N-benzyl-N-[(1-{[(benzyloxy)carbonyl]amino}cyclopropyl)carbonyl]-L-alaninate N,N'-dicyclohexylcarbodiimide (6.0 g, 29.0 mmol) was added to a dichloromethane (150 ml) solution of methyl N-benzyl-L-alaninate (5.20 g, 26.9 mmol) and 1-{[(benzyloxy)carbonyl]amino}cyclopropanecarboxylic acid (6.30 g, 26.7 mmol) under ice cooling and the resulting mixture was stirred overnight at room temperature. The reaction mixture was concentrated under reduced pressure and then diluted with ethyl acetate, insoluble matter was removed by filtration and then the filtrate was washed with 1 N aqueous hydrochloric acid solution and saturated brine and dried over anhydrous sodium sulfate. The solvent was evaporated under reduced pressure and the obtained residue was purified by silica gel column chromatography [n-hexane:ethyl acetate=1:3 (v/v)] to give the title compound (7.80 g, 71%) as a colorless oil.

$^1$H-NMR (400 MHz, CDCl$_3$, 70° C.) δ: 1.03-1.11 (2H, m), 1.37 (3H, d, J=7.1 Hz), 1.43-1.47 (2H, m), 3.72 (3H, s), 4.48 (1H, brs), 4.61 (1H, d, J=16.6 Hz), 4.91 (1H, d, J=16.6 Hz), 4.99 (2H, s), 5.20 (1H, brs), 7.20-7.34 (10H, m).

Step 2: (6S)-7-benzyl-6-methyl-4,7-diazaspiro[2.5]octane-5,8-dione

The compound obtained in Step 1 above was reacted in the same way as in Step 2 of Reference Example 2 to give the title compound as a colorless oil.

$^1$H-NMR (400 MHz, CDCl$_3$) δ: 0.98-1.07 (2H, m), 1.36 (1H, m), 1.47 (3H, d, J=7.1 Hz), 1.85 (1H, m), 3.91 (1H, q, J=7.1 Hz), 4.06 (1H, d, J=14.9 Hz), 5.21 (1H, d, J=14.9 Hz), 7.26-7.37 (5H, m).

Step 3: (6S)-7-benzyl-6-methyl-4,7-diazaspiro[2.5]octane

The compound obtained in Step 2 above was reacted in the same way as in Step 3 of Reference Example 2 to give the title compound as a colorless solid.

$^1$H-NMR (400 MHz, CDCl$_3$) δ: 0.30-0.34 (1H, m), 0.36-0.40 (1H, m), 0.48-0.53 (1H, m), 0.55-0.61 (1H, m), 1.16 (3H, d, J=6.3 Hz), 2.12 (1H, d, J=11.7 Hz), 2.26-2.33 (2H, m), 2.74 (1H, dd, J=13.2, 9.3 Hz), 2.90 (1H, dd, J=13.2, 3.4 Hz), 3.15 (1H, d, J=13.4 Hz), 4.07 (1H, d, J=13.4 Hz), 7.20-7.34 (6H, m).

Step 4: (6S)-7-benzyl-6-methyl-4-(trifluoroacetyl)-4,7-diazaspiro[2.5]octane

The compound obtained in Step 3 above was reacted in the same way as in Step 4 of Reference Example 2 to give the title compound as a colorless oil.

$^1$H-NMR (400 MHz, CDCl$_3$) δ: 0.68 (1H, m), 0.79 (1H, m), 0.93 (1H, m), 1.21 (3H, d, J=6.1 Hz), 1.33 (1H, m), 2.17 (1H, d, J=12.0 Hz), 2.49 (1H, d, J=12.0 Hz), 2.59 (1H, m), 3.16 (1H, d, J=13.4 Hz), 3.33 (1H, dd, J=13.4, 9.3 Hz), 3.77 (1H, d, J=13.4 Hz), 4.04 (1H, d, J=13.4 Hz), 7.23-7.34 (5H, m).

Step 5: (6S)-6-methyl-4-(trifluoroacetyl)-4,7-diazaspiro[2.5]octane hydrochloride The compound obtained in Step 4 above was reacted in the same way as in Step 5 of Reference Example 2 to give the title compound as a colorless solid.

$^1$H-NMR (400 MHz, DMSO-d$_6$) δ: 0.95 (1H, brs), 1.12 (1H, brs), 1.27 (1H, m), 1.33 (3H, d, J=6.3 Hz), 1.41 (1H, brs), 2.90 (1H, m), 3.38-3.59 (3H, m), 4.03 (1H, brs).

MS (ESI) m/z: 223 [(M+H)$^+$].

Reference Example 5

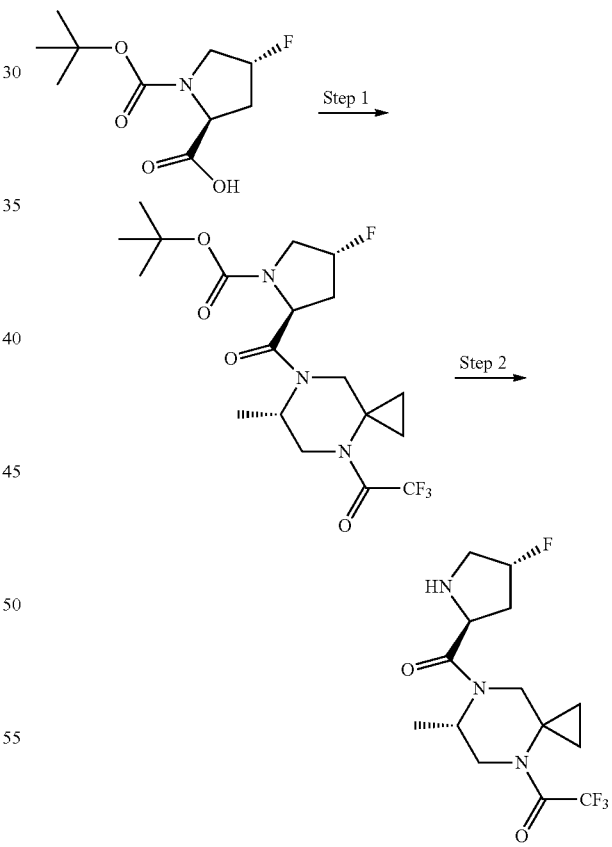

Step 1: tert-butyl (2S,4R)-4-fluoro-2-{[(6S)-6-methyl-4-(trifluoroacetyl)-4,7-diazaspiro[2.5]oct-7-yl]carbonyl}pyrrolidine-1-carboxylate The compound obtained in Step 5 of Reference Example 4 instead of the compound obtained in Step 5 of Reference Example 2 was reacted in the same way as in Step 1 of Reference Example 3 to give the title compound as a pale yellow oil.

¹H-NMR (400 MHz, DMSO-d₆, 100° C.) δ: 0.69-0.71 (2H, m), 1.11 (3H, d, J=6.6 Hz), 1.28-1.32 (2H, m), 1.37 (9H, s), 1.49 (1H, m), 2.05 (1H, m), 3.49-3.68 (5H, m), 3.88 (1H, brs), 4.67-4.75 (2H, m), 5.27 (1H, d, J=54.0 Hz).

MS (ESI) m/z: 460 [(M+Na)⁺].

Step 2: (6S)-7-[(4R)-4-fluoro-L-prolyl]-6-methyl-4-(trifluoroacetyl)-4,7-diazaspiro[2.5]octane The compound obtained in Step 1 above was reacted in the same way as in Step 2 of Reference Example 3 to give the title compound as a pale yellow oil.

¹H-NMR (400 MHz, DMSO-d₆, 100° C.) δ: 0.68-0.77 (2H, m), 1.12 (3H, d, J=6.6 Hz), 1.28 (1H, dd, J=17.0, 7.1 Hz), 1.49 (1H, dd, J=17.0, 7.1 Hz), 2.01-2.24 (2H, m), 2.65-2.68 (1H, m), 3.00-3.14 (1H, m), 3.42-3.61 (3H, m), 3.90 (1H, brs), 4.08 (1H, t, J=7.6 Hz), 4.66-4.69 (1H, m), 5.25 (1H, dt, J=55.6, 4.5 Hz).

Reference Example 6

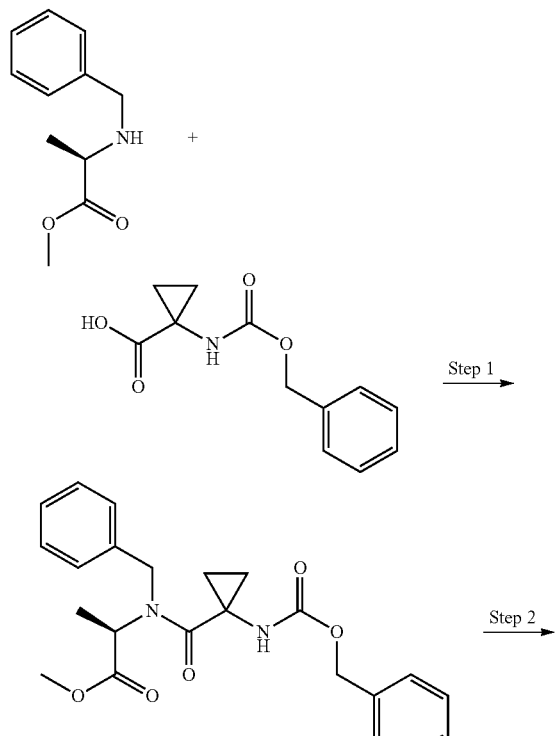

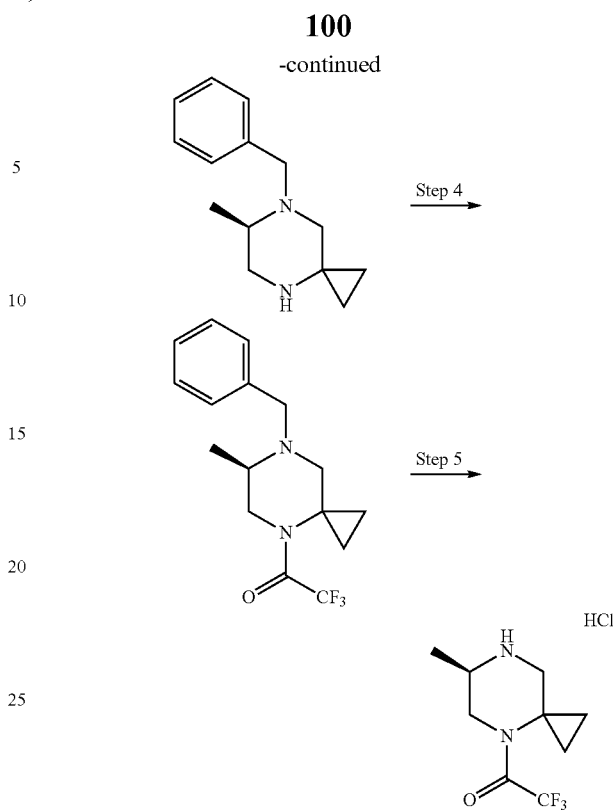

Step 1: methyl N-benzyl-N-[(1-[(benzyloxy)carbonyl]amino}cyclopropyl)carbonyl]-D-alaninate Methyl N-benzyl-D-alaninate instead of methyl N-benzyl-L-alaninate was reacted in the same way as in Step 1 of Reference Example 4 to give the title compound as a colorless oil.

¹H-NMR (400 MHz, CDCl₃) δ: 1.07 (2H, brs), 1.36 (3H, d, J=7.1 Hz), 1.43 (2H, brs), 3.61 (3H, s), 4.48-4.52 (1H, m), 4.61 (1H, d, J=17.4 Hz), 4.87 (1H, d, J=17.4 Hz), 4.98 (2H, s), 5.12 (1H, brs), 7.20-7.32 (10H, m).

MS (ESI) m/z: 411 [(M+H)⁺].

Step 2: (6R)-7-benzyl-6-methyl-4,7-diazaspiro[2.5]octane-5,8-dione

The compound obtained in Step 1 above was reacted in the same way as in Step 2 of Reference Example 2 to give the title compound as a colorless oil.

¹H-NMR (400 MHz, CDCl₃) δ: 0.97-1.03 (2H, m), 1.34-1.41 (2H, m), 1.47 (3H, d, J=7.1 Hz), 1.81-1.88 (1H, m), 4.06 (1H, d, J=14.9 Hz), 5.19 (1H, d, J=14.9 Hz), 6.74 (1H, brs), 7.25-7.37 (5H, m).

Step 3: (6R)-7-benzyl-6-methyl-4,7-diazaspiro[2.5]octane

The compound obtained in Step 2 above was reacted in the same way as in Step 3 of Reference Example 2 to give the title compound as a colorless solid.

¹H-NMR (400 MHz, CDCl₃) δ: 0.30-0.40 (2H, m), 0.48-0.61 (2H, m), 1.16 (3H, d, J=6.3 Hz), 1.58 (1H, brs), 2.12 (1H, d, J=11.5 Hz), 2.25-2.33 (2H, m), 2.73 (1H, dd, J=13.1, 9.3 Hz), 2.90 (1H, dd, J=13.1, 3.0 Hz), 3.15 (1H, d, J=13.4 Hz), 4.08 (1H, d, J=13.4 Hz), 7.20-7.33 (5H, m).

Step 4: (6R)-7-benzyl-6-methyl-4-(trifluoroacetyl)-4,7-diazaspiro[2.5]octane

The compound obtained in Step 3 above was reacted in the same way as in Step 4 of Reference Example 2 to give the title compound as a colorless oil.
$^1$H-NMR (400 MHz, CDCl$_3$) δ: 0.64-0.92 (3H, m), 1.20 (3H, d, J=6.1 Hz), 1.30-1.36 (1H, m), 2.16 (1H, d, J=12.0 Hz), 2.48 (1H, d, J=12.0 Hz), 2.58 (1H, brs), 3.15 (1H, d, J=13.4 Hz), 3.31 (1H, dd, J=13.4, 9.5 Hz), 3.76 (1H, d, J=13.4 Hz), 4.02 (1H, d, J=13.4 Hz), 7.23-7.33 (5H, m).

Step 5: (6R)-6-methyl-4-(trifluoroacetyl)-4,7-diazaspiro[2.5]octane hydrochloride The compound obtained in Step 4 above was reacted in the same way as in Step 5 of Reference Example 2 to give the title compound as a colorless solid.
$^1$H-NMR (400 MHz, DMSO-d$_6$, 70° C.) δ: 0.93 (1H, brs), 1.17 (1H, brs), 1.24-1.30 (1H, m), 1.34 (3H, d, J=6.3 Hz), 1.40 (1H, brs), 2.89 (1H, d, J=12.0 Hz), 3.14 (1H, brs), 3.40-3.46 (2H, m), 4.04 (1H, brs), 9.84 (2H, brs).
MS (ESI) m/z: 223 [(M+H)$^+$].

Reference Example 7

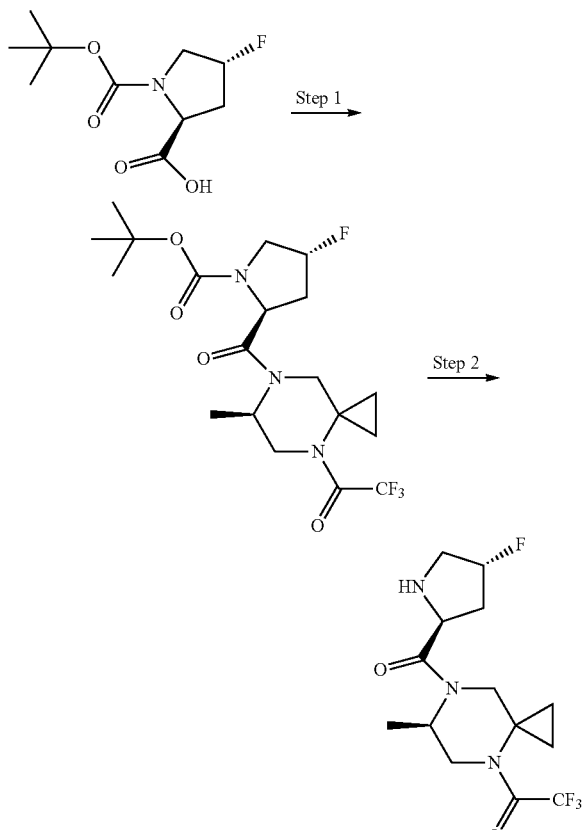

Step 1: tert-butyl (2S,4R)-4-fluoro-2-{[(6R)-6-methyl-4-(trifluoroacetyl)-4,7-diazaspiro[2.5]oct-7-yl]carbonyl}pyrrolidine-1-carboxylate The compound obtained in Step 5 of Reference Example 6 instead of the compound obtained in Step 5 of Reference Example 2 was reacted in the same way as in Step 1 of Reference Example 3 to give the title compound as a colorless solid.
$^1$H-NMR (400 MHz, DMSO-d$_6$, 100° C.) δ: 0.68-0.71 (2H, m), 1.09 (3H, brs), 1.28-1.31 (2H, m), 1.36 (9H, s), 1.47 (1H, m), 1.95 (1H, brs), 3.46-3.68 (5H, m), 3.91 (1H, brs), 4.69-4.71 (2H, m), 5.23 (1H, d, J=54.6 Hz).

Step 2: (6R)-7-[(4R)-4-fluoro-L-prolyl]-6-methyl-4-(trifluoroacetyl)-4,7-diazaspiro[2.5]octane The compound obtained in Step 1 above was reacted in the same way as in Step 2 of Reference Example 3 to give the title compound as a pale yellow oil.
$^1$H-NMR (400 MHz, DMSO-d$_6$, 100° C.) δ: 0.67-0.73 (1H, m), 0.86 (1H, brs), 1.12 (3H, d, J=5.9 Hz), 1.28 (1H, dt, J=12.4, 5.0 Hz), 1.49 (1H, dt, J=12.4, 5.2 Hz), 1.94-2.22 (2H, m), 2.65-2.68 (1H, m), 3.13 (1H, ddd, J=32.5, 13.0, 4.2 Hz), 3.43-3.61 (3H, m), 3.92 (1H, brs), 4.04-4.06 (1H, m), 4.65 (1H, brs), 5.24 (1H, dt, J=55.6, 4.6 Hz).

Reference Example 8

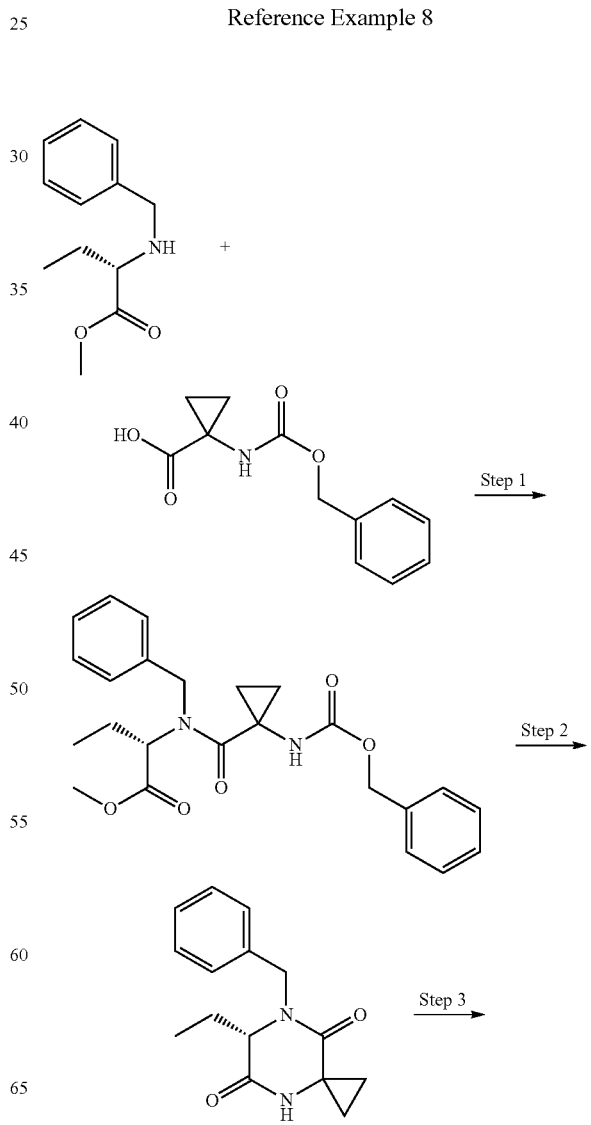

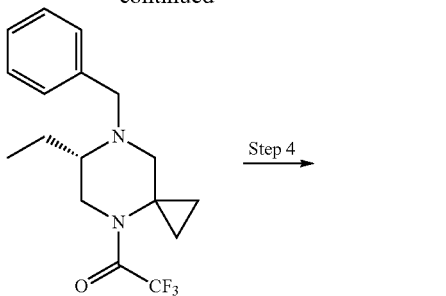

Step 1: methyl (2S)-2-{benzyl[(1-{[(benzyloxy)carbonyl]amino}cyclopropyl)carbonyl]amino}butanoate Methyl (2S)-2-(benzylamino)butanoate instead of methyl N-benzyl-L-alaninate was reacted in the same way as in Step 1 of Reference Example 4 to give the title compound as a colorless solid.
$^1$H-NMR (400 MHz, DMSO-$d_6$, 90° C.) δ: 0.70 (3H, t, J=7.4 Hz), 0.83-0.89 (1H, m), 1.00-1.06 (1H, m), 1.09-1.16 (1H, m), 1.30-1.37 (1H, m), 1.58-1.68 (1H, m), 1.83-1.92 (1H, m), 2.87-2.92 (1H, m), 3.48 (3H, s), 4.50-4.56 (1H, m), 4.64 (1H, d, J=15.9 Hz), 5.00 (2H, q, J=12.1 Hz), 7.17-7.33 (10H, m), 7.76 (1H, brs).
MS (ESI) m/z: 425 [(M+H)$^+$].

Step 2: (6S)-7-benzyl-6-ethyl-4,7-diazaspiro[2.5]octane-5,8-dione

The compound obtained in Step 1 above was reacted in the same way as in Step 2 of Reference Example 2 to give the title compound as a colorless solid.
$^1$H-NMR (400 MHz, CDCl$_3$) δ: 0.93-0.98 (2H, m), 0.99 (3H, t, J=7.4 Hz), 1.35-1.40 (1H, m), 1.79-1.86 (1H, m), 1.91-1.97 (2H, m), 3.90 (1H, t, J=5.4 Hz), 3.94 (1H, d, J=14.9 Hz), 5.35 (1H, d, J=14.9 Hz), 7.25-7.36 (5H, m), 7.39 (1H, brs).
MS (ESI) m/z: 259 [(M+H)$^+$].

Step 3: (6S)-7-benzyl-6-ethyl-4-(trifluoroacetyl)-4,7-diazaspiro[2.5]octane

The compound obtained in Step 2 above was reacted in the same way as in Step 3 of Reference Example 2 and then the compound obtained was reacted in the same way as in Step 4 of Reference Example 2 to give the title compound as a colorless oil.
$^1$H-NMR (400 MHz, DMSO-$d_6$, 90° C.) δ: 0.65-0.70 (1H, m), 0.85-0.90 (2H, m), 0.91 (3H, t, J=7.4 Hz), 1.18-1.23 (1H, m), 1.46-1.53 (1H, m), 1.66-1.75 (1H, m), 2.31-2.36 (1H, m), 2.38-2.45 (2H, m), 3.32 (1H, d, J=13.9 Hz), 3.40-3.47 (1H, m), 3.84 (1H, d, J=11.7 Hz), 3.97 (1H, d, J=13.9 Hz), 7.18-7.23 (1H, m), 7.27-7.31 (4H, m).
MS (ESI) m/z: 327 [(M+H)$^+$].

Step 4: (6S)-6-ethyl-4-(trifluoroacetyl)-4,7-diazaspiro[2.5]octane hydrochloride The compound obtained in Step 3 above was reacted in the same way as in Step 5 of Reference Example 2 to give the title compound as a colorless solid.
$^1$H-NMR (400 MHz, DMSO-$d_6$, 90° C.) δ: 0.89-0.94 (1H, m), 0.99 (3H, t, J=7.6 Hz), 1.16-1.21 (1H, m), 1.25-1.31 (1H, m), 1.41-1.48 (1H, m), 1.66-1.74 (1H, m), 1.77-1.85 (1H, m), 2.86 (1H, d, J=12.9 Hz), 3.24-3.32 (1H, m), 3.37-3.44 (1H, m), 3.45 (1H, d, J=12.9 Hz), 4.06-4.14 (1H, m).
MS (ESI) m/z: 237 [(M+H)$^+$].

Reference Example 9

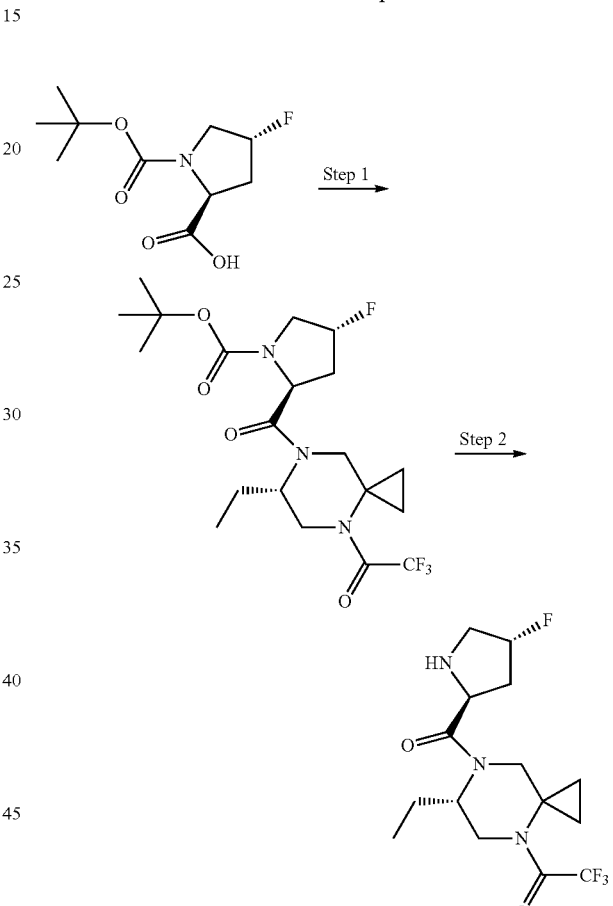

Step 1: tert-butyl (2S,4R)-2-{[(6S)-6-ethyl-4-(trifluoroacetyl)-4,7-diazaspiro[2.5]oct-7-yl]carbonyl}-4-fluoropyrrolidine-1-carboxylate 1-chloro-N,N,2-trimethyl-1-propenylamine (0.35 ml, 2.68 mmol) was added to a dichloromethane (8 ml) solution of (4R)-1-(tert-butoxycarbonyl)-4-fluoro-L-proline (520 mg, 2.23 mmol) under ice cooling. The resulting mixture was stirred at the same temperature for 1 hour, then the compound (730 mg, 2.68 mmol) obtained in Step 4 of Reference Example 8 and triethylamine (0.78 ml, 5.58 mmol) were added and the resulting mixture was further stirred at room temperature for 3 hours. The reaction mixture was diluted with chloroform and the organic layer was washed with saturated aqueous sodium bicarbonate solution and saturated brine and dried over anhydrous sodium sulfate. The solvent was evaporated under reduced pressure and the residue obtained was purified by silica gel column chromatography [n-hexane:ethyl acetate=2:1 (v/v)] to give the title compound (780 mg, 77%) as a colorless solid.

$^1$H-NMR (400 MHz, DMSO-d$_6$, 90° C.) δ: 0.67-0.73 (2H, m), 0.83-0.88 (3H, m), 1.29-1.33 (1H, m), 1.39 (9H, s), 1.45-1.52 (3H, m), 2.07-2.17 (1H, m), 2.43-2.47 (1H, m), 3.36-3.77 (6H, m), 4.40-4.55 (1H, m), 4.70-4.86 (1H, m), 5.30 (1H, d, J=54.9 Hz).

MS (ESI) m/z: 452 [(M+H)$^+$].

Step 2: (6S)-6-ethyl-7-[(4R)-4-fluoro-L-prolyl]-4-(trifluoroacetyl)-4,7-diazaspiro[2.5]octane The compound obtained in Step 1 above was reacted in the same way as in Step 2 of Reference Example 3 to give the title compound as a colorless solid.

$^1$H-NMR (400 MHz, DMSO-d$_6$, 90° C.) δ: 0.66-0.75 (2H, m), 0.83 (3H, t, J=7.2 Hz), 1.24-1.31 (1H, m), 1.43-1.53 (3H, m), 1.96-2.08 (1H, m), 2.16-2.32 (1H, m), 2.67-2.74 (1H, m), 2.91-2.99 (1H, m), 3.38-3.57 (4H, m), 4.05-4.16 (1H, m), 4.43-4.53 (1H, m), 5.24 (1H, d, J=56.1 Hz).

MS (ESI) m/z: 352 [(M+H)$^+$].

Reference Example 10

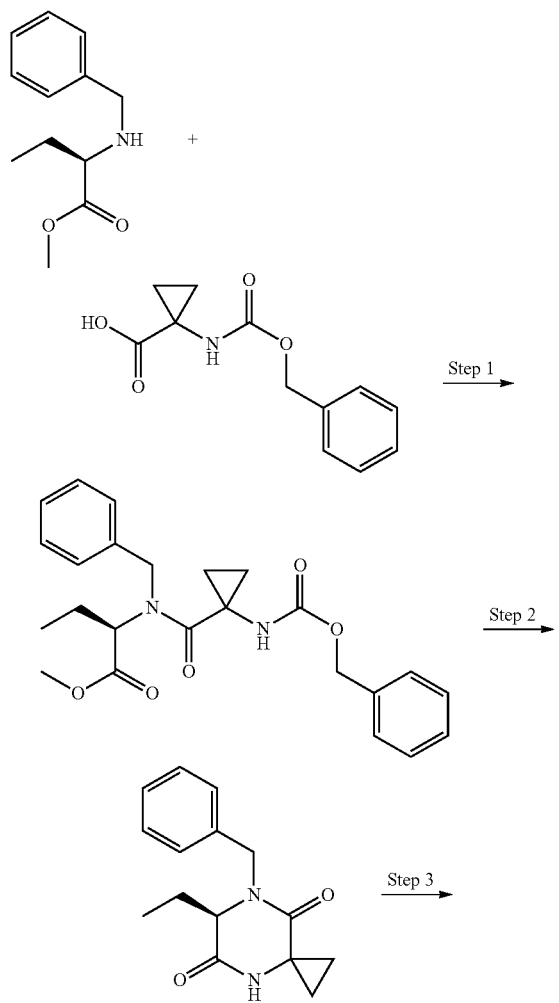

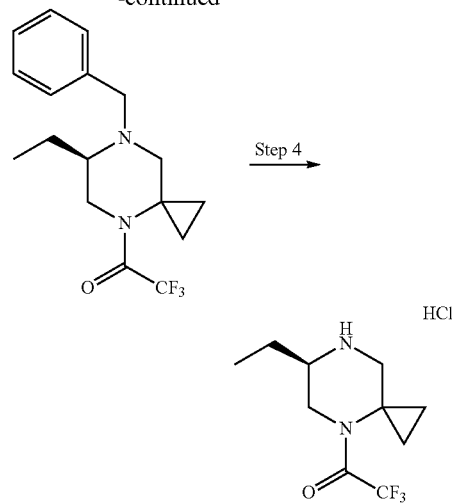

Step 1: methyl (2R)-2-{benzyl[(1-{[(benzyloxy)carbonyl]amino}cyclopropyl)carbonyl]amino}butanoate Methyl (2R)-2-(benzylamino)butanoate instead of methyl N-benzyl-L-alaninate was reacted in the same way as in Step 1 of Reference Example 4 to give the title compound as a pale yellow solid.

$^1$H-NMR (400 MHz, DMSO-d$_6$, 90° C.) δ: 0.71 (3H, t, J=7.4 Hz), 0.85-0.90 (1H, m), 1.02-1.08 (1H, m), 1.11-1.16 (1H, m), 1.32-1.38 (1H, m), 1.59-1.68 (1H, m), 1.84-1.93 (1H, m), 3.49 (3H, s), 4.30-4.38 (1H, m), 4.49-4.57 (1H, m), 4.65 (1H, d, J=16.1 Hz), 5.01 (2H, q, J=12.2 Hz), 7.18-7.34 (10H, m), 7.77 (1H, brs).

MS (ESI) m/z: 425 [(M+H)$^+$].

Step 2: (6R)-7-benzyl-6-ethyl-4,7-diazaspiro[2.5]octane-5,8-dione

The compound obtained in Step 1 above was reacted in the same way as in Step 2 of Reference Example 2 to give the title compound as a colorless solid.

$^1$H-NMR (400 MHz, CDCl$_3$) δ: 0.93-0.98 (2H, m), 0.99 (3H, t, J=7.6 Hz), 1.35-1.40 (1H, m), 1.80-1.86 (1H, m), 1.91-1.98 (2H, m), 3.89 (1H, t, J=5.2 Hz), 3.94 (1H, d, J=14.9 Hz), 5.35 (1H, d, J=14.9 Hz), 7.25-7.35 (5H, m), 7.51 (1H, brs).

MS (ESI) m/z: 259 [(M+1)$^+$].

Step 3: (6R)-7-benzyl-6-ethyl-4-(trifluoroacetyl)-4,7-diazaspiro[2.5]octane

The compound obtained in Step 2 above was reacted in the same way as in Step 3 of Reference Example 2 and then the compound obtained was reacted in the same way as in Step 4 of Reference Example 2 to give the title compound as a colorless oil.

$^1$H-NMR (400 MHz, DMSO-d$_6$, 90° C.) δ: 0.65-0.70 (1H, m), 0.85-0.90 (2H, m), 0.91 (3H, t, J=7.4 Hz), 1.18-1.23 (1H, m), 1.46-1.53 (1H, m), 1.66-1.75 (1H, m), 2.31-2.36 (1H, m), 2.38-2.45 (2H, m), 3.32 (1H, d, J=13.9 Hz), 3.40-3.47 (1H, m), 3.84 (1H, d, J=11.7 Hz), 3.97 (1H, d, J=13.9 Hz), 7.18-7.23 (1H, m), 7.27-7.31 (4H, m).

MS (ESI) m/z: 327 [(M+H)$^+$].

Step 4: (6R)-6-ethyl-4-(trifluoroacetyl)-4,7-diazaspiro[2.5]octane hydrochloride The compound obtained in Step 3 above was reacted in the same way as in Step 5 of Reference Example 2 to give the title compound as a colorless solid.

$^1$H-NMR (400 MHz, DMSO-d$_6$, 70° C.) δ: 0.89-0.94 (1H, m), 0.99 (3H, t, J=7.6 Hz), 1.16-1.21 (1H, m), 1.25-1.31 (1H, m), 1.41-1.48 (1H, m), 1.66-1.74 (1H, m), 1.77-1.85 (1H, m), 2.86 (1H, d, J=12.9 Hz), 3.24-3.32 (1H, m), 3.37-3.44 (1H, m), 3.45 (1H, d, J=12.9 Hz), 4.06-4.14 (1H, m).

MS (ESI) m/z: 237 [(M+H)$^+$].

Reference Example 11

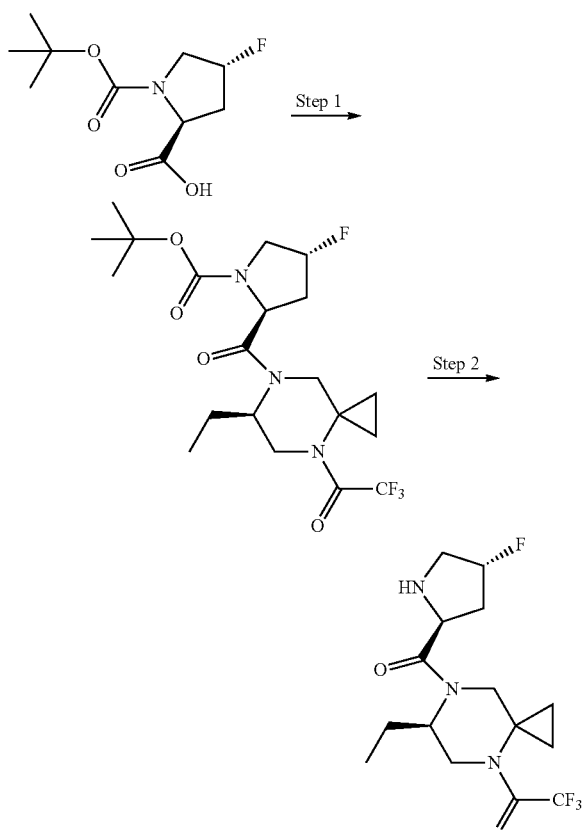

Step 1: tert-butyl (2S,4R)-2-{[(6R)-6-ethyl-4-(trifluoroacetyl)-4,7-diazaspiro[2.5]oct-7-yl]carbonyl}-4-fluoropyrrolidine-1-carboxylate The compound obtained in Step 4 of Reference Example 10 instead of the compound obtained in Step 4 of Reference Example 8 was reacted in the same way as in Step 1 of Reference Example 9 to give the title compound as a colorless solid.

$^1$H-NMR (400 MHz, DMSO-d$_6$, 100° C.) δ: 0.69-0.73 (1H, m), 0.76-0.84 (2H, m), 0.93-0.98 (1H, m), 1.30-1.38 (3H, m), 1.39 (9H, s), 1.44-1.51 (2H, m), 1.85-2.08 (2H, m), 3.25-3.61 (4H, m), 3.66-3.77 (1H, m), 4.00-4.07 (1H, m), 4.58-4.80 (2H, m), 5.25 (1H, d, J=51.3 Hz).

MS (ESI) m/z: 474 [(M+Na)$^+$].

Step 2: (6R)-6-ethyl-7-[(4R)-4-fluoro-L-prolyl]-4-(trifluoroacetyl)-4,7-diazaspiro[2.5]octane The compound obtained in Step 1 above was reacted in the same way as in Step 2 of Reference Example 3 to give the title compound as a pale yellow solid.

$^1$H-NMR (400 MHz, DMSO-d$_6$, 100° C.) δ: 0.65-0.72 (1H, m), 0.79-0.85 (3H, m), 1.24-1.32 (1H, m), 1.42-1.55 (4H, m), 1.89-2.05 (1H, m), 2.12-2.20 (1H, m), 2.64-2.69 (1H, m), 2.91 (1H, t, J=12.5 Hz), 3.07-3.20 (1H, m), 3.38-3.58 (3H, m), 3.97-4.09 (1H, m), 4.51-4.64 (1H, m), 5.23 (1H, d, J=55.7 Hz).

MS (ESI) m/z: 352 [(M+H)$^+$].

Reference Example 12

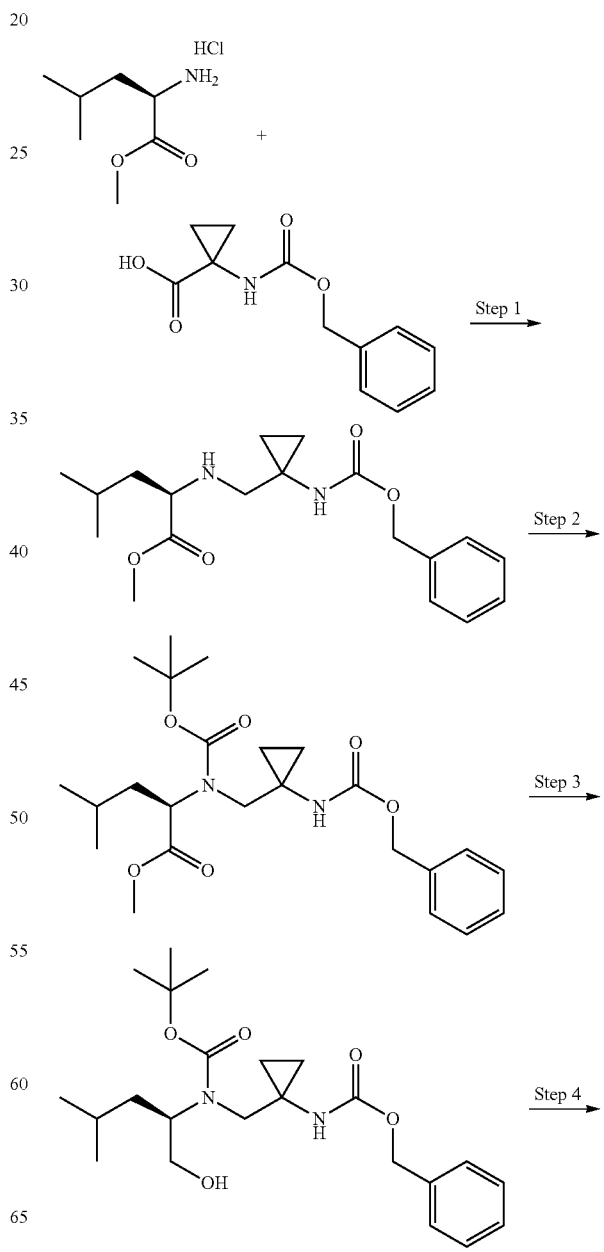

-continued

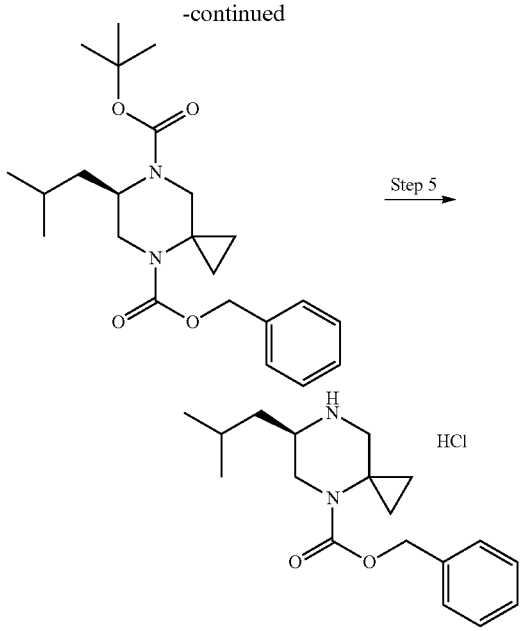

Step 1: methyl N-[(1-{[(benzyloxy)carbonyl]amino}cyclopropyl)methyl]-D-leucinate Methyl D-leucinate hydrochloride (2.73 g, 15.1 mmol), zinc chloride (2.8 g, 20.5 mmol), and sodium triacetoxyborohydride (9.16 g, 41.1 mmol) were added to a dichloromethane (200 ml) solution of benzyl (1-formylcyclopropyl)carbamate (3.0 g, 13.7 mmol) and the resulting mixture was stirred at room temperature for 18 hours. The reaction mixture was concentrated under reduced pressure, the residue obtained was diluted with ethyl acetate and washed with saturated aqueous sodium bicarbonate solution and saturated brine and then the organic layer was dried over anhydrous magnesium sulfate. The solvent was evaporated under reduced pressure and the residue obtained was purified by silica gel column chromatography [n-hexane:ethyl acetate=2:1 (v/v)] to give the title compound (2.24 g, 47%) as a pale yellow oil.

$^1$H-NMR (400 MHz, CDCl$_3$) δ: 0.62-0.94 (4H, m), 0.88 (3H, d, J=6.6 Hz), 0.91 (3H, d, J=6.6 Hz), 1.37-1.66 (2H, m), 1.70-1.77 (1H, m), 2.46 (1H, d, J=12.9 Hz), 2.82 (1H, d, J=12.9 Hz), 3.24 (1H, t, J=7.4 Hz), 3.68 (3H, s), 5.08 (1H, brs), 5.11 (2H, s), 7.22-7.42 (5H, m).

Step 2: methyl N-[(1-{[(benzyloxy)carbonyl]amino}cyclopropyl)methyl]-N-(tert-butoxycarbonyl)-D-leucinate The compound obtained in Step 1 above was reacted in the same way as in Step 2 of Reference Example 1 to give the title compound as a colorless oil.

$^1$H-NMR (400 MHz, CDCl$_3$) δ: 0.64-0.76 (1H, m), 0.78-0.97 (2H, m), 0.87 (3H, d, J=6.6 Hz), 0.90 (3H, d, J=6.6 Hz), 1.32-1.40 (1H, m), 1.41 (9H, s), 1.42-1.67 (1H, m), 1.72-1.89 (2H, m), 3.00-3.19 (1H, m), 3.39-3.72 (1H, m), 3.73 (3H, s), 3.74-4.18 (1H, m), 5.03 (1H, d, J=11.7 Hz), 5.13 (1H, d, J=11.7 Hz), 5.92-6.08 (1H, m), 7.25-7.41 (5H, m).

Step 3: benzyl[1-({(tert-butoxycarbonyl)[(1R)-1-(hydroxymethyl)-3-methylbutyl]amino}methyl)cyclopropyl]carbamate A tetrahydrofuran (30 ml) solution of the compound (1.95 g, 4.35 mmol) obtained in Step 2 above was added dropwise to a tetrahydrofuran (20 ml) suspension of lithium aluminum hydride (0.50 g, 12.2 mmol) under ice cooling and the resulting mixture was stirred at the same temperature for 1 hour. Water and 10% aqueous citric acid solution were added to terminate the reaction. Then, the reaction mixture was diluted with ethyl acetate, washed with saturated brine, and then dried over anhydrous magnesium sulfate. The solvent was evaporated under reduced pressure and the residue obtained was purified by silica gel column chromatography [n-hexane:ethyl acetate=2:3 (v/v)] to give the title compound (1.26 g, 64%) as a colorless oil.

$^1$H-NMR (400 MHz, CDCl$_3$) δ: 0.69-1.01 (10H, m), 1.35-1.43 (1H, m), 1.44 (9H, s), 1.45-1.53 (1H, m), 1.56-1.63 (2H, m), 3.09-4.00 (5H, m), 4.98-5.13 (2H, m), 5.60 (1H, brs), 7.24-7.38 (5H, m).

Step 4: 4-benzyl 7-tert-butyl (6R)-6-isobutyl-4,7-diazaspiro[2.5]octane-4,7-dicarboxylate Triphenylphosphine (1.57 g, 5.99 mmol) and diisopropyl azodicarboxylate (0.93 ml, 4.49 mmol) were added to a toluene (100 ml) solution of the compound (1.26 g, 3.00 mmol) obtained in Step 3 above under ice cooling and the resulting mixture was gradually returned to room temperature while being stirred for 18 hours. Further triphenylphosphine (1.57 g, 5.99 mmol) and diisopropyl azodicarboxylate (0.93 ml, 4.49 mmol) were added and the resulting mixture was heated to reflux for 4 hours. The reaction mixture was concentrated under reduced pressure and the residue obtained was purified by silica gel column chromatography [n-hexane:ethyl acetate=3:1 (v/v)] to give the title compound (0.57 g, 47%) as a colorless oil.

$^1$H-NMR (400 MHz, CDCl$_3$, 60° C.) δ: 0.45-0.54 (1H, m), 0.61-0.71 (1H, m), 0.85 (3H, d, J=6.6 Hz), 0.86 (3H, d, J=6.6 Hz), 0.96-1.05 (1H, m), 1.21-1.62 (13H, m), 3.11-3.26 (2H, m), 3.42 (1H, d, J=14.0 Hz), 3.99 (1H, d, J=14.0 Hz), 4.19 (1H, s), 5.12 (2H, s), 7.23-7.39 (5H, m).

Step 5: benzyl (6R)-6-isobutyl-4,7-diazaspiro[2.5]octane-4-carboxylate hydrochloride 4 N hydrochloric acid/dioxane (8 ml) was added to a dioxane (10 ml) solution of the compound (0.57 g, 1.42 mmol) obtained in Step 4 above under ice cooling and the resulting mixture was gradually returned to room temperature while being stirred for 24 hours. The reaction mixture was concentrated under reduced pressure to give the title compound as a colorless solid.

Reference Example 13

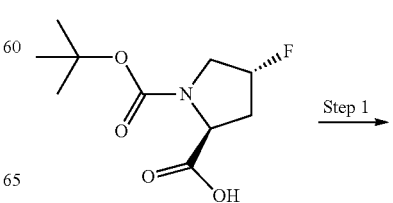

-continued

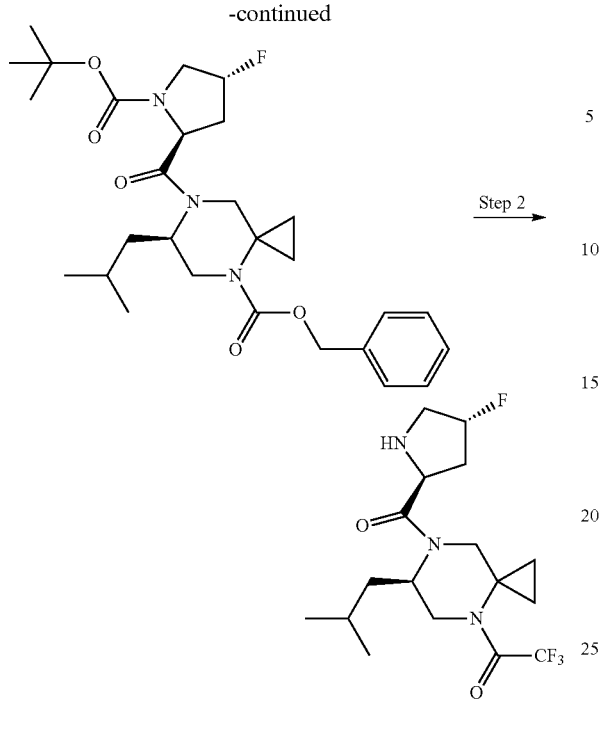

Step 1: benzyl (6R)-7-{[(2S,4R)-1-(tert-butoxycarbonyl)-4-fluoropyrrolidin-2-yl]carbonyl}-6-isobutyl-4,7-diazaspiro[2.5]octane-4-carboxylate The compound obtained in Step 5 of Reference Example 12 instead of the compound obtained in Step 4 of Reference Example 8 was reacted in the same way as in Step 1 of Reference Example 9 to give the title compound as a pale yellow oil.

$^1$H-NMR (400 MHz, DMSO-d$_6$, 100° C.) δ: 0.44-0.59 (1H, m), 0.76-0.96 (7H, m), 1.04-1.58 (15H, m), 1.65-2.23 (1H, m), 2.86-3.09 (2H, m), 3.17 (1H, d, J=11.2 Hz), 3.34-3.80 (3H, m), 4.01 (1H, d, J=13.2 Hz), 4.45-4.82 (1H, m), 5.03-5.39 (1H, m), 5.11 (2H, s), 7.28-7.45 (5H, m).

Step 2: tert-butyl (2S,4R)-4-fluoro-2-{[(6R)-6-isobutyl-4-(trifluoroacetyl)-4,7-diazaspiro[2.5]oct-7-yl]carbonyl}pyrrolidine-1-carboxylate 5% palladium carbon (0.10 g) was added to an ethanol (20 ml) solution of the compound (0.65 g, 1.25 mmol) obtained in Step 1 above and the resulting mixture was subjected to catalytic reduction at room temperature for 18 hours in a hydrogen atmosphere. The catalyst was removed by filtration through celite and then the filtrate was concentrated under reduced pressure. The residue obtained was dissolved in dichloromethane (20 ml), diisopropylamine (1.3 ml, 7.52 mmol) was added and trifluoroacetic anhydride (0.53 ml, 3.76 mmol) was added under ice cooling. The resulting mixture was gradually returned to room temperature while being stirred for 2 hours and the reaction mixture was concentrated under reduced pressure. The residue obtained was diluted with ethyl acetate and washed with saturated aqueous sodium bicarbonate solution, 10% aqueous citric acid solution, and saturated brine and then the organic layer was dried over anhydrous magnesium sulfate. The solvent was evaporated under reduced pressure, the residue obtained was dissolved in dichloromethane (20 ml), trifluoroacetic acid (10 ml) was added under ice cooling and the resulting mixture was stirred at room temperature for 2 hours. The reaction mixture was concentrated under reduced pressure, then the residue obtained was diluted with chloroform and washed with saturated aqueous sodium bicarbonate solution and saturated brine and then the organic layer was dried over anhydrous magnesium sulfate. The solvent was evaporated under reduced pressure and the residue obtained was purified by silica gel column chromatography [ethyl acetate:ethanol=4:1 (v/v)] to give the title compound (0.28 g, 59%) as a pale yellow oil.

MS (ESI) m/z: 380 [(M+H)$^+$].

Reference Example 14

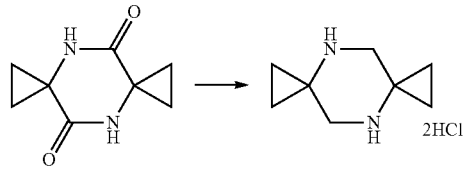 [SMILES: O=C1NC2(CC2)C(=O)NC12CC2 ; C1CC12CNC1(CC1)CN2]

4,9-diazadispiro[2.2.2.2]decane dihydrochloride

A borane-tetrahydrofuran complex (1.02 M tetrahydrofuran solution) (41 ml, 41.6 mmol) was added dropwise to a tetrahydrofuran (20 ml) solution of 4,9-diazadispiro[2.2.2.2]decane-5,10-dione (1.70 g, 10.4 mmol) under ice cooling and then the resulting mixture was heated to reflux for 18.5 hours. Methanol (50 ml) was added to the reaction mixture under ice cooling, the resulting mixture was stirred for 60 minutes and then the solvent was concentrated under reduced pressure. Ethanol (50 ml), water (25 ml), and triethylamine (25 ml) were added to the residue obtained, the resulting mixture was heated to reflux for 4 hours and then the solvent was concentrated under reduced pressure. The residue obtained was dissolved in tetrahydrofuran (20 ml), triethylamine (4.3 ml, 31.2 mmol) and di-tert-butyl dicarbonate (6.80 g, 31.2 mmol) were added under ice cooling and the resulting mixture was stirred at room temperature for 14 hours. The solvent was concentrated under reduced pressure and the residue obtained was diluted with ethyl acetate, washed with aqueous solution of saturated ammonium chloride and saturated brine, and then dried over anhydrous sodium sulfate. The solvent was evaporated under reduced pressure, trifluoroacetic acid (20 ml) was added to a chloroform (20 ml) solution of the residue obtained and the resulting mixture was stirred at room temperature for 1 hour. The solvent was concentrated under reduced pressure, 4 N hydrochloric acid/dioxane (50 ml) was added to the residue obtained and the resulting mixture was stirred for 2 hours. The solvent was evaporated under reduced pressure, diethyl ether was added to the residue and the deposited solid was collected by filtration to give the title compound (2.00 g, 91%) as a colorless solid.

$^1$H-NMR (400 MHz, DMSO-d$_6$) δ: 1.02 (4H, t, J=6.5 Hz), 1.24 (4H, t, J=6.3 Hz), 3.41 (4H, s), 10.30 (2H, s).

MS (ESI) m/z: 212 [(M+H)$^+$].

Reference Example 15

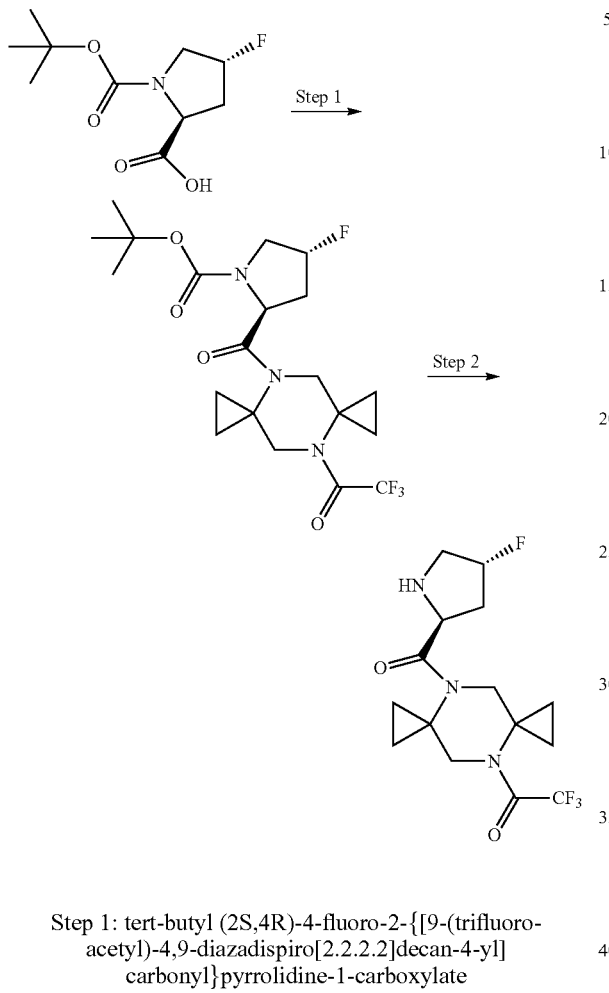

Step 1: tert-butyl (2S,4R)-4-fluoro-2-{[9-(trifluoro-acetyl)-4,9-diazadispiro[2.2.2.2]decan-4-yl]carbonyl}pyrrolidine-1-carboxylate Diisopropylethylamine (1.15 ml, 6.60 mmol) and (benzotriazol-1-yloxy)tripyrrolidinophosphonium hexafluorophosphate (1.14 g, 2.20 mmol) were added to a dimethylformamide (10 ml) solution of (4R)-1-(tert-butoxycarbonyl)-4-fluoro-L-proline (466 mg, 2.00 mmol) and the compound (422 mg, 2.00 mmol) obtained in Reference Example 14 under ice cooling. The resulting mixture was stirred at room temperature for 19 hours and then the reaction mixture was diluted with ethyl acetate, washed with an aqueous solution of saturated ammonium chloride, saturated aqueous sodium bicarbonate solution, and saturated brine, and then dried over anhydrous sodium sulfate. The solvent was evaporated under reduced pressure, then the residue obtained was dissolved in dichloromethane (10 ml) and triethylamine (0.56 ml, 4.00 mmol) was added. After ice cooling, trifluoroacetic anhydride (0.28 ml, 2.00 mmol) was added. The resulting mixture was stirred at room temperature for 7 hours and then the reaction mixture was concentrated under reduced pressure, diluted with ethyl acetate, washed with an aqueous solution of saturated ammonium chloride and saturated brine, and then dried over anhydrous sodium sulfate. The solvent was evaporated under reduced pressure and the residue was purified by silica gel column chromatography [n-hexane:ethyl acetate=1:1 (v/v)] to give the title compound (349 mg, 39%) as a pale yellow oil.

$^1$H-NMR (400 MHz, DMSO-d$_6$, 100° C.) δ: 1.15-1.33 (18H, m), 2.04 (1H, dt, J=35.5, 7.0 Hz), 2.53 (1H, s), 3.59-3.69 (5H, m), 4.97 (1H, s), 5.31 (1H, d, J=54.2 Hz).
MS (ESI) m/z: 472 [(M+Na)$^+$].

Step 2: 4-[(4R)-4-fluoro-L-prolyl]-9-(trifluoroacetyl)-4,9-diazadispiro[2.2.2.2]decane The compound obtained in Step 1 above was reacted in the same way as in Step 2 of Reference Example 3 to give the title compound as a pale yellow solid.

$^1$H-NMR (400 MHz, CDCl$_3$) δ: 1.08-1.23 (8H, m), 2.13 (1H, s), 2.63 (1H, s), 3.67-3.73 (5H, m), 5.16 (1H, s), 5.41 (1H, d, J=53.5 Hz), 5.91 (2H, s).
MS (ESI) m/z: 350 [(M+H)$^+$].

Reference Example 16

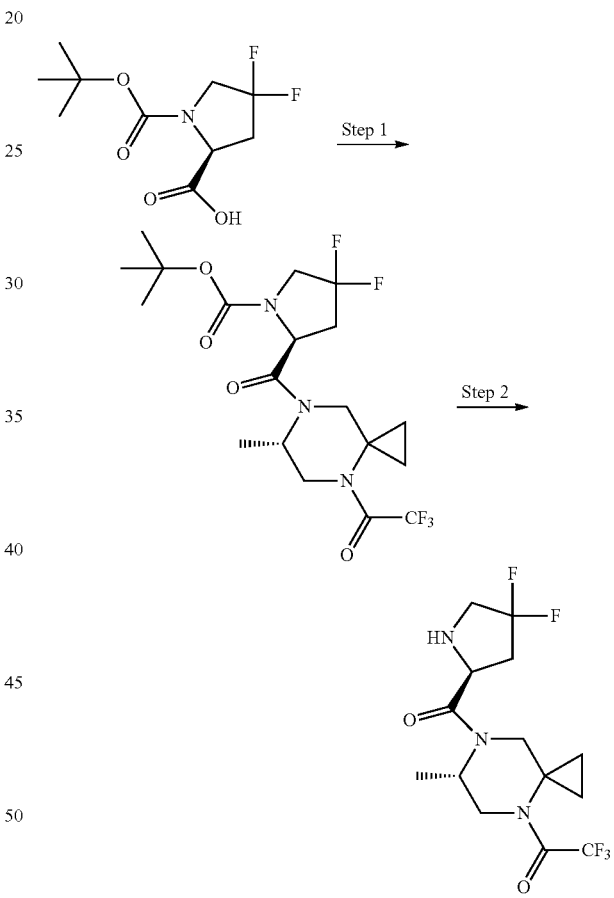

Step 1: tert-butyl (2S)-4,4-difluoro-2-{[(6S)-6-methyl-4-(trifluoroacetyl)-4,7-diazaspiro[2.5]oct-7-yl]carbonyl}pyrrolidine-1-carboxylate 1-(tert-butoxycarbonyl)-4,4-difluoro-L-proline instead of (4R)-1-(tert-butoxycarbonyl)-4-fluoro-L-proline and the compound obtained in Step 5 of Reference Example 4 instead of the compound obtained in Step 5 of Reference Example 2 were reacted in the same way as in Step 1 of Reference Example 3 to give the title compound as a colorless solid.

$^1$H-NMR (400 MHz, DMSO-d$_6$, 80° C.) δ: 0.72 (2H, brs), 1.11 (3H, brs), 1.25-1.29 (2H, m), 1.38 (9H, s), 1.48 (1H, brs), 2.21-2.33 (1H, m), 2.87 (1H, brs), 3.02-3.10 (2H, m), 3.54 (2H, brs), 3.65-3.75 (1H, m), 3.79-3.87 (1H, m), 4.64 (1H, brs).
MS (ESI) m/z: 456 [(M+H)$^+$].

Step 2: (6S)-7-(4,4-difluoro-L-prolyl)-6-methyl-4-(trifluoroacetyl)-4,7-diazaspiro[2.5]octane The compound obtained in Step 1 above was reacted in the same way as in Step 2 of Reference Example 3 to give the title compound as a colorless oil.
$^1$H-NMR (400 MHz, DMSO-d$_6$, 80° C.) δ: 0.70-0.74 (2H, m), 1.11 (3H, d, J=6.6 Hz), 1.23-1.29 (1H, m), 1.45-1.51 (1H, m), 2.32-2.45 (2H, m), 2.92-3.08 (2H, m), 3.16-3.26 (1H, m), 3.56 (3H, brs), 3.88 (1H, brs), 4.02-4.07 (1H, m), 4.64 (1H, brs).
MS (ESI) m/z: 356 [(M+H)$^+$].

Reference Example 17

$^1$H-NMR (400 MHz, DMSO-d$_6$, 100° C.) δ: 0.72 (2H, brs), 1.11 (3H, brs), 1.25-1.31 (2H, m), 1.38 (9H, s), 1.46-1.52 (2H, m), 2.07 (1H, brs), 2.82-2.92 (1H, m), 3.53 (2H, brs), 3.64-3.86 (3H, m), 4.82 (1H, brs).
MS (ESI) m/z: 478 [(M+Na)$^+$].

Step 2: (6R)-7-(4,4-difluoro-L-prolyl)-6-methyl-4-(trifluoroacetyl)-4,7-diazaspiro[2.5]octane The compound obtained in Step 1 above was reacted in the same way as in Step 2 of Reference Example 3 to give the title compound as a colorless oil.
$^1$H-NMR (400 MHz, DMSO-d$_6$, 100° C.) δ: 0.66-0.83 (2H, m), 1.10 (3H, d, J=6.5 Hz), 1.22-1.28 (1H, m), 1.44-1.51 (1H, m), 2.23-2.46 (2H, m), 2.92-3.01 (2H, m), 3.22-3.26 (1H, m), 3.43-3.60 (3H, m), 4.14 (1H, brs), 4.61 (1H, brs).
MS (ESI) m/z: 356 [(M+H)$^+$].

Reference Example 18

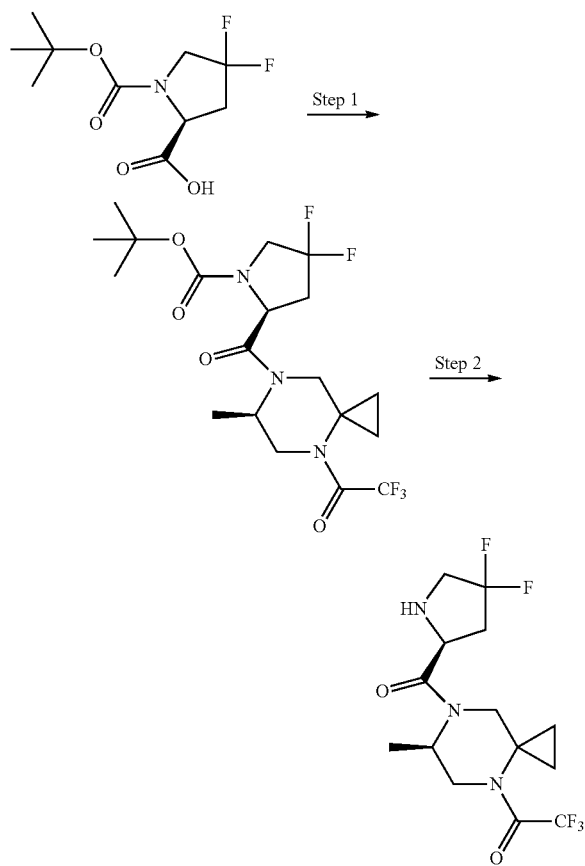

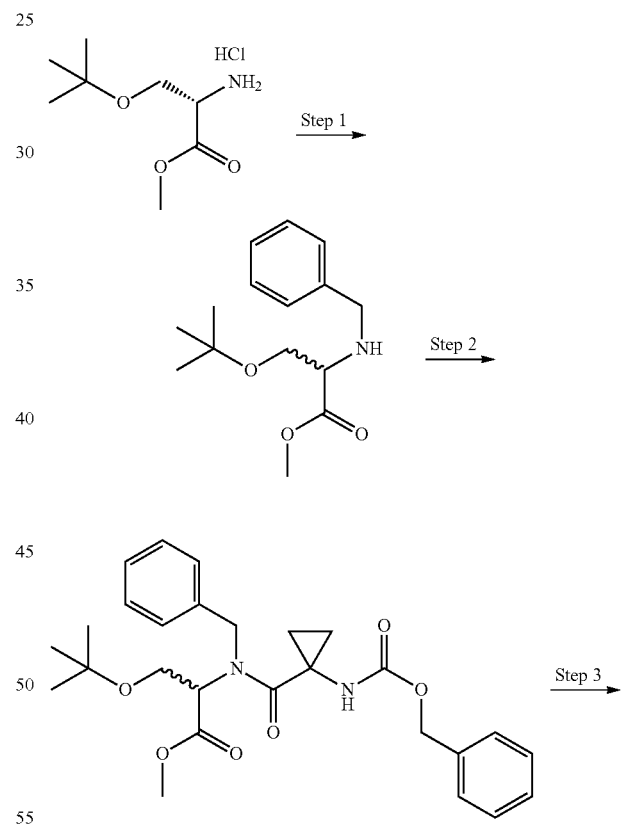

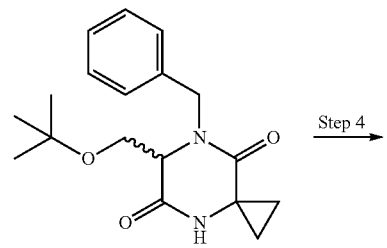

Step 1: tert-butyl (2S)-4,4-difluoro-2-{[(6R)-6-methyl-4-(trifluoroacetyl)-4,7-diazaspiro[2.5]-oct-7-yl]carbonyl}pyrrolidine-1-carboxylate 1-(tert-butoxycarbonyl)-4,4-difluoro-L-proline instead of (4R)-1-(tert-butoxycarbonyl)-4-fluoro-L-proline and the compound obtained in Step 5 of Reference Example 6 instead of the compound obtained in Step 5 of Reference Example 2 were reacted in the same way as in Step 1 of Reference Example 3 to give the title compound as a colorless solid.

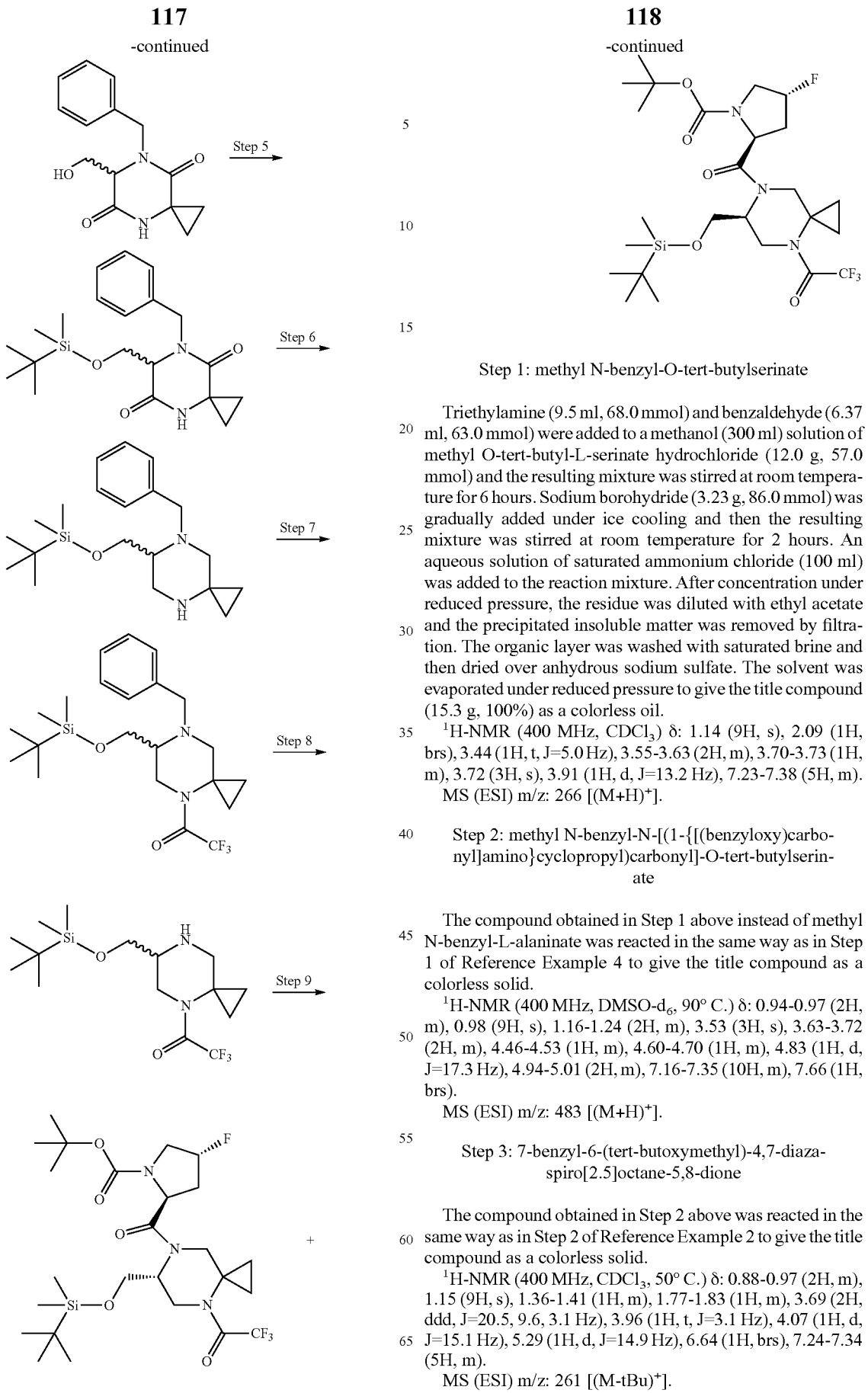

Step 1: methyl N-benzyl-O-tert-butylserinate

Triethylamine (9.5 ml, 68.0 mmol) and benzaldehyde (6.37 ml, 63.0 mmol) were added to a methanol (300 ml) solution of methyl O-tert-butyl-L-serinate hydrochloride (12.0 g, 57.0 mmol) and the resulting mixture was stirred at room temperature for 6 hours. Sodium borohydride (3.23 g, 86.0 mmol) was gradually added under ice cooling and then the resulting mixture was stirred at room temperature for 2 hours. An aqueous solution of saturated ammonium chloride (100 ml) was added to the reaction mixture. After concentration under reduced pressure, the residue was diluted with ethyl acetate and the precipitated insoluble matter was removed by filtration. The organic layer was washed with saturated brine and then dried over anhydrous sodium sulfate. The solvent was evaporated under reduced pressure to give the title compound (15.3 g, 100%) as a colorless oil.

$^1$H-NMR (400 MHz, CDCl$_3$) δ: 1.14 (9H, s), 2.09 (1H, brs), 3.44 (1H, t, J=5.0 Hz), 3.55-3.63 (2H, m), 3.70-3.73 (1H, m), 3.72 (3H, s), 3.91 (1H, d, J=13.2 Hz), 7.23-7.38 (5H, m).

MS (ESI) m/z: 266 [(M+H)$^+$].

Step 2: methyl N-benzyl-N-[(1-{[(benzyloxy)carbonyl]amino}cyclopropyl)carbonyl]-O-tert-butylserinate The compound obtained in Step 1 above instead of methyl N-benzyl-L-alaninate was reacted in the same way as in Step 1 of Reference Example 4 to give the title compound as a colorless solid.

$^1$H-NMR (400 MHz, DMSO-d$_6$, 90° C.) δ: 0.94-0.97 (2H, m), 0.98 (9H, s), 1.16-1.24 (2H, m), 3.53 (3H, s), 3.63-3.72 (2H, m), 4.46-4.53 (1H, m), 4.60-4.70 (1H, m), 4.83 (1H, d, J=17.3 Hz), 4.94-5.01 (2H, m), 7.16-7.35 (10H, m), 7.66 (1H, brs).

MS (ESI) m/z: 483 [(M+H)$^+$].

Step 3: 7-benzyl-6-(tert-butoxymethyl)-4,7-diazaspiro[2.5]octane-5,8-dione

The compound obtained in Step 2 above was reacted in the same way as in Step 2 of Reference Example 2 to give the title compound as a colorless solid.

$^1$H-NMR (400 MHz, CDCl$_3$, 50° C.) δ: 0.88-0.97 (2H, m), 1.15 (9H, s), 1.36-1.41 (1H, m), 1.77-1.83 (1H, m), 3.69 (2H, ddd, J=20.5, 9.6, 3.1 Hz), 3.96 (1H, t, J=3.1 Hz), 4.07 (1H, d, J=15.1 Hz), 5.29 (1H, d, J=14.9 Hz), 6.64 (1H, brs), 7.24-7.34 (5H, m).

MS (ESI) m/z: 261 [(M-tBu)$^+$].

Step 4: 7-benzyl-6-(hydroxymethyl)-4,7-diazaspiro[2.5]octane-5,8-dione

Trifluoroacetic acid (30 ml) was added to a chloroform (50 ml) solution of the compound (10.5 g, 33.0 mmol) obtained in Step 3 above and the resulting mixture was stirred at room temperature for 1 hour and then further stirred under heating at 40° C. for 6 hours. The solvent was concentrated under reduced pressure, then the reaction mixture was subjected to azeotropic distillation with toluene and the residue was diluted with ethyl acetate, then washed with saturated aqueous sodium bicarbonate solution and saturated brine, and dried over anhydrous magnesium sulfate. The solvent was evaporated under reduced pressure and the residue obtained was purified by silica gel column chromatography [chloroform:methanol=15:1 (v/v)] to give the title compound (7.15 g, 83%) as a colorless solid.

$^1$H-NMR (400 MHz, CDCl$_3$) δ: 0.96-1.06 (2H, m), 1.36-1.42 (1H, m), 1.74-1.80 (1H, m), 2.98-3.05 (1H, m), 3.91 (1H, s), 3.91-4.00 (1H, m), 4.11 (1H, d, J=15.1 Hz), 5.28 (1H, d, J=15.1 Hz), 7.25-7.42 (6H, m).

MS (ESI) m/z: 261 [(M+H)$^+$].

Step 5: 7-benzyl-6-({[tert-butyl(dimethyl)silyl]oxy}methyl)-4,7-diazaspiro[2.5]octane-5,8-dione 4-dimethylaminopyridine (660 mg, 5.00 mmol) and tert-butyldimethylchlorosilane (4.90 g, 32.0 mmol) were added to a dimethylformamide (100 ml) solution of the compound (7.15 g, 27.0 mmol) obtained in Step 4 above and triethylamine (4.5 ml, 32.0 mmol). The resulting mixture was stirred at room temperature for 16 hours, then ice water (200 ml) was added to the reaction mixture and the precipitated solid was collected by filtration. The solid obtained was purified by silica gel column chromatography [n-hexane:ethyl acetate=3:1 (v/v)] to give the title compound (8.63 g, 85%) as a colorless solid.

$^1$H-NMR (400 MHz, CDCl$_3$) δ: 0.04 (3H, s), 0.05 (3H, s), 0.89 (9H, s), 0.91-1.00 (2H, m), 1.40-1.46 (1H, m), 1.74-1.81 (1H, m), 3.90-3.94 (2H, m), 4.00 (1H, dd, J=11.1, 3.5 Hz), 4.08 (1H, d, J=15.1 Hz), 5.32 (1H, d, J=15.1 Hz), 7.25-7.38 (5H, m).

MS (ESI) m/z: 375 [(M+H)$^+$].

Step 6: 7-benzyl-6-({[tert-butyl(dimethyl)silyl]oxy}methyl)-4,7-diazaspiro[2.5]octane The compound obtained in Step 5 above was reacted in the same way as in Step 3 of Reference Example 2 to give the title compound as a colorless oil.

$^1$H-NMR (400 MHz, CDCl$_3$) δ: 0.05 (3H, s), 0.06 (3H, s), 0.31-0.38 (2H, m), 0.51-0.59 (2H, m), 0.89 (9H, s), 2.23 (1H, d, J=11.7 Hz), 2.30 (1H, d, J=11.7 Hz), 2.40-2.45 (1H, m), 2.81 (1H, dd, J=13.2, 8.3 Hz), 3.16 (1H, dd, J=13.2, 3.4 Hz), 3.34 (1H, d, J=13.9 Hz), 3.65 (1H, dd, J=10.4, 6.5 Hz), 3.96 (1H, dd, J=10.3, 4.4 Hz), 4.10 (1H, d, J=13.7 Hz), 7.21-7.37 (5H, m).

MS (ESI) m/z: 347 [(M+H)$^+$].

Step 7: 7-benzyl-6-({[tert-butyl(dimethyl)silyl]oxy}methyl)-4-(trifluoroacetyl)-4,7-diazaspiro[2.5]octane The compound obtained in Step 6 above was reacted in the same way as in Step 4 of Reference Example 2 to give the title compound as a pale yellow oil.

$^1$H-NMR (400 MHz, DMSO-d$_6$, 90° C.) δ: 0.00 (3H, s), 0.01 (3H, s), 0.61-0.68 (1H, m), 0.84 (9H, s), 0.85-0.90 (2H, m), 1.18-1.25 (1H, m), 2.28 (1H, d, J=11.7 Hz), 2.45-2.49 m), 2.54-2.58 (1H, m), 3.34-3.41 (2H, m), 3.50 (1H, dd, J=10.3, 7.8 Hz), 3.91 (1H, dd, J=11.5, 5.1 Hz), 3.95 (1H, d, J=14.2 Hz), 4.03 (1H, d, J=14.2 Hz), 7.16-7.20 (1H, m), 7.24-7.28 (4H, m).

MS (ESI) m/z: 443 [(M+H)$^+$].

Step 8: 6-({[tert-butyl(dimethyl)silyl]oxy}methyl)-4-(trifluoroacetyl)-4,7-diazaspiro[2.5]octane The compound obtained in Step 7 above was reacted in the same way as in Step 5 of Reference Example 2 to give the title compound as a colorless solid.

$^1$H-NMR (400 MHz, DMSO-d$_6$, 90° C.) δ: 0.08 (6H, s), 0.76-0.80 (1H, m), 0.90 (9H, s), 0.91-0.94 (1H, m), 1.10-1.16 (1H, m), 1.36-1.42 (1H, m), 2.54 (1H, d, J=12.9 Hz), 3.04-3.09 (1H, m), 3.22-3.29 (2H, m), 3.66 (1H, dd, J=10.4, 7.0 Hz), 3.74 (1H, dd, J=10.5, 4.9 Hz), 4.04-4.12 (1H, m).

MS (ESI) m/z: 353 [(M+H)$^+$].

Step 9: tert-butyl (2S,4R)-2-{[(6R)-6-({[tert-butyl(dimethyl)silyl]oxy}methyl)-4-(trifluoroacetyl)-4,7-diazaspiro[2.5]oct-7-yl]carbonyl}-4-fluoropyrrolidine-1-carboxylate (isomer A) and tert-butyl (2S,4R)-2-{[(6S)-6-({[tert-butyl(dimethyl)silyl]oxy}methyl)-4-(trifluoroacetyl)-4,7-diazaspiro[2.5]oct-7-yl]carbonyl}-4-fluoropyrrolidine-1-carboxylate (isomer B)

The compound obtained in Step 8 above instead of the compound obtained in Step 4 of Reference Example 8 was reacted in the same way as in Step 1 of Reference Example 9 and then the mixture of diastereomers obtained was resolved by silica gel column chromatography [n-hexane:ethyl acetate=3:1 (v/v)] to respectively give the title compounds as a colorless solid.

Isomer A: $^1$H-NMR (400 MHz, DMSO-d$_6$, 90° C.) δ: 0.00 (3H, s), 0.01 (3H, s), 0.68-0.76 (1H, m), 0.84 (9H, s), 0.85-0.87 (1H, m), 1.23-1.30 (1H, m), 1.35 (9H, s), 1.40-1.45 (1H, m), 1.99-2.16 (1H, m), 2.31-2.49 (1H, m), 3.33-3.77 (7H, m), 4.12-4.28 (1H, m), 4.34-4.48 (1H, m), 4.60-4.76 (1H, m), 5.26 (1H, d, J=52.7 Hz).

MS (ESI) m/z: 590 [(M+Na)$^+$].

Isomer B: $^1$H-NMR (400 MHz, DMSO-d$_6$, 90° C.) δ: −0.01 (3H, s), 0.01 (3H, s), 0.66-0.75 (1H, m), 0.83 (9H, s), 1.26-1.34 (3H, m), 1.35 (9H, s), 1.74-1.96 (2H, m), 3.27-3.73 (7H, m), 4.12-4.28 (1H, m), 4.38-4.52 (1H, m), 4.68-4.78 (1H, m), 5.20 (1H, d, J=55.2 Hz).

MS (ESI) m/z: 590 [(M+Na)$^+$].

Reference Example 19

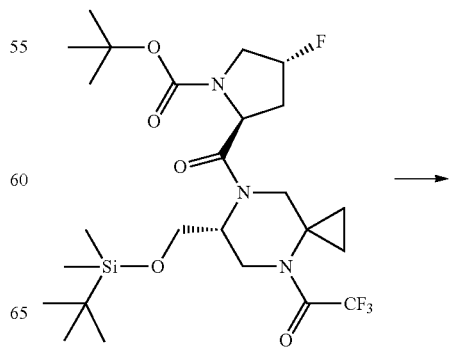

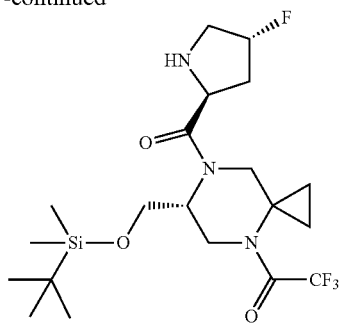

(6R)-6-({[tert-butyl(dimethyl)silyl]oxy}methyl)-7-[(4R)-4-fluoro-L-prolyl]-4-(trifluoroacetyl)-4,7-diazaspiro[2.5]octane The compound (isomer A) obtained in Step 9 of Reference Example 18 was reacted in the same way as in Step 2 of Reference Example 3 to give the title compound as a colorless solid.

$^1$H-NMR (400 MHz, DMSO-d$_6$, 90° C.) δ: 0.01 (6H, s), 0.66-0.79 (2H, m), 0.83 (9H, s), 1.20-1.31 (1H, m), 1.37-1.47 (1H, m), 1.92-2.07 (1H, m), 2.09-2.26 (1H, m), 2.80-2.92 (2H, m), 3.39-3.71 (6H, m), 3.98-4.18 (1H, m), 4.35-4.53 (1H, m), 5.22 (1H, d, J=55.4 Hz).

MS (ESI) m/z: 468 [(M+H)$^+$].

Reference Example 20

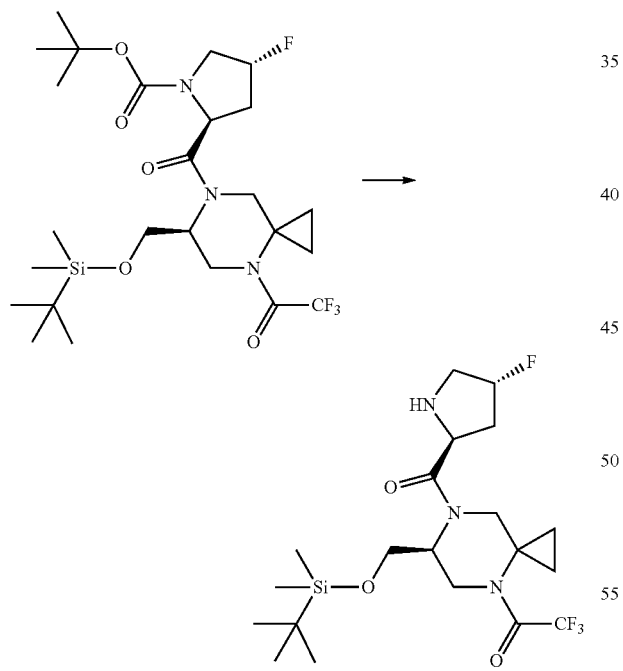

(6S)-6-({[tert-butyl(dimethyl)silyl]oxy}methyl)-7-[(4R)-4-fluoro-L-prolyl]-4-(trifluoroacetyl)-4,7-diazaspiro[2.5]octane The compound (isomer B) obtained in Step 9 of Reference Example 18 was reacted in the same way as in Step 2 of Reference Example 3 to give the title compound as a colorless solid.

$^1$H-NMR (400 MHz, DMSO-d$_6$, 90° C.) δ: 0.01 (6H, s), 0.67-0.73 (1H, m), 0.83 (9H, s), 1.20-1.28 (2H, m), 1.38-1.47 (1H, m), 1.89-2.15 (2H, m), 2.68-2.80 (1H, m), 2.85-2.92 (1H, m), 3.08-3.18 (1H, m), 3.39-3.72 (4H, m), 4.02-4.19 (2H, m), 4.39-4.53 (1H, m), 5.21 (1H, d, J=55.7 Hz).

MS (ESI) m/z: 468 [(M+H)$^+$].

Reference Example 21

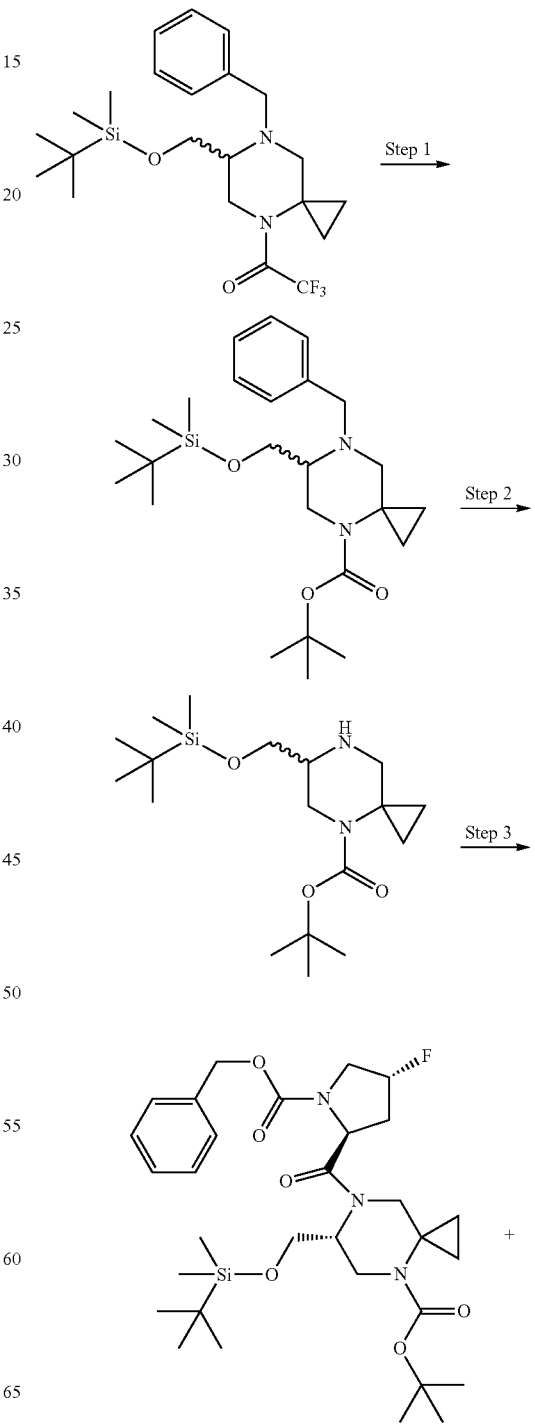

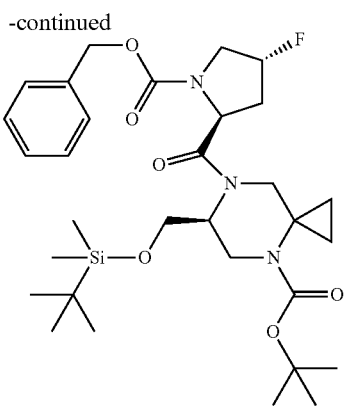

Step 1: tert-butyl 7-benzyl-6-({[tert-butyl(dimethyl)silyl]oxy}methyl)-4,7-diazaspiro[2.5]octane-4-carboxylate The compound obtained in Step 7 of Reference Example 18 was reacted in the same way as in Step 2 of Example 1 and then reacted in the same way as in Step 2 of Reference Example 1 to give the title compound as a colorless oil.

$^1$H-NMR (400 MHz, DMSO-$d_6$, 90° C.) δ: 0.00 (6H, s), 0.39-0.46 (1H, m), 0.60-0.70 (2H, m), 0.84 (9H, s), 0.97-1.02 (1H, m), 1.35 (9H, s), 2.16 (1H, d, J=11.7 Hz), 2.27 (1H, d, J=11.7 Hz), 3.08 (1H, dd, J=12.9, 8.3 Hz), 3.32 (1H, d, J=14.2 Hz), 3.49 (1H, dd, J=10.5, 6.6 Hz), 3.79-3.88 (2H, m), 3.95 (1H, d, J=14.2 Hz), 7.13-7.16 (1H, m), 7.21-7.27 (4H, m).

MS (ESI) m/z: 447 [(M+1)]$^+$.

Step 2: tert-butyl 6-({[tert-butyl(dimethyl)silyl]oxy}methyl)-4,7-diazaspiro[2.5]octane-4-carboxylate The compound obtained in Step 1 above was reacted in the same way as in Step 5 of Reference Example 2 to give the title compound as a pale yellow oil.

$^1$H-NMR (400 MHz, DMSO-$d_6$, 90° C.) δ: 0.06 (6H, s), 0.48-0.57 (2H, m), 0.78-0.83 (1H, m), 0.89 (9H, s), 1.14-1.20 (1H, m), 1.40 (9H, s), 2.16 (1H, d, J=12.5 Hz), 2.62-2.68 (1H, m), 2.75 (1H, dd, J=12.5, 10.0 Hz), 2.96 (1H, dd, J=12.5, 2.0 Hz), 3.47 (1H, dd, J=10.1, 6.2 Hz), 3.54 (1H, dd, J=10.0, 5.1 Hz), 3.87 (1H, dd, J=12.5, 2.9 Hz).

MS (ESI) m/z: 357 [(M+1)]$^+$.

Step 3: tert-butyl (6R)-7-({(2S,4R)-1-[(benzyloxy)carbonyl]-4-fluoropyrrolidin-2-ylcarbonyl)-6-({[tert-butyl(dimethyl)silyl]oxy}methyl)-4,7-diazaspiro[2.5]octane-4-carboxylate (isomer A) and tert-butyl (6S)-7-({(2S,4R)-1-[(benzyloxy)carbonyl]-4-fluoropyrrolidin-2-ylcarbonyl)-6-({[tert-butyl(dimethyl)silyl]oxy}methyl)-4,7-diazaspiro[2.5]octane-4-carboxylate (isomer B)

The compound obtained in Step 2 above instead of the compound obtained in Step 4 of Reference Example 8 was reacted in the same way as in Step 1 of Reference Example 9 and then the mixture of diastereomers obtained was resolved by silica gel column chromatography in the same way as in Step 9 of Reference Example 18 to give the title compounds respectively as colorless solids.

Isomer A: $^1$H-NMR (400 MHz, DMSO-$d_6$, 90° C.) δ: −0.06 (3H, brs), 0.00 (3H, s), 0.46-0.52 (1H, m), 0.82 (9H, s), 0.94-1.04 (1H, m), 1.15-1.28 (2H, m), 1.36 (9H, s), 1.92-2.12 (2H, m), 2.71-2.83 (1H, m), 3.21-3.29 (1H, m), 3.42-3.64 (4H, m), 3.69-3.78 (1H, m), 4.10-4.24 (1H, m), 4.57-5.12 (4H, m), 5.28 (1H, d, J=52.7 Hz), 7.24-7.33 (5H, m).

MS (ESI) m/z: 628 [(M+Na)]$^+$.

Isomer B: $^1$H-NMR (400 MHz, DMSO-$d_6$, 90° C.) δ: −0.01 (3H, s), 0.00 (3H, s), 0.74-0.79 (1H, m), 0.79-0.85 (1H, m), 0.82 (9H, s), 0.95-1.04 (1H, m), 1.22-1.30 (1H, m), 1.37 (9H, s), 1.80-2.01 (2H, m), 3.19-3.26 (1H, m), 3.34-3.60 (4H, m), 3.67-3.83 (2H, m), 3.98-4.13 (1H, m), 4.31-4.45 (1H, m), 4.78-4.84 (1H, m), 4.87-5.10 (2H, m), 5.21, 5.28 (1H, each d, J=55.2, 54.2 Hz), 7.23-7.34 (5H, m).

MS (ESI) m/z: 628 [(M+Na)]$^+$.

Reference Example 22

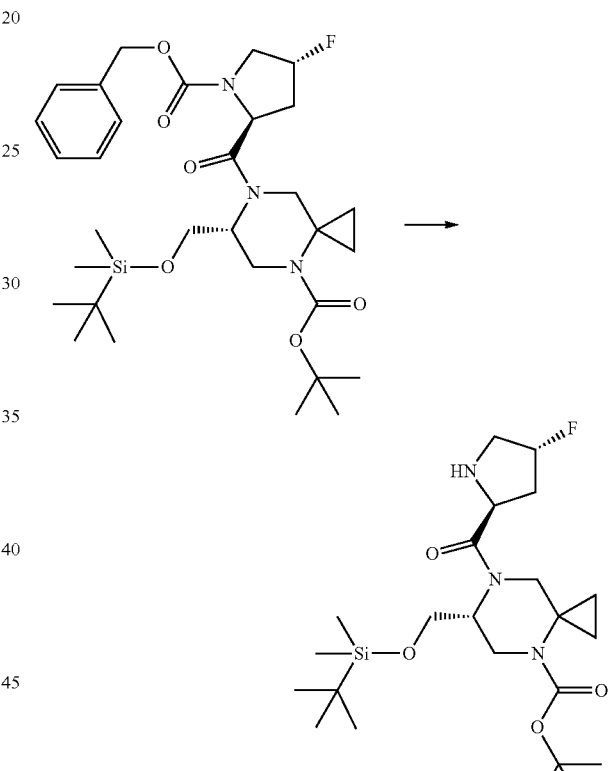

tert-butyl (6R)-6-({[tert-butyl(dimethyl)silyl]oxy}methyl)-7-[(4R)-4-fluoro-L-prolyl]-4,7-diazaspiro[2.5]octane-4-carboxylate The compound (isomer A) obtained in Step 3 of Reference Example 21 was reacted in the same way as in Step 5 of Reference Example 2 to give the title compound as a colorless solid.

$^1$H-NMR (400 MHz, DMSO-$d_6$, 90° C.) δ: 0.06 (6H, s), 0.49-0.59 (2H, m), 0.87 (9H, s), 1.07-1.14 (1H, m), 1.31-1.39 (1H, m), 1.42 (9H, s), 2.16-2.34 (2H, m), 3.00-3.43 (6H, m), 3.55-3.77 (2H, m), 3.95-4.17 (1H, m), 4.29-4.38 (1H, m), 5.37 (1H, d, J=54.4 Hz).

MS (ESI) m/z: 472 [(M+1)]$^+$.

125

Reference Example 23

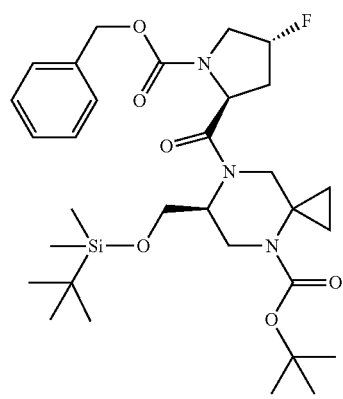

→

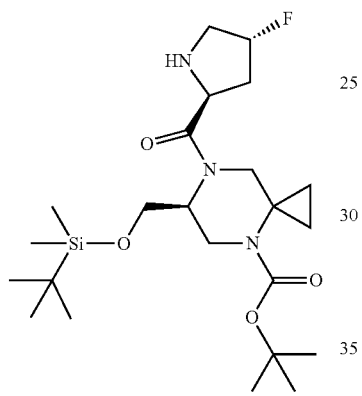

tert-butyl (6S)-6-({[tert-butyl(dimethyl)silyl]oxy}methyl)-7-[(4R)-4-fluoro-L-prolyl]-4,7-diazaspiro[2.5]octane-4-carboxylate The compound (isomer B) obtained in Step 3 of Reference Example 21 was reacted in the same way as in Step 5 of Reference Example 2 to give the title compound as a colorless solid.

$^1$H-NMR (400 MHz, DMSO-d$_6$, 90° C.) δ: 0.05 (6H, s), 0.51-0.58 (1H, m), 0.87 (9H, s), 1.07-1.16 (1H, m), 1.30-1.40 (2H, m), 1.43 (9H, s), 1.94-2.13 (2H, m), 3.03-3.20 (3H, m), 3.27-3.41 (1H, m), 3.45-3.56 (1H, m), 3.59-3.74 (1H, m), 3.90-4.11 (2H, m), 4.43-4.63 (2H, m), 5.39 (1H, d, J=53.5 Hz).

MS (ESI) m/z: 472 [(M+1)]$^+$.

Reference Example 24

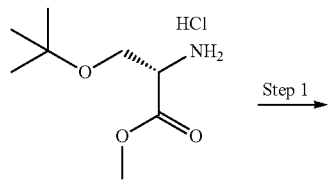 Step 1 →

126

-continued

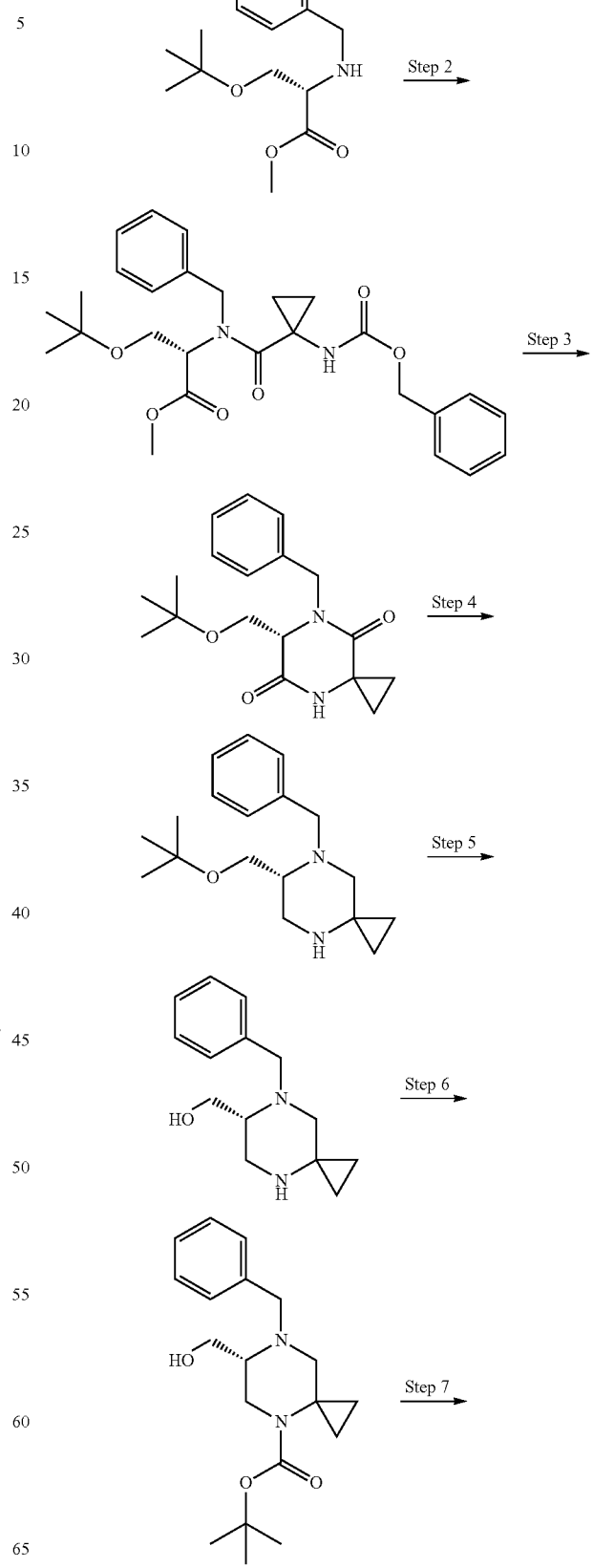

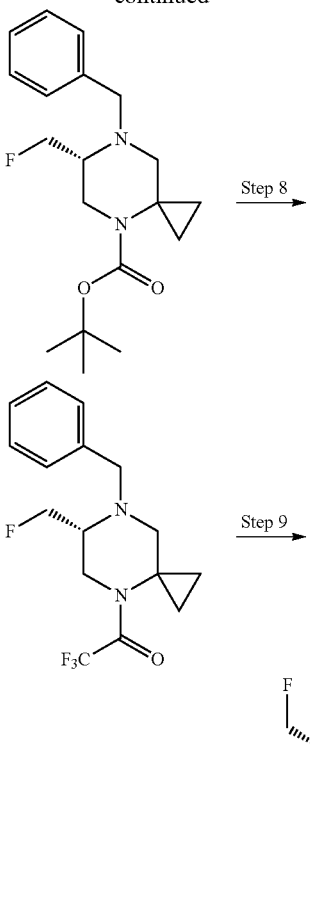

Step 1: methyl N-benzyl-O-tert-butyl-L-serinate

Methyl O-tert-butyl-L-serinate hydrochloride (12 g, 56.7 mmol) was dissolved in methanol (120 ml), acetic acid (6.50 ml, 114 mmol), benzaldehyde (6.25 ml, 61.8 mmol), and sodium cyanoborohydride (1 M tetrahydrofuran solution, 75 ml) were added and the resulting mixture was stirred at room temperature for 48 hours. The reaction mixture was concentrated, diluted with water, and neutralized with sodium bicarbonate under ice cooling, followed by extraction with chloroform. The organic layer was dried over anhydrous magnesium sulfate, then the drying agent was removed by filtration and the solvent was concentrated under reduced pressure. The residue obtained was purified by silica gel chromatography [ethyl acetate:n-hexane=1:4 (v/v)] to give the title compound (7.75 g, 52%) as a colorless solid.

$^1$H-NMR (400 MHz, CDCl$_3$) δ: 1.14 (9H, s), 2.09 (1H, brs), 3.44 (1H, t, J=5.0 Hz), 3.55-3.63 (2H, m), 3.70-3.73 (1H, m), 3.72 (3H, s), 3.91 (1H, d, J=13.2 Hz), 7.23-7.38 (5H, m).
MS (ESI) m/z: 266 [(M+1)]$^+$.

Step 2: methyl N-benzyl-N-[(1-{[(benzyloxy)carbonyl]amino}cyclopropyl)carbonyl]-O-tert-butyl-L-serinate The compound obtained in Step 1 above instead of methyl N-benzyl-L-alaninate was reacted in the same way as in Step 1 of Reference Example 4 to give the title compound as a colorless oil.

$^1$H-NMR (400 MHz, DMSO-d$_6$) δ: 0.94-0.98 (2H, m), 0.98 (9H, s), 1.16-1.24 (2H, m), 3.53 (3H, s), 3.63-3.72 (2H, m), 4.46-4.53 (1H, m), 4.60-4.70 (1H, m), 4.83 (1H, d, J=17.3 Hz), 4.94-5.01 (2H, m), 7.16-7.35 (10H, m), 7.66 (1H, brs).
MS (ESI) m/z: 483 [(M+1)]$^+$.

Step 3: (6S)-7-benzyl-6-(tert-butoxymethyl)-4,7-diazaspiro[2.5]octane-5,8-dione The compound obtained in Step 2 above was reacted in the same way as in Step 2 of Reference Example 2 to give the title compound as a colorless solid.

$^1$H-NMR (400 MHz, CDCl$_3$) δ: 0.88-0.97 (2H, m), 1.15 (9H, s), 1.36-1.41 (1H, m), 1.77-1.83 (1H, m), 3.69 (2H, ddd, J=20.5, 9.6, 3.1 Hz), 3.96 (1H, t, J=3.1 Hz), 4.07 (1H, d, J=15.1 Hz), 5.29 (1H, d, J=14.9 Hz), 6.64 (1H, brs), 7.24-7.34 (5H, m).
MS (ESI) m/z: 317 [(M+1)]$^+$.

Step 4: (6R)-7-benzyl-6-(tert-butoxymethyl)-4,7-diazaspiro[2.5]octane

The compound obtained in Step 3 above was reacted in the same way as in Step 3 of Reference Example 2 to give the title compound as a colorless solid.

$^1$H-NMR (400 MHz, CDCl$_3$) δ: 0.30-0.38 (2H, m), 0.48-0.59 (2H, m), 1.19 (9H, s), 1.62 (1H, br), 2.27 (2H, AB type d, J=11.9 Hz), 2.40-2.48 (1H, m), 2.80 (1H, dd, J=13.3, 8.2 Hz), 3.14 (1H, dd, J=7.3, 3.2 Hz), 3.34-3.41 (2H, m), 3.69 (1H, dd, J=9.3, 4.6 Hz), 4.12 (1H, d, J=13.7 Hz), 7.21-7.35 (5H, m).
MS (ESI) m/z: 289 [(M+1)]$^+$.

Step 5: [(6R)-7-benzyl-4,7-diazaspiro[2.5]oct-6-yl]methanol

The compound obtained in Step 4 above was reacted in the same way as in Step 4 of Reference Example 18 to give the title compound as a colorless solid.

$^1$H-NMR (400 MHz, CDCl$_3$) δ: 0.33-0.43 (2H, m), 0.52-0.61 (2H, m), 1.71 (1H, br), 2.36-2.45 (3H, m), 3.06 (2H, d, J=6.0 Hz), 3.36 (1H, d, J=13.7 Hz), 3.60 (1H, dd, J=11.0, 3.5 Hz), 3.95 (1H, dd, J=11.0, 4.5 Hz), 4.15 (1H, d, J=13.7 Hz), 7.24-7.32 (5H, m).
MS (ESI) m/z: 233 [(M+1)]$^+$.

Step 6: tert-butyl (6R)-7-benzyl-6-(hydroxymethyl)-4,7-diazaspiro[2.5]octane-4-carboxylate The compound obtained in Step 5 above was reacted in the same way as in Step 2 of Reference Example 1 to give the title compound as a colorless solid.

$^1$H-NMR (400 MHz, d$_6$-DMSO, 100° C.) δ: 0.44-0.49 (1H, m), 0.62-0.72 (2H, m), 1.00-1.05 (1H, m), 1.39 (9H, s), 2.18 (1H, d, J=11.7 Hz), 2.28 (1H, dd, J=11.7, 1.2 Hz), 2.41-2.46 (1H, m), 3.13 (1H, dd, J=13.2, 8.5 Hz), 3.34 (1H, d, J=14.0 Hz), 3.40-3.46 (1H, m), 3.66-3.72 (1H, m), 3.82 (1H, dd, J=13.2, 3.5 Hz), 4.02 (1H, d, J=14.0 Hz), 4.14 (1H, t, J=5.4 Hz), 7.16-7.30 (5H, m).
MS (ESI) m/z: 333 [(M+1)]$^+$.

Step 7: tert-butyl (6R)-7-benzyl-6-(fluoromethyl)-4,7-diazaspiro[2.5]octane-4-carboxylate A dichloromethane (8 ml) solution of the compound (360 mg, 1.08 mmol) obtained in Step 6 above was cooled to −78° C. Subsequently, bis(2-methoxyethyl)aminosulfur trifluoride (0.26 ml, 1.41 mmol) was added dropwise and the resulting mixture was gradually heated and stirred for 20 hours. The reaction mixture was neutralized with saturated aqueous sodium bicarbonate solution, followed by extraction with chloroform. The organic layer was dried over anhydrous sodium sulfate, then the drying agent was removed by filtration and the solvent was concentrated under reduced pressure. The residue obtained was purified by silica gel chromatography [ethyl acetate:n-hexane=1:10 (v/v)] to give the title compound (325 mg, 90%) as a colorless oil.

$^1$H-NMR (400 MHz, d$_6$-DMSO, 100° C.) δ: 0.60-0.67 (2H, m), 0.79-0.90 (2H, m), 1.40 (9H, s), 2.45 (1H, d, J=12.7 Hz), 2.64 (1H, d, J=12.7 Hz), 2.83-2.93 (2H, m), 3.35-3.45 (1H, m), 3.71 (2H, d, J=3.2 Hz), 3.72-3.79 (1H, m), 4.66-4.81 (1H, m), 7.19-7.31 (5H, m).

MS (ESI) m/z: 335 [(M+1)]$^+$.

Step 8: (6R)-7-benzyl-6-(fluoromethyl)-4-(trifluoroacetyl)-4,7-diazaspiro[2.5]octane The compound obtained in Step 7 above was reacted in the same way as in Step 5 of Reference Example 12 and then reacted in the same way as in Step 4 of Reference Example 2 to give the title compound as a colorless oil.

$^1$H-NMR (400 MHz, d$_6$-DMSO, 100° C.) δ: 0.84 (2H, brs), 0.92 (2H, br), 2.55, 2.76 (1H, each br), 2.94 (2H, s), 2.95-2.98 (1H, m), 3.72 (2H, s), 3.73-3.94 (2H, m), 4.74, 4.86 (1H, each br), 7.20-7.31 (5H, m).

Step 9: (6R)-6-(fluoromethyl)-4-(trifluoroacetyl)-4,7-diazaspiro[2.5]octane hydrochloride The compound obtained in Step 8 above was reacted in the same way as in Step 5 of Reference Example 2 to give the title compound as a colorless solid.

$^1$H-NMR (400 MHz, d$_6$-DMSO, 100° C.) δ: 1.06-1.11 (4H, m), 2.65-2.90 (3H, m), 3.37-3.65 (2H, m), 3.92 (1H, br), 5.21-5.34 (1H, m), 9.55 (2H, br).

MS (ESI) m/z: 241 [(M+1)]$^+$.

Reference Example 25

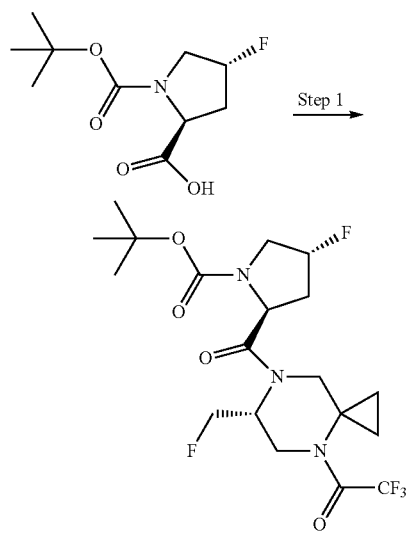

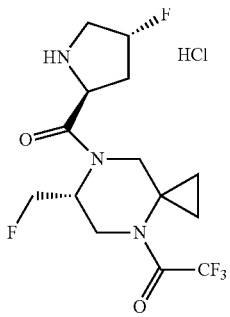

Step 1: tert-butyl (2S,4R)-4-fluoro-2-{[(6R)-6-(fluoromethyl)-4-(trifluoroacetyl)-4,7-diazaspiro[2.5]oct-7-yl]carbonyl}-4-fluoropyrrolidine-1-carboxylate The compound obtained in Step 9 of Reference Example 24 instead of the compound obtained in Step 4 of Reference Example 8 was reacted in the same way as in Step 1 of Reference Example 9 to give the title compound as a colorless solid.

MS (ESI) m/z: 456 [(M+1)]$^+$.

Step 2: (6R)-6-(fluoromethyl)-7-[(4R)-4-fluoro-L-prolyl]-4-(trifluoroacetyl)-4,7-diazaspiro[2.5]octane hydrochloride The compound obtained in Step 1 above was reacted in the same way as in Step 5 of Reference Example 12 to give the title compound as a colorless solid.

$^1$H-NMR (400 MHz, d$_6$-DMSO, 100° C.) δ: 1.07-1.11 (4H, m), 2.04-2.31 (1H, m), 2.65-2.73 (1H, m), 3.13-3.23 (2H, m), 3.43-3.58 (2H, m), 3.62-3.75 (2H, m), 4.20-4.37 (2H, m), 4.57-4.78 (1H, m), 4.92-4.98 (1H, m), 5.46 (1H, d, J=53.2 Hz), 9.77 (2H, br).

MS (ESI) m/z: 356 [(M+1)]$^+$.

Reference Example 26

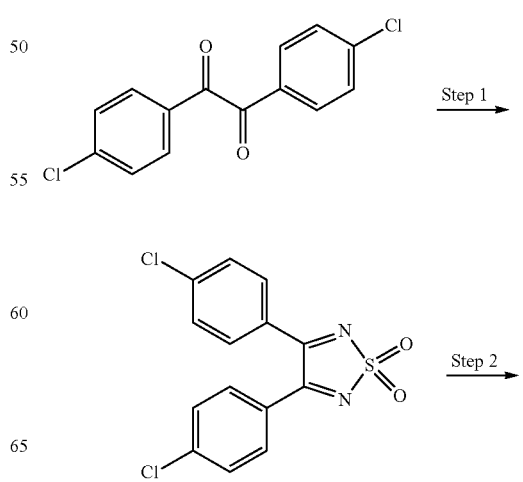

-continued

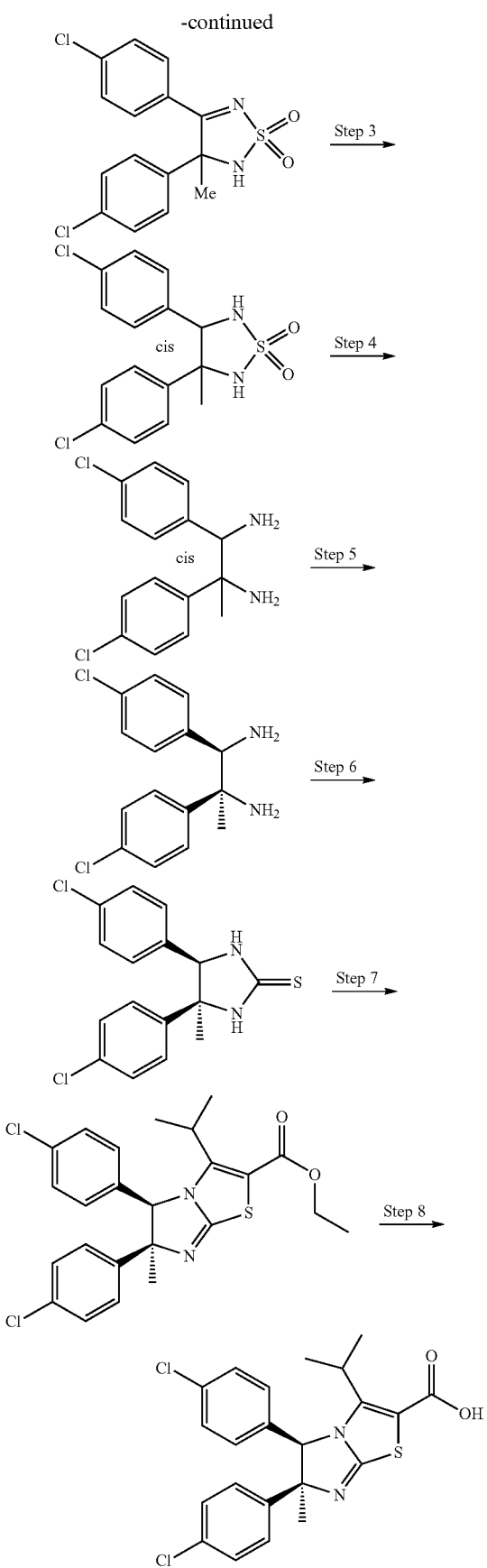

Step 1: 3,4-bis(4-chlorophenyl)-1,2,5-thiadiazole 1,1-dioxide 1,2-bis(4-chlorophenyl)ethane-1,2-dione was used as a starting material and reacted in the same way as in Step 7 of Reference Example 1 to give the title compound as a pale yellow solid.
$^1$H-NMR (400 MHz, CDCl$_3$) δ: 7.47 (4H, d, J=8.8 Hz), 7.53 (4H, d, J=8.8 Hz).

Step 2: 3,4-bis(4-chlorophenyl)-3-methyl-2,3-dihydro-1,2,5-thiadiazole 1,1-dioxide Methyl magnesium bromide (0.89 M tetrahydrofuran solution, 43.1 ml) was added dropwise to a toluene (200 ml) suspension of the compound (10.0 g, 29.5 mmol) obtained in Step 1 above at 0° C. The resulting mixture was stirred at room temperature for 1 hour and then 1 N aqueous hydrochloric acid solution was added, followed by extraction with ethyl acetate. Then, the organic layer was washed with saturated aqueous sodium bicarbonate solution and saturated brine and dried over anhydrous sodium sulfate and the solvent was evaporated under reduced pressure to give the title compound (11.1 g, quantitative) as a colorless oil.
$^1$H-NMR (400 MHz, CDCl$_3$) δ: 2.06 (3H, s), 4.70 (1H, s), 7.30-7.48 (6H, m), 7.63 (2H, d, J=9.0 Hz).

Step 3: (3S*,4R*)-3,4-bis(4-chlorophenyl)-3-methyl-1,2,5-thiadiazolidine 1,1-dioxide The compound obtained in Step 2 above was reacted in the same way as in Step 8 of Reference Example 1 to give the title compound as a colorless solid.
$^1$H-NMR (400 MHz, CDCl$_3$) δ: 1.85 (3H, s), 4.63 (1H, d, J=6.8 Hz), 4.72 (1H, s), 4.93 (1H, d, J=6.8 Hz), 6.77 (2H, d, J=8.5 Hz), 7.01 (2H, d, J=8.5 Hz), 7.17 (2H, d, J=8.5 Hz), 7.18 (2H, d, J=8.5 Hz).

Step 4: (1R*,2S*)-1,2-bis(4-chlorophenyl)propane-1,2-diamine

The compound obtained in Step 3 above was reacted in the same way as in Step 9 of Reference Example 1 to give the title compound as a colorless solid.
$^1$H-NMR (400 MHz, CDCl$_3$) δ: 1.49 (3H, s), 4.08 (1H, s), 6.98 (2H, d, J=8.5 Hz), 7.17 (2H, d, J=8.3 Hz), 7.25-7.28 (4H, m).

Step 5: (1R,2S)-1,2-bis(4-chlorophenyl)propane-1,2-diamine

The compound obtained in Step 4 above was optically resolved in the same way as in Step 10 of Reference Example 1 to give the title compound as a colorless solid.
[α]D=+69.2° (c.1.05, methanol, 23° C.)

Step 6: (4S,5R)-4,5-bis(4-chlorophenyl)-4-methylimidazolidine-2-thione

The compound obtained in Step 5 above was reacted in the same way as in Step 11 of Reference Example 1 to give the title compound as a colorless solid.
$^1$H-NMR (400 MHz, DMSO-d$_6$) δ: 1.71 (3H, s), 4.94 (1H, s), 6.89 (2H, dt, J=8.9, 2.1 Hz), 6.97 (2H, dt, J=8.9, 2.1 Hz), 7.17-7.12 (4H, m), 8.74 (1H, s), 8.92 (1H, s).

Step 7: ethyl (5R,6S)-5,6-bis(4-chlorophenyl)-3-isopropyl-6-methyl-5,6-dihydroimidazo[2,1-b][1,3]thiazole-2-carboxylate The compound obtained in Step 6 above was reacted in the same way as in Step 12 of Reference Example 1 to give the title compound as a colorless solid.

$^1$H-NMR (400 MHz, CDCl$_3$) δ: 1.03 (3H, d, J=7.0 Hz), 1.03 (3H, d, J=7.0 Hz), 1.37 (3H, t, J=7.1 Hz), 2.10 (3H, s), 3.28-3.47 (1H, m), 4.33 (2H, q, J=7.1 Hz), 5.57 (1H, s), 6.45-7.18 (8H, m).

Step 8: (5R,6S)-5,6-bis(4-chlorophenyl)-3-isopropyl-6-methyl-5,6-dihydroimidazo[2,1-b][1,3]thiazole-2-carboxylic acid The compound obtained in Step 7 above was reacted in the same way as in Step 13 of Reference Example 1 to give the title compound as a colorless solid.

$^1$H-NMR (400 MHz, DMSO-d$_6$) δ: 0.83 (3H, d, J=7.1 Hz), 0.93 (3H, d, J=7.1 Hz), 1.78 (3H, s), 2.99-3.67 (1H, m), 5.79 (1H, s), 6.44-7.43 (8H, m).

MS (ESI) m/z: 447 [(M+1)]$^+$.

Reference Example 27

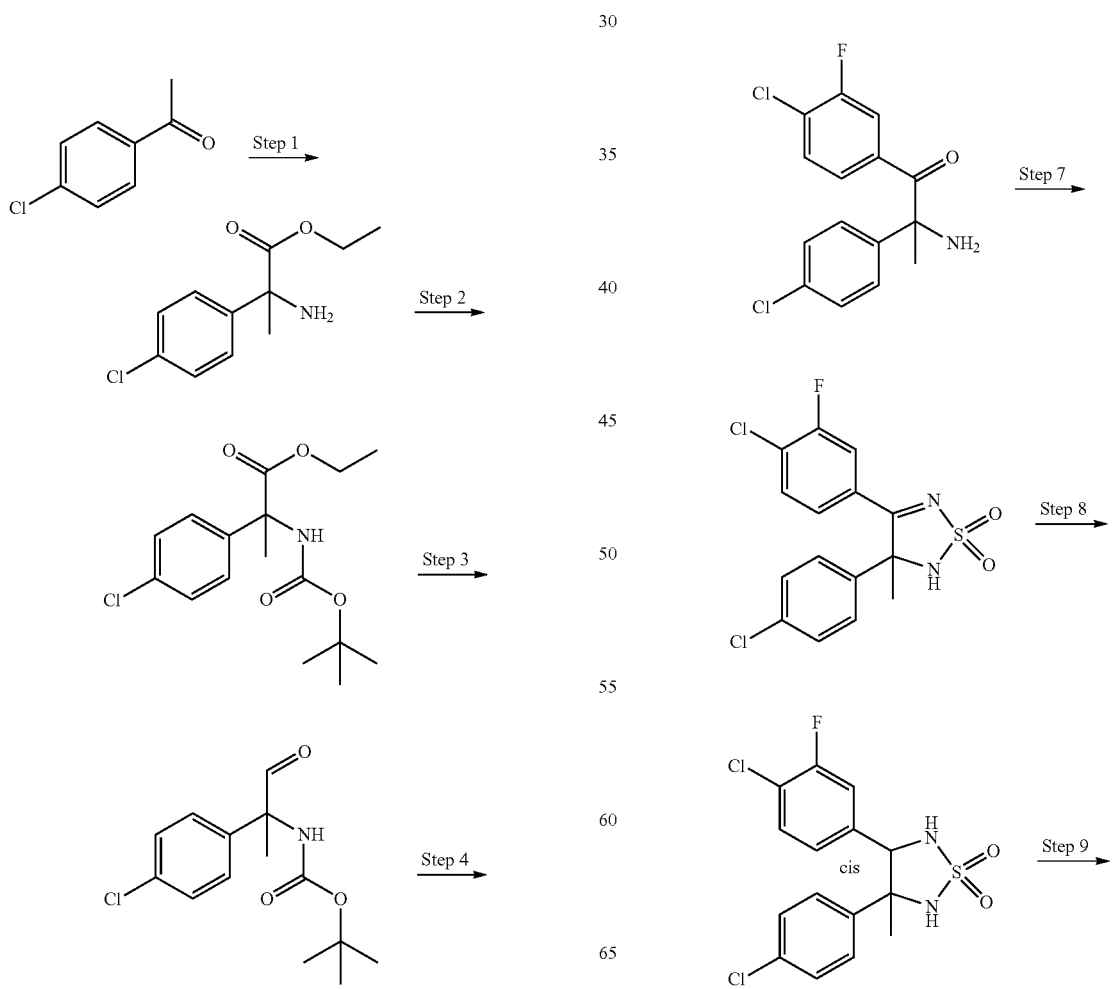

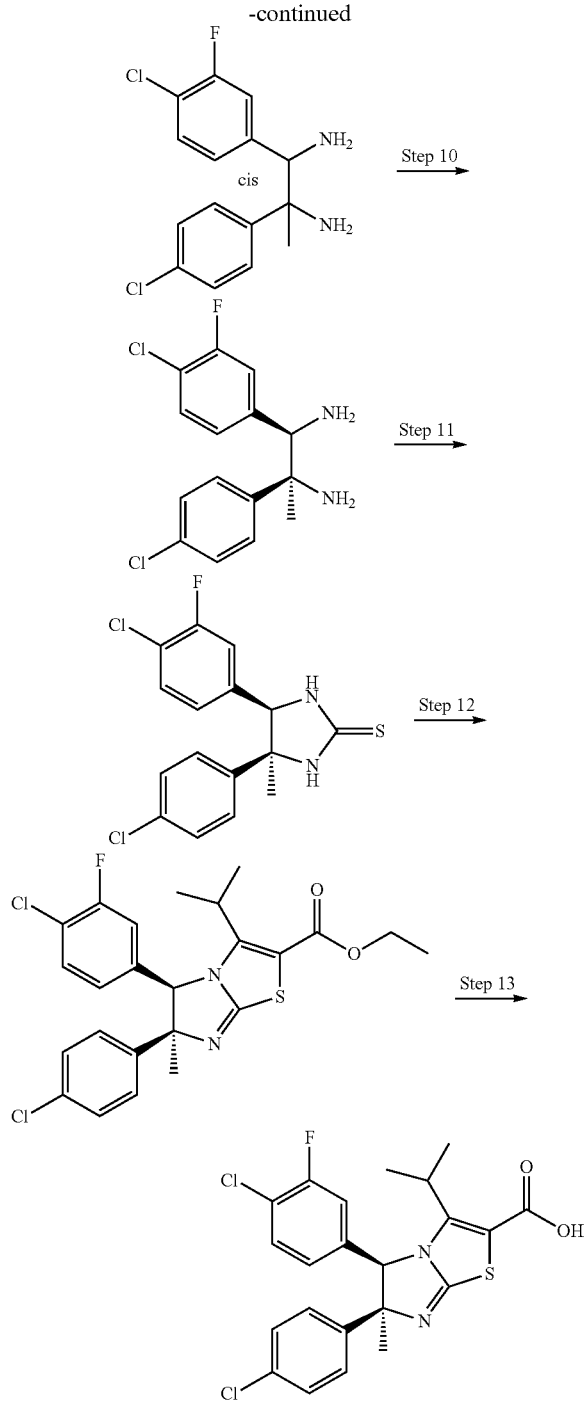

Step 1: ethyl 2-amino-2-(4-chlorophenyl)propionate

4'-chloroacetophenone instead of 1-(6-chloropyridin-3-yl)ethanone was reacted in the same way as in Step 1 of Reference Example 1 to give the title compound as a yellow oil.
MS (ESI) m/z: 228 [(M+1)]⁺.

Step 2: ethyl 2-[(tert-butoxycarbonyl)amino]-2-(4-chlorophenyl)propionate

The compound obtained in Step 1 above was reacted in the same way as in Step 2 of Reference Example 1 to give the title compound as a colorless solid.
¹H-NMR (400 MHz, CDCl₃) δ: 1.17 (3H, t, J=7.3 Hz), 1.37 (9H, brs), 1.97 (3H, s), 4.08-4.21 (2H, m), 5.92 (1H, br), 7.29-7.33 (2H, m), 7.36-7.41 (2H, m).
MS (ESI) m/z: 350 [(M+Na)]⁺.

Step 3: tert-butyl[1-(4-chlorophenyl)-1-methyl-2-oxoethyl]carbamate

The compound obtained in Step 2 above was reacted in the same way as in Step 3 of Reference Example 1 to give the title compound as a colorless solid.
¹H-NMR (400 MHz, CDCl₃) δ: 1.42 (9H, brs), 1.81 (3H, s), 5.71 (1H, br), 7.31-7.39 (4H, m), 9.27 (1H, s).

Step 4: tert-butyl[2-(4-chloro-3-fluorophenyl)-1-(4-chlorophenyl)-2-hydroxy-1-methylethyl]carbamate The compound obtained in Step 3 above was reacted in the same way as in Step 4 of Reference Example 1 to give the title compound as a colorless solid.
¹H-NMR (400 MHz, CDCl₃) δ: 1.43 (9H, brs), 1.55 (3H, brs), 5.08 (2H, br), 5.40 (1H, br), 6.80 (1H, br), 7.02-7.07 (1H, m), 7.24-7.35 (5H, m).
MS (ESI) m/z: 436 [(M+Na)]⁺.

Step 5: tert-butyl[2-(4-chloro-3-fluorophenyl)-1-(4-chlorophenyl)-1-methyl-2-oxoethyl]carbamate The compound obtained in Step 4 above was reacted in the same way as in Step 5 of Reference Example 1 to give the title compound as a colorless solid.
¹H-NMR (400 MHz, CDCl₃) δ: 1.29 (9H, brs), 1.96 (3H, s), 6.19 (1H, br), 7.28-7.42 (7H, m).
MS (ESI) m/z: 434 [(M+Na)]⁺.

Step 6: 2-amino-1-(4-chloro-3-fluorophenyl)-2-(4-chlorophenyl)propan-1-one

The compound obtained in Step 5 above was reacted in the same way as in Step 6 of Reference Example 1 to give the title compound as a colorless solid.
MS (ESI) m/z: 312 [(M+1)]⁺.

Step 7: 4-(4-chloro-3-fluorophenyl)-3-(4-chlorophenyl)-3-methyl-2,3-dihydro-1,2,5-thiadiazole 1,1-dioxide The compound obtained in Step 6 above was reacted in the same way as in Step 7 of Reference Example 1 to give the title compound as a colorless solid.
¹H-NMR (400 MHz, CDCl₃) δ: 2.06 (3H, s), 4.74 (1H, br), 7.34-7.54 (7H, m).

Step 8: (3S*,4R*)-4-(4-chloro-3-fluorophenyl)-3-(4-chlorophenyl)-3-methyl-1,2,5-thiadiazole 1,1-dioxide The compound obtained in Step 7 above was reacted in the same way as in Step 8 of Reference Example 1 to give the title compound as a colorless solid.
¹H-NMR (400 MHz, CDCl₃) δ: 1.78 (3H, s), 4.93 (1H, d, J=2.3 Hz), 6.95 (1H, d, J=8.5 Hz), 7.07-7.14 (3H, m), 7.21 (2H, d, J=8.8 Hz), 7.35 (1H, t, J=8.1 Hz), 7.94-7.97 (2H, m).
MS (ESI) m/z: 375 [(M+1)]⁺.

Step 9: (1R*,2S*)-1-(4-chloro-3-fluorophenyl)-2-(4-chlorophenyl)propane-1,2-diamine The compound obtained in Step 8 above was reacted in the same way as in Step 9 of Reference Example 1 to give the title compound as a colorless solid.

$^1$H-NMR (400 MHz, CDCl$_3$) δ: 1.49 (3H, s), 1.50 (4H, rbs), 4.08 (1H, s), 6.75 (1H, d, J=8.2 Hz), 6.94 (1H, dd, J=10.5, 1.3 Hz), 7.19 (1H, t, J=7.8 Hz), 7.26 (4H, s).
MS (ESI) m/z: 313 [(M+1)]$^+$.

Step 10: (1R,2S)-1-(4-chloro-3-fluorophenyl)-2-(4-chlorophenyl)propane-1,2-diamine The compound obtained in Step 9 above was optically resolved in the same way as in Step 10 of Reference Example 1 to give the title compound as a pale yellow oil.
MS (ESI) m/z: 313 [(M+1)]$^+$.
[α]$_D$=+67.4° (c=1.0, chloroform, 25° C.)

Step 11: (4S,5R)-5-(4-chloro-3-fluorophenyl)-4-(4-chlorophenyl)-4-methylimidazolidine-2-thione The compound obtained in Step 10 above was reacted in the same way as in Step 11 of Reference Example 1 to give the title compound as a pale yellow oil. This compound was used in next reaction without being purified.

Step 12: ethyl (5R,6S)-5-(4-chloro-3-fluorophenyl)-6-(4-chlorophenyl)-3-isopropyl-6-methyl-5,6-dihydroimidazo[2,1-b][1,3]thiazole-2-carboxylate The compound obtained in Step 11 above was reacted in the same way as in Step 12 of Reference Example 1 to give the title compound as a pale yellow solid.

$^1$H-NMR (400 MHz, CDCl$_3$) δ: 0.90 (3H, d, J=7.3 Hz), 1.02 (3H, d, J=7.1 Hz), 1.34 (3H, t, J=7.2 Hz), 1.80 (3H, s), 3.35-3.37 (1H, m), 4.25 (2H, q, J=7.1 Hz), 5.03 (1H, s), 6.54 (2H, brs), 7.07-7.12 (5H, m).

Step 13: (5R,6S)-5-(4-chloro-3-fluorophenyl)-6-(4-chlorophenyl)-3-isopropyl-6-methyl-5,6-dihydroimidazo[2,1-b][1,3]thiazole-2-carboxylic acid The compound obtained in Step 12 above was reacted in the same way as in Step 13 of Example 1 to give the title compound as a colorless solid.

$^1$H-NMR (400 MHz, DMSO-d$_6$) δ: 0.91 (3H, d, J=7.3 Hz), 0.98 (3H, d, J=7.1 Hz), 1.18 (1H, td, J=7.1, 0.9 Hz), 1.89 (3H, s), 5.98 (1H, s), 7.20-7.38 (7H, m).

Reference Example 28

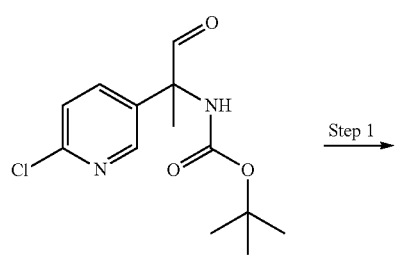

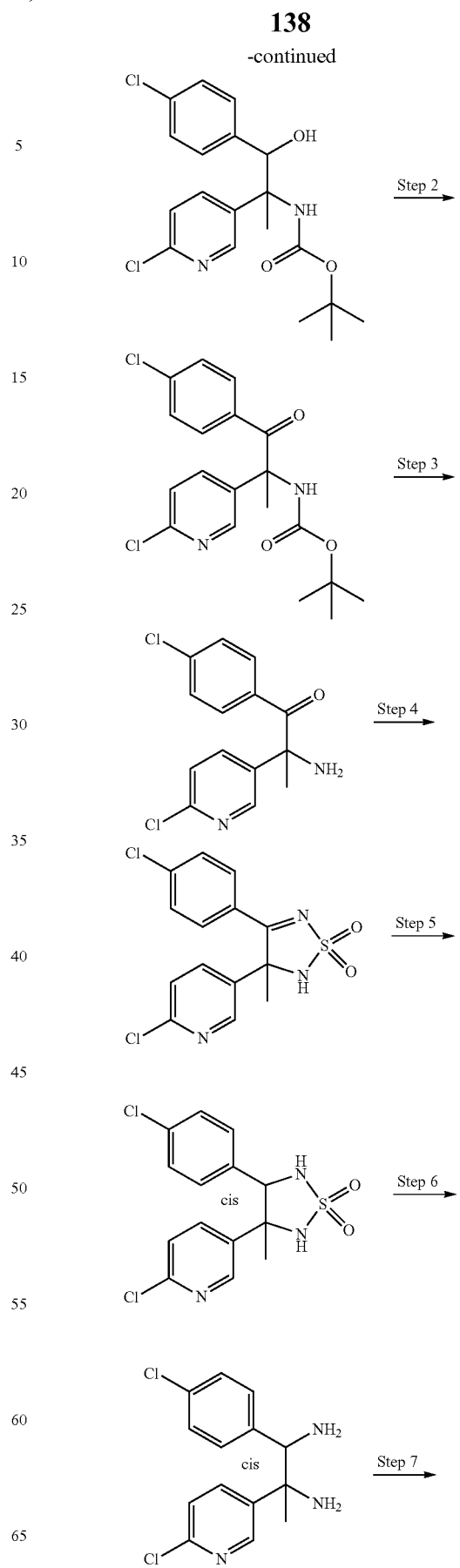

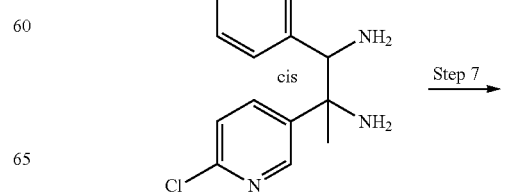

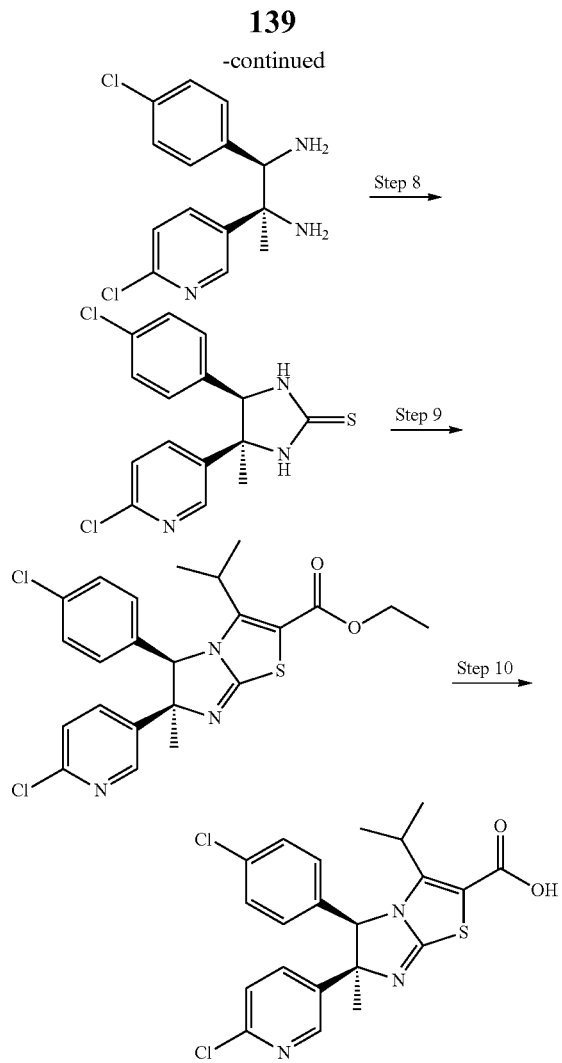

Step 1: tert-butyl[2-(4-chlorophenyl)-1-(6-chloropyridin-3-yl)-2-hydroxy-1-methylethyl]carbamate 4-chlorophenyl magnesium bromide instead of 4-chloro-3-fluorophenyl magnesium bromide was reacted in the same way as in Step 4 of Reference Example 1 to give the title compound as a colorless solid.
$^1$H-NMR (400 MHz, CDCl$_3$) δ: 1.45 (9H, brs), 1.57 (3H, s), 4.89 (1H, br), 5.01 (1H, br), 5.17 (1H, br), 6.74-6.81 (1H, m), 7.09 (1H, brs), 7.17-7.21 (1H, m), 7.28-7.36 (2H, m), 7.64 (1H, br), 8.40 (1H, br).

Step 2: tert-butyl[2-(4-chlorophenyl)-1-(6-chloropyridin-3-yl)-1-methyl-2-oxoethyl]carbamate The compound obtained in Step 1 above was reacted in the same way as in Step 5 of Example 1 to give the title compound as a colorless solid.
$^1$H-NMR (400 MHz, CDCl$_3$) δ: 1.31 (9H, brs), 2.04 (3H, s), 6.45 (1H, br), 7.28-7.35 (3H, m), 7.54 (2H, d, J=7.6 Hz), 7.71 (1H, br), 8.46 (1H, s).

Step 3: 2-amino-1-(4-chlorophenyl)-2-(6-chloropyridin-3-yl)propan-1-one

The compound obtained in Step 2 above was reacted in the same way as in Step 6 of Example 1 to give the title compound as a colorless oil.
MS (ESI) m/z: 295 [(M+1)]$^+$.

Step 4: 2-chloro-5-[4-(4-chlorophenyl)-3-methyl-1,1-dioxido-2,3-dihydro-1,2,5-thiadiazol-3-yl]pyridine The compound obtained in Step 3 above was reacted in the same way as in Step 7 of Example 1 to give the title compound as a colorless solid.
$^1$H-NMR (400 MHz, CDCl$_3$) δ: 2.07 (3H, s), 7.53-7.62 (3H, m), 7.72-7.80 (3H, m), 8.53 (1H, d, J=2.2 Hz), 9.11 (1H, br).
MS (ESI) m/z: 356 [(M+H)]$^+$.

Step 5: (3S*,4R*)-2-chloro-5-[(3S,4R)-4-(4-chlorophenyl)-3-methyl-1,1-dioxido-1,2,5-thiadiazolidin-3-yl]pyridine The compound obtained in Step 4 above was reacted in the same way as in Step 8 of Example 1 to give the title compound as a colorless solid.
$^1$H-NMR (400 MHz, CDCl$_3$) δ: 1.77 (3H, s), 4.95 (1H, d, J=5.0 Hz), 7.09 (2H, d, J=8.2 Hz), 7.25 (2H, d, J=8.2 Hz), 7.32 (1H, d, J=8.5 Hz), 7.48-7.50 (1H, m), 7.95 (1H, d, J=5.0 Hz), 8.01-8.06 (2H, m).
MS (ESI) m/z: 358 [(M+1)]$^+$.

Step 6: (1R*,2S*)-1-(4-chlorophenyl)-2-(6-chloropyridin-3-yl)propane-1,2-diamine The compound obtained in Step 5 above was reacted in the same way as in Step 9 of Example 1 to give the title compound as a pale yellow oil.
$^1$H-NMR (400 MHz, CDCl$_3$) δ: 1.52 (3H, s), 1.58 (4H, brs), 4.08 (1H, s), 6.96 (2H, d, J=8.3 Hz), 7.17-7.22 (3H, m), 7.57 (1H, dd, J=8.4, 2.6 Hz), 8.33 (1H, d, J=2.4 Hz).
MS (ESI) m/z: 296 [(M+1)]$^+$.

Step 7: (1R,2S)-1-(4-chlorophenyl)-2-(6-chloropyridin-3-yl)propane-1,2-diamine

The compound obtained in Step 6 above was optically resolved in the same way as in Step 10 of Example 1 to give the title compound as a yellow oil.
$^1$H-NMR (400 MHz, CDCl$_3$) δ: 1.52 (3H, s), 1.58 (4H, brs), 4.08 (1H, s), 6.96 (2H, d, J=8.3 Hz), 7.17-7.22 (3H, m), 7.57 (1H, dd, J=8.4, 2.6 Hz), 8.33 (1H, d, J=2.4 Hz).
$[α]_D$=+69.4° (c=2.0, chloroform, 24° C.)

Step 8: (4S,5R)-5-(4-chlorophenyl)-4-(6-chloropyridin-3-yl)-4-methylimidazolidine-2-thione The compound obtained in Step 7 above was reacted in the same way as in Step 11 of Example 1 to give the title compound as a colorless solid.
$^1$H-NMR (400 MHz, CDCl$_3$) δ: 1.93 (3H, s), 5.02 (1H, s), 6.36 (1H, brs), 6.70 (1H, brs), 6.85 (2H, d, J=8.5 Hz), 7.12 (1H, d, J=8.3 Hz), 7.15 (2H, d, J=8.3 Hz), 7.25-7.30 (1H, m), 7.97 (1H, d, J=2.7 Hz).
MS (ESI) m/z: 338 [(M+1)]$^+$.

Step 9: ethyl (5R,6S)-5-(4-chlorophenyl)-6-(6-chloropyridin-3-yl)-3-isopropyl-6-methyl-5,6-dihydroimidazo[2,1-b][1,3]thiazole-2-carboxylate The compound obtained in Step 8 above was reacted in the same way as in Step 12 of Example 1 to give the title compound as a colorless solid.
$^1$H-NMR (400 MHz, CDCl$_3$) δ: 0.88 (3H, d, J=7.1 Hz), 1.01 (3H, d, J=7.1 Hz), 1.33 (3H, t, J=7.1 Hz), 1.83 (3H, s), 3.32-3.43 (1H, m), 4.26 (2H, q, J=7.2 Hz), 5.12 (1H, s), 6.68-6.81 (2H, brm), 7.00 (1H, d, J=8.3 Hz), 7.09 (2H, d, J=8.8 Hz), 7.49 (1H, dd, J=8.3, 2.7 Hz), 8.20 (1H, d, J=2.7 Hz).

MS (ESI) m/z: 476 [(M+1)]$^+$.

Step 10: (5R,6S)-5-(4-chlorophenyl)-6-(6-chloropyridin-3-yl)-3-isopropyl-6-methyl-5,6-dihydroimidazo[2,1-b][1,3]thiazole-2-carboxylic acid The compound obtained in Step 9 above was reacted in the same way as in Step 13 of Example 1 to give the title compound as a colorless solid.

$^1$H-NMR (400 MHz, DMSO-d$_6$) δ: 0.76 (3H, d, J=7.1 Hz), 0.96 (3H, d, J=7.1 Hz), 1.72 (3H, s), 5.70 (1H, s), 6.46-6.62 (2H, m), 7.15-7.29 (3H, m), 7.65 (1H, dd, J=8.2, 2.3 Hz), 8.25 (1H, s).

MS (ESI) m/z: 448 [(M+1)]$^+$.

Test Example 1

Mdm2/P53 Binding Assay

A protein dilution containing 6.25 nM each of His-p53 (fusion protein of a p53 partial protein having p53 amino acids at positions 1 to 132, with a histidine protein) and GST-Mdm2 (fusion protein of a Mdm2 partial protein, having Mdm2 amino acids at positions 25 to 108 with leucine residue 33 substituted by glutamic acid, with glutathione transferase) proteins was prepared using a protein buffer solution (20 mM HEPES pH 7.4, 150 mM NaCl, 0.1% BSA). This protein dilution was added in an amount of 8 μL/well to a 384-well plate (384-well low volume NBC, Corning Inc., catalog No: 3676).

Next, a test compound was diluted with DMSO to produce protein buffer solution containing 10% dilution, and this buffer solution was added in an amount of 4 μL/well to the plate.

Subsequently, a solution containing an XL665-labeled anti-His antibody (HTRF monoclonal anti-6HIS antibody labeled with XL665 (catalog No: 61HISXLB), Schering/Cisbio Bioassays) and a europium (Eu)-labeled anti-GST antibody (HTRF monoclonal anti-GST antibody labeled with europium cryptate, Schering/Cisbio Bioassays, catalog No: 61GSTKLB) at concentrations of 2.5 μg/mL and 0.325 μg/mL, respectively, was prepared using an antibody diluting buffer solution (20 mM HEPES pH 7.4, 150 mM NaCl, 0.1% BSA, 0.5 M KF). These dilutions were added in an amount of 8 μL/well (total reaction solution volume: 20 μl/well). Then, the plate was left at 25° C. for 1 hour.

Time-resolved fluorescence at 620 and 665 nm was measured at an excitation wavelength of 320 nm using a plate reader (ARVOsx, PerkinElmer Co., Ltd. or PHERAstar, BMG LABTECH). Ratio (R) was calculated using the measured values (RFU 620 nm and RFU 665 nm) according to the following formula:

$R=(RFU\ 665\ nm-BI-C\times RFU\ 620\ nm)/RFU\ 620\ nm$

BI: measured value at 665 nm of reaction solution (only each buffer solution) nonsupplemented with each protein, the compound, and the antibodies $C(\text{correction factor})=(A-BI)/D$ A and D: each measured value at 665 nm and 620 nm of reaction solution supplemented with only Eu-labeled anti-GST antibody solution.

The R value calculated from the well supplemented with His-p53, GST-Mdm2, the test compound, and each antibody was defined as R (sample). The R value calculated from the well supplemented with His-p53, GST-Mdm2, and each antibody but without the test compound was defined as R (control). The R value calculated from the well supplemented with GST-Mdm2, the test compound, and each antibody but without His-p53 was defined as R (background). T/C was calculated from the formula shown below. An IC$_{50}$ value for Mdm2/p53 binding was calculated by sigmoid fitting. The results are shown in Table 1.

$T/C=(R(\text{sample})-R(\text{background}))/(R(\text{control})-R(\text{background}))$ The results are shown in Table 20.

TABLE 20

|  | IC50 (μM) |
|---|---|
| Compound of Example 1 | 0.0028 |
| Compound of Example 2 | 0.0022 |
| Compound of Example 3 | 0.0039 |
| Compound of Example 4 | 0.0025 |
| Compound of Example 5 | 0.0053 |
| Compound of Example 6 | 0.0024 |
| Compound of Example 7 | 0.0036 |
| Compound of Example 8 | 0.0022 |
| Compound of Example 9 | 0.0041 |
| Compound of Example 10 | 0.014 |
| Compound of Example 11 | 0.0032 |
| Compound of Example 12 | 0.0050 |
| Compound of Example 13 | 0.0054 |
| Compound of Example 14 | 0.016 |
| Compound of Example 15 | 0.0027 |
| Compound of Example 16 | 0.0023 |
| Compound of Example 17 | 0.0033 |
| Compound of Example 18 | 0.0016 |
| Compound of Example 19 | 0.0016 |
| Compound of Example 20 | 0.0014 |
| Compound of Example 21 | 0.0022 |
| Compound of Example 22 | 0.0026 |
| Compound of Example 23 | 0.0016 |
| Compound of Example 24 | 0.0012 |
| Compound of Example 25 | 0.0017 |
| Compound of Example 26 | 0.0027 |
| Compound of Example 27 | 0.0019 |
| Compound of Example 28 | 0.0031 |
| Compound of Example 29 | 0.0026 |
| Compound of Example 30 | 0.0031 |
| Compound of Example 31 | 0.0031 |

Test Example 2

Cell Growth Inhibition Assay

A cell growth inhibition assay was conducted using human lung cancer-derived cell line NCI-H460 having wild-type p53.

NCI-H460 cells were suspended in a medium (RPMI1640 medium containing 10% fetal bovine serum) and the suspension was inoculated in an amount of 500 cells/150 μL/well to a 96-well multiwell plate. A test compound was dissolved in DMSO and this solution was diluted with medium to prepare a sample solution (DMSO concentration: 1% or lower). On the next day of inoculation, medium nonsupplemented with the test compound or the sample solution was added in an amount of 50 μL/well. The MTT assay was conducted immediately after the medium was added in an amount of 50 μL on the next day of cell inoculation, and after the sample solution or the medium was added to cells followed by culturing at 37° C. for 3 days in a 5% CO$_2$ atmosphere. The MTT assay was conducted as shown below.

A 5 mg/mL MTT (3-(4,5-dimethylthiazol-2-yl)-2,5-diphenyltetrazolium bromide, Sigma-Aldrich Co., M-2128) solution was prepared using a phosphate buffer solution (Dulbecco's Phosphate-buffered Saline). This MTT solution was added in an amount of 20 μL/well. Then, the plate was cultured at 37° C. for 4 hours in a 5% CO$_2$ atmosphere. The plate was centrifuged at 1200 rpm for 5 minutes and then the culture supernatant was removed by aspiration using a dispenser. DMSO was added in an amount of 150 μL/well to dissolve generated formazan. The plate was stirred using a plate mixer for uniform color development from each well. The absorbance of each well was measured under conditions of OD 540 nm and reference 660 nm using a plate reader (SpectraMax PLUS384, Molecular Devices, CA, USA).

The OD value measured on the day of adding the sample solution was defined as S. The OD value measured three days after addition of the sample solution was defined as T. The OD value measured three days after addition of the DMSO dilution was defined as C. T/C (%) was determined at each concentration according to the calculation formula shown below to prepare a dose response curve, from which 50% growth inhibition concentration ($GI_{50}$ value) was calculated.

$$T/C(\%) = (T-S)/(C-S) \times 100$$

The compounds of Examples 1 to 6, 8 to 10, 15, 16, 18 to 25, 27, 29, and 31 exhibited anti-cellular effect of $GI_{50}$ (μM)<0.4. The compounds of Examples 7, 11 to 14, 17, 26, 28, and 30 exhibited anti-cellular effect of $0.4 \leq GI_{50} < 2.5$ (μM).

Test Example 3

Anti-Tumor Activity Test

A human osteosarcoma cell line SJSA-1 or SJSA-1-RE (cells in which a p53 reporter gene was incorporated in SJSA-1) was subcutaneously transplanted to nude mice (BALB/C-nu/nu SLC, male, Japan SLC, Inc.). At the point in time when the tumor size reached approximately 100 to 200 mm³, the mice were divided into groups (6 mice/group). A test compound was suspended in 0.5% methylcellulose solution and orally administered twice a day (bid) at a dose of 50 mg/kg for 4 consecutive days. After 2-day drug holiday, the mice were dissected, the tumors were excised and then their weights were measured.

The anti-tumor effect (IR (%)) was calculated according to the following formula:

IR(%)=[1−(average tumor weight of compound-administered group/average tumor weight of untreated control group)]×100.

The compound of Example 2 exhibited anti-tumor effect of 50<IR (%)<70. The compounds of Examples 3, 4, 6, and 9 exhibited anti-tumor effect of 70<IR (%)<100.

Test Example 4

Metabolic Stability Test

100 μL of 100 mM phosphate buffer solution (pH 7.4) containing 3 μM test compound was added to 100 μL of reaction solution containing 100 mM phosphate buffer solution (pH 7.4), 30 mM glucose 6-phosphate, 10 mM $MgCl_2 \cdot 6H_2O$, 3 units/mL glucose 6-phosphate 1-dehydrogenase, and 0.3 to 1.5 mgP/mL human liver microsomes and the mixture was incubated at 37° C. for 20 minutes. Then, 70 μL of 100 mM phosphate buffer solution (pH 7.4) containing 3 mM NADP+ was added and the mixture was further incubated at 37° C. for 30 minutes to conduct a microsomal metabolism test. The compound was quantified by the internal standard method using a quadrupole mass spectrometer connected to a high performance liquid chromatography apparatus. The metabolic stability (residual percentage of compound: MS %) was determined according to the following formula:

MS(human)(%)=(peak area ratio of test compound after addition of NADP+ and incubation for 30 minutes)/(peak area ratio of test compound before addition of NADP+)×100.

(peak area ratio: peak area of test compound divided by that of internal standard substance)

The results are shown in Table 21.

TABLE 21

|  | MS (human) % |
|---|---|
| Compound of Example 1 | 77 |
| Compound of Example 2 | 100 |
| Compound of Example 3 | 68 |
| Compound of Example 4 | 100 |
| Compound of Example 5 | ND |
| Compound of Example 6 | 69 |
| Compound of Example 7 | 100 |
| Compound of Example 8 | 95 |
| Compound of Example 9 | 80 |
| Compound of Example 10 | 48 |
| Compound of Example 11 | 100 |
| Compound of Example 12 | 69 |
| Compound of Example 13 | 100 |
| Compound of Example 14 | 100 |
| Compound of Example 15 | 44 |
| Compound of Example 16 | 56 |
| Compound of Example 17 | 44 |
| Compound of Example 18 | 6 |
| Compound of Example 19 | 93 |
| Compound of Example 20 | 36 |
| Compound of Example 21 | 96 |
| Compound of Example 22 | 60 |
| Compound of Example 23 | 24 |
| Compound of Example 24 | 89 |
| Compound of Example 25 | 47 |
| Compound of Example 26 | 57 |
| Compound of Example 27 | 91 |
| Compound of Example 28 | 51 |
| Compound of Example 29 | 96 |
| Compound of Example 30 | 62 |
| Compound of Example 31 | 6 |

(ND: Not Determined)

What is claimed is:

1. A compound represented by formula (1) or a pharmaceutically acceptable salt thereof:

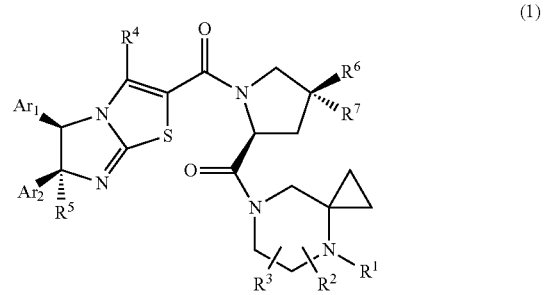

(1)

wherein
$Ar_1$ represents a phenyl group optionally substituted with one or more substituents each independently selected from a halogen atom, a cyano group, and a $C_1$-$C_6$ alkyl group;
$Ar_2$ represents a phenyl group optionally substituted with one or more substituents each independently selected from a halogen atom, a $C_1$-$C_6$ alkyl group, and a cyano group; or a pyridyl group optionally substituted with one or more substituents each independently selected from a halogen atom, a $C_1$-$C_6$ alkyl group, and a cyano group;
$R^1$ represents a $C_1$-$C_6$ alkyl group optionally substituted with one or more substituents each independently selected from a halogen atom, a hydroxy group, a $C_1$-$C_6$ alkoxy group, a carbamoyl group, an amino group, a $C_1$-$C_6$ alkanoyl group, and a cyano group; or a $C_1$-$C_6$ alkanoyl group optionally substituted with one or more substituents each independently selected from a halogen atom, a hydroxy group, a $C_1$-$C_6$ alkoxy group, a carbamoyl group, an amino group, and a cyano group; a hydrogen atom; or a hydroxy group;

R² and R³ each independently represent a $C_1$-$C_6$ alkyl group optionally substituted with one or more substituents each independently selected from a halogen atom, a hydroxy group, a $C_1$-$C_6$ alkoxy group, a carbamoyl group, an amino group, a $C_1$-$C_6$ alkanoyl group, and a cyano group; a carboxy group; or a hydrogen atom; or R² and R³ may together form an oxo group; or R² and R³ together with the carbon atoms to which R² and R³ are respectively bonded may form a 3- to 5-membered saturated hydrocarbon ring in a spiro form;

R⁴ represents a $C_1$-$C_6$ alkyl group optionally substituted with one or more substituents each independently selected from a halogen atom, a hydroxy group, a $C_1$-$C_6$ alkoxy group, a carbamoyl group, an amino group, a $C_1$-$C_6$ alkanoyl group, and a cyano group;

R⁵ represents a $C_1$-$C_6$ alkyl group optionally substituted with one or more substituents each independently selected from a halogen atom, a hydroxy group, a $C_1$-$C_6$ alkoxy group, a carbamoyl group, an amino group, a $C_1$-$C_6$ alkanoyl group, and a cyano group;

R⁶ represents a halogen atom or a hydrogen atom; and R⁷ represents a halogen atom.

2. A compound according to claim 1 represented by general formula (2) or a pharmaceutically acceptable salt thereof:

(2)

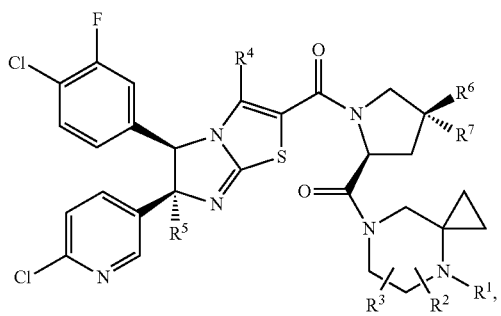

wherein R¹, R², R³, R⁴, R⁵, R⁶, and R⁷ are as defined in claim 1.

3. A compound according to claim 1 or a pharmaceutically acceptable salt thereof, wherein R¹ is a $C_1$-$C_6$ alkyl group, a $C_1$-$C_6$ alkanoyl group optionally substituted with one or more halogen atoms, or a hydrogen atom.

4. A compound according to claim 1 or a pharmaceutically acceptable salt thereof, wherein R⁴ is a $C_1$-$C_6$ alkyl group.

5. A compound according to claim 1 or a pharmaceutically acceptable salt thereof, wherein R⁵ is a $C_1$-$C_6$ alkyl group.

6. A pharmaceutical composition comprising a compound according to claim 1 or a pharmaceutically acceptable salt thereof and a pharmaceutically acceptable carrier.

7. A compound represented by the following formula or a pharmaceutically acceptable salt thereof:

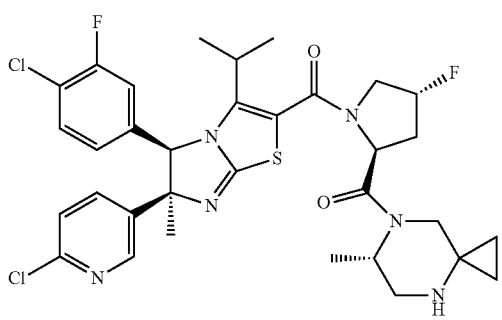

8. A compound represented by the following formula or a pharmaceutically acceptable salt thereof:

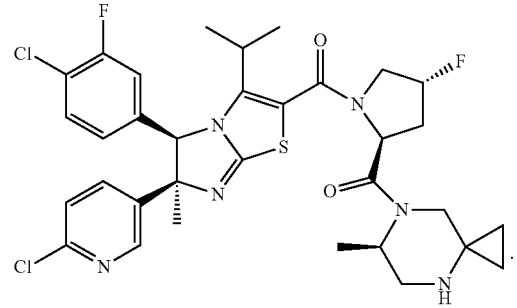 [SMILES: CC(C)C1=C(C(=O)N2C[C@H](F)C[C@H]2C(=O)N2CC3(CC3)NC[C@H]2C)SC2=N[C@@](C)(c3ccc(Cl)nc3)[C@@H](c3ccc(Cl)c(F)c3)N21]

9. A compound represented by the following formula or a pharmaceutically acceptable salt thereof:

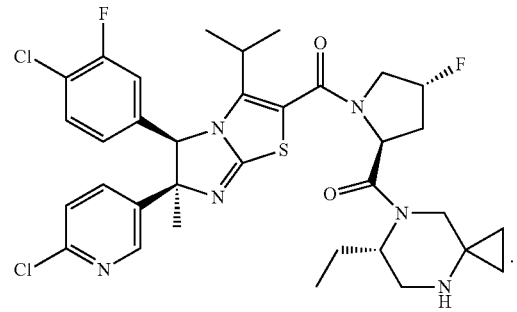 [SMILES: CC[C@H]1CNC2(CC2)CN1C(=O)[C@@H]1C[C@@H](F)CN1C(=O)C1=C(C(C)C)N2C(=N[C@@](C)(c3ccc(Cl)nc3)[C@H]2c2ccc(Cl)c(F)c2)S1]

10. A compound represented by the following formula or a pharmaceutically acceptable salt thereof:

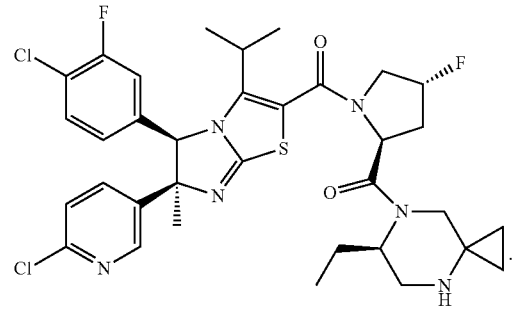

11. A compound represented by the following formula or a pharmaceutically acceptable salt thereof:

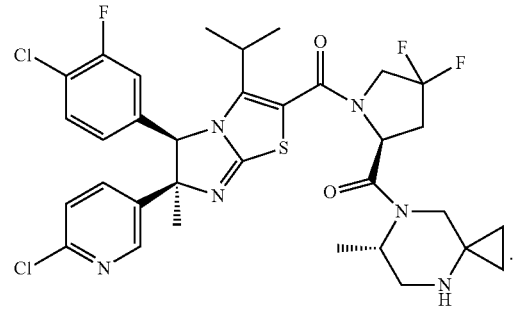 [SMILES: CC(C)C1=C(C(=O)N2CC(F)(F)C[C@H]2C(=O)N2CC3(CC3)NC[C@@H]2C)SC2=N[C@@](C)(c3ccc(Cl)nc3)[C@@H](c3ccc(Cl)c(F)c3)N21]

* * * * *